(12) United States Patent
Reader et al.

(10) Patent No.: US 9,187,465 B2
(45) Date of Patent: Nov. 17, 2015

(54) OXAZOLE TYROSINE KINASE INHIBITORS

(71) Applicant: Sareum Limited, Cambridge (GB)

(72) Inventors: John Charles Reader, Linton (GB); John Mark Ellard, Royston (GB); Helen Boffey, Debden (GB); Susanne Taylor, Cambridge (GB); Andrew David Carr, Great Chesterford (GB); Michael Cherry, Haddenham (GB); Michelle Wilson, Cambridge (GB); Richard Boakye Owoare, London (GB)

(73) Assignee: SAREUM LIMITED (GB)

(*) Notice: Subject to any disclaimer, the term of this patent is extended or adjusted under 35 U.S.C. 154(b) by 0 days.

(21) Appl. No.: 14/529,902

(22) Filed: Oct. 31, 2014

(65) Prior Publication Data

US 2015/0057282 A1 Feb. 26, 2015

Related U.S. Application Data

(60) Continuation of application No. 14/294,263, filed on Jun. 3, 2014, now Pat. No. 8,921,544, which is a continuation of application No. 13/705,659, filed on Dec. 5, 2012, now abandoned, which is a division of application No. 12/599,653, which is a continuation of application No. PCT/GB2008/001612, filed on May 9, 2008, now Pat. No. 8,378,095.

(60) Provisional application No. 60/917,191, filed on May 10, 2007, provisional application No. 60/987,273, filed on Nov. 12, 2007.

(30) Foreign Application Priority Data

May 10, 2007 (GB) .................................. 0709031.9

(51) Int. Cl.
| | |
|---|---|
| C07D 263/48 | (2006.01) |
| C07D 413/12 | (2006.01) |
| C07D 413/14 | (2006.01) |
| C07D 233/90 | (2006.01) |
| C07D 263/34 | (2006.01) |
| C07D 401/04 | (2006.01) |
| C07D 403/04 | (2006.01) |
| C07D 409/04 | (2006.01) |
| C07D 413/04 | (2006.01) |
| C07D 413/10 | (2006.01) |
| C07D 451/04 | (2006.01) |
| C07D 453/02 | (2006.01) |
| C07D 471/04 | (2006.01) |
| C07D 451/02 | (2006.01) |

(52) U.S. Cl.
CPC ............ *C07D 413/14* (2013.01); *C07D 233/90* (2013.01); *C07D 263/34* (2013.01); *C07D 263/48* (2013.01); *C07D 401/04* (2013.01); *C07D 403/04* (2013.01); *C07D 409/04* (2013.01); *C07D 413/04* (2013.01); *C07D 413/10* (2013.01); *C07D 413/12* (2013.01); *C07D 451/02* (2013.01); *C07D 451/04* (2013.01); *C07D 453/02* (2013.01); *C07D 471/04* (2013.01)

(58) Field of Classification Search
None
See application file for complete search history.

(56) References Cited

U.S. PATENT DOCUMENTS

| 7,125,891 B2 | 10/2006 | Breslin |
|---|---|---|
| 8,378,095 B2 | 2/2013 | Reader |

FOREIGN PATENT DOCUMENTS

| DE | 2301030 | 2/1974 |
|---|---|---|
| DE | 19653355 | 6/1998 |
| DK | 20060313 | 3/2006 |
| GB | 1374345 | 11/1974 |
| JP | 6310767 | 1/1988 |
| JP | 86155456 | 1/1988 |
| WO | 0158890 | 8/2001 |
| WO | 0200649 | 1/2002 |

(Continued)

OTHER PUBLICATIONS

Golub et al. Science (1999), vol. 286, pp. 531-536.*

(Continued)

*Primary Examiner* — Alicia L Otton
(74) *Attorney, Agent, or Firm* — Heslin Rothenberg Farley & Mesiti, P.C.

(57) ABSTRACT

The invention provides a compound which is an amide of the formula (1), or a salt, solvate, N-oxide or tautomer thereof; wherein: a is 0 or 1; b is 0 or 1: provided that the sum of a and b is 0 or 1; T is O or NH Ar$^1$ is a monocyclic or bicyclic 5- to 10-membered aryl or heteroaryl group containing up to 4 heteroatoms selected from O, N and S, and being optionally substituted by one or more substituents R$^1$; Ar$^2$ Js a monocyclic or bicyclic 5- to 10-membered aryl or heteroaryl group containing up to 4 heteroatoms selected from O, N and S and being optionally substituted by one or more substituents R$^2$; and R$^1$ and R$^2$ are as defined in the claims. The compounds are inhibitors of kinases and in particular FLT3, FLT4 and Aurora kinases.

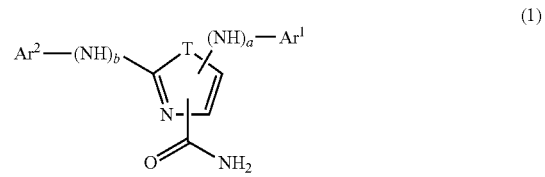

8 Claims, No Drawings

(56) References Cited

FOREIGN PATENT DOCUMENTS

| WO | 2004005283 | 1/2004 |
|----|------------|--------|
| WO | 2005040139 | 5/2005 |
| WO | 2006095159 | 9/2006 |
| WO | 2007043400 | 4/2007 |
| WO | 2007131953 | 11/2007 |
| WO | 2008024980 | 2/2008 |

OTHER PUBLICATIONS

Huff, Joel R. HIV Protease: A novel chemotherapeutic target for AIDS. Journal of Medicinal Chemistry, 34(8) (1991), 2305-2314.*

Lala et al. Cancer and Metastasis Reviews (1998), 17(1), 91-106.*
J. Lykkeberg et al., Acta Chemica Scandinavica, Series B: Organic Chemistry and Biochemistry (1975) B29(7), 793-5.
Ponomarev et al., Zhurnal Fizicheskoi Khimii (1990) 64(10), 2723-9 (Chem Abs. 114:100938).
Ozaki et al., Chem. Pharm. Bull. (1983) 31(12), 4417-24.
Spiekermann et al., Neoplasia, vol. 101, Feb. 15, 2003, pp. 1494-1504.
Harrington et al., Nature Medicine, vol. 10, No. 3, Mar. 2004, pp. 262-267.
Franchetti et al., J. Med. Chem., 1990, 33, 2849-2852.
Morwick et al., J. Med. Chem., 2006, 49, 2898-2908.
Jansen et al., J. Chem. Soc. (1961), 405-11.

* cited by examiner

OXAZOLE TYROSINE KINASE INHIBITORS

CROSS REFERENCE TO RELATED APPLICATIONS

This application is a continuation of U.S. patent application Ser. No. 14/294,263, filed on Jun. 3, 2014, which is a continuation application of U.S. patent application Ser. No. 13/705,659, filed on Dec. 5, 2012, which is a divisional application of U.S. patent application Ser. No. 12/599,653, which issued as U.S. Pat. No. 8,378,095 on Feb. 19, 2013. U.S. patent application Ser. No. 12/599,653 was a national phase filing under 35 U.S.C. §371 of PCT International Application PCT/GB2008/001612, filed May 9, 2008, and published under PCT Article 21(2) in English as WO 2008/139161 A1 on Nov. 20, 2008. PCT/GB2008/001612 claimed priority from British application No. 0709031.9 filed on May 10, 2007, U.S. provisional application No. 60/917,191 filed on May 10, 2007 and 60/987,273 filed on Nov. 12, 2007. The entire contents of each of the prior applications are incorporated herein by reference.

This invention relates to compounds that inhibit or modulate the activity of kinases such as FLT3, FLT4 and Aurora kinases, to the use of the compounds in the treatment or prophylaxis of disease states or conditions mediated by kinases. Also provided are pharmaceutical compositions containing the compounds, processes for their preparation and novel chemical intermediates.

BACKGROUND OF THE INVENTION

Protein kinases constitute a large family of structurally related enzymes that are responsible for the control of a wide variety of signal transduction processes within the cell (Hardie and Hanks (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks and Hunter, *FASEB J.*, (1995) 9. 576-596; Knighton, et al., *Science*, (1991) 253, 407-414; Hiles, et al., *Cell*, (1992) 70, 419-429; Kunz, et al., *Cell*, (1993) 73, 585-596; Garcia-Bustos, et al., *EMBO J.*, (1994) 13, 2352-2361).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. The appropriate protein kinase functions in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, disease and conditions of the immune system, disease and conditions of the central nervous system, and angiogenesis.

Aurora Kinases

Three members of the Aurora kinase family have been found in mammals so far (Nigg, *Nat. Rev. Mol. Cell. Biol.* (2001) 2, 21-32). Aurora A kinase (also referred to in the literature as Aurora 2) is a serine/threonine kinase that is involved in the G2 and M phases of the cell cycle, and is an important regulator of mitosis. Aurora kinase A is believed to play a part in mitotic checkpoint control, chromosome dynamics and cytokinesis (Adams et al., *Trends Cell Biol.*, (2001) 11, 49-54). The kinases are located at the centrosomes of interphase cells, at the poles of the bipolar spindle and in the mid-body of the mitotic apparatus.

The other two currently known Aurora kinases are Aurora B (also referred to in the literature as Aurora 1) and Aurora C (also referred to in the literature as Aurora 3). The Aurora kinases have highly homologous catalytic domains but differ considerably in their N-terminal portions (Katayama et al, *Cancer Metastasis Rev.* (2003) 22(4), 451-64).

The substrates of the Aurora kinases A and B have been identified as including a kinesin-like motor protein, spindle apparatus proteins, histone H3 protein, kinetochore protein and the tumour suppressor protein p53.

Aurora A kinases are believed to be involved in spindle formation and become localised on the centrosome during the early G2 phase where they phosphorylate spindle-associated proteins (Prigent et al., *Cell* (2003) 114, 531-535). Hirota et al, (*Cell*, (2003) 114, 585-598) found that cells depleted of Aurora A protein kinase were unable to enter mitosis. Furthermore, it has been found (Adams, 2001) that mutation or disruption of the Aurora A gene in various species leads to mitotic abnormalities, including centrosome separation and maturation defects, spindle aberrations and chromosome segregation defects.

Aurora kinase A is generally expressed at a low level in the majority of normal tissues, the exceptions being tissues with a high proportion of dividing cells such as the thymus and testis. However, elevated levels of Aurora kinases have been found in many human cancers (Giet et al., *J. Cell. Sci.* (1999) 112, 3591 and Katayama (2003)). Furthermore, Aurora A kinase maps to the chromosome 20q13 region that has frequently been found to be amplified in many human cancers.

Thus, for example, significant Aurora A over-expression has been detected in human breast, ovarian and pancreatic cancers (see Zhou et al., *Nat. Genet.* (1998) 20, 189-193; Tanaka et al., *Cancer Res.* (1999) 59, 2041-2044 and Han et al., *Cancer Res.* (2002) 62, 2890-2896).

Moreover, Isola (*American Journal of Pathology* (1995) 147, 905-911) has reported that amplification of the Aurora A locus (20q13) correlates with poor prognosis for patients with node-negative breast cancer.

Amplification and/or over-expression of Aurora-A is observed in human bladder cancers and amplification of Aurora-A is associated with aneuploidy and aggressive clinical behaviour (see Sen et al., *J. Natl. Cancer Inst.* (2002) 94, 1320-1329).

Elevated expression of Aurora-A has been detected in over 50% of colorectal cancers (see Bischoff et al., *EMBO J.* (1998) 17, 3052-3065 and Takahashi et al., *Jpn. J. Cancer Res.* (2000) 91, 1007-1014), ovarian cancers (see Gritsko et al., *Clin. Cancer Res.* (2003) 9, 1420-1426) and gastric tumours (see Sakakura et al., *British Journal of Cancer* (2001) 84, 824-831).

Tanaka et al., (*Cancer Research* (1999) 59, 2041-2044) found evidence of over-expression of Aurora A in 94% of invasive duct adenocarcinomas of the breast.

High levels of Aurora A kinase have also been found in renal, cervical, neuroblastoma, melanoma, lymphoma, pancreatic and prostate tumour cell lines (Bischoff et al., (1998), *EMBO J.* (1998) 17, 3052-3065; Kimura et al., *J. Biol. Chem.* (1999) 274, 7334-7340; Zhou et al., *Nature Genetics,* 20: 189-193 (1998); Li et al., Clin Cancer Res. 9 (3): 991-7 (2003).

Royce et al (*Cancer*. (2004) 100(1), 12-19) report that the expression of the Aurora 2 gene (known as STK15 or BTAK) has been noted in approximately one-fourth of primary breast tumours.

Reichardt et al (*Oncol Rep*. (2003) 10(5), 1275-9) have reported that quantitative DNA analysis by PCR to search for Aurora amplification in gliomas revealed that 5 out of 16 tumours (31%) of different WHO grade (1× grade II, 1× grade III, 3× grade IV) showed DNA amplification of the Aurora 2 gene. It was hypothesized that amplification of the Aurora 2 gene may be a non-random genetic alteration in human gliomas playing a role in the genetic pathways of tumourigenesis.

Results by Hamada et al (*Br. J. Haematol.* (2003) 121(3), 439-47) also suggest that Aurora 2 is an effective candidate to indicate not only disease activity but also tumourigenesis of non-Hodgkin's lymphoma. Retardation of tumour cell growth resulting from the restriction of this gene's functions could be a therapeutic approach for non-Hodgkin's lymphoma.

In a study by Gritsko et al (*Clin Cancer Res*. (2003) 9(4), 1420-6), the kinase activity and protein levels of Aurora A were examined in 92 patients with primary ovarian tumours. In vitro kinase analyses revealed elevated Aurora A kinase activity in 44 cases (48%). Increased Aurora A protein levels were detected in 52 (57%) specimens. High protein levels of Aurora A correlated well with elevated kinase activity.

Results obtained by Li et al (*Clin. Cancer Res.* 2003 March; 9(3):991-7) showed that the Aurora A gene is over-expressed in pancreatic tumours and carcinoma cell lines and suggest that overexpression of Aurora A may play a role in pancreatic carcinogenesis.

Similarly, it has been shown that Aurora A gene amplification and associated increased expression of the mitotic kinase it encodes are associated with aneuploidy and aggressive clinical behaviour in human bladder cancer. (*J. Natl. Cancer Inst.* (2002) 94(17), 1320-9).

Investigation by several groups (Dutertre and Prigent, *Mol. Interv*. (2003) 3(3), 127-30 and Anand et al., *Cancer Cell.* (2003) 3(1), 51-62) suggests that overexpression of Aurora kinase activity is associated with resistance to some current cancer therapies. For example overexpression of Aurora A in mouse embryo fibroblasts can reduce the sensitivity of these cells to the cytotoxic effects of taxane derivatives. Therefore Aurora kinase inhibitors may find particular use in patients who have developed resistance to existing therapies.

On the basis of work carried out to date, it is envisaged that inhibition of Aurora A kinase will prove an effective means of arresting tumour development.

It has also been shown that there is an increase in expression of Aurora B in tumour cells compared to normal cells (Adams et al., *Chromasoma*. (2001) 110, 65-74). One report suggests that overexpression of Aurora B induces aneuploidy through increased phosphorylation of histone H3 at serine 10, and that cells overexpressing Aurora B form more aggressive tumours and have a higher tendency to form metastatic tumours (Ota et al., *Cancer Res*. (2002) 62, 5168-5177).

Aurora B is required for both spindle checkpoint function and metaphase chromosome alignment in human cells (Adams et al. *J. Cell Biol*. (2001) 153, 865-880; Kallio et al., *Curr. Biol*. (2002) 12, 900-905 and Murata-Hori and Wang *Curr. Biol*. (2002) 12, 894-899). It has been demonstrated that suppression of Aurora B kinase activity compromises chromosome alignment, spindle checkpoint function and cytokinesis (Ditchfield et al., *J. Cell Biol*. (2003) 161, 267-280 and Hauf et al., *J. Cell Biol*. (2003), 161, 281-294). Consequently, after a brief delay cells exit mitosis without dividing and with a 4N DNA content, whereupon they rapidly lose their proliferative potential.

Harrington et al (*Nat. Med*. (2004) 10(3), 262-7) have demonstrated that an inhibitor of the Aurora kinases suppresses tumour growth and induces tumour regression in vivo. In the study, the Aurora kinase inhibitor blocked cancer cell proliferation, and also triggered cell death in a range of cancer cell lines including leukaemic, colorectal and breast cell lines. In addition, it has shown potential for the treatment of leukemia by inducing apoptosis in leukemia cells. VX-680 potently killed treatment-refractory primary Acute Myelogenous Leukemia (AML) cells from patients (Andrews, *Oncogene* (2005) 24, 5005-5015).

Manfredi et al (*PNAS* (2007) 104, 4106-4111) have demonstrated that a small-molecule inhibitor of Aurora A suppresses tumour growth in vivo. In the study, dose-dependent tumour growth inhibition was demonstrated in HCT-116 tumour bearing mice and PC-3 tumour bearing mice versus vehicle treated mice. Tumour growth inhibition of up to 84% against HCT-116 and 93% against PC-3 cell xenografts was observed.

Mortlock et al (*Clin Cancer Res*. (2007) 13(12), 3682-3688) have demonstrated that a small molecule inhibitor of Aurora B suppresses tumour growth in vivo. Immunodeficient mice bearing established SW620, HCT-116, Colo205, A549, Calu-6 or HL-60 tumour xenografts were dosed over 48 h via sub-cutaneous mini-pump infusion with the small molecule inhibitor AZD1152. The inhibition of tumour growth in all cases ranged from 55% to 100% with complete tumour regression observed in 8 of 11 animals bearing the HL-60 xenograft.

On the basis of evidence obtained to date, it is considered likely that Aurora kinase inhibitors should be particularly useful in arresting tumour development and treating cancers such as breast, bladder, colorectal, pancreatic and ovarian cancers, non-Hodgkin's lymphoma, gliomas, nonendometrioid endometrial carcinomas, Acute Myelogenous Leukemia (AML), Chronic Myelogenous Leukaemia (CML), B-cell lymphoma (Mantle cell), and Acute Lymphoblastic Leukemia (ALL).

FLT3

FMS-like tyrosine kinase 3 (FLT3) is a receptor tyrosine kinase involved in the proliferation, differentiation and apoptosis of hematopoietic and non-hematopoietic cells (Scheijen and Griffin, *Oncogene* (2002) 21, 3314-3333 and Reilly, *British Journal of Haematology* (2002) 116, 744-757). As a result of the natural ligand (FL) binding, the FLT3 receptor dimerises resulting in activation of its tyrosine kinase domain, receptor autophosphorylation and recruitment of downstream signalling molecules such as the p85 subunit of PI3K (phosphatidylinositol 3 kinase), PLC-gamma (Phospholipase-C gamma), STAT5a (signal transducer and activator of transcription 5a), and SRC family tyrosine kinases (Gilliland and Griffin, *Blood* (2002) 100(5), 1532-42; Drexler, *Leukemia* (1996) 10(4), 588-99 and Ravandi et al., *Clin Cancer Res*. (2003) 9(2), 535-50).

Activation of these downstream signalling molecules by phosphorylation leads to the proliferative and pro-survival effects of FLT3 (Gilliland and Griffin (2002) and Levis and Small, *Leukemia* (2003) 17(9), 1738-52).

Somatic mutations of FLT3 involving internal tandem duplications in the juxtamembrane region of the receptor, or through point mutation of D835 in the activation loop have been demonstrated in approximately 30% of patients with acute myeloid leukaemia (AML), a cancer of the white blood cells caused through overproduction of immature myeloid white blood cells (Nakao et al., *Leukemia* (1996) 10(12), 1911-8; Thiede et al., *Blood* (2002) 99(12), 4326-35; Yamamoto et al., *Blood* (2001) 97(8), 2434-9; Abu-Duhier et al., *Br. J. Haematol.* (2000) 111(1), 190-5 and Abu-Duhier et al., *Br. J. Haematol.* (2001) 113(4), 983-8).

Other ligand independent activating mutations of FLT3 have recently been described, contributing to the leukaemic transformation in AML. Presence of such mutations at diagnosis has been linked to inferior prognosis in some patients (Jiang et al., *Blood* (2004) 104(6), 1855-8 and Kindler et al., *Blood* (2005) 105(1), 335-40).

FLT4

FLT4 is a receptor tyrosine kinase closely related in structure to the products of the VEGFR-1 and VEGFR-2 genes. FLT4 is activated by its ligand VEGF-C resulting in the promotion of angiogenesis and lymphangiogenesis (Alitalo and Carmeliet, *Cancer Cell* (2002) 1, 219-227; Plate, *Nat. Med.* (2001) 7, 151-152 and Skobe et al., *Nat. Med.*, (2001) 7, 192-198).

FLT4 has been found to be expressed in a variety of human malignancies including lung adenocarcinoma (Li et al., *Chin. Med. J.* (2003) 116, 727-730), colorectal adenocarcinoma (Witte et al., *Anticancer Res.*, (2002) 22, 1463-1466), prostate carcinoma (Kaushal et al., *Clin. Cancer Res.* (2005) 11, 584), head and neck carcinomas (Neuchrist et al., *Head Neck* (2003) 25, 464), leukaemia (Dias et al., *Blood* (2002) 99, 2179) and Kaposi's sarcoma (Weninger et al., *Lab. Invest.*, (1999) 79, 243-251). Expression of FLT4 has also been shown to correlate with the different stages of cervical carcinogenesis (Van Trappen et al, *J. Pathol.*, (2003) 201, 544-554).

Expression levels of VEGF-C and FLT4 were found to correlate with the stage and lymph node metastasis and survival of cancer patients with lung adenocarcinomas. The VEGF-C/FLT4 axis was shown to promote the migration and invasiveness of cancer cells (Kuo et al., 2006, Cancer Cell, 9, 209-223).

J. Lykkeberg et al., *Acta Chemica Scandinavica, Series B: Organic Chemistry and Biochemistry* (1975) B29(7), 793-5 describes the preparation of some 2,4-disubstituted imidazole-5-carboxamides by thermolysis of β-substituted α-(1-tetrazolyl)acrylamides. Amongst the compounds disclosed in the article are 2,5-diphenyl-1H-imidazole-4-carboxylic acid amide and 2-phenyl-5-thiophen-2-yl-1H-imidazole-4-carboxylic acid amide.

Ponomarev et al., *Zhurnal Fizicheskoi Khimii* (1990) 64(10), 2723-9 (Chem. Abs. 114:100938) describes the electronic absorption spectra of fused oxazole compounds. Amongst the compounds disclosed in the article is 2,5-diphenyl-oxazole-4-carboxylic acid amide.

Ozaki et al., *Chem. Pharm. Bull.* (1983) 31(12), 4417-24 discloses a series of 2-substituted oxazole compounds as blood platelet aggregation inhibitors. One of the compounds exemplified in the article is 2-phenyl-5-(3,4,5-trimethoxyphenyl)-oxazole-4-carboxylic acid amide.

JP 63-10767 and JP 86-155456 (Yoshitomi) disclose diaryl imidazoles as analgesic and anti-inflammatory agents. The compound 2-(4-fluorophenyl)-5-(4-methoxyphenyl)-1H-imidazole-4-carboxylic acid amide is specifically disclosed.

WO 2006/095159 (AstraZeneca) discloses imidazolyl-anilino-pyrimidines as cell proliferation inhibitors.

WO 02/00649 (AstraZeneca) discloses substituted quinazolines as Aurora kinase inhibitors.

WO 2004/005283 (Vertex) discloses pyridyl and pyrimidinyl substituted oxazoles, thiazoles and imidazoles as protein kinase inhibitors.

WO 2007/043400 (Kissei) discloses aryl and heteroaryl pyrazole derivatives as xanthine oxidase inhibitors. The compound 2-(4-methylphenyl)-5-phenyl-oxazole-4-carboxylic acid amide is specifically disclosed as a chemical intermediate.

WO 2005/040139 (AB Science et al.) and WO 2007/131953 (AB Science) disclose 2-phenylamino-oxazoles as inhibitors of various tyrosine kinases.

WO 2008/024980 (Serenex Inc.) discloses pyrrole, thiophene, furan, imidazole, oxazole and thiazole derivatives that have Hsp90 inhibiting activity and which are useful for treating a range of diseases including cancer.

SUMMARY OF THE INVENTION

The invention provides compounds that have kinase modulating or inhibiting activity, and which it is envisaged will be useful in preventing or treating disease states or conditions mediated by the kinases.

The compounds of the invention are defined and described below and in the claims appended hereto.

Accordingly, in one aspect, the invention provides a compound which is an amide of the formula (1):

$$Ar^2-(NH)_b \underset{N-}{\overset{T}{\diagdown}} (NH)_a-Ar^1$$
$$\underset{O}{\diagdown} NH_2$$

(1)

or a salt, solvate, N-oxide or tautomer thereof; wherein:

a is 0 or 1;

b is 0 or 1:

provided that the sum of a and b is 0 or 1;

T is O or NH

Ar$^1$ is a monocyclic or bicyclic 5- to 10-membered aryl or heteroaryl group containing up to 4 heteroatoms selected from O, N and S, and being optionally substituted by one or more substituents R$^1$;

Ar$^2$ is a monocyclic or bicyclic 5- to 10-membered aryl or heteroaryl group containing up to 4 heteroatoms selected from O, N and S and being optionally substituted by one or more substituents R$^2$;

R$^1$ is halogen; cyano; nitro; a group R$^a$-R$^b$; or a 3 to 8-membered carbocyclic or heterocyclic ring containing up to 4 heteroatoms (e.g. up to 2 heteroatoms) selected from O, N and S and being optionally substituted by one or more substituents R$^3$;

R$^a$ is a bond, O, CO, X$^1$C(X$^2$), C(X$^2$)X$^1$, X$^1$C(X$^2$)X$^1$, S, SO, SO$_2$, NR$^c$, SO$_2$NR$^c$ or NR$^c$SO$_2$;

R$^b$ is:

hydrogen; or a 3 to 8-membered carbocyclic or heterocyclic ring containing up to 4 heteroatoms (e.g. up to 2 heteroatoms)

selected from O, N and S and being optionally substituted by one or more substituents $R^3$; or a $C_{1-12}$ acyclic hydrocarbon group optionally substituted by one or more substituents selected from hydroxy; oxo; halogen; cyano; nitro; carboxy; amino; $N(R^c)_2$; and 3 to 8-membered carbocyclic or heterocyclic rings containing up to 4 heteroatoms (e.g. up to 2 heteroatoms) selected from O, N and S and being optionally substituted by one or more substituents $R^3$; wherein one to three but not all of the carbon atoms of the $C_{1-12}$ acyclic hydrocarbon group may optionally be replaced by O, CO, $X^1C(X^2)$, $C(X^2)X^1$, $X^1C(X^2)X^1$, S, SO, $SO_2$, $NR^c$, $SO_2NR^c$ or $NR^cSO_2$;

$R^c$ is hydrogen or a $C_{1-4}$ hydrocarbon group;

$X^1$ is O, S or $NR^c$;

$X^2$ is =O, =S or =$NR^c$;

$R^2$ is halogen; cyano; nitro; or a group $R^a$-$R^d$;

$R^d$ is hydrogen; a $C_{1-4}$ alkyl group optionally substituted by one or more fluorine atoms; or a benzyl group wherein the benzene ring of the benzyl group is optionally substituted with one to three substituents selected from halogen, cyano, $C_{1-4}$ alkyl and $C_{1-4}$ alkoxy, and wherein the $C_{1-4}$ alkyl and $C_{1-4}$ alkoxy substituents on the benzene ring are each optionally substituted with one or more fluorine atoms;

$R^3$ is $X^2$; halogen; cyano; nitro; a group $R^a$-$R^e$; or a 3 to 7-membered carbocyclic or heterocyclic ring containing up to 4 heteroatoms (e.g. up to 2 heteroatoms) selected from O, N and S and being optionally substituted by a group $R^4$;

$R^e$ is:

hydrogen; or a $C_{1-6}$ acyclic hydrocarbon group optionally substituted by one or more substituents selected from hydroxy; oxo; halogen; cyano; nitro; carboxy; amino; and $N(R^c)_2$; wherein one to three but not all of the carbon atoms of the $C_{1-6}$ acyclic hydrocarbon group may optionally be replaced by O, S, SO, $SO_2$, $NR^c$, $X^1C(X^2)$, $C(X^2)X^1$ or $X^1C(X^2)X^1$; or a benzyl group wherein the benzene ring of the benzyl group is optionally substituted with one to three substituents selected from halogen, cyano, $C_{1-4}$ alkyl and $C_{1-4}$ alkoxy, and wherein the $C_{1-4}$ alkyl and $C_{1-4}$ alkoxy groups are each optionally substituted with one or more fluorine atoms; and $R^4$ is selected from halogen, cyano, nitro and a group $R^a$-$R^d$;

provided that when a is 0, $Ar^1$ is other than a 2-aminopyridin-4-yl or 2-amino-pyrimidin-4-yl group wherein the 2-amino moiety is optionally substituted;

and that neither $Ar^2$—$(NH)_b$— nor $Ar^1$—$(NH)_a$— form an optionally substituted quinoxalin-4-ylamino group;

and that when a is 1 and b is 0, then $Ar^2$ is other than a bicyclic group containing a pyrrole or pyrazole ring fused to a non-aromatic six-membered carbocyclic ring wherein the point of attachment of $Ar^2$ is a nitrogen atom of the pyrrole or pyrazole ring;

but excluding the compounds:

2,5-diphenyl-1H-imidazole-4-carboxylic acid amide and tautomers thereof;

2-(4-fluorophenyl)-5-(4-methoxyphenyl)-1H-imidazole-4-carboxylic acid amide and tautomers thereof;

2-phenyl-5-thiophen-2-yl-1H-imidazole-4-carboxylic acid amide and tautomers thereof;

2-phenyl-5-(3,4,5-trimethoxy-phenyl)-oxazole-4-carboxylic acid amide;

2,5-diphenyl-oxazole-4-carboxylic acid amide; and 2-(4-methylphenyl)-5-phenyl-oxazole-4-carboxylic acid amide.

In one embodiment, the invention provides a compound which is an amide of the formula (1a):

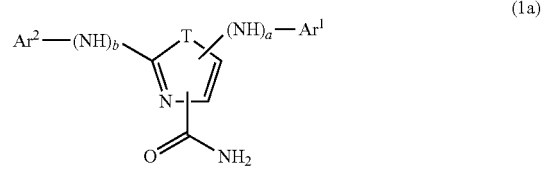

(1a)

or a salt, solvate, N-oxide or tautomer thereof; wherein:

a is 0 or 1;

b is 0 or 1;

provided that the sum of a and b is 0 or 1;

T is O or NH $Ar^1$ is a monocyclic or bicyclic 5- to 10-membered aryl or heteroaryl group containing up to 4 heteroatoms selected from O, N and S, and being optionally substituted by one or more substituents $R^1$;

$Ar^2$ is a monocyclic or bicyclic 5- to 10-membered aryl or heteroaryl group containing up to 4 heteroatoms selected from O, N and S and being optionally substituted by one or more substituents $R^2$;

$R^1$ is halogen; cyano; nitro; a group $R^a$-$R^b$; or a 3 to 7-membered carbocyclic or heterocyclic ring containing up to 4 heteroatoms selected from O, N and S and being optionally substituted by one or more substituents $R^3$;

$R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$;

$R^b$ is:

hydrogen; or a 3 to 7-membered carbocyclic or heterocyclic ring containing up to 4 heteroatoms selected from O, N and S and being optionally substituted by one or more substituents $R^3$; or a $C_{1-12}$ acyclic hydrocarbon group optionally substituted by one or more substituents selected from hydroxy; oxo; halogen; cyano; nitro; carboxy; amino; $N(R^c)_2$; and 3 to 7-membered carbocyclic or heterocyclic rings containing up to 4 heteroatoms selected from O, N and S and being optionally substituted by one or more substituents $R^3$; wherein one to three but not all of the carbon atoms of the $C_{1-12}$ acyclic hydrocarbon group may optionally be replaced by O, CO, $X^1C(X^2)$, $C(X^2)X^1$, $X^1C(X^2)X^1$, S, SO, $SO_2$, $NR^c$, $SO_2NR^c$ or $NR^cSO_2$;

$R^c$ is hydrogen or a $C_{1-4}$ hydrocarbon group;

$X^1$ is O, S or $NR^c$;

$X^2$ is =O, =S or =$NR^c$;

$R^2$ is halogen; cyano; nitro; or a group $R^a$-$R^d$;

$R^d$ is hydrogen or a $C_{1-4}$ alkyl group optionally substituted by one or more fluorine atoms;

$R^3$ is $X^2$; halogen; cyano; nitro; a group $R^a$-$R^e$; or a 3 to 7-membered carbocyclic or heterocyclic ring containing up to 4 heteroatoms selected from O, N and S and being optionally substituted by a group $R^4$;

$R^e$ is:

hydrogen; or a $C_{1-6}$ acyclic hydrocarbon group optionally substituted by one or more substituents selected from hydroxy; oxo; halogen; cyano; nitro; carboxy; amino; and $N(R^c)_2$; wherein one to three but not all of the carbon atoms of the $C_{1-6}$ acyclic hydrocarbon group may optionally be replaced by O, S, SO, SO₂, NR$^c$, X$^1$C(X$^2$), C(X$^2$)X$^1$ or X$^1$C(X$^2$)X$^1$; and R$^4$ is selected from halogen, cyano, nitro and a group R$^a$-R$^d$;
provided that when a is 0, Ar$^1$ is other than a 2-aminopyridin-4-yl or 2-amino-pyrimidin-4-yl group wherein the 2-amino moiety is optionally substituted;
and that neither Ar$^2$—(NH)$_b$— nor Ar$^1$—(NH)$_a$— form an optionally substituted quinoxalin-4-ylamino group;
but excluding the compounds:
2,5-diphenyl-1H-imidazole-4-carboxylic acid amide and tautomers thereof;
2-(4-fluorophenyl)-5-(4-methoxyphenyl)-1H-imidazole-4-carboxylic acid amide and tautomers thereof;
2-phenyl-5-thiophen-2-yl-1H-imidazole-4-carboxylic acid amide and tautomers thereof;
2-phenyl-5-(3,4,5-trimethoxy-phenyl)-oxazole-4-carboxylic acid amide;
2,5-diphenyl-oxazole-4-carboxylic acid amide; and
2-(4-methylphenyl)-5-phenyl-oxazole-4-carboxylic acid amide.

In one sub-group of compounds, a and b are both 0 and therefore the compound is an amide of the formula (2):

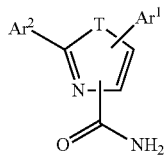

(2)

or a salt, solvate, N-oxide or tautomer thereof; wherein T, Ar$^1$ and Ar$^2$ are as hereinbefore defined in each of formulae (1) and (1a);
but excluding the compounds:
2,5-diphenyl-1H-imidazole-4-carboxylic acid amide and tautomers thereof;
2-(4-fluorophenyl)-5-(4-methoxyphenyl)-1H-imidazole-4-carboxylic acid amide and tautomers thereof;
2-phenyl-5-thiophen-2-yl-1H-imidazole-4-carboxylic acid amide and tautomers thereof;
2-phenyl-5-(3,4,5-trimethoxy-phenyl)-oxazole-4-carboxylic acid amide;
2,5-diphenyl-oxazole-4-carboxylic acid amide; and 2-(4-methylphenyl)-5-phenyl-oxazole-4-carboxylic acid amide.

Within formula (2), one group of compounds consists of amides of the formula (2a):

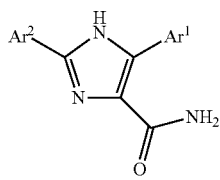

(2a)

and salts, solvates, N-oxides and tautomers thereof; wherein Ar$^1$ and Ar$^2$ are as hereinbefore defined in each of formulae (1) and (1a), but excluding the compounds 2,5-diphenyl-1H-imidazole-4-carboxylic acid amide and tautomers thereof;
2-(4-fluorophenyl)-5-(4-methoxyphenyl)-1H-imidazole-4-carboxylic acid amide and tautomers thereof;
and 2-phenyl-5-thiophen-2-yl-1H-imidazole-4-carboxylic acid amide and tautomers thereof.

Another group of compounds consists of amides of the formula (2b):

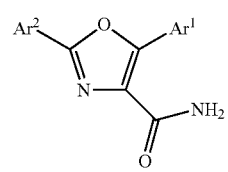

(2b)

and salts, solvates, N-oxides and tautomers thereof; wherein Ar$^1$ and Ar$^2$ are as hereinbefore defined in each of formulae (1) and (1a), but excluding the compounds 2-phenyl-5-(3,4,5-trimethoxy-phenyl)-oxazole-4-carboxylic acid amide;
2,5-diphenyl-oxazole-4-carboxylic acid amide and 2-(4-methylphenyl)-5-phenyl-oxazole-4-carboxylic acid amide.

A further group of compounds consists of amides of the formula (2c):

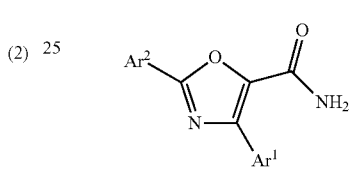

(2c)

and salts, solvates, N-oxides and tautomers thereof; wherein Ar$^1$ and Ar$^2$ are as hereinbefore defined in each of formulae (1) and (1a).

In another subgroup of compounds, a is 1 and b is 0 and therefore the compound is an amide of the formula (3):

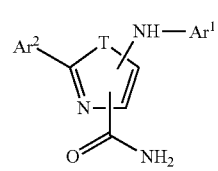

(3)

or a salt, solvate, N-oxide or tautomer thereof; wherein T, Ar$^1$ and Ar$^2$ are as hereinbefore defined in each of formulae (1) and (1a).

Within formula (3), one group of compounds consists of amides of the formula (3a):

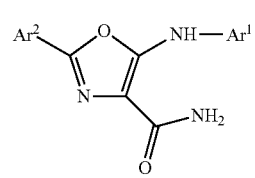

(3a)

and salts, solvates, N-oxides and tautomers thereof; wherein Ar$^1$ and Ar$^2$ are as hereinbefore defined in each of formulae (1) and (1a).

In a further sub-group of compounds, a is 0 and b is 1 and therefore the compound is an amide of the formula (4):

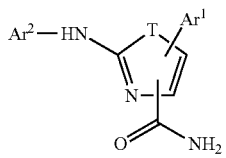

(4)

or a salt, solvate, N-oxide or tautomer thereof; wherein T, Ar¹ and Ar² are as hereinbefore defined in each of formulae (1) and (1a).

Within formula (4), one group of compounds consists of amides of the formula (4a):

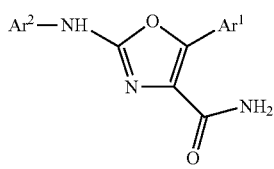

(4a)

and salts, solvates, N-oxides and tautomers thereof; wherein Ar¹ and Ar² are as hereinbefore defined in each of formulae (1) and (1a).

In another aspect, the invention provides a compound for use in medicine, for example for use in the prophylaxis or treatment of a proliferative disease such as cancer or a disease mediated by a kinase selected from FLT3, FLT4 and Aurora kinase, wherein the compound is a compound of the formula (1), (1a), (2), (2a), (2b), (2c), (3), (3a), (4) or (4a) as hereinbefore defined but further including the compounds:

2,5-diphenyl-1H-imidazole-4-carboxylic acid amide and tautomers thereof;
2-(4-fluorophenyl)-5-(4-methoxyphenyl)-1H-imidazole-4-carboxylic acid amide and tautomers thereof;
2-phenyl-5-thiophen-2-yl-1H-imidazole-4-carboxylic acid amide and tautomers thereof;
2-phenyl-5-(3,4,5-trimethoxy-phenyl)-oxazole-4-carboxylic acid amide;
2,5-diphenyl-oxazole-4-carboxylic acid amide; and 2-(4-methylphenyl)-5-phenyl-oxazole-4-carboxylic acid amide.

Further aspects of the invention and particular and preferred embodiments of the invention are as set out below or as defined in the claims appended hereto.

GENERAL PREFERENCES AND DEFINITIONS

In this specification, references to formula (1) include not only formula (1) per se but also formulae (1a), (2), (2a), (2b), (2c), (3), (3a), (4), (4a) and (5) and sub-groups, examples or embodiments thereof, unless the context requires otherwise.

Thus for example, references to therapeutic uses, pharmaceutical formulations and processes for making compounds, where they refer to formula (1), are also to be taken as referring to formulae (1a), (2), (2a), (2b), (2c), (3), (3a), (4), (4a) and (5) and sub-groups, examples or embodiments thereof.

Similarly, where preferences, embodiments and examples are given for compounds of the formula (1), they are also applicable to formulae (1a), (2), (2a), (2b), (2c), (3), (3a), (4), (4a) and (5) unless the context requires otherwise.

As used herein, the term "modulation", as applied to the activity of a kinase such as FLT3, FLT4 or an Aurora kinase, is intended to define a change in the level of biological activity of the kinase(s). Thus, modulation encompasses physiological changes which effect an increase or decrease in the relevant kinase activity. In the latter case, the modulation may be described as "inhibition".

The term "upregulation" as used herein in relation to a kinase is defined as including elevated expression or overexpression of the kinase, including gene amplification (i.e. multiple gene copies) and increased expression by a transcriptional effect, and hyperactivity and activation of the kinase, including activation by mutations.

References herein to a disease state or condition being "mediated" by a particular kinase are intended to operate limitatively so that the various disease states or conditions to which the term is applied are those in which the kinase in question plays a biological role. The biological role played by the kinase may be direct or indirect and may be necessary and/or sufficient for the manifestation of the symptoms of the disease, state or condition (or its aetiology or progression).

The following general preferences and definitions shall apply to each of the moieties T, Ar¹, Ar², R¹ to R⁴ and any sub-definition, sub-group or embodiment thereof, unless the context indicates otherwise.

The term "halogen" as used herein refers to fluorine, chlorine, bromine and iodine and does not include astatine.

The term "aryl" as used herein refers to a carbocyclic ring or group having aromatic character and the term "heteroaryl" is used herein to denote a heterocyclic group having aromatic character. The terms "aryl" and "heteroaryl" (e.g. as used in relation to the moieties Ar¹ and Ar²) embrace aromatic monocyclic ring systems and polycyclic (e.g. bicyclic) ring systems containing one or more aromatic rings. The term covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety (e.g. the five membered ring containing N and T) by the aromatic ring, or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;

b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) an imidazole ring fused to a 5- or 6-membered ring containing 1 or 2 ring heteroatoms;
g) an oxazole ring fused to a 5- or 6-membered ring containing 1 or 2 ring heteroatoms;
h) an isoxazole ring fused to a 5- or 6-membered ring containing 1 or 2 ring heteroatoms;
i) a thiazole ring fused to a 5- or 6-membered ring containing 1 or 2 ring heteroatoms;
j) an isothiazole ring fused to a 5- or 6-membered ring containing 1 or 2 ring heteroatoms;
k) a thiophene ring fused to a 5- or 6-membered ring containing 1, 2 or 3 ring heteroatoms;
l) a furan ring fused to a 5- or 6-membered ring containing 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of carbocyclic aryl groups include phenyl, naphthyl, indenyl, and tetrahydronaphthyl groups.

References to "carbocyclic" and "heterocyclic" rings or groups as used herein (for example in relation to the substituent group $R^3$) shall, unless the context indicates otherwise, include both aromatic and non-aromatic ring systems. Thus, for example, the term "carbocyclic and heterocyclic" includes within its scope aromatic, non-aromatic, unsaturated, partially saturated and fully saturated carbocyclic and heterocyclic ring systems.

The carbocyclic or heterocyclic rings or groups can be aryl or heteroaryl rings or groups as hereinbefore defined The term "non-aromatic group" embraces unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclic groups include cycloalkyl groups as defined below. Partially saturated carbocyclic groups include cycloalkenyl groups as defined below, for example cyclopentenyl, cycloheptenyl and cyclooctenyl. A further example of a cycloalkenyl group is cyclohexenyl.

Examples of non-aromatic heterocyclic groups include heterocyclic groups having from 3 to 7 ring members, typically 4 to 7 ring members, and more usually from 5 to 6 ring members. Such groups typically have 1, 2, 3 or 4 heteroatom ring members selected from nitrogen, oxygen and sulphur.

Further examples of non-aromatic heterocyclic rings include bridged bicyclic ring systems such as bicycloalkanes and azabicycloalkanes. By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged ring systems include bicyclo[2.2.1]heptane, aza-bicyclo[2.2.1]heptane, bicyclo[2.2.2]octane, aza-bicyclo[2.2.2]octane (e.g. quinuclidine), bicyclo[3.2.1]octane and aza-bicyclo[3.2.1]octane. Particular examples of bridged bicyclic ring systems are quinuclidine and 8-methyl-8-aza-bicyclo[3.2.1]octane.

When sulphur is present, it may, where the nature of the adjacent atoms and groups permits, exist as —S—, —S(O)— or —S(O)$_2$—.

The heterocyclic groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ester moieties (e.g. as in butyrolactone), cyclic sulphones (e.g. as in sulpholane and sulpholene), cyclic sulphoxides, cyclic sulphonamides and combinations thereof (e.g. morpholine and thiomorpholine and its S-oxide and S,S-dioxide), and cyclic ureas (e.g. as in imidazolidin-2-one).

Examples of monocyclic non-aromatic heterocyclic groups include 4, 5, 6 and 7-membered monocyclic heterocyclic groups. Particular examples include azetidine, pyrrolidine (e.g. 1-pyrrolidinyl, 2-pyrrolidinyl and 3-pyrrolidinyl), piperidine (e.g. 1-piperidinyl, 2-piperidinyl, 3-piperidinyl and 4-piperidinyl), azepine, pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, morpholine, piperazine, N-alkyl piperazines such as N-methyl piperazine, thiomorpholine and its S-oxide and S,S-dioxide, piperidone, piperazone, and N-alkyl piperidines such as N-methyl piperidine.

One sub-set of non-aromatic heterocyclic groups consists of saturated groups such as azetidine, pyrrolidine, piperidine, morpholine, thiomorpholine, thiomorpholine S,S-dioxide, piperazine, N-alkyl piperazines, and N-alkyl piperidines.

Examples of non-aromatic carbocyclic groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

Preferred non-aromatic carbocyclic groups are saturated monocyclic rings. Typical examples are 3, 4, 5 and 6 membered saturated carbocyclic rings, e.g. optionally substituted cyclopentyl and cyclohexyl rings.

One sub-set of non-aromatic carbocyclic groups includes monocyclic groups and particularly saturated monocyclic groups, e.g. cycloalkyl groups. Examples of such cycloalkyl groups include cyclopropyl, cyclobutyl, cyclopentyl, cyclohexyl and cycloheptyl; more typically cyclopropyl, cyclobutyl, cyclopentyl and cyclohexyl, particularly cyclohexyl.

Further examples of non-aromatic cyclic groups include bridged ring systems such as bicycloalkanes and azabicycloalkanes although such bridged ring systems are generally less preferred. By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged ring systems include bicyclo[2.2.1]heptane, azabicyclo[2.2.1]heptane, bicyclo[2.2.2]octane, aza-bicyclo[2.2.2]octane, bicyclo[3.2.1]octane and aza-bicyclo[3.2.1]octane. A particular example of a bridged ring system is the 1-aza-bicyclo[2.2.2]octan-3-yl group.

In the definition of the compounds of the formula (1) above and as used hereinafter, the term "hydrocarbon" is used in its conventional sense to denote aliphatic, alicyclic and aromatic groups having an all-carbon backbone and consisting of carbon and hydrogen atoms, except where otherwise stated.

In certain cases, as defined herein, one or more of the carbon atoms making up the carbon backbone may be replaced by a specified atom or group of atoms.

Examples of hydrocarbon groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. The examples and preferences expressed below apply to each of the hydrocarbon substituent groups or hydrocarbon-containing substituent groups referred to in the various definitions of substituents for compounds of the formula (1) unless the context indicates otherwise.

The term "acyclic hydrocarbon group" as used herein (e.g. in the phrase "$C_{1-12}$ acyclic hydrocarbon group") encompasses alkyl, alkenyl, alkynyl and mixed alkenyl-alkynyl groups.

Preferred non-aromatic hydrocarbon groups are saturated groups such as alkyl and cycloalkyl groups.

Generally by way of example, the hydrocarbon groups can have up to twelve carbon atoms, unless the context requires otherwise. Subsets of hydrocarbon groups are $C_{1-8}$ hydrocarbon groups, $C_{1-6}$ hydrocarbon groups, $C_{1-4}$ hydrocarbon groups, $C_{1-3}$ hydrocarbon groups and $C_{1-2}$ hydrocarbon groups, specific examples being any individual value or combination of values selected from $C_1$, $C_2$, $C_3$, $C_4$, $C_5$, $C_6$, $C_7$ and $C_8$ hydrocarbon groups.

The term "alkyl" covers both straight chain and branched chain alkyl groups. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers. Subsets of alkyl groups are $C_{1-8}$ alkyl groups, $C_{1-6}$ alkyl groups, $C_{1-4}$ alkyl groups, $C_{1-3}$ alkyl groups and $C_{1-2}$ alkyl groups.

Examples of cycloalkyl groups are those derived from cyclopropane, cyclobutane, cyclopentane, cyclohexane and cycloheptane. Within the sub-set of cycloalkyl groups the cycloalkyl group will have from 3 to 8 carbon atoms, particular examples being $C_{3-6}$ cycloalkyl groups.

Examples of alkenyl groups include, but are not limited to, ethenyl (vinyl), 1-propenyl, 2-propenyl (allyl), isopropenyl, butenyl, buta-1,4-dienyl, pentenyl, and hexenyl. Within the sub-set of alkenyl groups, the alkenyl group may have 2 to 8 carbon atoms, particular examples being $C_{2-6}$ alkenyl groups, such as $C_{2-4}$ alkenyl groups.

Examples of cycloalkenyl groups include, but are not limited to, cyclopropenyl, cyclobutenyl, cyclopentenyl, cyclopentadienyl and cyclohexenyl. Within the sub-set of cycloalkenyl groups, the cycloalkenyl groups may have from 3 to 8 carbon atoms, and particular examples are $C_{3-6}$ cycloalkenyl groups.

Examples of alkynyl groups include, but are not limited to, ethynyl and 2-propynyl (propargyl) groups. Within the sub-set of alkynyl groups the alkynyl groups may have 2 to 8 carbon atoms, particular examples being $C_{2-6}$ alkynyl groups and $C_{2-4}$ alkynyl groups.

Examples of carbocyclic aryl groups include substituted and unsubstituted phenyl groups.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

Where stated, 1 to 3 carbon atoms of a hydrocarbon group may optionally be replaced by O, S, SO, $SO_2$, $NR^c$, $X^1C(X^2)$, $C(X^2)X^1$ or $X^1C(X^2)X^1$ (or a sub-group thereof) wherein $X^1$ and $X^2$ are as hereinbefore defined, provided that at least one carbon atom of the hydrocarbon group remains. For example, 1, 2, 3 or 4 carbon atoms of the hydrocarbon group may be replaced by one of the atoms or groups listed, and the replacing atoms or groups may be the same or different. In general, the number of linear or backbone carbon atoms replaced will correspond to the number of linear or backbone atoms in the group replacing them. Examples of groups in which one or more carbon atom of the hydrocarbon group have been replaced by a replacement atom or group as defined above include ethers and thioethers (C replaced by O or S), amides, esters, thioamides and thioesters (C—C replaced by $X^1C(X^2)$ or $C(X^2)X^1$), sulphones and sulphoxides (C replaced by SO or $SO_2$), amines (C replaced by $NR^c$). Further examples include ureas, carbonates and carbamates (C—C—C replaced by $X^1C(X^2)X^1$).

The term "aza-cycloalkyl" as used herein refers to a cycloalkyl group in which one of the carbon ring members has been replaced by a nitrogen atom. Thus examples of aza-cycloalkyl groups include piperidine and pyrrolidine. The term "oxa-cycloalkyl" as used herein refers to a cycloalkyl group in which one of the carbon ring members has been replaced by an oxygen atom. Thus examples of oxa-cycloalkyl groups include tetrahydrofuran and tetrahydropyran. In an analogous manner, the terms "diaza-cycloalkyl", "dioxa-cycloalkyl" and "aza-oxa-cycloalkyl" refer respectively to cycloalkyl groups in which two carbon ring members have been replaced by two nitrogen atoms, or by two oxygen atoms, or by one nitrogen atom and one oxygen atom.

The definition "$R^a$-$R^b$" as used herein, either with regard to substituents present on a carbocyclic or heterocyclic moiety, or with regard to other substituents present at other locations on the compounds of the formula (1), includes inter alia compounds wherein $R^a$ is selected from a bond, O, CO, OC(O), SC(O), $NR^cC(O)$, OC(S), SC(S), $NR^cC(S)$, $OC(NR^c)$, $SC(NR^c)$, $NR^cC(NR^c)$, C(O)O, C(O)S, $C(O)NR^c$, C(S)O, C(S)S, $C(S)NR^c$, $C(NR^c)O$, $C(NR^c)S$, $C(NR^c)NR^c$, OC(O)O, SC(O)O, NR$^c$C(O)O, OC(S)O, SC(S)O, NR$^c$C(S)O, OC(NR$^c$)O, SC(NR$^c$)O, NR$^c$C(NR$^c$)O, OC(O)S, SC(O)S, NR$^c$C(O)S, OC(S)S, SC(S)S, NR$^c$C(S)S, OC(NR$^c$)S, SC(NR$^c$)S, NR$^c$C(NR$^c$)S, OC(O)NR$^c$, SC(O)NR$^c$, NR$^c$C(O)NR$^c$, OC(S)NR$^c$, SC(S)NR$^c$, NR$^c$C(S)NR$^c$, OC(NR$^c$)NR$^c$, SC(NR$^c$)NR$^c$, NR$^c$C(NR$^c$NR$^c$, S, SO, SO$_2$, NR$^c$, SO$_2$NR$^c$ and NR$^c$SO$_2$ wherein R$^c$ is as hereinbefore defined.

The moiety R$^b$ can be hydrogen or it can be a group selected from carbocyclic and heterocyclic groups having from 3 to 7 ring members (usually 4 to 7 and more usually 5 to 6), and a C$_{1-12}$ hydrocarbon group optionally substituted as defined. Examples of hydrocarbon, carbocyclic and heterocyclic groups are as set out above.

When R$^a$ is O and R$^b$ is a C$_{1-12}$ hydrocarbon group, R$^a$ and R$^b$ together form a hydrocarboxy group. Preferred hydrocarboxy groups include saturated hydrocarboxy such as alkoxy (e.g. C$_{1-6}$ alkoxy, more usually C$_{1-4}$ alkoxy such as ethoxy and methoxy, particularly methoxy), cycloalkoxy (e.g. C$_{3-6}$ cycloalkoxy such as cyclopropyloxy, cyclobutyloxy, cyclopentyloxy and cyclohexyloxy) and cycloalkylalkoxy (e.g. C$_{3-6}$ cycloalkyl-C$_{1-2}$ alkoxy such as cyclopropylmethoxy).

The hydrocarboxy groups can be substituted by various substituents as defined herein. For example, the alkoxy groups can be substituted by halogen (e.g. as in difluoromethoxy and trifluoromethoxy), hydroxy (e.g. as in hydroxyethoxy), C$_{1-2}$ alkoxy (e.g. as in methoxyethoxy), hydroxy-C$_{1-2}$ alkyl (as in hydroxyethoxyethoxy) or a cyclic group (e.g. a cycloalkyl group or non-aromatic heterocyclic group as hereinbefore defined). Examples of alkoxy groups bearing a non-aromatic heterocyclic group as a substituent are those in which the heterocyclic group is a saturated cyclic amine such as morpholine, piperidine, pyrrolidine, piperazine, C$_{1-4}$-alkyl-piperazines, C$_{3-7}$-cycloalkyl-piperazines, tetrahydropyran or tetrahydrofuran and the alkoxy group is a C$_{1-4}$ alkoxy group, more typically a C$_{1-3}$ alkoxy group such as methoxy, ethoxy or n-propoxy.

Alkoxy groups substituted by a monocyclic group such as pyrrolidine, piperidine, morpholine and piperazine and N-substituted derivatives thereof such as N-benzyl, N—C$_{1-4}$ acyl and N—C$_{1-4}$ alkoxycarbonyl. Particular examples include pyrrolidinoethoxy, piperidinoethoxy and piperazinoethoxy.

When R$^a$ is a bond and R$^b$ is a C$_{1-12}$ hydrocarbon group, examples of hydrocarbon groups R$^a$-R$^b$ are as hereinbefore defined. The hydrocarbon groups may be saturated groups such as cycloalkyl and alkyl and particular examples of such groups include methyl, ethyl and cyclopropyl. The hydrocarbon (e.g. alkyl) groups can be substituted by various groups and atoms as defined herein. Examples of substituted alkyl groups include alkyl groups substituted by one or more halogen atoms such as fluorine and chlorine (particular examples including bromoethyl, chloroethyl and trifluoromethyl), or hydroxy (e.g. hydroxymethyl and hydroxyethyl), C$_{1-8}$ acyloxy (e.g. acetoxymethyl and benzyloxymethyl), amino and mono- and dialkylamino (e.g. aminoethyl, methylaminoethyl, dimethylaminomethyl, dimethylaminoethyl and tert-butylaminomethyl), alkoxy (e.g. C$_{1-2}$ alkoxy such as methoxy—as in methoxyethyl), and cyclic groups such as cycloalkyl groups, aryl groups, heteroaryl groups and non-aromatic heterocyclic groups as hereinbefore defined).

Particular examples of alkyl groups substituted by a cyclic group are those wherein the cyclic group is a saturated cyclic amine such as morpholine, piperidine, pyrrolidine, piperazine, C$_{1-4}$-alkyl-piperazines, C$_{3-7}$-cycloalkyl-piperazines, tetrahydropyran or tetrahydrofuran and the alkyl group is a C$_{1-4}$ alkyl group, more typically a C$_{1-3}$ alkyl group such as methyl, ethyl or n-propyl. Specific examples of alkyl groups substituted by a cyclic group include pyrrolidinomethyl, pyrrolidinopropyl, morpholinomethyl, morpholinoethyl, morpholinopropyl, piperidinylmethyl, piperazinomethyl and N-substituted forms thereof as defined herein.

Particular examples of alkyl groups substituted by aryl groups and heteroaryl groups include benzyl and pyridylmethyl groups.

When R$^a$ is SO$_2$NR$^c$, R$^b$ can be, for example, hydrogen or an optionally substituted C$_{1-8}$ hydrocarbon group, or a carbocyclic or heterocyclic group. Examples of R$^a$-R$^b$ where R$^a$ is SO$_2$NR$^b$ include aminosulphonyl, C$_{1-4}$ alkylaminosulphonyl and di-C$_{1-4}$ alkylaminosulphonyl groups, and sulphonamides formed from a cyclic amino group such as piperidine, morpholine, pyrrolidine, or an optionally N-substituted piperazine such as N-methyl piperazine.

Examples of groups R$^a$-R$^b$ where R$^a$ is SO$_2$ include alkylsulphonyl, heteroarylsulphonyl and arylsulphonyl groups, particularly monocyclic aryl and heteroaryl sulphonyl groups. Particular examples include methylsulphonyl, phenylsulphonyl and toluenesulphonyl.

When R$^a$ is NR$^c$, R$^b$ can be, for example, hydrogen or an optionally substituted C$_{1-8}$ hydrocarbon group, or a carbocyclic or heterocyclic group. Examples of R$^a$-R$^b$ where R$^a$ is NR$^c$ include amino, C$_{1-4}$ alkylamino (e.g. methylamino, ethylamino, propylamino, isopropylamino, tert-butylamino), alkylamino (e.g. dimethylamino and diethylamino) and cycloalkylamino (e.g. cyclopropylamino, cyclopentylamino and cyclohexylamiho).

In one general embodiment, when T is N and a is 0, Ar$^1$ may be other than a pyrimidin-4-yl group bearing a substituent at the 2-position thereof.

Specific Embodiments of and Preferences for Ar$^1$, Ar$^2$, and R$^1$ to R$^4$

In this section, the various definitions of Ar$^1$, Ar$^2$, and R$^1$ to R$^4$ set out below apply to each of the general formulae (1), (1a), (2), (2a), (2b), (2c), (3), (3a), (4), (4a) and (5) unless the context indicates otherwise. Each of the various definitions of Ar$^1$, Ar$^2$, and R$^1$ to R$^4$ set out below may be combined with each other and with each of the general formulae (1), (1a), (2), (2a), (2b), (2c), (3), (3a), (4), (4a) and (5).

Ar$^1$

Ar$^1$ is a monocyclic or bicyclic 5- to 10-membered aryl or heteroaryl group containing up to 4 (more preferably up to 3, for example up to 2) heteroatoms selected from O, N and S, and being optionally substituted by one or more substituents R$^1$.

The 5- to 10-membered aryl or heteroaryl groups may be as set out above in the General Preferences and Definitions section.

Preferred aryl and heteroaryl groups are monocyclic 5- and 6-membered rings containing up to 2 and more preferably up to 1 heteroatom selected from O, N and S.

Particular aryl and heteroaryl rings are optionally substituted phenyl, thiophene (e.g. 2-thienyl & 3-thienyl), furan (e.g. 2-furyl & 3-furyl), pyridine (e.g. 2-pyridyl, 3-pyridyl & 4-pyridyl), and pyrazole (e.g. 3-pyrazolyl & 4-pyrazolyl) rings.

More particularly, the aryl and heteroaryl rings are selected from phenyl, 2-thienyl, 3-thienyl, 2-furyl, 3-furyl, 2-pyridyl, 3-pyridyl and 4-pyridyl rings, each optionally substituted by one or more substituent groups R$^1$.

R$^1$

The aryl or heteroaryl ring Ar$^1$ can be optionally substituted by one or more substituents R$^1$.

Typically, each aryl or heteroaryl ring is substituted by 0, 1, 2 or 3 substituents R$^1$.

More typically, each aryl or heteroaryl ring is substituted by 0, 1 or 2 substituents $R^1$ and more preferably by 0 or 1 substituents.

In one embodiment, the aryl or heteroaryl ring is unsubstituted.

In another embodiment, the aryl or heteroaryl ring is substituted by 1 substituent $R^1$.

In another embodiment, the aryl or heteroaryl ring is substituted by 2 substituents $R^1$.

$R^1$ is halogen; cyano; nitro; a group $R^a$-$R^b$; or a 3 to 8-membered (e.g. 3 to 7-membered) carbocyclic or heterocyclic ring containing up to 2 heteroatoms selected from O, N and S and being optionally substituted by one or more substituents $R^3$.

The definitions of halogen, $R^a$-$R^b$; and 3 to 8-membered (e.g. 3 to 7-membered) carbocyclic or heterocyclic rings may be as set out above in the General Preferences and Definitions section.

In a preferred group of compounds, $R^1$ is halogen; cyano; or a group $R^{aa}$-$R^{bb}$;
$R^{aa}$ is a bond, O, CO, OC(O), C(O)O, $NR^{cc}$C(O), C(O)$NR^{cc}$, $NR^{cc}$, OC(O)O, $NR^{cc}$C(O)O, OC(O)$NR^{cc}$, $NR^{cc}$C(O)$NR^{cc}$, S, SO, $SO_2$, $SO_2NR^{cc}$ or $NR^{cc}SO_2$ wherein
$R^{bb}$ is:
  hydrogen; or
  a 3 to 8-membered non-aromatic carbocyclic or heterocyclic ring containing up to 2 heteroatoms selected from O, N and S and being optionally substituted by one or more substituents $R^{3a}$; or
  a 5- or 6-membered aryl or heteroaryl group containing up to 4 (e.g up to 2) heteroatoms selected from O, N and S and being optionally substituted by one or more substituents $R^{3a}$; or
  a $C_{1-12}$ acyclic hydrocarbon group optionally substituted by one or more substituents selected from:
  hydroxy;
  oxo;
  halogen;
  cyano;
  carboxy;
  $N(R^{cc})_2$;
  3 to 8-membered non-aromatic carbocyclic or heterocyclic rings containing up to 2 heteroatoms selected from O, N and S and being optionally substituted by one or more substituents $R^{3a}$;
  5- or 6-membered aryl or heteroaryl groups each containing up to 4 (e.g. up to 2) heteroatoms selected from O, N and S and being optionally substituted by one or more substituents $R^{3a}$;
  wherein one to three but not all of the carbon atoms of the $C_{1-12}$ acyclic hydrocarbon group may optionally be replaced by O, CO, OC(O), $NR^{cc}$C(O), OC($NR^{cc}$), C(O)O, C(O)$NR^{cc}$, $NR^{cc}$, OC(O)O, $NR^{cc}$C(O)O, OC($NR^{cc}$)O, OC(O)$NR^{cc}$, $NR^{cc}$C(O)$NR^{cc}$, S, SO, $SO_2$, $NR^{cc}$, $SO_2NR^{cc}$ and $NR^{cc}SO_2$;
$R^{cc}$ is hydrogen or a saturated $C_{1-4}$ hydrocarbon group;
$R^{3a}$ is oxo; halogen; cyano; a group $R^{aa}$-$R^{ee}$; or a 3 to 8-membered carbocyclic or heterocyclic ring containing up to 2 heteroatoms selected from O, N and S and being optionally substituted by $C_{1-4}$ alkyl, $C_{1-4}$ acyl, $C_{1-4}$ alkoxycarbonyl or $C_{1-4}$ alkylsulphonyl;
$R^{ee}$ is:
  hydrogen; or
  a $C_{1-6}$ acyclic saturated hydrocarbon group optionally substituted by one or more substituents selected from hydroxy; oxo; halogen; cyano; carboxy; and $N(R^{cc})_2$; or
  a benzyl group wherein the benzene ring of the benzyl group is optionally substituted with one to three substituents selected from halogen, cyano, $C_{1-4}$ alkyl and $C_{1-4}$ alkoxy, and wherein the $C_{1-4}$ alkyl and $C_{1-4}$ alkoxy groups are each optionally substituted with one or more fluorine atoms.

In another preferred group of compounds, $R^1$ is halogen; cyano; or a group $R^{aa}$-$R^{bb'}$;
$R^{aa}$ is a bond, O, CO, OC(O), C(O)O, $NR^{cc}$C(O), C(O)$NR^{cc}$, $NR^{cc}$, OC(O)O, $NR^{cc}$C(O)O, OC(O)$NR^{cc}$, $NR^{cc}$C(O)$NR^{cc}$, S, SO, $SO_2$, $SO_2NR^{cc}$ or $NR^{cc}SO_2$ wherein
$R^{bb'}$ is:
  hydrogen; or
  a 3 to 7-membered non-aromatic carbocyclic or heterocyclic ring containing up to 2 heteroatoms selected from O, N and S and being optionally substituted by one or more substituents $R^{3a}$; or
  a 5- or 6-membered aryl or heteroaryl group containing up to 4 (e.g up to 2) heteroatoms selected from O, N and S and being optionally substituted by one or more substituents $R^{3a}$; or
  a $C_{1-12}$ acyclic hydrocarbon group optionally substituted by one or more substituents selected from:
  hydroxy;
  oxo;
  halogen;
  cyano;
  carboxy;
  $N(R^{cc})_2$,
  3 to 7-membered non-aromatic carbocyclic or heterocyclic rings containing up to 2 heteroatoms selected from O, N and S and being optionally substituted by one or more substituents $R^{3a}$;
  5- or 6-membered aryl or heteroaryl groups each containing up to 4 (e.g. up to 2) heteroatoms selected from O, N and S and being optionally substituted by one or more substituents $R^{3a}$;
  wherein one to three but not all of the carbon atoms of the $C_{1-12}$ acyclic hydrocarbon group may optionally be replaced by O, CO, OC(O), $NR^{cc}$C(O), OC($NR^{cc}$), C(O)O, C(O)$NR^{cc}$, $NR^{cc}$, OC(O)O, $NR^{cc}$C(O)O, OC($NR^{cc}$)O, OC(O)$NR^{cc}$, $NR^{cc}$C(O)$NR^{cc}$, S, SO, $SO_2$, $NR^{X}$, $SO_2NR^{cc}$ and $NR^{cc}SO_2$;
$R^{cc}$ is hydrogen or a saturated $C_{1-4}$ hydrocarbon group;
$R^{3a}$ is oxo; halogen; cyano; a group $R^{aa}$-$R^{ee'}$; or a 3 to 7-membered carbocyclic or heterocyclic ring containing up to 2 heteroatoms selected from O, N and S and being optionally substituted by $C_{1-4}$ alkyl, $C_{1-4}$ acyl, $C_{1-4}$ alkoxycarbonyl or $C_{1-4}$ alkylsulphonyl;
$R^{ee'}$ is hydrogen; or a $C_{1-6}$ acyclic saturated hydrocarbon group optionally substituted by one or more substituents selected from hydroxy; oxo; halogen; cyano; carboxy; and $N(R^{cc})_2$.

In the foregoing definitions of $R^{bb}$ and $R^{bb'}$, the $C_{1-12}$ acyclic hydrocarbon group may be unsubstituted or substituted. Where it is substituted, preferably it bears no more than 3 substituents, and preferably no more than one of the substituents is a cyclic group.

In the foregoing definitions of $R^{bb}$ and $R^{bb'}$, the 3 to 8-membered (e.g. 3 to 7-membered) non-aromatic carbocyclic or heterocyclic ring (whether attached directly to $R^{aa}$ or via the $C_{1-12}$ acyclic hydrocarbon group) is preferably selected from azetidine, pyrrolidine, piperidine, piperazine, tetrahydropyran, tetrahydrothiopyran, morpholine, thiomorpholine (and the S-oxide and the S,S-dioxides thereof) each optionally substituted by up to 2, and more preferably up to 1 substituents $R^{3a}$.

In an alternative embodiment within $R^{bb}$, the 3 to 8-membered non-aromatic carbocyclic or heterocyclic ring (whether attached directly to $R^{aa}$ or via the $C_{1-12}$ acyclic hydrocarbon group) is a bridged bicyclic ring such as an aza-bicyclo[2.2.2]octane or aza-bicyclo[3.2.1]octane group, each optionally substituted by one or two $C_{1-4}$ alkyl (e.g. methyl) groups.

In another preferred group of compounds, $R^1$ is selected from:

halogen;

$CO_2R^5$ wherein $R^5$ is hydrogen or $C_{1-6}$ alkyl;

$SO_2R^5$;

$C_{1-4}$ alkyl optionally substituted by hydroxy or $C_{1-2}$ alkoxy or one or more fluorine atoms;

$C_{1-4}$ alkoxy optionally substituted by hydroxy or $C_{1-2}$ alkoxy or one or more fluorine atoms; or a group Q, C(O)NHQ, HNC(O)Q, C(O)NH-Alk-Q, HNC(O)-Alk-Q, NH-Alk-Q, $CH_2Q$, S(O)Q, $SO_2Q$, C(O)Q or O-Alk(OH)$_p$-Q where Alk is a straight or branched chain alkylene group of 2 to 5 carbon atoms and p is 0 or 1 provided that there are at least 2 carbon atoms in line between O and Q, or OH and Q, or O and OH;

and Q is selected from:

a saturated or partially unsaturated 4 to 8 membered (e.g. 4 to 7 membered) heterocyclic ring Het$^1$ containing a nitrogen ring member and optionally a further heteroatomic ring member selected from O, N and S, wherein the heterocyclic ring Het$^1$ is optionally substituted by one or more substituents selected from =O, OH, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

hydroxy;

$NR^7R^8$ where $R^7$ is hydrogen or $C_{1-4}$ alkyl; and $R^8$ is hydrogen, $C_{1-4}$ alkyl, $SO_2R^9$ or $COR^9$ wherein the $C_{1-4}$ alkyl moieties in each case are optionally substituted by OH, amino, mono- or di-$C_{1-4}$ alkylamino or phenyl;

O-Alk-Q' where Alk is as defined above and Q' is an optionally substituted saturated 4 to 8 membered (e.g. 4 to 7 membered) heterocyclic ring Het$^1$ as hereinbefore defined or a group $NR^7R^8$;

O-Q" where Q" is a saturated or partially unsaturated 4 to 8 membered (e.g. 4 to 7 membered) heterocyclic ring Het$^1$ containing a nitrogen ring member and optionally a further heteroatomic ring member selected from O, N and S, wherein the heterocyclic ring Het$^1$ is optionally substituted by one or more substituents selected from =O, OH, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

a 5- or 6-membered monocyclic heteroaryl ring containing 1 to 4 heteroatom ring members selected from O, N and S, of which at least one is N, the heteroaryl ring being optionally substituted by one or more substituents selected from OH, halogen, CN, $CF_3$, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl; and $R^9$ is $C_{1-4}$ alkyl optionally substituted by a 5- or 6-membered aryl or heteroaryl group containing up to 2 heteroatoms selected from O, N and S and wherein the aryl and heteroaryl groups are optionally substituted by $C_{1-4}$ alkyl, halogen, $C_{1-4}$ alkoxy or cyano.

In a more preferred group of compounds, $R^1$ is selected from: halogen;

$CO_2R^{5a}$ wherein $R^{5a}$ is $C_{1-6}$ alkyl;

$SO_2R^5$;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group Q, $CH_2Q$, S(O)Q, $SO_2Q$, C(O)Q or O-Alk(OH)$_p$-Q where Alk is a straight or branched chain alkylene group of 2 to 5 carbon atoms and p is 0 or 1 provided that there are at least 2 carbon atoms in line between O and Q, or OH and Q, or O and OH;

and Q is selected from:

a saturated or partially unsaturated 4 to 7 membered heterocyclic ring Het$^1$ containing a nitrogen ring member and optionally a further heteroatomic ring member selected from O, N and S, wherein the heterocyclic ring Het$^1$ is optionally substituted by one or more substituents selected from =O, OH, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

hydroxy;

$NR^7R^8$ where $R^7$ is hydrogen or $C_{1-4}$ alkyl; and $R^8$ is hydrogen, $C_{1-4}$ alkyl, $SO_2R^9$ or $COR^9$ wherein the $C_{1-4}$ alkyl moieties in each case are optionally substituted by OH, amino, mono- or di-$C_{1-4}$ alkylamino or phenyl;

O-Alk-Q' where Alk is as defined above and Q' is an optionally substituted saturated 4 to 7 membered heterocyclic ring Het$^1$ as hereinbefore defined or a group $NR^7R^8$;

O-Q" where Q" is a saturated or partially unsaturated 4 to 7 membered heterocyclic ring Het$^1$ containing a nitrogen ring member and optionally a further heteroatomic ring member selected from O, N and S, wherein the heterocyclic ring Het$^1$ is optionally substituted by one or more substituents selected from =O, OH, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

a 5- or 6-membered monocyclic heteroaryl ring containing 1 to 4 heteroatom ring members selected from O, N and S, of which at least one is N, the heteroaryl ring being optionally substituted by one or more substituents selected from OH, halogen, CN, $CF_3$, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl; and $R^9$ is $C_{1-4}$ alkyl optionally substituted by a 5- or 6-membered aryl or heteroaryl group containing up to 2 heteroatoms selected from O, N and S and wherein the aryl and heteroaryl groups are optionally substituted by $C_{1-4}$ alkyl, halogen, $C_{1-4}$ alkoxy or cyano.

In another preferred group of compounds, $R^1$ is selected from:

halogen;

$CO_2R^{5a}$ wherein $R^{5a}$ is $C_{1-6}$ alkyl;

$SO_2R^5$;

$C_{1-4}$ alkyl optionally substituted by hydroxy or $C_{1-2}$ alkoxy;

$C_{1-4}$ alkoxy optionally substituted by hydroxy or $C_{1-2}$ alkoxy; or a group Q, $CH_2Q$, $S(O)Q$, $SO_2Q$, $C(O)Q$ or O-Alk-Q where Alk is a straight or branched chain alkylene group of 2 to 5 carbon atoms provided that there are at least 2 carbon atoms in line between O and Q;

and Q is selected from:

a saturated 4 to 7 membered heterocyclic ring $Het^1$ containing a nitrogen ring member and optionally a further heteroatomic ring member selected from O, N and S, wherein the heterocyclic ring $Het^1$ is optionally substituted by one or more substituents selected from $C_{1-4}$ alkyl, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

hydroxy;

$NR^7R^8$ where $R^7$ is hydrogen or $C_{1-4}$ alkyl; and $R^8$ is hydrogen, $C_{1-4}$ alkyl, $SO_2R^9$ or $COR^9$;

O-Alk-Q' where Alk is as defined above and Q' is an optionally substituted saturated 4 to 7 membered heterocyclic ring $Het^1$ as hereinbefore defined or a group $NR^7R^8$; and $R^9$ is $C_{1-4}$ alkyl optionally substituted by a 5- or 6-membered aryl or heteroaryl group containing up to 2 heteroatoms selected from O, N and S and wherein the aryl and heteroaryl groups are optionally substituted by $C_{1-4}$ alkyl, halogen, $C_{1-4}$ alkoxy or cyano.

When $R^1$ is a group O-Alk-Q, the moiety Alk may typically be selected from $CH_2CH_2$, $CH_2CH_2CH_2$, $CH_2CH(Me)$, $CH_2CMe_2$, $CH_2CH_2CH(Me)$ and $CH_2CH_2CMe_2$, and preferably is selected from $CH_2CH_2$ and $CH_2CH_2CH_2$.

In one embodiment, the group Q is selected from:

a saturated 5 or 6 membered heterocyclic ring selected from pyrrolidine, morpholine, piperidine and piperazine, each being optionally substituted by one or more substituents selected from $C_{1-4}$ alkyl, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

$SO_2R^{5a}$;

hydroxy; and $NR^7R^8$ where $R^7$ is hydrogen or $C_{1-4}$ alkyl; and $R^8$ is hydrogen, $C_{1-4}$ alkyl, $SO_2R^9$ or $COR^9$; where $R^9$ is as hereinbefore defined.

In another embodiment, the group Q is selected from:

a saturated 5 or 6 membered heterocyclic ring selected from pyrrolidine, morpholine, piperidine and piperazine, each being optionally substituted by one or more substituents selected from $C_{1-4}$ alkyl, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl;

hydroxy; and $NR^7R^8$ where $R^7$ is hydrogen or $C_{1-4}$ alkyl; and $R^8$ is hydrogen, $C_{1-4}$ alkyl, $SO_2R^9$ or $COR^9$; where $R^9$ is as hereinbefore defined.

One preferred group of substituents $R^1$ is represented by the formula:

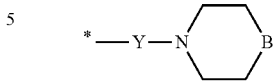

where the asterisk indicates the point of attachment to the group $Ar^1$;

Y is a bond, O-Alk- (where Alk is as hereinbefore defined), or a $C_{1-3}$ alkylene group; and B is O, NH, $CH_2$ or a group $NR^{10}$; and $R^{10}$ is selected from $C_{1-4}$ alkyl, $C_{1-4}$ acyl, carbamoyl, mono- and di-$C_{1-4}$ alkylcarbamoyl, $C_{1-4}$ alkoxycarbonyl and $C_{1-4}$ alkylsulphonyl.

When $Ar^1$ is a phenyl or other 6-membered aromatic ring such as pyridyl, it is preferred that a substituent $R^1$ is present at the para or 4-position of the ring. It is further preferred that only a single substituent $R^1$ is present and that the said single substituent is located at the para or 4-position of the ring.

Particular groups $R^1$ are those found in the compounds set out below in the Examples section of this application.

$Ar^2$ $Ar^2$ is a monocyclic or bicyclic 5- to 10-membered aryl or heteroaryl group containing up to 4 (more preferably up to 3, for example up to 2) heteroatoms selected from O, N and S and being optionally substituted by one or more substituents $R^2$.

The 5- to 10-membered aryl or heteroaryl rings may be as set out above in the General Preferences and Definitions section.

Preferred aryl and heteroaryl rings are monocyclic 5- and 6-membered rings containing up to 2 and more preferably up to 1 heteroatom selected from O, N and S, and bicyclic 6.5 fused rings containing up to 2 heteroatoms and more preferably up to 1 heteroatom selected from O, N and S.

In one embodiment, the aryl and heteroaryl rings are selected from phenyl, thiophene, furan, indole, indazole, benzoimidazole, benzofuran, pyridine, pyrrolopyridine and pyrazole rings, each optionally substituted by one or more substituents $R^2$. In another embodiment, the aryl and heteroaryl rings are selected from phenyl, thiophene, furan, indole, indazole, benzoimidazole, benzofuran, pyridine and pyrazole rings, each optionally substituted by one or more substituents $R^2$. For example, in another embodiment, the aryl and heteroaryl rings can be selected from phenyl, 2-thienyl, 3-thienyl, 2-furyl, 3-furyl, 3-pyrazole, 4-pyrazole, 5-pyrazole, 2-pyridyl, 3-pyridyl, 4-pyridyl, 3-indolyl, 4-indolyl, 5-indolyl, 6-indolyl, 3-indazolyl, 4-indazolyl, 5-indazolyl, 6-indazolyl, benzimidazol-4-yl, 3-benzofuranyl, 4-benzofuranyl and pyrrolo[2,3-b]pyridine (e.g. pyrrolo[2,3-b]pyridin-4-yl) rings, each optionally substituted by one or more substituent groups $R^2$.

In another embodiment, the aryl and heteroaryl rings can be selected from phenyl, 2-thienyl, 3-thienyl, 2-furyl, 3-furyl, 3-pyrazole, 4-pyrazole, 2-pyridyl, 3-pyridyl, 4-pyridyl, 3-indolyl, 4-indolyl, 3-indazolyl, 4-indazolyl, benzimidazol-4-yl, 3-benzofuranyl and 4-benzofuranyl rings, each optionally substituted by one or more substituent groups $R^2$.

In another embodiment, the aryl and heteroaryl rings are optionally substituted phenyl, thiophene (e.g. 2-thienyl & 3-thienyl), furan (e.g. 2-furyl & 3-furyl), indole (e.g. 3-indolyl & 4-indolyl), benzofuran (e.g. 3-benzofuranyl & 4-benzofuranyl), pyridine (e.g. 2-pyridyl, 3-pyridyl & 4-pyridyl), and pyrazole (e.g. 3-pyrazolyl & 4-pyrazolyl) rings. More particularly, within this embodiment, the aryl and heteroaryl rings are selected from phenyl, 2-thienyl, 3-thienyl, 2-furyl, 3-furyl, 3-pyrazolyl, 4-pyrazolyl, 2-pyridyl, 3-pyridyl, 4-pyridyl, 3-indolyl, 4-indolyl, 3-benzofuranyl and 4-benzofuranyl rings, each optionally substituted by one or more substituent groups $R^2$.

Particularly preferred groups $Ar^2$ are optionally substituted phenyl rings.

$R^2$

The aryl or heteroaryl ring $Ar^2$ can be optionally substituted by one or more substituents $R^2$.

Typically, each aryl or heteroaryl ring is substituted by 0, 1, 2 or 3 substituents $R^2$.

More typically, each aryl or heteroaryl ring is substituted by 0, 1 or 2 substituents $R^2$.

In one embodiment, each aryl or heteroaryl ring is unsubstituted.

In another embodiment, each aryl or heteroaryl ring is substituted by 1 substituent $R^2$.

In a further embodiment, each aryl or heteroaryl ring is substituted by 2 substituents $R^2$.

$R^2$ is halogen; cyano; nitro; or a group $R^a$-$R^d$; where $R^a$ is a bond, O, CO, $X^1C(X^2)$, $C(X^2)X^1$, $X^1C(X^2)X^1$, S, SO, $SO_2$, $NR^c$, $SO_2NR^c$ or $NR^cSO_2$; and $R^d$ is hydrogen or a $C_{1-4}$ alkyl group optionally substituted by one or more fluorine atoms.

The moiety $R^a$ may be as set out in the General Preferences and Definitions section above.

More typically, $R^2$ is absent or is selected from halogen; $C_{1-4}$ alkyl optionally substituted with one or more fluorine atoms; $C_{1-4}$ alkoxy optionally substituted with one or more fluorine atoms; cyclopropyl; cyclopropoxy; cyano; $CONH_2$; $C_{1-4}$ alkylsulphonyl; $C_{1-4}$ acylamino; $C_{1-4}$ alkylsulphonylamino.

More preferably, $R^2$ is absent or is selected from fluorine; chlorine; bromine; methyl optionally substituted with one or more fluorine atoms; methoxy optionally substituted with one or more fluorine atoms; cyano; methylsulphonyl; acetylamino; and methylsulphonylamino.

When $Ar^2$ is a phenyl group, preferably it is unsubstituted or substituted by 1, 2 or 3 substituents selected from fluorine; chlorine; bromine; methyl optionally substituted with one or more fluorine atoms; methoxy optionally substituted with one or more fluorine atoms; cyano; methylsulphonyl; acetylamino; and methylsulphonylamino.

When one substituent is present on the phenyl ring, it is preferred that the substituent is present at an ortho-position on the ring.

When two substituents are present on the phenyl ring, it is preferred that at least one, and preferably both are located at an ortho-position on the ring.

One sub-set of particularly preferred groups $Ar^2$ (which are unsubstituted except where specified) consists of phenyl, 2,6-difluorophenyl, 2-chlorophenyl, 2-fluorophenyl, 2-chloro-6-fluorophenyl, 2,6-dichlorophenyl, 2,6-dimethylphenyl, 3-indolyl, 4-indolyl, 3-pyrazolyl, 4-pyrazolyl, 2-thienyl and 3-thienyl.

Another sub-set of particularly preferred groups $Ar^2$ (which are unsubstituted except where specified) consists of phenyl, 2,6-difluorophenyl, 2-chloro-6-fluorophenyl, 2-chlorophenyl, 2-fluorophenyl, 3-indolyl, 4-indolyl, 2-pyrazolyl, 5-pyrazolyl, 2-thienyl and 3-thienyl.

When b is 1, $Ar^2$ may be other than a phenyl group bearing a substituent at the meta-position thereof wherein the substituent is an optionally substituted alkyl group, an optionally substituted amino group or a group containing the moiety C(O)—N where the carbon atom of the carbonyl group is attached to the meta-position of the phenyl group. The term "optionally substituted amino group" in this context includes any group (apart from nitro) containing a nitrogen atom wherein the said nitrogen atom is attached to the meta-position of the phenyl group.

The compound of the formula (1) may be other than a compound wherein T is O, b is 0 and $Ar^2$ is a 4-methylphenyl group.

Alternatively or additionally, the compound of the formula (1) may be other than a compound wherein b is 0 and $Ar^2$ is a bicyclic group containing at least one nitrogen ring member, the said nitrogen ring member being attached directly to the ring containing the moiety T.

Alternatively, or additionally, the compound of formula (1) may be other than:

2-(3-chlorophenyl)-4-(4-methoxyphenyl)-1H-imidazole-5-carboxamide; and/or 2-(4-chlorophenyl)-4-(4-methoxyphenyl)-1H-imidazole-5-carboxamide; and/or 2-(2,6-difluorophenyl)-4-(3-(hydroxymethyl)phenyl)-1H-imidazole-5-carboxamide; and/or 2-(furan-3-yl)-4-(thiophen-2-yl)-1H-imidazole-5-carboxamide; and/or 2-(benzo[b]thiophen-3-yl)-5-(thiophen-2-yl)oxazole-4-carboxamide; and/or 2-(benzo[b]thiophen-3-yl)-5-(4-methoxyphenyl)oxazole-4-carboxamide; and/or 2-(1H-benzo[d]imidazol-2-yl)-5-(4-methoxyphenyl)oxazole-4-carboxamide; and/or 2-(2-methoxyphenyl)-5-(4-methoxyphenyl)oxazole-4-carboxamide; and/or 2-(3-cyanophenyl)-5-(4-methoxyphenyl)oxazole-4-carboxamide; and/or 2-(4-(dimethylamino)phenyl)-5-(4-methoxyphenyl)oxazole-4-carboxamide; and/or 5-(4-methoxyphenyl)-2-(quinolin-3-yl)oxazole-4-carboxamide; and/or 2-(3-methoxyphenyl)-5-(4-methoxyphenyl)oxazole-4-carboxamide; and/or 2,5-bis(4-methoxyphenyl)oxazole-4-carboxamide; and/or 2-(2,6-difluorophenyl)-5-(3-methoxyphenyl)oxazole-4-carboxamide; and/or 2-(2,6-difluorophenyl)-5-(2-methoxyphenyl)oxazole-4-carboxamide; and/or tert-butyl 4-(4-carbamoyl-2-(2,6-difluorophenyl)oxazol-5-yl)benzylcarbamate.

Alternatively, or additionally, the compound of formula (1) may be other than any one or more (in any combination) of:

2-(2,6-difluorophenyl)-5-(2,4-dimethoxyphenyl)oxazole-4-carboxamide;

2-(2,6-difluorophenyl)-5-(2-fluoro-4-methoxyphenyl)oxazole-4-carboxamide;

2-(2,6-difluorophenyl)-5-(3,4,5-trimethoxyphenyl)oxazole-4-carboxamide;

2-(2,6-difluorophenyl)-5-(2,4-dimethoxyphenylamino)oxazole-4-carboxamide; and 2-(2,6-difluorophenyl)-5-(4-(piperidin-1-yl)phenyl)oxazole-4-carboxamide.

Preferred Sub-Groups of Compounds

One preferred sub-group of compounds is the group of compounds represented by the formula (5):

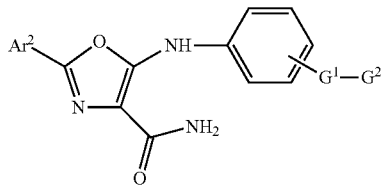

(5)

or salts, solvates or tautomers thereof;
wherein $G^1$ is C(O), C(O)NH or HNC(O); and
- (i) when $G^1$ is C(O), then $G^2$ is selected from OH and a group Het where Het is a 5 to 7 membered non-aromatic heterocyclic ring containing a nitrogen atom ring member and optionally one further heteroatom ring member selected from O, N and S: the group Het being linked to the C(O) group by a nitrogen ring member and being optionally substituted by one or two substituents selected from $C_{1-4}$ alkyl, hydroxy-$C_{1-4}$ alkyl, hydroxy, amino-$C_{1-4}$ alkyl, and mono- or di-$C_{1-2}$-alkylamino-$C_{1-4}$ alkyl; or
- (ii) when $G^1$ is C(O)NH or HNC(O), then $G^2$ is selected from:
  a 5 to 8 membered non-aromatic heterocyclic ring Het' containing a nitrogen atom ring member and optionally one further heteroatom ring member selected from O, N and S: the heterocyclic ring being optionally substituted by one or two substituents selected from $C_{1-4}$ alkyl, hydroxy-$C_{1-4}$ alkyl, hydroxy, amino-$C_{1-4}$ alkyl, and mono- or di-$C_{1-2}$-alkylamino-$C_{1-4}$ alkyl; and
  $C_{1-4}$ alkyl substituted by a group Het' or a group $NR^7R^8$, where $R^7$ and $R^8$ are the same or different and each is hydrogen or $C_{1-4}$ alkyl; and Het' is as hereinbefore defined.

Within formula (5), one sub-group of compounds is the sub-group wherein b is 0. Within this sub-group, preferred compounds are the compounds wherein $Ar^2$ is an optionally substituted phenyl ring as hereinbefore defined. Particularly preferred compounds are those wherein $Ar^2$ is a 2,6-difluorophenyl ring.

General

For the avoidance of doubt, it is to be understood that each general and specific preference, embodiment and example of the groups $Ar^1$ may be combined with each general and specific preference, embodiment and example of the group $Ar^2$ as defined herein and that all such combinations are embraced by this application.

The various functional groups and substituents making up the compounds of the formula (I) are typically chosen such that the molecular weight of the compound of the formula (I) does not exceed 1000. More usually, the molecular weight of the compound will be less than 750, for example less than 700, or less than 650, or less than 600, or less than 550. More preferably, the molecular weight is less than 525 and, for example, is 500 or less.

Particular compounds of the invention are as illustrated in the examples below.

Salts, Solvates, Tautomers, Isomers, N-Oxides, Esters, Prodrugs and Isotopes

Unless otherwise specified, a reference to a particular compound also includes ionic, salt, solvate, and protected forms thereof, for example, as discussed below.

Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds.

Salt forms may be selected and prepared according to methods described in *Pharmaceutical Salts Properties, Selection, and Use*, P. Heinrich Stahl (Editor), Camille G. Wermuth (Editor), ISBN: 3-90639-026-8, Hardcover, 388 pages, August 2002.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-aminosalicylic, sebacic, stearic, succinic, sulphuric, tannic, (+)-L-tartaric, thiocyanic, p-toluenesulphonic, undecylenic and valeric acids, as well as acylated amino acids and cation exchange resins.

One particular group of salts consists of salts formed from hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages 1200-12-1. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I) wherein T is NH, the imidazole group may take either of the following two tautomeric forms A and B. For simplicity, the general formula (I) illustrates form A but the formula is to be taken as embracing both tautomeric forms.

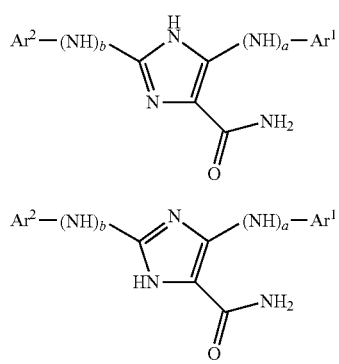

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl
(e.g., -Me, -Et, -nPr, -iPr, -nBu, -sBu, -iBu, -tBu);
$C_{1-7}$aminoalkyl
(e.g., aminoethyl; 2-(N,N-diethylamino)ethyl; 2-(4-morpholino)ethyl); and
acyloxy-$C_{1-7}$alkyl
(e.g., acyloxymethyl;
acyloxyethyl;
pivaloyloxymethyl;
acetoxymethyl;
1-acetoxyethyl;
1-(1-methoxy-1-methyl)ethyl-carbonyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;

1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Biological Activity

Compounds of the invention have various therapeutic uses.

Accordingly, the invention provides a compound of the formula (1) or any sub-groups or examples thereof as defined herein for use in medicine.

More particularly, compounds of the invention are inhibitors of kinases, for example kinases selected from FLT3, FLT4 and an Aurora kinase (such as Aurora kinase A or Aurora kinase B).

Therefore, in further aspects, the invention provides:

A compound of the formula (1) or any sub-groups or examples thereof as defined herein for use in the prophylaxis or treatment of a disease state or condition mediated by a kinase selected from FLT3, FLT4 and an Aurora kinase (such as Aurora kinase A or Aurora kinase B).

A compound of the formula (1) or any sub-groups or examples thereof as defined herein for use in the prophylaxis or treatment of a disease state or condition characterised by abnormal expression (e.g. over-expression) of a kinase selected from FLT3, FLT4 and an Aurora kinase (such as Aurora kinase A or Aurora kinase B).

The use of a compound of the formula (1) or any sub-groups or examples thereof as defined herein for the manufacture of a medicament for the prophylaxis or treatment of a disease state or condition mediated by a kinase selected from FLT3, FLT4 and an Aurora kinase (such as Aurora kinase A or Aurora kinase B).

The use of a compound of the formula (1) or any sub-groups or examples thereof as defined herein for the manufacture of a medicament for the prophylaxis or treatment of a disease state or condition characterised by abnormal expression (e.g. over-expression) of a kinase selected from FLT3, FLT4 and an Aurora kinase (such as Aurora kinase A or Aurora kinase B).

A method for the prophylaxis or treatment of a disease state or condition mediated by a kinase selected from FLT3, FLT4 and an Aurora kinase (such as Aurora kinase A or Aurora kinase B), which method comprises administering to a subject in need thereof a compound of the formula (1) or any sub-groups or examples thereof as defined herein.

A method for the prophylaxis or treatment of a disease state or condition characterised by abnormal expression (e.g. over-expression) of a kinase selected from FLT3, FLT4 and an Aurora kinase (such as Aurora kinase A or Aurora kinase B), which method comprises administering to a subject in need thereof a compound of the formula (1) or any sub-groups or examples thereof as defined herein.

A method for alleviating or reducing the incidence of a disease state or condition mediated by a kinase selected from FLT3, FLT4 and an Aurora kinase (such as Aurora kinase A or Aurora kinase B), which method comprises administering to a subject in need thereof a compound of the formula (1) or any sub-groups or examples thereof as defined herein.

A method of inhibiting a kinase selected from FLT3, FLT4 and an Aurora kinase (such as Aurora kinase A or Aurora kinase B), which method comprises contacting the kinase with a kinase-inhibiting compound of the formula (1) or any sub-groups or examples thereof as defined herein.

A method of modulating a cellular process (for example cell division) by inhibiting the activity of a kinase selected from FLT3, FLT4 and an Aurora kinase (such as Aurora kinase A or Aurora kinase B) using a compound of the formula (1) or any sub-groups or examples thereof as defined herein.

As a consequence of their activity in modulating and in particular inhibiting FLT3, FLT4 and Aurora kinases, they are expected to be useful in treating or preventing proliferative disorders such as cancers.

Accordingly, the invention further provides:

A compound of the formula (1) or any sub-groups or examples thereof as defined herein for use in the prophylaxis or treatment of a proliferative disease such as a cancer.

The use of a compound of the formula (1) or any sub-groups or examples thereof as defined herein for the manufacture of a medicament for use in the prophylaxis or treatment of a proliferative disease such as a cancer.

A method for treating a proliferative disease such as cancer in a subject, which method comprises administering to the subject (e.g. a mammal such as a human) a compound of the formula (1) or any sub-groups or examples thereof as defined herein.

A compound of the formula (1) or any sub-groups or examples thereof as defined herein for use in the prophylaxis or treatment of a disease or condition comprising or arising from abnormal cell growth.

The use of a compound of the formula (1) or any sub-groups or examples thereof as defined herein for the manufacture of a medicament for use in the prophylaxis or treatment of a disease or condition comprising or arising from abnormal cell growth.

A method for treating a disease or condition comprising or arising from abnormal cell growth in a mammal, which method comprises administering to the mammal a compound of the formula (1) or any sub-groups or examples thereof as defined herein in an amount effective in inhibiting abnormal cell growth.

A method for alleviating or reducing the incidence of a disease or condition comprising or arising from abnormal cell growth in a mammal, which method comprises administering to the mammal a compound of the formula (1) or any sub-groups or examples thereof as defined herein in an amount effective in inhibiting abnormal cell growth.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma, a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more kinases, e.g. kinases selected from FLT3 kinase, FLT4 kinase and an Aurora kinase such as Aurora A kinase or Aurora B kinase.

Cancers which are susceptible to inhibition of Aurora A kinase include breast, bladder, colorectal, pancreatic and ovarian cancers, non-Hodgkin's lymphoma, gliomas, nonendometrioid endometrial carcinomas, Acute Myelogenous Leukemia (AML), Chronic Myelogenous Leukaemia (CML), B-cell lymphoma (Mantle cell), and Acute Lymphoblastic Leukemia (ALL).

Cancers which are susceptible to inhibition of Aurora B kinase include colorectal, lung, Acute Myeloid Leukaemia, Acute Lymphoblastic Leukemia, and Acute Eosinophilic Leukemia.

Cancers which are susceptible to inhibition of FLT3 kinase include Acute Myeloid Leukemia (AML).

Cancers which are susceptible to inhibition of FLT4 kinase include lung adenocarcinoma, colorectal adenocarcinoma, prostate carcinoma, head and neck carcinomas, leukemia and Kaposi's sarcoma.

Whether or not a particular cancer is one which is sensitive to inhibition by a kinase may be determined by means of a cell growth assay, for example an assay as described in the example below or by a method as set out in the section headed "Methods of Diagnosis".

The activity of the compounds of the invention as inhibitors of kinases can be measured using the assays set forth in the examples below and the level of activity exhibited by a given compound can be defined in terms of the $IC_{50}$ value. Preferred compounds of the present invention are compounds having an $IC_{50}$ value of less than 10 µM, more preferably less than 1 µM.

In further aspects, the invention provides:

A compound of the formula (1) or any sub-groups or examples thereof as defined herein for use in the prophylaxis or treatment of a disease state as described herein.

The use of a compound of the formula (1) or any sub-groups or examples thereof as defined herein for the manufacture of a medicament, wherein the medicament is for any one or more of the uses defined herein.

A compound as defined herein for any of the uses and methods set forth above, and as described elsewhere herein.

Methods for the Preparation of Compounds of the Invention

In another aspect, the invention provides a process for the preparation of a compound of the formula (1) and subgroups and examples thereof as defined herein, which process comprises:

(a) the reaction of a compound of the formula (6A):

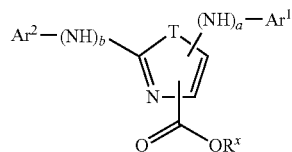

wherein $R^x$ is hydrogen or a $C_{1-4}$ alkyl group (preferably methyl or ethyl), with ammonia under conditions suitable for forming a primary amide group; or (b) the partial hydrolysis of a compound of the formula (6B):

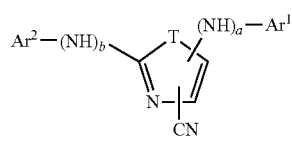

or (c) when a is 0, the reaction of a compound of the formula (6C):

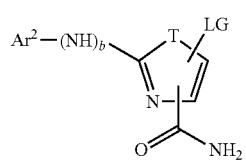

wherein LG is chlorine, bromine, iodine or trifluoromethanesulphonate; with a boronic acid or boronate ester or organometallic reagent (e.g. an organotin reagent) suitable for introduction of a group $Ar^1$, in the presence of a metal catalyst and in particular a palladium catalyst (for example under Suzuki coupling or Stille reaction conditions); or (d) when a is 1, the reaction of a compound of the formula (6C):

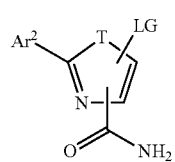

wherein LG is chlorine, bromine, iodine or trifluoromethanesulphonate; with an amine of the formula $NH_2—Ar^1$, in the presence of a metal catalyst and in particular a palladium catalyst; or (e) when b is 0, the reaction of a compound of the formula (6D):

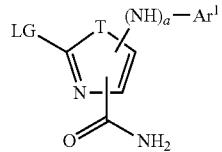

wherein LG is chlorine, bromine, iodine or trifluoromethanesulphonate; with a boronic acid or boronate ester or organometallic reagent (e.g. an organotin reagent) suitable for introduction of a group Ar², in the presence of a metal catalyst and in particular a palladium catalyst; or (f) when b is 1, the reaction of a compound of the formula (6D):

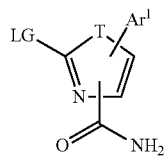

wherein LG is chlorine, bromine, iodine or trifluoromethanesulphonate; with an amine of the formula $NH_2$—$Ar^2$, in the presence of a metal catalyst and in particular a palladium catalyst; and (g) optionally converting one compound of the formula (1) into another compound of the formula (1).

Compounds in which a and b are both 0 and T is NH can be prepared by the sequence of reactions shown in Scheme 1.

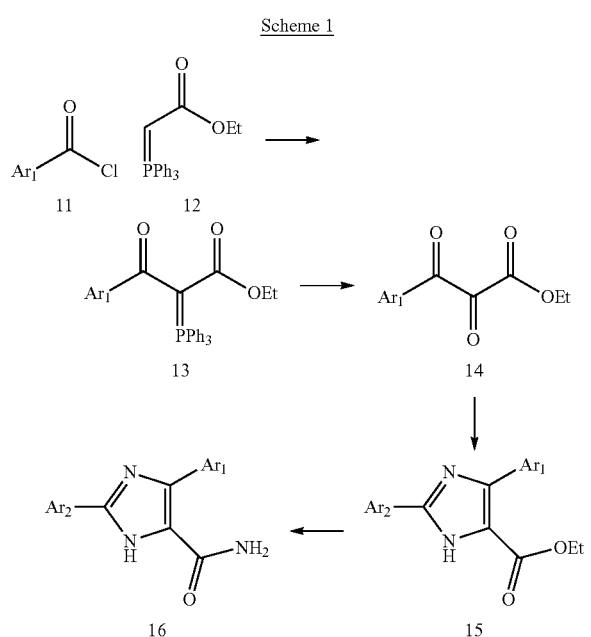

As shown in Scheme 1, the (carbethoxymethylene)triphenyl phosphorane 12 is reacted with the aroyl or heteroaroyl chloride 11 to give the triphenylphosphoranylidene derivative 13. The reaction is typically carried out in a non-protic solvent such as dichloromethane at a low temperature, for example at around 0° C., in the presence of the trimethylsilylating agent N,O-bis(trimethylsilyl)acetamide. The triphenylphosphoranylidene moiety is then oxidatively cleaved using an oxidising agent such as potassium peroxymonosulphate (Oxone®) in water/THF to give the substituted dioxopropionate ester 14. The ester 14 is then reacted with an aryl or heteroaryl aldehyde Ar²—CHO and ammonium acetate in acetic acid at an elevated temperature in excess of 100° C. (e.g. up to about 160° C.) in order to form the imidazole ester 15. Treatment of the imidazole ester 15 with aqueous ammonia at an elevated temperature (e.g. up to about 150° C.) gives the imidazolyl carboxamide 16.

As an alternative to forming the carboxamide group by reacting the imidazolyl ester 15 with ammonia, it may instead be hydrolysed to the carboxylic acid 17 which is then converted to the carboxamide 16 as shown in Scheme 2.

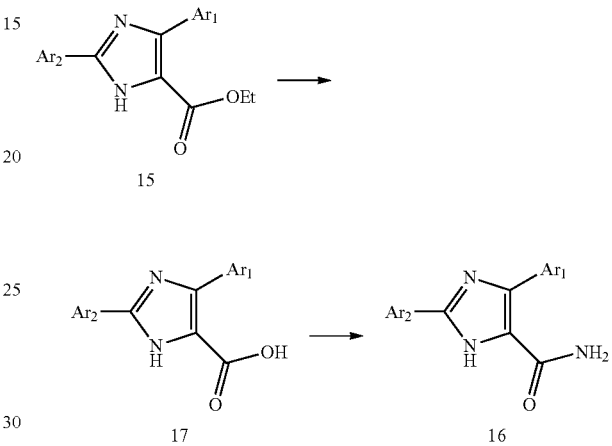

Hydrolysis of the imidazolyl ester 15 may conveniently be carried out in standard manner using an alkali metal hydroxide such as aqueous potassium hydroxide with moderate heating, for example to a temperature in the range 50-60° C.

The carboxylic acid 17 can be converted to the carboxamide 15 by reaction with ammonia in the presence of a reagent of the type commonly used in the formation of amide bonds. Examples of such reagents include 1,3-dicyclohexylcarbodiimide (DCC) (Sheehan et al, J. Amer. Chem. Soc. 1955, 77, 1067), 1-ethyl-3-(3'-dimethylaminopropyl)-carbodiimide (EDAC) (Sheehan et al, J. Org. Chem. (1961) 26, 2525), uronium-based coupling agents such as O-(7-azabenzotriazol-1-yl)-N,N,N',N'-tetramethyluronium hexafluorophosphate (HATU) and phosphonium-based coupling agents such as 1-benzo-triazolyloxytris-(pyrrolidino)phosphonium hexafluorophosphate (PyBOP) (Castro et al, Tetrahedron Letters (1990) 31, 205). Carbodiimide-based coupling agents are advantageously used in combination with 1-hydroxy-7-azabenzotriazole (HOAt) (Carpino, J. Amer. Chem. Soc. (1993) 115, 4397) or 1-hydroxybenzotriazole (HOBt) (Konig et al, Chem. Ber., (1970) 103, 708, 2024-2034). A preferred coupling reagent is EDAC in combination with HOAt or HOBt.

The coupling reaction is typically carried out in a non-aqueous, non-protic solvent such as acetonitrile, dioxan, dimethylsulphoxide, dichloromethane, dimethylformamide or N-methylpyrrolidine, or in an aqueous solvent optionally together with one or more miscible co-solvents. The reaction can be carried out at room temperature.

An alternative synthetic route to compounds of the formula (1) where a and b are both 0 and T is NH is illustrated in Scheme 3.

Scheme 3

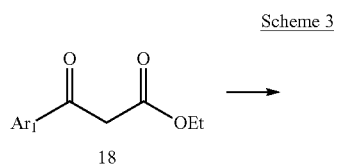

In Scheme 3, the β-keto-ester 18, which is either commercially available or can be made according to standard methods, is reacted with nitrous acid to give the oxime 19. The nitrous acid can be generated in known fashion from sodium nitrite and an acid such as acetic acid. The oxime 19 is converted to the imidazolyl ester 15 by reaction with an aryl or heteroaryl aldehyde Ar²—CHO and ammonium acetate in acetic acid at an elevated temperature in excess of 100° C. (e.g. up to about 160° C.). The imidazoyl ester 15 is then converted to the carboxamide 16 by the series of reactions illustrated in Scheme 2 above.

Compounds in which a and b are both 0 and T is O can be prepared by the sequence of reactions shown in Scheme 4, which is based on the synthetic route described in *J. Org. Chem.* (1960) 25, 1151-1154.

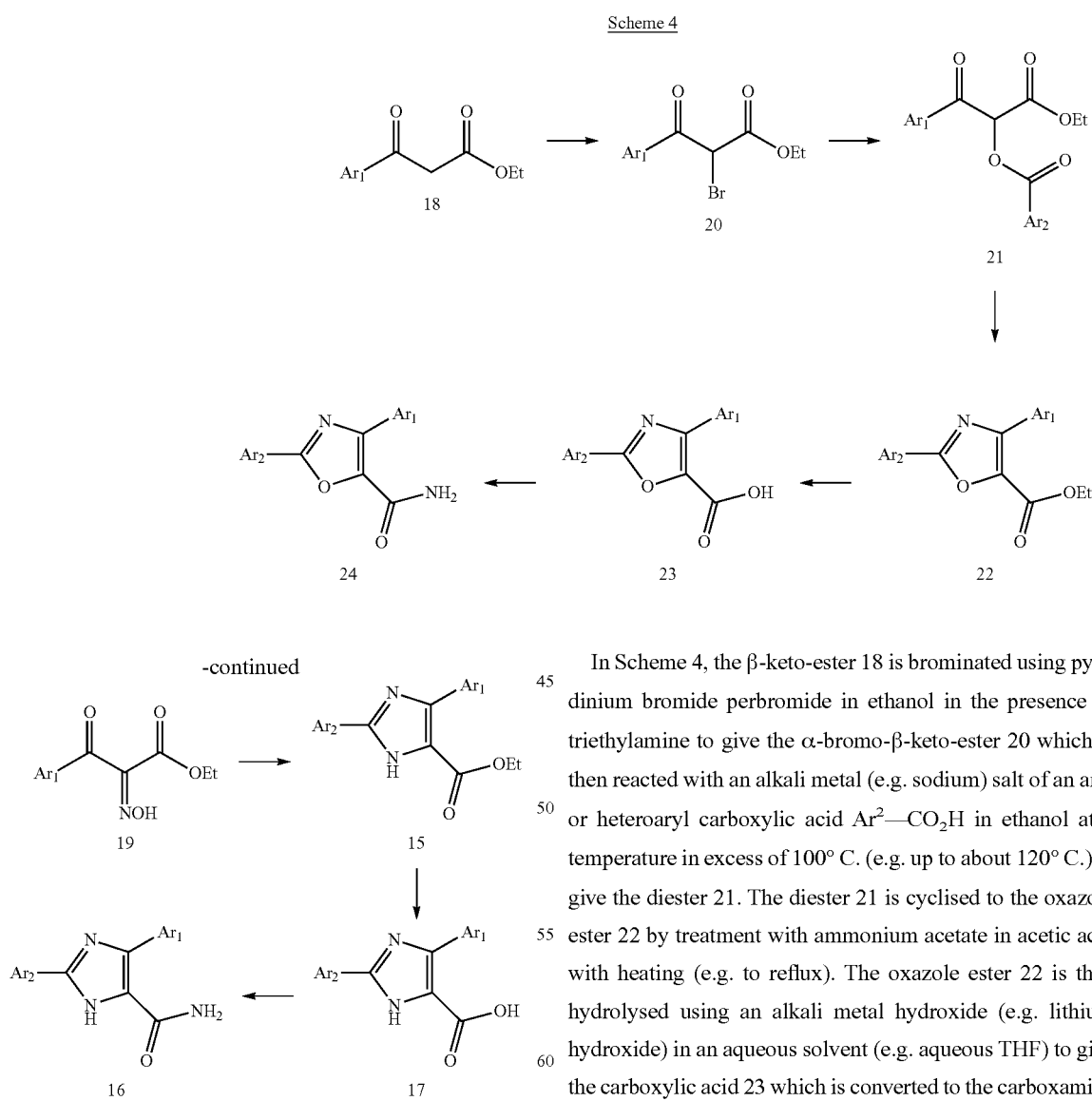

In Scheme 4, the β-keto-ester 18 is brominated using pyridinium bromide perbromide in ethanol in the presence of triethylamine to give the α-bromo-β-keto-ester 20 which is then reacted with an alkali metal (e.g. sodium) salt of an aryl or heteroaryl carboxylic acid Ar²—CO₂H in ethanol at a temperature in excess of 100° C. (e.g. up to about 120° C.) to give the diester 21. The diester 21 is cyclised to the oxazole ester 22 by treatment with ammonium acetate in acetic acid with heating (e.g. to reflux). The oxazole ester 22 is then hydrolysed using an alkali metal hydroxide (e.g. lithium hydroxide) in an aqueous solvent (e.g. aqueous THF) to give the carboxylic acid 23 which is converted to the carboxamide 24 by reaction with ammonia in the presence of EDAC and HOBt under conditions of the type described above.

An alternative route to compounds in which a and b are both 0 and T is O is shown in Scheme 5.

Scheme 5

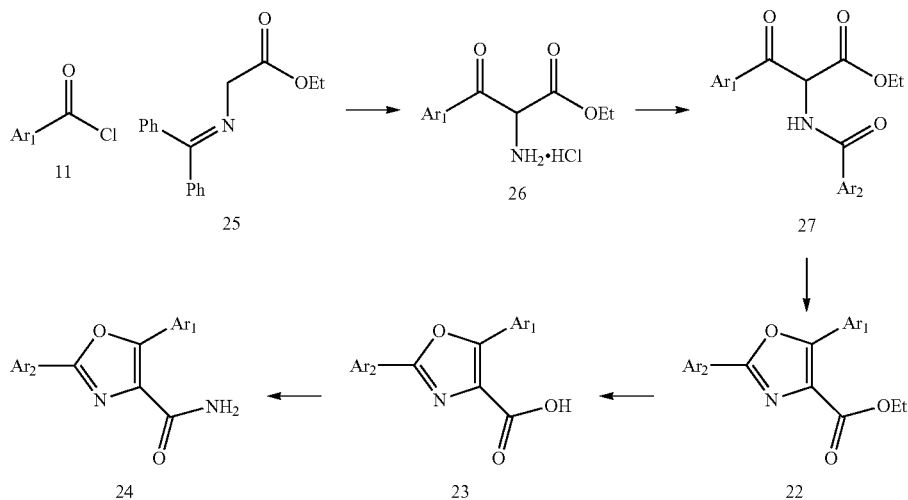

In Scheme 5, the N-(diphenylmethylene)glycine ethyl ester 25 is treated with a base such as potassium tert-butoxide in a dry solvent such as THF with cooling to a low temperature (e.g. a temperature of about −78° C.), followed by reaction with the acid chloride 11. The resulting α-amino-β-keto-ester 26 is converted to the amide 27 by reaction with a carboxylic acid $Ar^2$—$CO_2H$ in the presence of EDAC and HOBt under the amide forming conditions described above. The amide 27 is converted to the oxazole ester 22 by a cyclo-dehydration reaction brought about by heating with $POCl_3$. The oxazole ester 22 can then be hydrolysed (e.g. by using potassium hydroxide) to the carboxylic acid 23 and converted to the amide 24 as described above in relation to Scheme 4.

A further route to compounds of the formula 1 wherein a and b are both 0 and T is O is shown in Scheme 6.

cyano-oxazole 30 which is converted to the corresponding bromo-compound 31 by treatment with copper bromide and tert-butyl nitrite in dry acetonitrile. The nitrile group is then partially hydrolysed in concentrated sulphuric acid to give the bromo-oxazolyl carboxamide 32.

The aryl or heteroaryl group $Ar^1$ can be added by reacting the oxazolyl carboxamide 32 with a suitable aryl or heteroaryl boronic acid $Ar^1$—$B(OH)_2$ or boronate ester $Ar^1$—$B(OR)_2$ (where R is an alkyl group or the two groups R combine to form a linked divalent group such as a pinacol residue) under Suzuki coupling conditions or with an aryl or heteroaryl tin compound $Ar^1$—$SnR_3$ (where R is an alkyl group) under Stille reaction conditions.

Thus, for example, the bromo-oxazolyl carboxamide 32 may be reacted with a suitable aryl or heteroaryl boronate or

Scheme 6

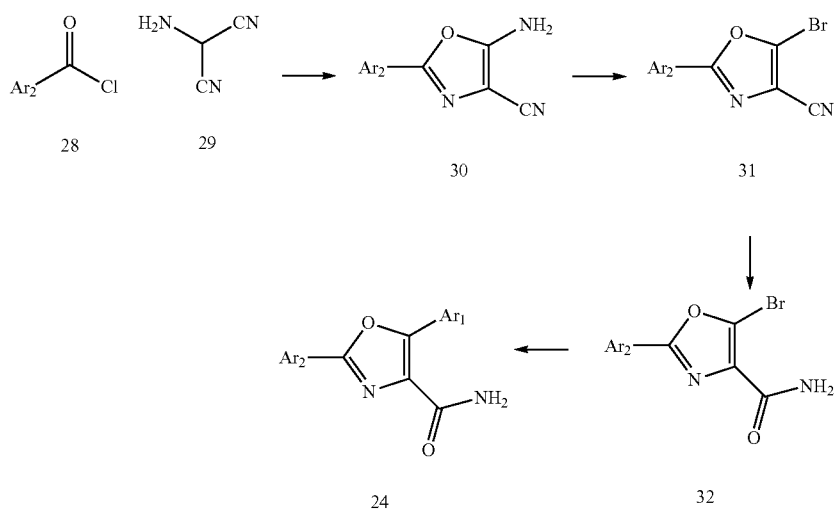

In Scheme 6, aminomalononitrile 29 is reacted with the aroyl or heteroaroyl chloride 28 in a high boiling polar aprotic solvent such as N-methylpyrrolidone at an elevated temperature above 100° C. (e.g. up to 120° C.) to give the amino-boronic acid $Ar^1$—$B(OH)_2$ or boronate ester $Ar^1$—$B(OR)_2$ in the presence of a palladium catalyst such as tetrakis(triphenylphosphine)palladium or bis (1,1'-bis(diphenylphosphino)-ferrocene)palladium dichloride ($Pd(dppf)_2Cl_2$) and a base (e.g. a carbonate such as potassium carbonate). The reaction may be carried out in a polar solvent, for example acetonitrile or an aqueous solvent such as aqueous ethanol, or an ether such as dimethoxyethane, and the reaction mixture is typically subjected to heating, for example to a temperature of 80° C. or more, e.g. a temperature in excess of 100° C., for example a temperature of up to about 150° C.

Many boronates suitable for use in preparing compounds of the invention are commercially available, for example from Boron Molecular Limited of Noble Park, Australia, or from Combi-Blocks Inc, of San Diego, USA. Where the boronates are not commercially available, they can be prepared by methods known in the art, for example as described in the review article by Miyaura and Suzuki, *Chem. Rev.* (1995) 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

The Stille reaction with an aryl or heteroaryl tin compound $Ar^1$—$SnR_3$ is typically carried out in the presence of a palladium catalyst, for example tetrakis(triphenylphosphine)palladium, in solvents and under conditions generally similar to those used for Suzuki coupling reactions.

give the oxazole ester 22. The oxazole ester 22 is then converted via the carboxylic acid 23 to the carboxamide 24 in the manner described above.

In a variation on the route described in Scheme 7 above, the iodo-oxazole ester 35 is hydrolysed to the carboxylic acid 36 and then converted to the carboxamide 37 before the Suzuki coupling step, as shown in Scheme 8.

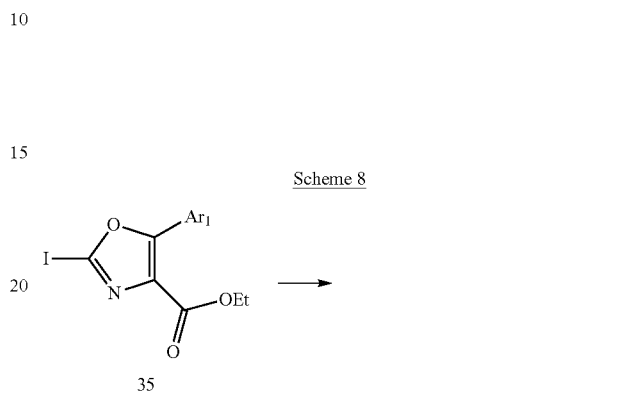

Scheme 8

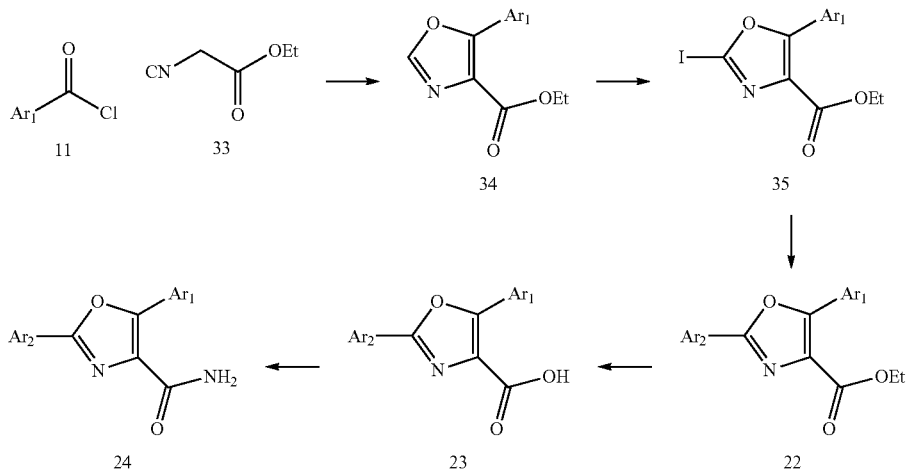

Scheme 7

In Scheme 7, ethyl isocyanoacetate 33 is reacted with the aroyl or heteroaryl chloride 11 to give the oxazole ester 34. The reaction is typically carried out in a polar aprotic solvent such as acetonitrile in the presence of a non-interfering base such as triethylamine or diazabicyclo[5.4.0]undec-7-ene (DBU), usually with heating, for example to a temperature in excess of 100° C. The conditions for this reaction step may be as described in *Organic Letters* (2006) 8, 5231-5234. The oxazole ester 34 is then converted to the iodo-oxazole ester 35 by reaction with lithium bis(trimethylsilyl)amide in THF at low temperature (e.g. −78° C.) followed by iodine.

The iodo-oxazole 35 is then used as substrate for a Suzuki coupling reaction with a boronic acid $Ar^2$—$B(OH)_2$ or boronate $Ar^2$—$B(OR)_2$ under the conditions described above to -continued

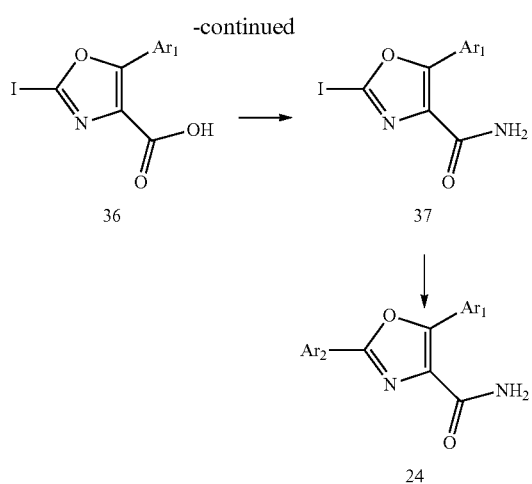

Compounds of the formula 1 wherein a is 1, b is 0 and T is O can be prepared by the route illustrated in Scheme 9.

An alternative route to compounds of the formula 1 wherein a is 1, b is 0 and T is O is illustrated in Scheme 10.

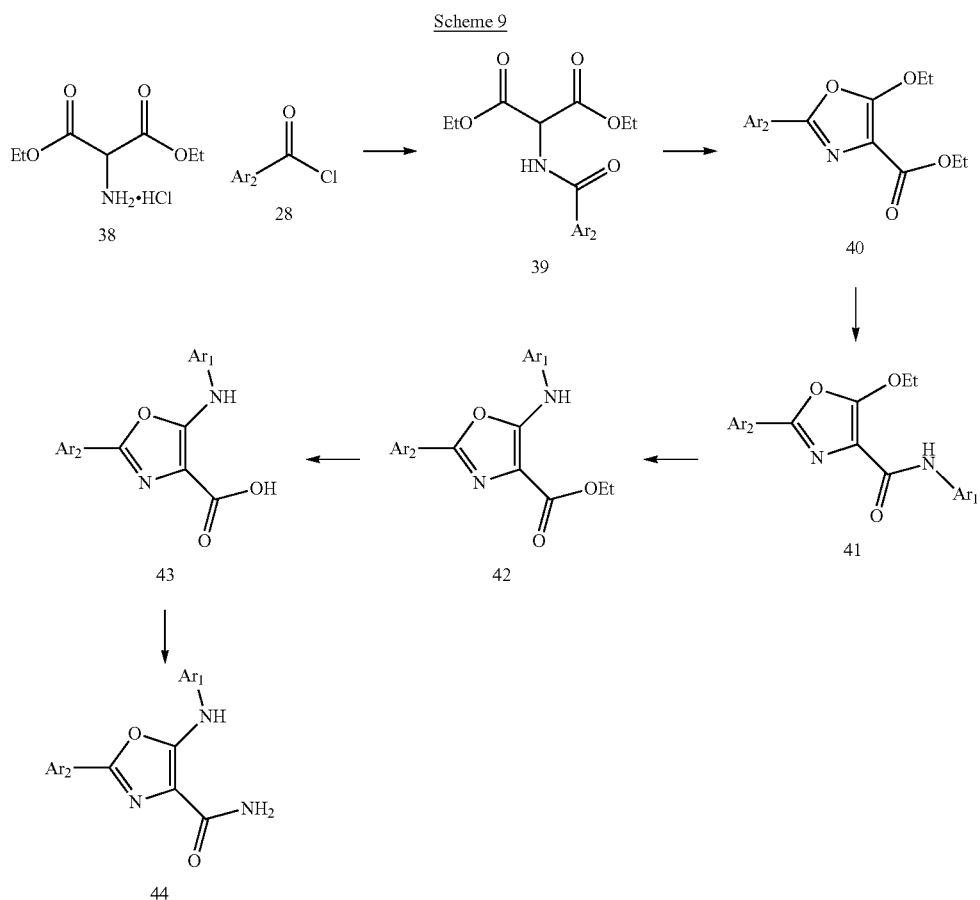

In Scheme 9, the synthesis of the key intermediate ethyl 2-aryl-5-(arylamino)oxazole-4-carboxylate 42 is based upon the method described in *Tetrahedron* (2006) 62, 4698-4707.

Thus, 2-amino diethylmalonate 38 is acylated using the acid chloride 28 in a non-protic solvent such as dichloromethane in the presence of non-interfering base such as triethylamine or diisopropylethylamine, to give the amide 39. Amide 39 is then cyclised to the ethoxy-oxazole ester 40 by treatment with trifluoroacetic anhydride in trifluorotoluene at an elevated temperature, e.g. a temperature in excess of 100° C., for example a temperature of up to about 160° C.

The ethoxy-oxazole ester 40 is hydrolysed using aqueous potassium hydroxide to give an intermediate carboxylic acid (not shown) which is then reacted with an aryl or heteroaryl amine Ar$^1$—NH$_2$ in the presence of HOBt and a carbodiimide derivative such as a PS-carbodiimide resin to give the amide 41. Heating the amide 41 in a high boiling inert solvent such as trifluorotoluene to an elevated temperature in excess of 160° C. (e.g. up to about 180° C.) leads to rearrangement of the amide to give the arylamino or heteroarylamino-oxazole ester 42.

The heteroarylamino-oxazole ester 42 is hydrolysed to the carboxylic acid 43, using a metal hydroxide (advantageously trimethyltin hydroxide in dichloroethane) and the carboxylic acid 43 is then converted to the carboxamide 44 by reaction with ammonia in the presence of EDAC and HOBt under conditions analogous to those described above.

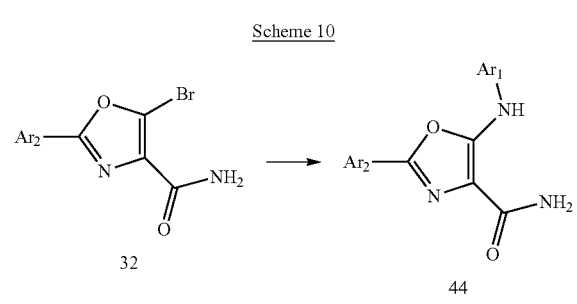

In Scheme 10, the bromo-oxazolyl carboxamide 32 (see Scheme 6 above) is subjected to a palladium catalysed amination by reaction with Ar$^1$—NH$_2$ in the presence of a palladium catalyst such as tris(dibenzylideneacetone)dipalladium (0)/bis(diphenylphosphino)-1,1''-binaphthalene and sodium tert-butoxide to give the product 44. The amination reaction is typically carried out at an elevated temperature, e.g. a temperature up to about 160° C., in a high boiling solvent such as trifluorotoluene.

A variation on the amination reaction sequence of Scheme 10 is illustrated in Scheme 11.

Scheme 11

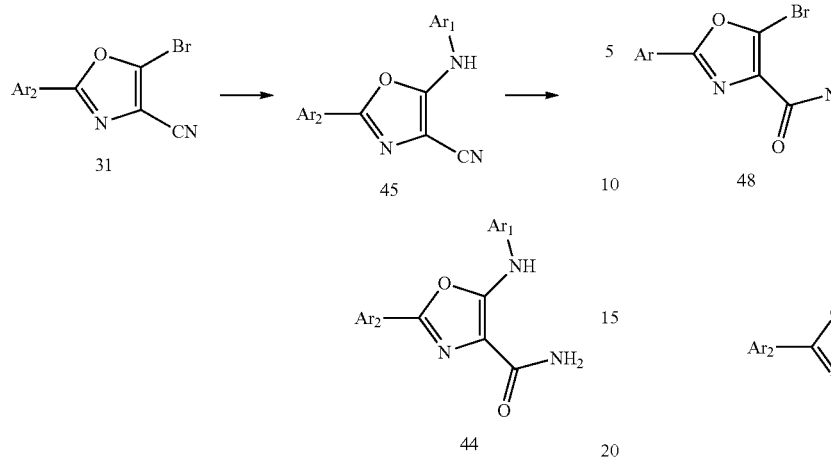

In Scheme 11, the bromo-compound 31 (see Scheme 6) is subjected to a palladium catalysed amination by reaction with Ar¹—NH₂ in the presence of a palladium catalyst to give the intermediate nitrile 45 which is then partially hydrolysed using acidic conditions such as concentrated sulphuric acid or basic conditions such as aqueous potassium hydroxide (typically with microwave heating) to give the product 44.

Compounds of the formula 1 wherein b is 1, a is 0 and T is O can be prepared by the reaction sequence set out in Scheme 12.

Scheme 12

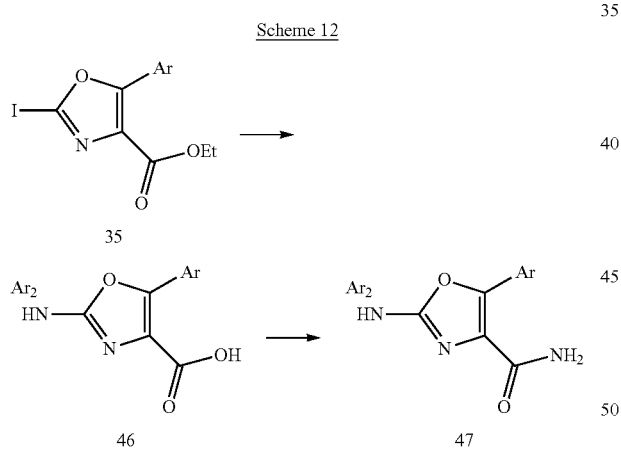

In Scheme 12, the iodo-oxazole ester 35 (see Scheme 8) is subjected to amination by reaction with Ar²—NH₂ in the presence of a palladium catalyst to give an intermediate ester (not shown). The ester is then hydrolysed using an alkali metal hydroxide such as potassium hydroxide as described above to give the oxazole carboxylic acid 46. The oxazole carboxylic acid 46 is then reacted with ammonia in the presence of EDAC and HOBt to give the amide product 47.

Compounds of the formula (1) wherein T is O, b is 0, a is 0 and Ar¹ is a phenyl group substituted by an aminoalkoxy substituent —(CH₂)ₙ—NR'''R''' (where each R''' is hydrogen or alkyl or NR'''R''' forms a cyclic group) can be prepared according to the synthetic route shown in Scheme 13.

Scheme 13

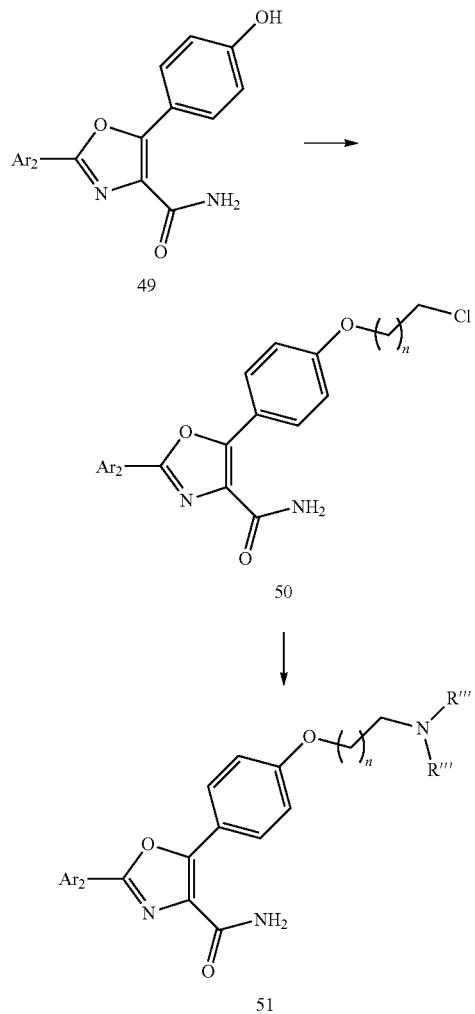

In Scheme 13, the starting material is the bromo-oxazole 48 which is reacted with 4-hydroxyphenylboronic acid in the presence of a palladium catalyst such as 1,1-bis(diphenylphosphino)ferrocene-palladium(II)dichloride and a base such as sodium carbonate in a polar solvent such as acetonitrile to give the hydroxyphenyloxazole compound 49. The hydroxyphenyloxazole compound 49 is then reacted with an alkylene dichloride Cl—(CH₂)ₙ—Cl where n is 2 or more (e.g. 2, 3 or 4) to give the chloroalkoxy compound 50. The chloroalkoxy compound is then reacted with an amine NR'''R''' in the presence of a non-interfering base such as triethylamine to give the product 51.

Compounds of the formula (1) wherein T is O, b is 0, a is 0 and Ar¹ is a phenyl group substituted by an amino(hydroxy)alkoxy substituent can be prepared according to the synthetic route shown in Scheme 14.

Scheme 14

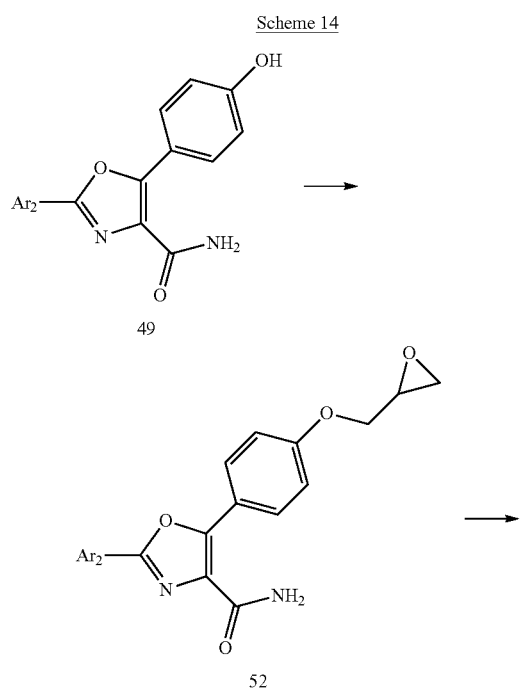

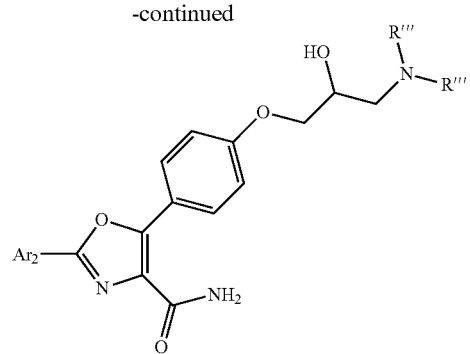

In Scheme 14, the hydroxyphenyloxazole compound 49 is treated with a base such as potassium carbonate followed by epichlorohydrin. The reaction is typically carried out in a polar solvent such as DMF at an elevated temperature (e.g. up to or in excess of 100° C.). The resulting oxirane 52 is then reacted with an amine HNR'''R''' in a polar solvent such as methanol at an elevated temperature (e.g. up to or in excess of 100° C.) to give the product 53.

Compounds of the formula (1) wherein T is O, b is 0, a is 1 and Ar¹ is a benzoic acid amide group can be prepared according to the synthetic route shown in Scheme 15.

Scheme 15

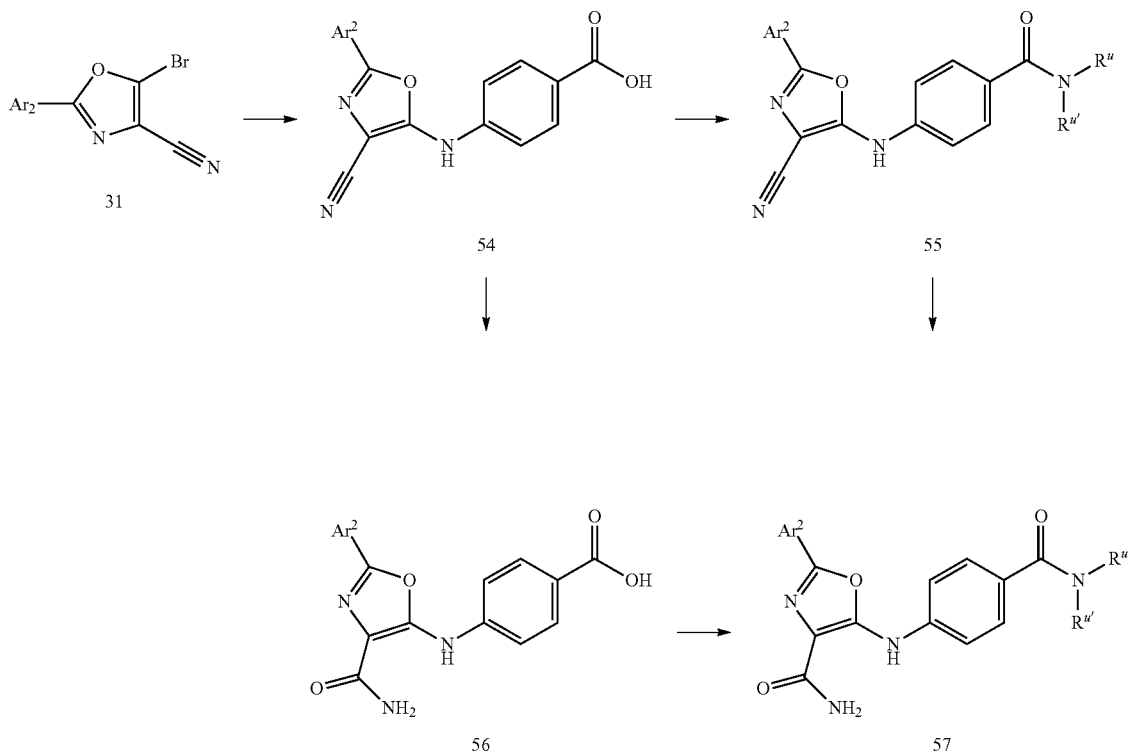

In Scheme 15, the bromo-cyano-oxaxole 31 (see Scheme 6) is subjected to a palladium catalysed amination by reaction with an aminobenzoic acid (4-aminobenzoic acid is specifically illustrated in the reaction scheme but the 2- and 3-isomers could be used instead) in the presence of a palladium catalyst such as tris(dibenzylideneacetone)dipalladium(0) in combination with 9,9-dimethyl-4,5-bis(diphenylphosphino)xanthene to give the substituted oxazolylaminobenzoic acid compound 54. The reaction may be carried out in a polar organic solvent such as a butanol:dioxane mixture in the presence of a base (e.g. an alkali metal carbonate such as caesium carbonate), typically with heating to a temperature in excess of 100° C. Compound 54 can then be treated with acid (e.g sulphuric acid) to hydrolyse the nitrile group to a carboxamide group to give a compound of the formula 56. The compound of formula 56 can then be reacted under amide-forming conditions (see Scheme 2 above) with an amine of the formula HNR$^u$R$^{u'}$ where R$^u$ and R$^{u'}$ are the same or different and each is hydrogen or a substituent or NR$^u$R$^{u'}$ forms a cyclic amine such as piperidine or morpholine, to give an amide of the formula 57.

Alternatively, the compound of formula 54 can be reacted under amide-forming conditions with an amine of the formula HNR$^u$R$^{u'}$ to give a compound of formula 55 which is then treated with acid to hydrolyse the nitrile group to a carboxamide group to give a compound of the formula 57.

The reverse amides of the compounds of formula 57 (i.e. compounds of the formula (1) in which T is O, b is 0, a is 1 and Ar$^1$ is an acylamino-phenyl group can be prepared according to the synthetic route shown in Scheme 16.

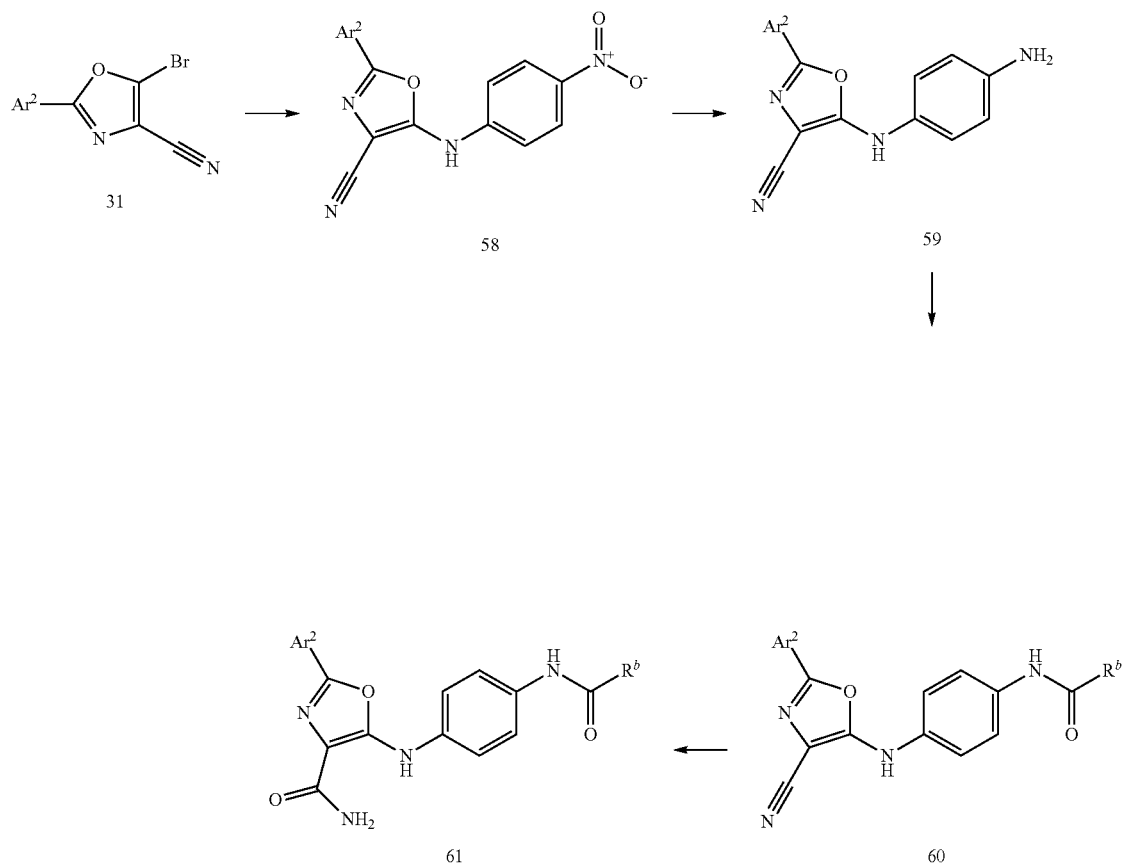

Scheme 16

In Scheme 16, the bromo-cyano-oxaxole 31 (see Scheme 6) is subjected to a palladium catalysed amination under conditions as described for Scheme 15 above, using a nitroaniline as the amine (the 4-nitroaniline is illustrated but other isomers could be used instead) to give the nitrophenylamine 58. The nitro group of the nitrophenylamine 58 is reduced to an amino group, for example by catalytic hydrogenation over palladium on carbon, to give the amine 59. The amine 59 can be converted to the acylamino compound 60 (where $R^b$ is as hereinbefore defined) by any of a variety of well known methods. For example, the amine 59 can be reacted with a carboxylic acid $R^bCO_2H$ under amide forming conditions as described above. Alternatively, when $R^b$ is a cyclic amine linked to the carbonyl group via a nitrogen atom (e.g. as in 1-piperidinyl, 4-morpholinyl or 4-piperazinyl), the amine 59 can be reacted with the cyclic amine in the presence of 1,1'-carbonyldiimidazole. The reaction is typically carried out at room temperature in a solvent such as dichloromethane in the presence of a non-interfering base such as triethylamine or diisopropylethylamine. The resulting intermediate, compound 60, is then treated with acid (e.g. sulphuric acid) as described above to hydrolyse the nitrile group to a carboxamide group thus giving the compound of formula 61.

Compounds of the formula (1) wherein T is O, b is 0, a is 0 and $Ar^1$ is a substituted aminomethyl-phenyl group can be prepared according to the synthetic route shown in Scheme 17.

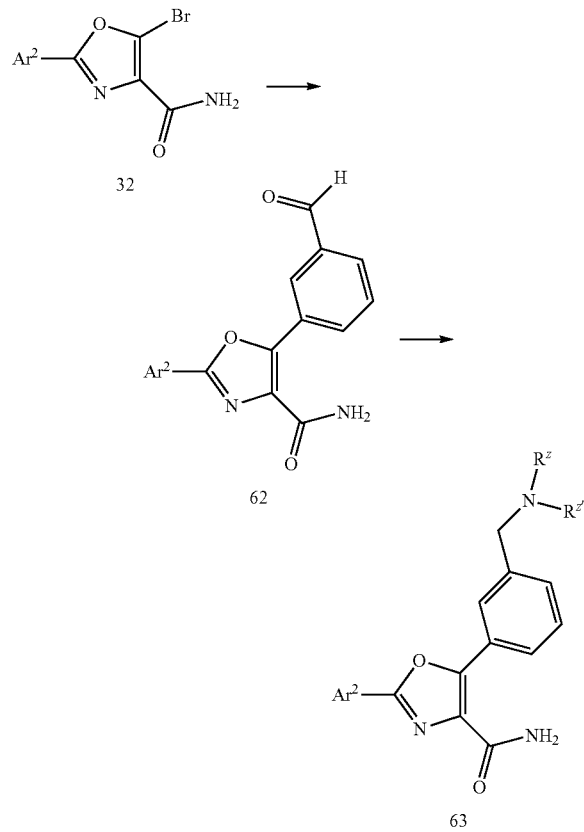

In Scheme 17, the bromo-oxazole carboxamide 32 (see Scheme 6 above) is reacted with a formyl-phenyl boronic acid (the 3-formyl-phenyl boronic acid is shown in the Scheme but the 2- or 4-isomers could be used instead) under Suzuki coupling conditions (see Scheme 6 above) to give the substituted benzaldehyde 62. The substituted benzaldehyde 62 is subjected to reductive amination with an amine $HNR^zR^{z'}$ in the presence of a borohydride reducing agent (such as sodium triacetoxyborohydride) in a chlorinated hydrocarbon solvent (such as 1,2-dichloroethane) containing acetic acid to give the substituted aminomethylphenyl oxazole compound 63 in which $NR^zR^{z'}$ can be, for example, a dialkylamino group or an optionally substituted cyclic amino group such as a morpholinyl, piperidinyl or piperazinyl group. The reductive amination reaction is typically carried out at room temperature.

Once formed, many compounds of the formula (1) can be converted into other compounds of the formula (1) using standard functional group interconversions.

Examples of functional group interconversions and reagents and conditions for carrying out such conversions can be found in, for example, *Advanced Organic Chemistry*, by Jerry March, 4$^{th}$ edition, 119, Wiley Interscience, New York, *Fiesers' Reagents for Organic Synthesis*, Volumes 1-17, John Wiley, edited by Mary Fieser (ISBN: 0-471-58283-2), and *Organic Syntheses*, Volumes 1-8, John Wiley, edited by Jeremiah P. Freeman (ISBN: 0-471-31192-8).

In many of the reactions described above, it may be necessary to protect one or more groups to prevent a reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

The compounds of the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Accordingly, in another aspect, the invention provides a pharmaceutical composition comprising a compound of the formula (1) or any sub-groups or examples thereof as defined herein and a pharmaceutically acceptable carrier.

The term "pharmaceutically acceptable" as used herein refers to compounds, materials, compositions, and/or dosage forms which are, within the scope of sound medical judgment, suitable for use in contact with the tissues of a subject (e.g. human) without excessive toxicity, irritation, allergic response, or other problems or complication, commensurate with a reasonable benefit/risk ratio. Each carrier, excipient, etc. must also be "acceptable" in the sense of being compatible with the other ingredients of the formulation.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

In one embodiment, the pharmaceutical composition is in a form suitable for i.v. administration, for example by injection or infusion.

In another embodiment, the pharmaceutical composition is in a form suitable for sub-cutaneous (s.c.) administration.

In a further embodiment, the pharmaceutical composition is in a form suitable for oral administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastrointestinal tract. Thus, the coating can be selected so as to degrade under certain pH conditions within the gastrointestinal tract, thereby selectively releasing the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Compositions for parenteral administration may be formulated for administration as discrete dosage units or may be formulated for administration by infusion.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 0.1 milligrams to 2 grams of active ingredient, more usually from 10 milligrams to 1 gram, for example, 50 milligrams to 500 milligrams.

The active compound will be administered to a patient in need thereof (for example a human or animal patient) in an amount sufficient to achieve the desired therapeutic effect.

Methods of Treatment

It is envisaged that the compounds of the formula (1) and sub-groups thereof defined herein will be useful in the prophylaxis or treatment of a range of disease states or conditions mediated by various kinase such as FLT3, FLT4 and Aurora kinases (particularly Aurora A kinase or Aurora B kinase). Examples of such disease states and conditions are set out above.

In particular, it is envisaged that the compounds of formula (1) will be useful in the prophylaxis and treatment of proliferative diseases such as cancers.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams) per kilogram of bodyweight although higher or lower doses may be administered where required. Ultimately, the quantity of compound administered and the type of composition used will be commensurate with the nature of the disease or physiological condition being treated and will be at the discretion of the physician.

The compounds of the formula (I) can be administered as the sole therapeutic agent or they can be administered in combination therapy with one of more other compounds for treatment of a particular disease state, for example a neoplastic disease such as a cancer as hereinbefore defined. Examples of other therapeutic agents that may be administered together (whether concurrently or at different time intervals) with the compounds of the formula (1) include but are not limited to topoisomerase inhibitors, alkylating agents, antimetabolites, DNA binders and microtubule inhibitors (tubulin targeting agents), such as cisplatin, cyclophosphamide, doxorubicin, irinotecan, fludarabine, 5FU, taxanes, mitomycin C, or radiotherapy. Alternatively, the compounds of the formula (I) can be administered in a combination therapy with monoclonal antibodies or signal transduction inhibitors.

Where the compound of the formula (1) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (1) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

Methods of Diagnosis

Prior to administration of a compound of the formula (1), a patient may be screened to determine whether a disease or condition from which the patient is or may be suffering is one which would be susceptible to treatment with a compound having activity against a particular kinase, for example FLT3, FLT4 and Aurora kinases.

Accordingly, the invention provides:

A compound of the formula (1) or a subgroup or example thereof as defined herein for use in the treatment or prophylaxis of a disease state or condition in a patient who has been screened and has been determined as suffering from, or being at risk of suffering from, a disease or condition which would be susceptible to treatment with a compound having activity against a kinase selected from FLT3, FLT4 and Aurora kinases.

The use of a compound of the formula (1) or a subgroup or example thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against a kinase selected from FLT3, FLT4 and Aurora kinases.

A method for the diagnosis and treatment of a disease state or condition mediated by a kinase selected from FLT3, FLT4 and Aurora kinases, which method comprises (i) screening a patient to determine whether a disease or condition from which the patient is or may be suffering is one which would be susceptible to treatment with a compound having activity against the kinase; and (ii) where it is indicated that the disease or condition from which the patient is thus susceptible, thereafter administering to the patient a compound of the formula (1) or a subgroup or example thereof as defined herein.

A biological sample taken from a patient may be subjected to diagnostic tests to determine whether a condition or disease, such as cancer, that the patient is or may be suffering from is one which is characterised by a genetic abnormality (e.g. a mutated kinase) or abnormal protein expression such as over-expression or upregulation of a particular kinase. The patient may be subjected to a diagnostic test to detect a marker characteristic of up-regulation of a particular kinase or the presence of a mutated kinase. Tumours with upregulation of a particular kinase may be particularly sensitive to inhibitors of that kinase. Therefore, tumours may preferentially be screened for upregulation of a particular kinase. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

Identification of individuals carrying a mutation in a particular kinase may mean that the patient would be particularly suitable for treatment with an inhibitor of the kinase. Tumours may preferentially be screened for presence of a variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel et al., eds. Current Protocols in Molecular Biology (2004) John Wiley & Sons Inc., or Innis, M. A. et al., eds. PCR Protocols: a guide to methods and applications (1990) Academic Press, San Diego. Reactions and manipulations involving nucleic acid techniques are also described in Sambrook et al., $3^{rd}$ Ed, Molecular Cloning: A Laboratory Manual (2001) Cold Spring Harbor Laboratory Press. Alternatively a commercially available kit for RT-PCR (for example Roche Molecular Biochemicals) may be used, or methodology as set forth in U.S. Pat. Nos.

4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in-situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel et al., eds. Current Protocols in Molecular Biology (2004) John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; (2004) pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies

EXAMPLES

The invention will now be illustrated, but not limited, by reference to the specific embodiments described in the following examples.

Liquid Chromatography—Mass Spectrometry (LC-MS) Methods

LC-MS (1) analyses were performed on a Micromass ZQ mass spectrometer/Waters Alliance 2795 HT HPLC with a Phenomenex Gemini 3 µm, C18, 30 mm×3 mm i.d. column at a temperature of 35° C. and a flow rate of 1.2 mL/minute using the following solvent gradient:
Solvent A: 0.02% Ammonia and 5% Solvent B in acetonitrile
Solvent B: 0.02% Ammonia and 0.063% ammonium formate in water.
0.00-2.50 minutes: 5% A/95% B to 95% A/5% B, 1.2 mL/minute
2.50-2.75 minutes: 95% A/5% B, 1.2 mL/minute
2.75-3.65 minutes: 95% A/5% B, 2.0 mL/minute
3.65-4.00 minutes: 95% A/5% B to 5% A/95% B, 2.0 mL/minute UV detection was at 220-400 nm using a Waters 996 photodiode array UV detector and ionisation was by positive or negative ion electrospray. Molecular weight scan range was 120-1000 amu.

LC-MS (2) analyses were performed on a Micromass ZQ mass spectrometer/Waters Alliance 2795 HT HPLC with a Phenomenex Gemini 5 µm, C18, 30 mm×4.6 mm i.d. column at a temperature of 35° C. and a flow rate of 2 mL/minute using the following solvent gradient:
Solvent A: 0.02% Ammonia and 5% Solvent B in acetonitrile.
Solvent B: 0.02% Ammonia and 0.063% ammonium formate in water.
0.00-4.25 minutes: 5% A/95% B to 95% A/5% B.
4.25-5.80 minutes: 95% A/5% B.
5.80-5.90 minutes: 95% A/5% B to 5% A/95% B.
5.90-7.00 minutes: 5% A/95% B.

UV detection was at 220-400 nm using a Waters 996 photodiode array UV detector and ionisation was by positive or negative ion electrospray. Molecular weight scan range was 80-1000 amu.

LC-MS (3) analyses were performed on a Micromass ZQ mass spectrometer/Waters Alliance 2795 HT HPLC with a XBridge C18 2.5 µm 3.0×30 mm i.d. column at a temperature of 35° C. and a flow rate of 1 mL/minute using the following solvent gradient:
Solvent A: 0.02% Ammonia and 5% Solvent B in acetonitrile.
Solvent B: 0.02% Ammonia and 0.063% ammonium formate in water.
0.00-2.5 minutes: 5% A/95% B to 95% A/5% B, flow rate 1 mL/min.
2.5-2.75 minutes: 95% A/5% B, flow rate 1 mL/min to 1.66 mL/min.
2.75-3.55 minutes: 95% A/5% B, flow rate 1.66 mL/min.
3.55-3.65 minutes: 95% A/5% B to 5% A/95% B, flow rate 1.66 mL/min.
3.65-4.00 minutes: 5% A/95% B, flow rate 1.66 mL/min to 1 mL/min.

UV detection was at 220-400 nm using a Waters 996 photodiode array UV detector and ionisation was by positive or negative ion electrospray. Molecular weight scan range was 120-1000 amu.

$^1$H NMR spectra were obtained using a Bruker DPX-400 spectrometer.

Microwave mediated reactions were performed in a Biotage Sixty microwave reactor at the temperature and times specified in the experimental section.

GLOSSARY OF TERMS

Et$_2$O—diethyl ether
MgSO$_4$—magnesium sulphate
MeOH—methanol
SPE—solid-phase extraction
MP—macroporous
TsOH—toluene sulphonic acid
HPLC—high performance liquid chromatography
EtOH—ethanol
HCl—hydrogen chloride
EtOAc—ethyl acetate
CDCl$_3$—deuterated chloroform
DMSO—dimethylsulphoxide
CD$_3$OD—deuterated methanol
THF—tetrahydrofuran
H$_2$O—water
d—doublet
dd—double doublet
s—singlet
br. s—broad singlet
t—triplet
q—quartet
m—multiplet
DMF—dimethylformamide
LCMS—liquid chromatography-mass spectrometry
NMR—nuclear magnetic resonance
NMP—N-methylpyrrolidine
DCE—dichloroethane
DCM—dichloromethane N₂—nitrogen
H₂SO₄—sulphuric acid
MP-SH—macroporous thiol
MP-CO₃—macroporous carbonate
Pd(dppf)₂Cl₂—[1,1'-bis(diphenylphosphino)ferrocene]dichloropalladium (II)
PS—polymer supported
uL or μL—microliter
mL—milliliter
mg—milligramme
nM—nanomolar
nm—nanometer
uM or μM—micromolar
mM—millimolar
pM—picomolar
Kda—kilo Daltons
ATP—adenosine triphosphate
MgCl₂—magnesium chloride
MnCl₂—manganese (II) chloride
GST—glutathione S-transferase
HEPES—4-(2-hydroxyethyl)-1-piperazineethanesulphonic acid
DTT—dithiothreitol
EDTA—ethylenediaminetetraacetic acid
BSA—bovine serum albumin
TBS—tris-buffered saline
Eu—N₁— europium N1 chelate. The reagent is the Eu³⁺-chelate of N¹-(p-iodoacetamido-benzyl)diethylenetriamine-N¹

General Method A

Examples A-1 to A-20 were prepared using General Method A which comprises the sequence of reactions set out in Scheme 1 above.

The tricarbonyl intermediate 14 in Scheme 1 was prepared following a procedure outlined in *J. Org. Chem.* (1995) 60, 8231-8235.

Example A-1

4-(4-methoxyphenyl)-2-phenyl-1H-imidazole-5-carboxamide

Step a—Ethyl 3-(4-methoxyphenyl)-3-oxo-2-(triphenylphosphoranylidene)propionate

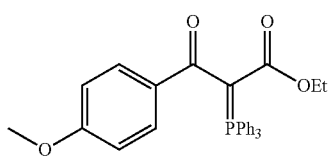

To a stirred solution of (carbethoxymethylene)triphenylphosphorane (0.500 g, 1.44 mmol) in DCM (7 ml) under an N₂ atmosphere was added N,O-bis(trimethylsilyl)acetamide (0.42 ml, 1.7 mmol). The solution was then cooled to 0° C. and p-anisoylchloride (0.250 g, 1.47 mmol) was added. The reaction mixture was then gradually warmed to room temperature and stirred overnight. The reaction was quenched by the addition of H₂O (3 ml) and the aqueous phase was extracted with DCM. The combined organic phases were dried over MgSO₄ and the solvent removed in vacuo to afford ethyl 3-(4-methoxyphenyl)-3-oxo-2-(triphenylphosphoranylidene)propionate. (0.637 g, 1.32 mmol, 92%) as an off white solid which was used without further purification. ¹H NMR (CDCl₃) δ 0.62 (3H, t), 3.69 (2H, q), 3.82 (3H, s), 6.86 (2H, d), 7.43-7.55 (9H, m), 7.71-7.80 (8H, m). LCMS (2) Rt: 3.65 min; m/z 483.

Step b—Ethyl 3-(4-methoxyphenyl)-2,3-dioxopropanoate

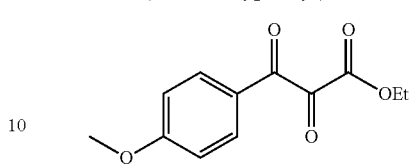

To a solution of ethyl 3-(4-methoxyphenyl)-3-oxo-2-(triphenylphosphoranylidene)propionate. (0.510 g, 1.1 mmol) in THF (10 ml) was added water (10 ml) followed by oxone (0.974 g, 1.6 mmol) in portions and the resulting mixture was stirred at room temperature overnight. The solid was removed by filtration and filtrate concentrated in vacuo and extracted with DCM. The combined organic phases were dried over MgSO₄ and the solvent removed in vacuo to afford crude ethyl 3-(4-methoxyphenyl)-2,3-dioxopropanoate as a yellow oil (0.500 g) as a mixture with triphenylphosphine oxide which was used without further purification. LCMS (2) 2.38 min; m/z 237.

Step c—Ethyl 4-(4-methoxyphenyl)-2-phenyl-1H-imidazole-5-carboxylate

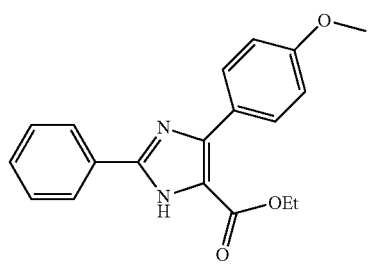 [SMILES: CCOC(=O)c1[nH]c(-c2ccccc2)nc1-c1ccc(OC)cc1]

A mixture of crude ethyl 3-(4-methoxyphenyl)-2,3-dioxopropanoate (0.050 g, approximately 0.11 mmol), ammonium acetate (0.082 g, 10.6 mmol) and benzaldehyde (11 μl, 0.11 mmol) in acetic acid (0.5 ml) was heated in the microwave at 160° C. for 5 minutes. The reaction mixture was diluted with MeOH and purified by SPE using a MP-TsOH cartridge (1000 mg). The solvent was removed in vacuo to afford ethyl 4-(4-methoxyphenyl)-2-phenyl-1H-imidazole-5-carboxylate (0.022 g, 0.07 mmol) which was used without further purification. LCMS (2) Rt: 3.29; m/z 323.

Step d—4-(4-methoxyphenyl)-2-phenyl-1H-imidazole-5-carboxamide

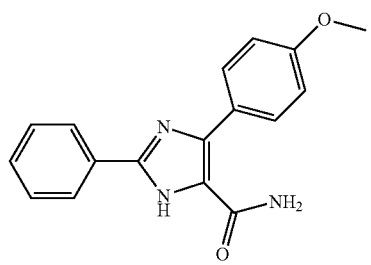 [SMILES: COc1ccc(-c2nc(-c3ccccc3)[nH]c2C(N)=O)cc1]

A suspension of ethyl 4-(4-methoxyphenyl)-2-phenyl-1H-imidazole-5-carboxylate (0.078 g, 0.23 mmol) in aqueous (28%) ammonia (4.5 ml) was heated in the microwave for 35 minutes at 150° C. The solvent was then removed in vacuo and the residue was purified by preparative HPLC to afford 4-(4-methoxyphenyl)-2-phenyl-1H-imidazole-5-carboxamide (0.0109 g, 0.04 mmol, 16%) as a white solid. ¹H NMR (DMSO) δ 3.82 (3H, s), 7.01 (2H, d), 7.10 (1H, br. s), 7.39-7.43 (2H, m), 7.49 (2H, dd), 7.85 (2H, d), 8.10 (2H, m). LCMS (2) Rt: 2.46 min; m/z (ES+) 294.

In a similar manner as described in example A-1, but using the appropriate aryl or heteroaryl aldehyde in place of benzaldehyde in Step c, the compounds described in examples A-2 to A-20 were prepared.

Example A-2

2-(2-chlorophenyl)-4-(4-methoxyphenyl)-1H-imidazole-5-carboxamide

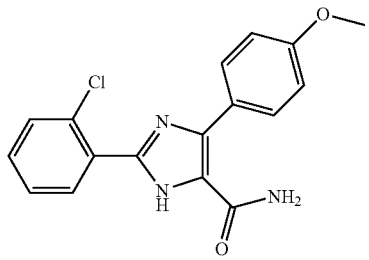 [SMILES: COc1ccc(-c2nc(-c3ccccc3Cl)[nH]c2C(N)=O)cc1]

¹N NMR (DMSO) δ 3.82 (3H, s), 7.00 (2H, d) 7.08 (1H, br. s), 7.33 (1H, br. s), 7.45-7.53 (2H, m), 7.62 (1H, m), 7.75 (1H, m), 7.86 (2H, d). LCMS (2) Rt: 2.55 min; m/z (ES+) 328/330.

Example A-3

2-(2-methoxyphenyl)-4-(4-methoxyphenyl)-1H-imidazole-5-carboxamide

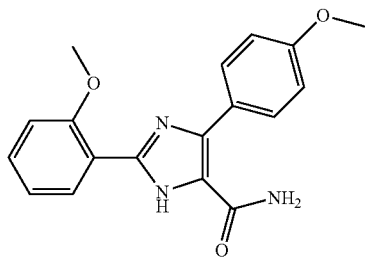 [SMILES: COc1ccc(-c2nc(-c3ccccc3OC)[nH]c2C(N)=O)cc1]

¹H NMR (DMSO) δ 3.82 (3H, s), 3.91 (3H, s), 7.00 (2H, d), 7.03 (1H, br. s), 7.07 (1H, m), 7.17 (1H, m), 7.39 (1H, br. s), 7.42 (1H, m), 7.80 (2H, d), 7.97 (1H, dd), 11.97 (1H, br. s). LCMS (2) Rt: 2.63 min; m/z (ES+) 324.

Example A-4

2-(3-methoxyphenyl)-4-(4-methoxyphenyl)-1H-imidazole-5-carboxamide

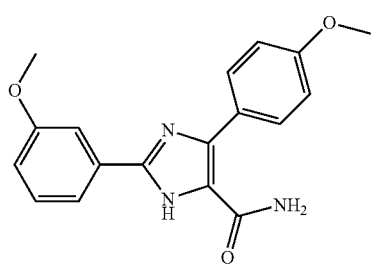 [SMILES: COc1ccc(-c2nc(-c3cccc(OC)c3)[nH]c2C(N)=O)cc1]

¹H NMR (DMSO) δ 3.82 (3H, s), 3.84 (3H, s), 6.97 (1H, ddd), 7.01 (2H, d), 7.08 (1H, br. s), 7.39 (1H, dd), 7.43 (1H, br. s), 7.67-7.71 (2H, m), 7.83 (2H, d), 12.70 (1H, br. s). LCMS (2) Rt: 2.48 min; m/z (ES+) 324.

Example A-5

2,4-bis(4-methoxyphenyl)-1H-imidazole-5-carboxamide

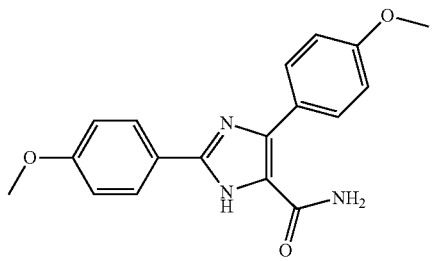

¹H NMR (DMSO) δ 3.82 (3H, s), 3.82 (3H, s), 7.01 (2H, d), 7.05 (3H, m), 7.38 (1H, br. s), 7.84 (2H, d), 8.03 (2H, d), 12.55 (1H, br. s). LCMS (2) Rt: 2.41 min; m/z (ES+) 324.

Example A-6

4-(4-methoxyphenyl)-2-o-tolyl-1H-imidazole-5-carboxamideHH

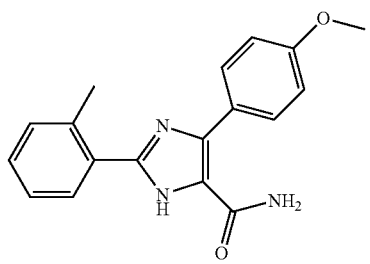 [SMILES: COc1ccc(-c2nc(-c3ccccc3C)[nH]c2C(N)=O)cc1]

¹H NMR (DMSO) δ 2.57 (3H, s), 3.82 (3H, s), 7.00 (2H, d), 7.04 (1H, br. s), 7.28-7.35 (4H, m), 7.67 (1H, d), 7.87 (2H, d), 12.55 (1H, br. s). LCMS (2) Rt: 2.51 min; m/z 308.

Example A-7

4-(4-methoxyphenyl)-2-m-tolyl-1H-imidazole-5-carboxamide

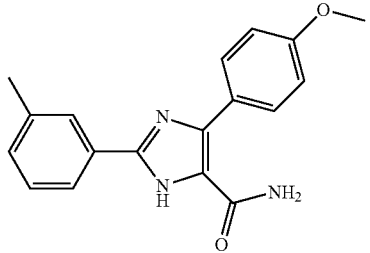 [SMILES: COc1ccc(-c2nc(-c3cccc(C)c3)[nH]c2C(N)=O)cc1]

¹H NMR (DMSO) δ 2.39 (3H, s), 3.82 (3H, s), 7.01 (2H, d), 7.08 (1H, br. s), 7.22 (1H, d), 7.37 (1H, dd), 7.40 (1H, br. s), 7.84 (2H, d), 7.89 (1H, d), 7.95 (1H, s). LCMS (2) Rt: 2.64 min; m/z (ES+) 308.

Example A-8

4-(4-methoxyphenyl)-2-p-tolyl-1H-imidazole-5-carboxamide

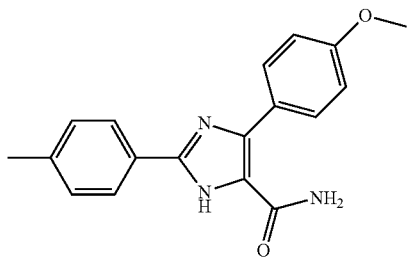

¹H NMR (DMSO) δ 2.35 (3H, s), 3.81 (3H, s), 7.00 (2H, d), 7.04 (1H, br. s), 7.29 (2H, d), 7.38 (1H, br. s), 7.83 (2H, d), 7.98 (2H, d), 12.63 (1H, br. s). LCMS (2) Rt: 2.62 min; m/z (ES+) 308.

Example A-9

2-(4-bromo-2-fluorophenyl)-4-(4-methoxyphenyl)-1H-imidazole-5-carboxamide

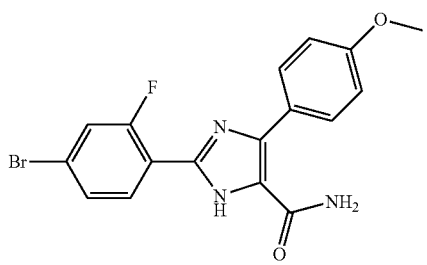 [SMILES: COc1ccc(-c2nc(-c3ccc(Br)cc3F)[nH]c2C(N)=O)cc1]

¹H NMR (DMSO) δ 3.82 (3H, s), 7.00 (2H, d), 7.12 (1H, br. s), 7.38 (1H, br. s), 7.58 (1H, dd), 7.75 (1H, dd), 7.81 (2H, d), 7.92 (1H, dd), 12.70 (1H, br. s). LCMS (2) Rt: 2.81 min; m/z (ES+) 390/392.

Example A-10

2-(2,6-dichlorophenyl)-4-(4-methoxyphenyl)-1H-imidazole-5-carboxamide

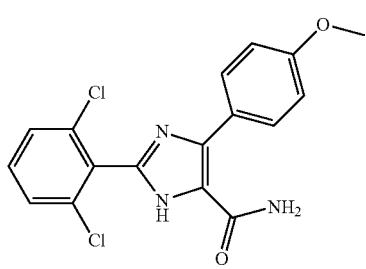 [SMILES: COc1ccc(-c2nc(-c3c(Cl)cccc3Cl)[nH]c2C(N)=O)cc1]

¹H NMR (DMSO) δ 3.81 (3H, s), 7.00 (2H, d), 7.06 (1H, br. s), 7.38 (1H, br. s), 7.58 (1H, dd), 7.64 (1H, d), 7.66 (1H, d), 7.87 (2H, d). LCMS (2) Rt: 2.34; m/z (ES+) 362/364/366.

Example A-11

2-(2-fluorophenyl)-4-(4-methoxyphenyl)-1H-imidazole-5-carboxamide

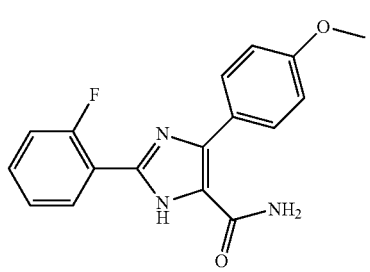

¹H NMR (DMSO) δ 3.82 (3H, s), 7.00 (2H, d), 7.11 (1H, br. s), 7.33-7.41 (3H, m), 7.50 (1H, m), 7.82 (2H, d), 7.95 (1H, m), 12.63 (1H, br. s).

Example A-12

4-(4-methoxyphenyl)-2-(pyridin-3-yl)-1H-imidazole-5-carboxamide

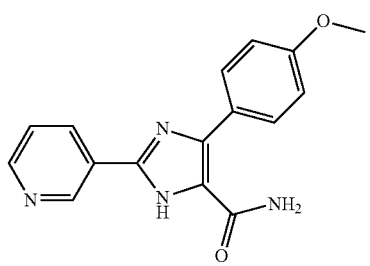

¹H NMR (DMSO) δ 3.83 (3H, s), 7.03 (2H, d), 7.14 (1H, br. s), 7.50 (1H, br. s), 7.53 (1H, dd), 7.85 (2H, d), 8.41 (1H, ddd), 8.60 (1H, dd), 9.28 (1H, d), 12.94 (1H, br. s).

Example A-13

2-(1H-indol-3-yl)-4-(4-methoxyphenyl)-1H-imidazole-5-carboxamide

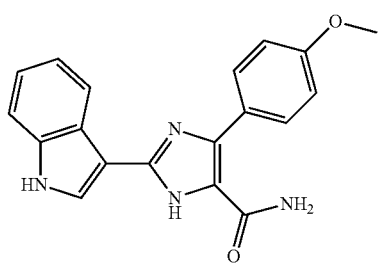 [SMILES: COc1ccc(-c2nc(-c3c[nH]c4ccccc34)[nH]c2C(N)=O)cc1]

$^1$H NMR (DMSO) δ 3.83 (3H, s), 7.02 (2H, d), 7.05 (1H, br. s), 7.11-7.20 (2H, m), 7.45 (1H, d), 7.47 (1H, br. s), 7.88 (2H, d), 8.06 (1H, d), 8.51 (1H, d), 11.41 (1H, br. s), 12.34 (1H, br. s).

Example A-14

2-(4-bromo-2,6-difluorophenyl)-4-(4-methoxyphenyl)-1H-imidazole-5-carboxamide

Step a—4-bromo-2,6-difluorobenzaldehyde

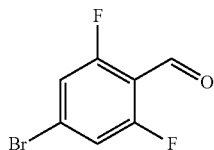 [SMILES: O=Cc1c(F)cc(Br)cc1F]

To a solution of 4-bromo-2,6-difluorobenzylalcohol (0.200 g, 0.9 mmol) in DCM (4 ml) and DMSO (0.440 ml) was added triethylamine (1 ml, 0.72 mmol) and sulfur trioxide pyridine complex (0.570 g, 3.6 mmol) and the resulting solution was stirred at room temperature for 3 hours. The solution was diluted with Et$_2$O and washed with 0.5M aqueous HCl, 1M sodium bicarbonate solution and brine. The organic phase was dried over MgSO$_4$ and the solvent removed in vacuo to afford 4-bromo-2,6-difluorobenzaldehyde (0.166 g, 0.75 mmol, 84%) as a white solid. $^1$H NMR (CDCl$_3$) δ 7.22 (2H, d), 10.29 (1H, br. s).

LCMS (2) Rt: 2.74 min.

Step b—2-(4-bromo-2,6-difluorophenyl)-4-(4-methoxyphenyl)-1H-imidazole-5-carboxamide

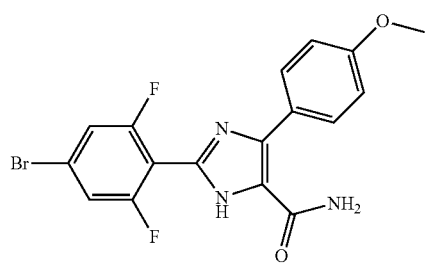 [SMILES: COc1ccc(-c2nc(-c3c(F)cc(Br)cc3F)[nH]c2C(N)=O)cc1]

The title compound was prepared according to the procedure described in example A-1 using 4-bromo-2,6-difluorobenzaldehyde in place of benzaldehyde in Step c. NMR (DMSO) δ 3.81 (3H, s), 7.01 (2H, d), 7.12 (1H, br. s), 7.35 (1H, br. s), 7.72 (2H, d), 7.81 (2H, d), 13.03 (1H, br. s). LCMS (2) Rt: 2.59 min; m/z (ES+) 408/410.

Example A-15

2-(2-chloro-6-fluorophenyl)-4-(4-methoxyphenyl)-1H-imidazole-5-carboxamide

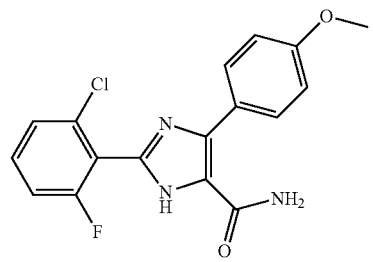 [SMILES: COc1ccc(-c2nc(-c3c(F)cccc3Cl)[nH]c2C(N)=O)cc1]

$^1$H NMR (DMSO) δ 3.81 (3H, s), 7.00 (2H, d), 7.08 (1H, br. s), 7.37 (1H, br. s), 7.43 (1H, dd), 7.52 (1H, d), 7.61 (1H, m), 7.85 (2H, d), 12.98 (1H, br. s). LCMS (2) Rt: 2.08 min; m/z (ES+) 346/348.

Example A-16

2-(2,6-difluorophenyl)-4-(thiophen-2-yl)-1H-imidazole-5-carboxamide

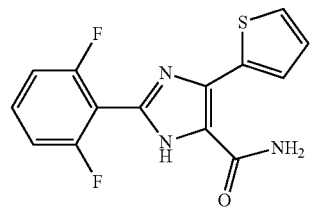 [SMILES: NC(=O)c1[nH]c(-c2c(F)cccc2F)nc1-c1cccs1]

LCMS (2) Rt: 1.92 min; m/z (ES+) 306.

Example A-17

2-(3,5-dimethoxyphenyl)-4-(4-methoxyphenyl)-1H-imidazole-5-carboxamide

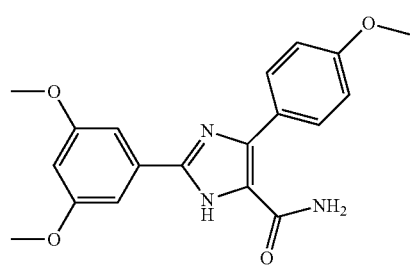

¹H NMR (DMSO) δ 3.82 (9H, s), 6.83 (1H, t), 7.02 (2H, d), 7.07 (1H, br. s), 7.32 (2H, d), 7.47 (1H, br. s), 7.81 (2H, d), 12.68 (1H, br. s). LCMS (2) Rt: 2.55 min; m/z (ES+) 354.

Example A-18

2-(2,6-difluorophenyl)-4-(2-fluorophenyl)-1H-imidazole-5-carboxamide

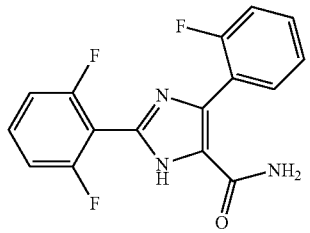 [SMILES: NC(=O)c1[nH]c(-c2c(F)cccc2F)nc1-c1ccccc1F]

LCMS (2) Rt: 1.97 min; m/z (ES+) 318.

Example A-19

2-(2,6-difluorophenyl)-4-phenyl-1H-imidazole-5-carboxamide

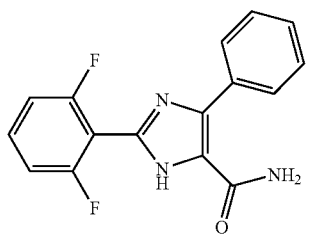 [SMILES: NC(=O)c1[nH]c(-c2c(F)cccc2F)nc1-c1ccccc1]

LCMS (2) Rt: 1.97 min; m/z (ES+) 300.

Example A-20

2-(2,6-difluorophenyl)-4-(3-methoxyphenyl)-1H-imidazole-5-carboxamide

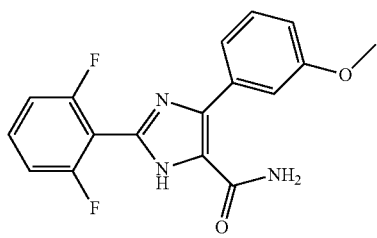 [SMILES: COc1cccc(-c2nc(-c3c(F)cccc3F)[nH]c2C(N)=O)c1]

¹H NMR (DMSO) δ 3.80 (3H, s), 6.95 (1H, ddd), 7.20 (1H, br. s), 7.31 (2H, t), 7.36 (1H, d), 7.41 (1H, br. s), 7.44 (1H, m), 7.56 (1H, m), 7.63 (1H, m). LCMS (2) Rt: 2.11 min; m/z (ES+) 330.

General Method B

General Method B comprises the series of reactions set out in Scheme 2 above.

Example B-1

4-(4-methoxyphenyl)-2-(pyridin-4-yl)-1H-imidazole-5-carboxamide

Step a—4-(4-methoxyphenyl)-2-(pyridin-4-yl)-1H-imidazole-5-carboxylic acid

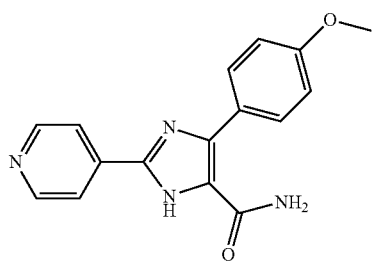 [SMILES: COc1ccc(-c2nc(-c3ccncc3)[nH]c2C(N)=O)cc1]

To a solution of ethyl 4-(4-methoxyphenyl)-2-(pyridin-4-yl)-1H-imidazole-5-carboxylate (0.089 g, 0.28 mmol, prepared (using pyridine-4-carboxaldehyde in place of benzaldehyde) according to the method outlined in Example A-1, step c), in methanol was added 1M aqueous potassium hydroxide (5 ml, 5.0 mmol) and the resulting mixture stirred at 55° C. for 48 hours. The solution was cooled to room temperature, neutralised by the addition of 0.5M aqueous HCl and extracted with DCM. The aqueous phase was then acidified by the addition of acetic acid and purified by SPE using MP-TsOH cartridges (2×1000 mg) to afford 4-(4-methoxyphenyl)-2-(pyridin-4-yl)-1H-imidazole-5-carboxylic acid (0.090 g) as an orange oil which was used without further purification.

LCMS (2) Rt: 1.20 min; m/z (ES+) 296.

Step b—4-(4-methoxyphenyl)-2-(pyridin-4-yl)-1H-imidazole-5-carboxamide

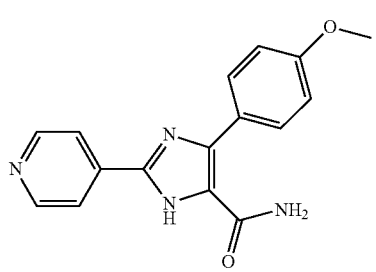 [SMILES: COc1ccc(-c2nc(-c3ccncc3)[nH]c2C(N)=O)cc1]

To a solution of 4-(4-methoxyphenyl)-2-(pyridin-4-yl)-1H-imidazole-5-carboxylic acid (0.090 g, 0.3 mmol) and hydroxybenzotriazole monohydrate (0.047 g, 0.3 mmol) in DMF (2.5 ml) was added 0.5M ammonia in dioxane (2 ml, 1.0 mmol) and the resulting solution stirred at room temperature for 10 minutes. 1-[3-(Dimethylamino)propyl]-3-ethylcarbodiimide (0.064 g, 0.33 mmol) was added and the reaction mixture stirred at room temperature overnight. The solvent was removed in vacuo and the residue purified by preparative HPLC to afford 4-(4-methoxyphenyl)-2-(pyridin-4-yl)-1H-imidazole-5-carboxamide (0.025 g, 0.08 mmol, 67%). ¹H NMR (DMSO) δ 3.83 (3H, s), 7.03 (2H, d), 7.20 (1H, br. s), 7.50 (1H, br. s), 7.84 (2H, d), 8.03 (2H, dd), 8.68 (2H, dd), 13.12 (1H, br. s). LCMS (2) Rt 1.68 min; m/z (ES+) 295.

In a similar manner as described in example B-1 the compounds described in examples B-2 to B-6 were prepared.

Example B-2

2-(5-methoxy-1H-indol-3-yl)-4-(4-methoxyphenyl)-1H-imidazole-5-carboxamide

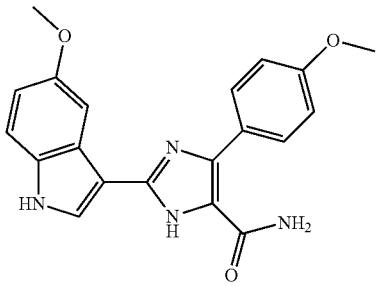 [SMILES: COc1ccc(-c2nc(-c3c[nH]c4ccc(OC)cc34)[nH]c2C(N)=O)cc1]

$^1$H NMR (DMSO) δ 3.82 (3H, s), 3.85 (3H, s), 6.82 (1H, dd), 7.02 (2H, d), 7.06 (1H, br. s), 7.34 (1H, d), 7.42 (1H, br. s), 7.87 (2H, d), 7.92 (1H, d), 8.01 (1H, d), 11.30 (1H, br. s), 12.32 (1H, br. s). LCMS (2) Rt: 2.25 min; m/z (ES+) 363.

Example B-3

2-(benzo[b]thiophen-3-yl)-4-(4-methoxyphenyl)-1H-imidazole-5-carboxamide

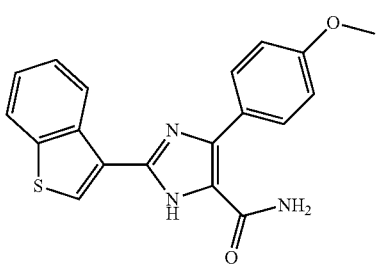 [SMILES: COc1ccc(-c2nc(-c3csc4ccccc34)[nH]c2C(N)=O)cc1]

$^1$H NMR (DMSO) δ 3.83 (3H, s), 7.04 (2H, d), 7.16 (1H, br. s), 7.50 (2H, m), 7.57 (1H, br. s), 7.87 (2H, d), 8.06 (1H, d), 8.41 (1H, s), 9.12 (1H, d), 12.84 (1H, br. s). LCMS (2) Rt: 2.77 min; m/z (ES+) 350.

Example B-4

4-(4-methoxyphenyl)-2-(1-methyl-1H-indol-3-yl)-1H-imidazole-5-carboxamide

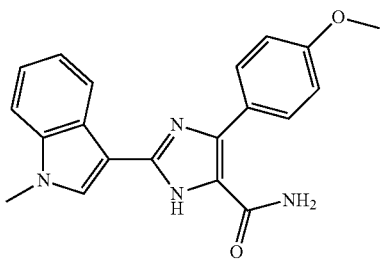

LCMS (2) Rt: 2.55 min; m/z (ES+) 347.

Example B-5

2-(2,6-difluorophenyl)-4-(4-methoxyphenyl)-1H-imidazole-5-carboxamide

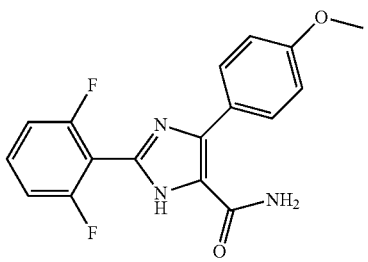 [SMILES: COc1ccc(-c2nc(-c3c(F)cccc3F)[nH]c2C(N)=O)cc1]

$^1$H NMR (DMSO) δ 3.84 (3H, s), 7.10 (2H, d), 7.39 (2H, t), 7.66 (1H, br. s), 7.67 (1H, br. s), 7.73 (1H, m), 8.24 (2H, d). LCMS (2) Rt: 2.99 min; m/z (ES+) 331.

Example B-6

4-(4-methoxyphenyl)-2-(pyridin-2-yl)-1H-imidazole-5-carboxamide

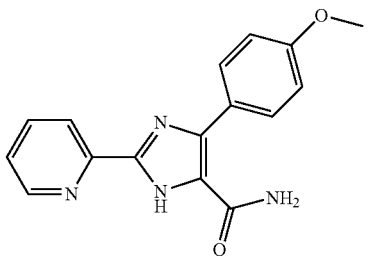

$^1$H NMR (DMSO) δ 3.81 (3H, s), 6.97 (2H, d), 7.14 (1H, br. s), 7.43 (1H, ddd), 7.47 (1H, br. s), 7.85 (2H, d), 7.95 (1H, ddd), 8.17 (1H, d), 8.65 (1H, d), 13.24 (1H, br. s). LCMS (2) Rt: 1.99 min; m/z (ES+) 295.

General Method C

General Method C comprises the series of reactions set out in Scheme 3 above.

Example C-1

2-(2,6-difluorophenyl)-4-(pyridin-2-yl)-1H-imidazole-5-carboxamide

Step a—ethyl 2-(hydroxyimino)-3-oxo-3-(pyridin-2-yl)propanoate

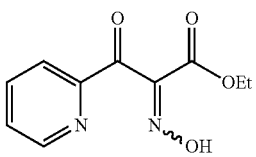 [SMILES: CCOC(=O)C(=NO)C(=O)c1ccccn1]

To a stirred solution of ethyl picolinoylacetate (0.500 g, 2.6 mmol) in acetic acid (0.5 mL) was added a solution of sodium nitrite (0.238 g, 3.4 mmol) in water (0.5 mL), dropwise. The resulting solution was stirred at room temperature for 2 hours after which water (0.5 mL) was added and the reaction was stirred for a further 2 hours. The mixture was extracted with Et$_2$O and the combined organic phase was washed with water, saturated sodium bicarbonate solution and brine, dried over MgSO$_4$ and the solvent removed in vacuo to afford ethyl 2-(hydroxyimino)-3-oxo-3-(pyridin-2-yl)propanoate (0.353 g, 1.6 mmol, 61%) as a white solid. $^1$H NMR (DMSO) δ 1.17 (3H, t), 4.22 (2H, q), 7.74 (1H, m), 8.04-8.11 (2H, m), 8.74 (1H, m), 12.87 (1H, s). LCMS (2) Rt: 1.09 min; m/z (ES+) 223.

Step b—ethyl 2-(2,6-difluorophenyl)-4-(pyridin-2-yl)-1H-imidazole-5-carboxylate

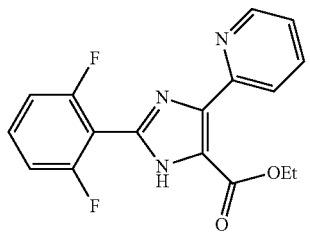 [SMILES: CCOC(=O)c1[nH]c(-c2c(F)cccc2F)nc1-c1ccccn1]

A mixture of ethyl 2-(hydroxyimino)-3-oxo-3-(pyridin-2-yl)propanoate (0.300 g, 1.4 mmol), ammonium acetate (0.104 g, 1.4 mmol) and 2,6-difluorobenzaldehyde (0.145 mL, 1.3 mmol) in acetic acid (6 mL) was heated in the microwave at 160° C. for 2 minutes. The reaction mixture was diluted with MeOH and purified by SPE using a MP-TsOH resin cartridge (2500 mg). The crude mixture obtained was purified by preparative HPLC to afford ethyl 2-(2,6-difluorophenyl)-4-(pyridin-2-yl)-1H-imidazole-5-carboxylate (0.029 g, 0.09 mmol, 7%) as a pale solid. LCMS (2) Rt: 2.46 min; m/z (ES+) 330.

Step c—2-(2,6-difluorophenyl)-4-(pyridin-2-yl)-1H-imidazole-5-carboxamide

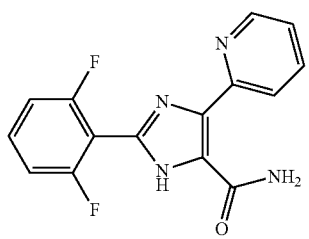 [SMILES: NC(=O)c1[nH]c(-c2c(F)cccc2F)nc1-c1ccccn1]

Prepared according to the method outlined in example B-1 from ethyl 2-(2,6-difluorophenyl)-4-(pyridin-2-yl)-1H-imidazole-5-carboxylate (0.029 g, 0.09 mmol) to afford 2-(2,6-difluorophenyl)-4-(pyridin-2-yl)-1'-1-imidazole-5-carboxamide (0.0025 g, 0.008 mmol, 9%). $^1$H NMR (DMSO) δ 7.27 (2H, t), 7.43 (1H, dd), 7.62 (1H, m), 7.86 (1H, br. s), 7.98 (1H, br. dd), 8.29 (1H, br. d), 8.65 (1H, ddd), 11.38 (1H, br. s), 13.28 (1H, br. s). LCMS (2) Rt: 2.28 min; m/z 301.

General Method D

General Method D comprises the series of reactions set out in Scheme 4 above. The reaction sequence is based on a route to diaryl substituted oxazoles described in *J. Org. Chem.* (1960) 25, 1151-1154.

Sodium 2,6-difluorobenzoate

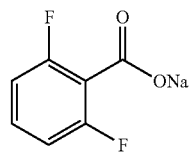

To a solution of 2,6-difluorobenzoic acid (1.00 g, 6.3 mmol) in EtOH and water (5:1, 60 mL) was added 1N aqueous sodium hydroxide solution (6.33 mL, 6.3 mmol). The reaction mixture was stirred for 10 minutes at room temperature and then solvents were removed in vacuo to yield sodium 2,6-difluorobenzoate (1.22 g, 6.3 mmol, quantitative) as an off white solid. $^1$H NMR (DMSO) δ 6.89 (2H, m), 7.15 (1H, m).

Example D-1

2-(2,6-difluorophenyl)-4-(4-methoxyphenyl)oxazole-5-carboxamide

Step a—ethyl 2-bromo-3-(4-methoxyphenyl)-3-oxopropanoate

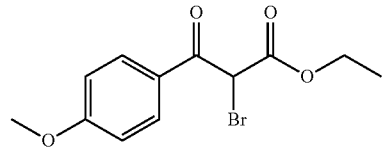 [SMILES: CCOC(=O)C(Br)C(=O)c1ccc(OC)cc1]

To a solution of ethyl p-anisoylacetate (1.00 g, 4.5 mmol) in ethanol (14 mL) at 50° C. was added triethylamine (0.63 mL, 4.5 mmol) followed by pyridinium hydrobromide perbromide (1.44 g, 4.5 mmol) and the resulting mixture was then stirred at 50° C. for 2 hours. The reaction was cooled to room temperature and poured into EtOAc. The organic phase was then washed with saturated sodium bicarbonate solution and 0.5M aqueous HCl, dried over MgSO$_4$ and the solvent removed in vacuo to afford ethyl 2-bromo-3-(4-methoxyphenyl)-3-oxopropanoate (1.209 g, 4.0 mmol, 89%) which was used without further purification. $^1$H NMR (CDCl$_3$) δ 1.26 (3H, t), 3.89 (3H, s), 4.28 (2H, q), 5.62 (1H, s), 6.96 (2H, d), 7.98 (2H, d). LCMS (2) Rt: 3.06 min; m/z (ES+) 301/303.

Step b—3-ethoxy-1-(4-methoxyphenyl)-1,3-dioxo-propan-2-yl-2,6-difluorobenzoate

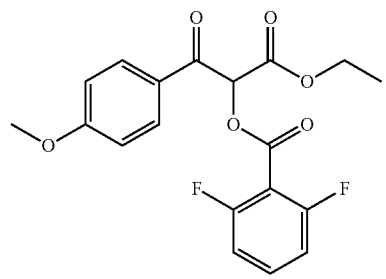 [SMILES: CCOC(=O)C(OC(=O)c1c(F)cccc1F)C(=O)c1ccc(OC)cc1]

A solution of ethyl 2-bromo-3-(4-methoxyphenyl)-3-oxo-propanoate (0.090 g, 0.3 mmol) and sodium 2,6-difluorobenzoate (0.054 g, 0.30 mmol) in ethanol (2 mL) was heated at 120° C. in the microwave for 10 minutes. The reaction mixture was diluted with EtOAc (25 mL) and water (25 mL). The organic phase was washed with water and brine, dried over MgSO$_4$ and the solvent evaporated in vacuo. The residue was purified by silica gel column chromatography using a gradient of 0-40% EtOAc in hexanes to afford 3-ethoxy-1-(4-methoxyphenyl)-1,3-dioxopropan-2-yl-2,6-difluorobenzoate (0.108 g, 0.29 mmol, 96%) as a clear film. $^1$H NMR (CDCl$_3$) δ 1.27 (3H, t), 3.89 (3H, s), 4.30 (2H, m), 6.47 (1H, s), 6.97 (4H, m), 7.46 (1H, m), 8.06 (2H, d). LCMS (1) Rt: 2.26 min; m/z (ES+) 379.

Step c—ethyl 2-(2,6-difluorophenyl)-4-(4-methoxyphenyl)oxazole-5-carboxylate

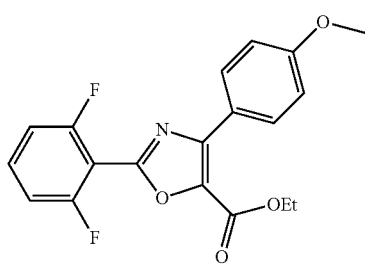

To a stirred solution of 3-ethoxy-1-(4-methoxyphenyl)-1,3-dioxopropan-2-yl 2,6-difluorobenzoate (0.082 g, 0.22 mmol) in acetic acid (3 mL) was added ammonium acetate (0.125 g, 1.62 mmol) and the reaction mixture heated to reflux for 3 hours. A further portion of ammonium acetate (0.017 g, 0.22 mmol) was added the reaction mixture heated to reflux for 1 hour. The reaction was diluted with water and extracted with EtOAc. The organic phase was washed with water and brine, dried over MgSO$_4$ and the solvent removed in vacuo. The residue was purified by silica gel column chromatography using 15% EtOAc in hexanes as eluent to afford ethyl 2-(2,6-difluorophenyl)-4-(4-methoxyphenyl)oxazole-5-carboxylate (0.041 g, 0.11 mmol, 53%) as a white crystalline solid. $^1$H NMR (CDCl$_3$) δ 1.41 (3H, t), 3.87 (3H, s), 4.43 (2H, q), 6.99 (2H, d), 7.07 (2H, t), 7.49 (1H, m), 8.15 (2H, d). LCMS (1) Rt: 2.46 min; m/z (ES+) 360.

Step d—2-(2,6-difluorophenyl)-4-(4-methoxyphenyl)oxazole-5-carboxylic acid

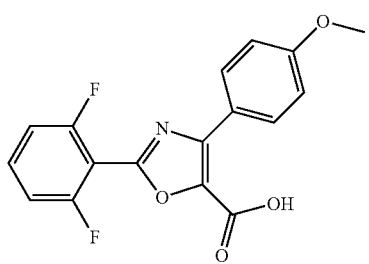 [SMILES: COc1ccc(-c2nc(-c3c(F)cccc3F)oc2C(=O)O)cc1]

To a stirred solution of ethyl 2-(2,6-difluorophenyl)-4-(4-methoxyphenyl)oxazole-5-carboxylate (0.030 g, 0.08 mmol) in THF and H$_2$O (1:1, 3 mL) was added lithium hydroxide hydrate (0.008 g, 0.33 mmol) and the reaction mixture stirred at room temperature for 2.5 hours. The THF was removed in vacuo and 1N aqueous HCl was added and the resultant precipitate collected by filtration to afford 2-(2,6-difluorophenyl)-4-(4-methoxyphenyl)oxazole-5-carboxylic acid (0.027 g, 0.08 mmol, 98%) as a white solid which was used without further purification. LCMS (1) Rt: 1.24 min; m/z (ES+) 332.

Step e—2-(2,6-difluorophenyl)-4-(4-methoxyphenyl)oxazole-5-carboxamide

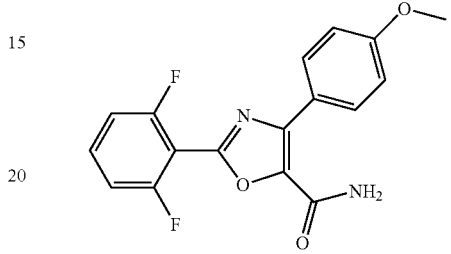

To a solution of 2-(2,6-difluorophenyl)-4-(4-methoxyphenyl)oxazole-5-carboxylic acid (0.026 g, 0.08 mmol) and hydroxybenzotriazole monohydrate (0.012 g, 0.08 mmol) in DMF (3 mL) was added 0.5M ammonia in dioxane (0.471 mL, 0.24 mmol) and the reaction mixture stirred at room temperature for 10 minutes. 1-[3-(dimethylamino)propyl]-3-ethylcarbodiimide (0.015 g, 0.08 mmol) was then added and the resulting reaction mixture stirred at room temperature overnight. After a further addition of hydroxybenzotriazole monohydrate (0.008 g, 0.05 mmol), 1-[3-(dimethylamino)propyl]-3-ethylcarbodiimide (0.010 g, 0.05 mmol) and 0.5M ammonia in dioxane (0.315 mL, 0.1116 mmol) the reaction mixture was stirred at room temperature for 4 hours. The solvent was evaporated in vacuo, and the residue was partitioned between DCM (10 mL) and water (10 mL). The organic phase was washed with water and brine, dried over MgSO$_4$ and the solvent removed in vacuo. The residue was purified by preparative HPLC to afford 2-(2,6-difluorophenyl)-4-(4-methoxyphenyl)oxazole-5-carboxamide (0.018 g, 0.05 mmol, 69%) as a white solid. $^1$H NMR (CD$_3$OD) δ 3.88 (3H, s), 7.03 (2H, d), 7.25 (2H, t), 7.68 (1H, m), 8.21 (2H, d). LCMS (2) Rt: 2.80; m/z (ES+) 331.

General Method E

General Method E comprises the series of reactions set out in Scheme 5 above.

Example E-1

2-(2,6-difluorophenyl)-5-(thiophen-2-yl)oxazole-4-carboxamide

Step a—ethyl 2-amino-3-oxo-3-(thiophen-2-yl)propanoate hydrochloride (see *J. Am. Chem. Soc.* (2005) 127, 5784-5785)

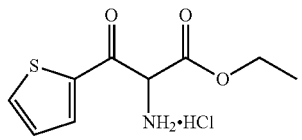

To a stirred solution of potassium tert-butoxide (0.84 g, 7.5 mmol) in dry THF (5.25 mL) under an $N_2$ atmosphere at −78° C. was added a cooled (−78° C.) solution of N-(diphenylmethylene)glycine ethyl ester (2.00 g, 7.5 mmol) in dry THF (3 mL), dropwise. The resulting solution was stirred at −78° C. for 30 minutes when it was added via canula to a stirred solution of 2-thiophene carbonyl chloride (0.80 mL, 7.5 mmol) in dry THF (3 mL) under an $N_2$ atmosphere at −78° C. The resulting mixture was stirred at −78° C. for 1 hour. The reaction was warmed to room temperature, 3N aqueous HCl (7.5 mL) was then added and the mixture stirred for 15 minutes. The resulting mixture was then concentrated in vacuo, diluted with water and washed with $Et_2O$. The aqueous phase was evaporated to dryness to afford ethyl 2-amino-3-oxo-3-(thiophen-2-yl)propanoate hydrochloride (1.345 g) as a pale solid which was used without further purification. LCMS (2) Rt: 1.44 min; m/z (ES+) 214.

Step b—ethyl 2-(2,6-difluorobenzamido)-3-oxo-3-(thiophen-2-yl)propanoate

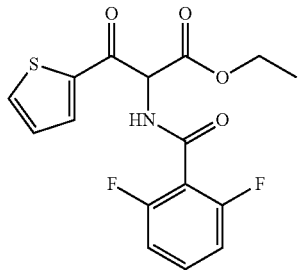 [SMILES: CCOC(=O)C(NC(=O)c1c(F)cccc1F)C(=O)c1cccs1]

To a stirred mixture of crude ethyl 2-amino-3-oxo-3-(thiophen-2-yl)propanoate hydrochloride (0.44 g), hydroxybenzotriazole monohydrate (0.417 g, 2.7 mmol) and 2,6-difluorobenzoic acid (0.431 g, 2.7 mmol) in DMF (5.5 mL) was added triethylamine (0.38 mL, 5.2 mmol) followed by 1-(3-(dimethylamino)propyl)-3-ethyl-carbodiimide hydrochloride (0.575 g, 3.0 mmol). The resulting mixture was stirred at room temperature overnight. The solvent was removed in vacuo and the residue was partitioned between water and DCM. The organic phase was separated, washed with water, dried over $MgSO_4$ and the solvent removed in vacuo. The residue was purified by silica gel column chromatography using 20% EtOAc in hexane as eluant to afford ethyl 2-(2,6-difluorobenzamido)-3-oxo-3-(thiophen-2-yl)propanoate (0.123 g, 0.35 mmol, 20%). $^1$H NMR ($CDCl_3$) δ 1.27 (3H, t), 4.28 (2H, m), 6.21 (1H, d), 7.00 (2H, t), 7.26 (1H, dd), 7.44 (2H, m), 7.83 (1H, dd), 8.20 (1H, dd). LCMS (1) Rt: 2.10 min; m/z (ES+) 354.

Step c—ethyl 2-(2,6-difluorophenyl)-5-(thiophen-2-yl)oxazole-4-carboxylate

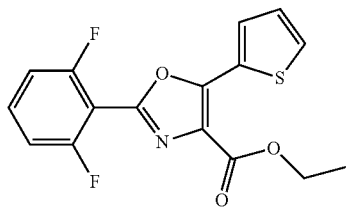 [SMILES: CCOC(=O)c1nc(-c2c(F)cccc2F)oc1-c1cccs1]

A solution of ethyl 2-(2,6-difluorobenzamido)-3-oxo-3-(thiophen-2-yl)propanoate (0.120 g, 0.34 mmol) in phosphorous oxychloride (0.4 mL, 4.29 mmol) was stirred at 75° C. overnight. The reaction was cooled to room temperature and then poured into ice-water. The resultant mixture was basified with solid sodium bicarbonate and then extracted with EtOAc. The combined organic phases were dried over $MgSO_4$ and the solvent removed in vacuo to afford 2-(2,6-difluorophenyl)-5-(thiophen-2-yl)oxazole-4-carboxylate (0.096 g, 0.29 mmol, 84%) as a brown solid. $^1$H NMR ($CDCl_3$) δ 1.40 (3H, t), 4.23 (2H, q), 7.00 (2H, t), 7.11 (1H, dd), 7.40 (1H, m), 7.45 (1H, dd), 8.07 (1H, dd). LCMS (1) Rt: 2.58 min; m/z (ES+) 336.

Step d—2-(2,6-difluorophenyl)-5-(thiophen-2-yl)oxazole-4-carboxylic acid

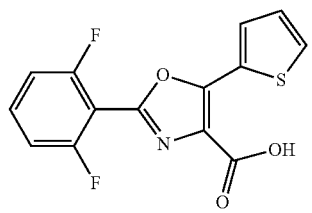 [SMILES: O=C(O)c1nc(-c2c(F)cccc2F)oc1-c1cccs1]

To a solution of ethyl 2-(2,6-difluorophenyl)-5-(thiophen-2-yl)oxazole-4-carboxylate (0.096 g, 0.29 mmol) in MeOH (6 mL) was added 1M potassium hydroxide solution (8 mL, 8.0 mmol) and the resulting mixture stirred at 55° C. overnight. The reaction was cooled to room temperature, acidified with 4N HCl and extracted with DCM. The combined organic phase was dried over $MgSO_4$ and the solvent removed in vacuo to afford 2-(2,6-difluorophenyl)-5-(thiophen-2-yl)oxazole-4-carboxylic acid (0.078 g, 0.25 mmol, 89%) as an off white solid which was used without further purification. LCMS (1) Rt: 1.41 min; m/z (ES+) 308.

Step e—2-(2,6-difluorophenyl)-5-(thiophen-2-yl)oxazole-4-carboxamide

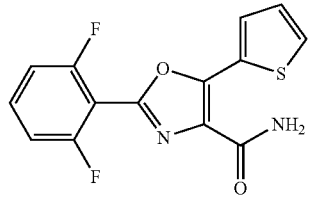 [SMILES: NC(=O)c1nc(-c2c(F)cccc2F)oc1-c1cccs1]

To a solution of 2-(2,6-difluorophenyl)-5-(thiophen-2-yl)oxazole-4-carboxylic acid (0.078 g, 0.25 mmol) and hydroxybenzotriazole monohydrate (0.039 g, 0.25 mmol) in DMF (2 mL) was added a 0.5M ammonia in dioxane solution (1.5 mL, 0.75 mmol) and the reaction mixture was stirred at room temperature for 10 minutes. 1-(3-(Dimethylamino)propyl)-3-ethyl-carbodiimide hydrochloride (0.054 g, 0.28 mmol) was then added and the resulting mixture stirred at room temperature overnight. The solvent was removed in vacuo and the residue was purified by preparative HPLC to afford 2-(2,6-difluorophenyl)-5-(thiophen-2-yl)oxazole-4-carboxamide (0.0031 g, 0.01 mmol, 4%) as a white solid. $^1$H NMR (DMSO) δ 7.25 (1H, dd), 7.40 (2H, t), 7.69-7.76 (3H, m), 7.84 (1H, dd), 8.17 (1H, dd). LCMS (2) Rt: 2.73 min; m/z (ES+) 307.

In a similar manner as described in example E-1 the compounds described in examples E-2 to E-4 were prepared.

Example E-2

2-(2,6-difluorophenyl)-5-(4-methoxyphenyl)oxazole-4-carboxamide

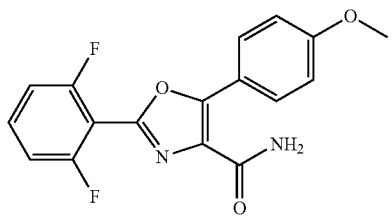 [SMILES: COc1ccc(-c2oc(-c3c(F)cccc3F)nc2C(N)=O)cc1]

$^1$H NMR (DMSO) δ 3.84 (3H, s), 7.10 (2H, d), 7.39 (2H, t), 7.66 (1H, br. s), 7.67 (1H, br. s), 7.73 (1H, m), 8.24 (2H, d). LCMS (2) Rt: 2.99 min; m/z (ES+) 331.

Example E-3

2-(1H-indol-3-yl)-5-(4-methoxyphenyl)oxazole-4-carboxamide

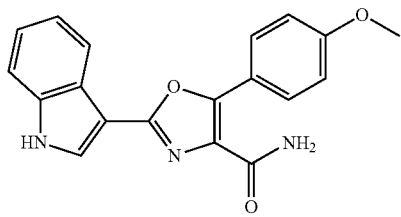 [SMILES: COc1ccc(-c2oc(-c3c[nH]c4ccccc34)nc2C(N)=O)cc1]

$^1$H NMR (DMSO) δ 3.85 (3H, s), 7.09 (2H, d), 7.25 (2H, m), 7.52 (1H, dd), 7.59 (1H, br. s), 7.79 (1H, br. s), 8.23 (1H, d), 8.39 (3H, m), 11.96 (1H, br. s). LCMS (2) Rt: 2.73 min; m/z (ES+) 334.

Example E-4

2-(1H-indol-3-yl)-5-(thiophen-2-yl)oxazole-4-carboxamide

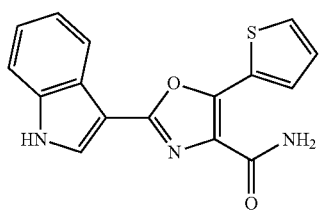 [SMILES: NC(=O)c1nc(-c2c[nH]c3ccccc23)oc1-c1cccs1]

$^1$H NMR (DMSO) δ 7.21-7.29 (3H, m), 7.53 (1H, dd), 7.64 (1H, br. s), 7.76 (1H, dd), 7.80 (1H, br.s), 8.20 (1H, dd), 8.22 (1H, d), 8.39 (1H, dd), 11.99 (1H, br. s). LCMS (2) Rt: 2.73 min; m/z (ES+) 310.

General Method F

General Method F comprises the series of reactions set out in Scheme 6 above.

Boronic Acid Synthesis 4-(2-(piperidin-1-yl)ethoxy)phenylboronic acid

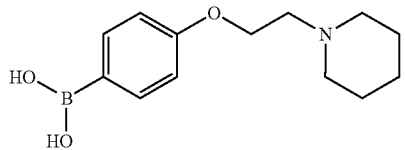 [SMILES: OB(O)c1ccc(OCCN2CCCCC2)cc1]

A mixture of 4-(4,4,5,5-tetramethyl-1,3,2-dioxaborolan-2-yl)phenol (0.120 g, 0.55 mmol), 1-(2-chloroethyl)piperidine hydrochloride (0.100 g, 0.54 mmol), potassium carbonate (0.226 g, 1.64 mmol) and 18-crown-6 (0.072 g, 0.27 mmol) in MeCN (3 mL) was heated in the microwave at 180° C. for 10 minutes. The mixture was diluted with MeOH and a small amount of water and purified by SPE using a MP-TsOH resin (1000 mg) cartridge. The solvent was removed in vacuo to afford 4-(2-(piperidin-1-yl)ethoxy)phenylboronic acid (0.129 g, 0.52 mmol, 95%) which was used without further purification. LCMS (1) Rt: 1.55; m/z (ES+) 250.

4-(2-(dimethylamino)ethoxy)phenylboronic acid

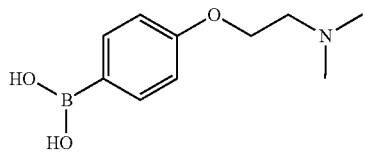

Prepared in a manner similar to that described for the preparation of 4-(2-(piperidin-1-yl)ethoxy)phenylboronic acid. LCMS (1) Rt: 1.19; m/z (ES+) 210.

4-(2-morpholinoethoxy)phenylboronic acid

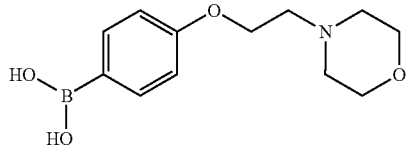 [SMILES: OB(O)c1ccc(OCCN2CCOCC2)cc1]

Prepared in a manner similar to that described for the preparation of 4-(2-(piperidin-1-yl)ethoxy)phenylboronic acid. LCMS (1) Rt: 1.18; m/z (ES+) 252.

4-((4-acetylpiperazin-1-yl)methyl)phenylboronic acid

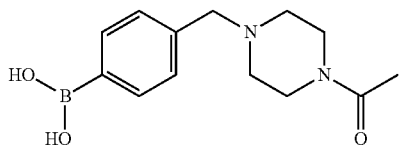 [SMILES: CC(=O)N1CCN(Cc2ccc(B(O)O)cc2)CC1]

To a stirred mixture of 2-(4-bromophenyl)-4,4,5,5-tetramethyl-1,3,2-dioxaborolane (0.120 g, 0.4 mmol) and potassium carbonate (0.056 g, 0.4 mmol) in DMF (3 mL) was added N-acetylpiperazine (0.052 g, 0.4 mmol) and the resulting reaction mixture stirred at room temperature for 2 hours. The solvent was removed in vacuo. The residue was suspended in MeOH and purified by SPE using an MP-TsOH resin (1000 mg) cartridge to afford 4-((4-acetylpiperazin-1-yl)methyl)phenylboronic acid as an oil which was used without further purification. LCMS (1) Rt: 1.04 min; m/z (ES+) 263.

4-((4-methylpiperazin-1-yl)methyl)phenylboronic acid

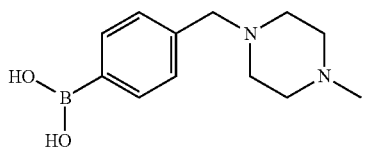 [SMILES: CN1CCN(Cc2ccc(B(O)O)cc2)CC1]

Prepared in a manner similar to that described for the preparation of 4-((4-acetylpiperazin-1-yl)methyl)phenylboronic acid. LCMS (1) Rt: 0.91 min; m/z (ES+) 235.

4-((2-morpholinoethoxy)methyl)phenylboronic acid

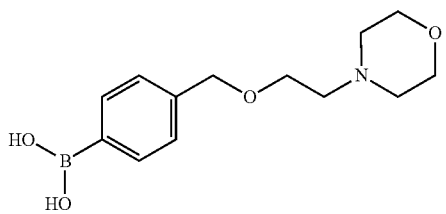 [SMILES: OB(O)c1ccc(COCCN2CCOCC2)cc1]

Prepared in a manner similar to that described for the preparation of 4-((4-acetylpiperazin-1-yl)methyl)phenylboronic acid. LCMS (1) Rt: 0.27 min; m/z (ES+) 266.

tert-butyl 4-(4-(4,4,5,5-tetramethyl-1,3,2-dioxaborolan-2-yl)benzyl)piperazine-1-carboxylate

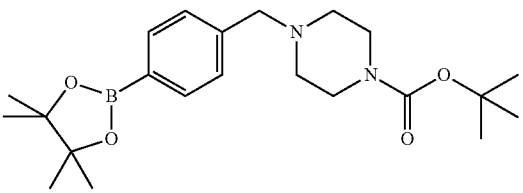 [SMILES: CC(C)(C)OC(=O)N1CCN(Cc2ccc(B3OC(C)(C)C(C)(C)O3)cc2)CC1]

To a stirred mixture of 2-(4-bromophenyl)-4,4,5,5-tetramethyl-1,3,2-dioxaborolane (0.114 g, 0.4 mmol) and potassium carbonate (0.060 g, 0.43 mmol) in DMF (3 mL) was added tert-Butyl 1-piperazinecarboxylate (0.071 g, 0.4 mmol) and the resulting reaction mixture stirred at room temperature for 2 hours. The solvent was removed in vacuo and the crude tert-butyl 4-(4-(4,4,5,5-tetramethyl-1,3,2-dioxaborolan-2-yl)benzyl)piperazine-1-carboxylate obtained was used without further purification. LCMS (1) Rt: 2.56 min; m/z (ES+) 403.

Example F-1

2-(2,6-difluorophenyl)-5-phenyloxazole-4-carboxamide

Step a—5-amino-2-(2,6-difluorophenyl)oxazole-4-carbonitrile

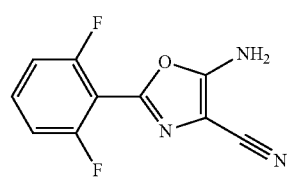 [SMILES: N#Cc1nc(-c2c(F)cccc2F)oc1N]

To a solution of aminomalononitrile p-toluenesulfonate (0.050 g, 0.2 mmol) in NMP (0.5 mL) was added 2,6-difluorobenzoyl chloride (27 ul, 0.21 mmol) and the resulting solution heated in the microwave at 120° C. for 5 minutes. The solution was diluted with EtOAc and water. The organic phase was washed with water and brine, dried over MgSO$_4$ and the solvent removed in vacuo to afford 5-amino-2-(2,6-difluorophenyl)oxazole-4-carbonitrile (0.030 g, 0.14 mmol, 69%) as an off-white solid. $^1$H NMR (DMSO) δ 7.30 (2H, t), 7.61 (1H, m), 8.14 (2H, br. s). LCMS (1) Rt: 1.59 min; m/z (ES+) 222.

Step b—5-bromo-2-(2,6-difluorophenyl)oxazole-4-carbonitrile

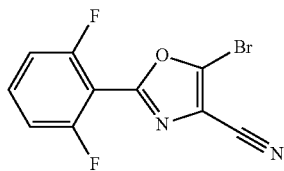 [SMILES: N#Cc1nc(-c2c(F)cccc2F)oc1Br]

To a stirred solution of copper bromide (2.02 g, 9.0 mmol) in dry acetonitrile (64 mL) under an $N_2$ atmosphere at 0° C. was added tert-butyl nitrite (0.60 mL, 5.0 mmol). 5-Amino-2-(2,6-difluorophenyl)oxazole-4-carbonitrile was then added in portions. The resulting solution was stirred at 0° C. for 30 minutes and then warmed to room temperature and stirred for a further 30 minutes. The reaction was partitioned between water and $Et_2O$. The organic layer was washed with 1M HCl and the combined aqueous phases extracted with $Et_2O$. The combined organic phases were dried over $MgSO_4$ and the solvent removed in vacuo. The residue was purified by silica gel chromatography using a gradient of 0-20% EtOAc in hexane to afford 5-bromo-2-(2,6-difluorophenyl)oxazole-4-carbonitrile (0.487 g, 1.7 mmol, 38%) as a white solid. $^1$H NMR ($CDCl_3$) δ 7.02 (2H, t), 7.47 (1H, m). LCMS (1) Rt: 2.20 min.

Step c—5-bromo-2-(2,6-difluorophenyl)oxazole-4-carboxamide

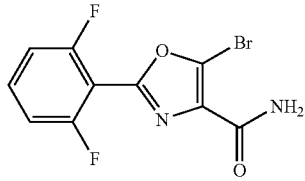 [SMILES: NC(=O)c1nc(-c2c(F)cccc2F)oc1Br]

A solution of 5-bromo-2-(2,6-difluorophenyl)oxazole-4-carbonitrile (0.010 g, 0.04 mmol) in concentrated $H_2SO_4$ (0.4 mL) was stirred at room temperature for 4 hours. The reaction was neutralised with saturated sodium bicarbonate solution and extracted with EtOAc. The organic phase was dried over $MgSO_4$ and the solvent removed in vacuo to afford 5-bromo-2-(2,6-difluorophenyl)oxazole-4-carboxamide (0.010 g, 0.03 mmol, 94%) as a white solid. $^1$H NMR ($CDCl_3$) δ 5.79 (1H, br. s), 6.95 (1H, br. s), 7.07 (2H, t), 7.49 (1H, m). LCMS (1) Rt: 1.59 min; m/z (ES+) 303/305.

Step d—2-(2,6-difluorophenyl)-5-phenyloxazole-4-carboxamide

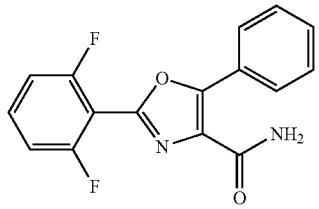 [SMILES: NC(=O)c1nc(-c2c(F)cccc2F)oc1-c1ccccc1]

A mixture of 5-bromo-2-(2,6-difluorophenyl)oxazole-4-carboxamide (0.060 g, 0.2 mmol), phenyl boronic acid (0.048 g, 0.4 mmol), Pd(dppf)$_2$Cl$_2$ (0.008 g, 0.01 mmol) and 1M sodium carbonate solution (0.395 mL, 0.4 mmol) in acetonitrile (4 mL) was heated in the microwave at 150° C. for 15 minutes. The reaction mixture was partitioned between 1M sodium hydroxide solution and EtOAc and the aqueous phase washed with EtOAc. The organic phase was passed through a MP-SH resin cartridge. (0.5 g) and the solvent removed in vacuo. The residue was purified by preparative HPLC to afford 2-(2,6-difluorophenyl)-5-phenyloxazole-4-carboxamide (0.0047 g, 0.02 mmol, 8%) as a white solid. $^1$H NMR (DMSO) δ 7.40 (2H, t,), 7.54 (3H, m), 7.75 (3H, m), 8.24 (2H, m). LCMS (2) Rt: 2.89 min; m/z (ES+) 301.

Example F-2

2-(2,6-difluorophenyl)-5-(pyridin-2-yl)oxazole-4-carboxamide

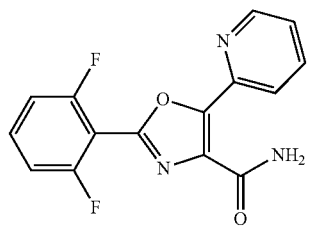 [SMILES: NC(=O)c1nc(-c2c(F)cccc2F)oc1-c1ccccn1]

A mixture of 5-bromo-2-(2,6-difluorophenyl)oxazole-4-carbonitrile (0.050 g, 0.16 mmol), tri-n-butyl(2-pyridyl)tin (0.120 g, 0.32 mmol) and tetrakis(triphenylphosphine)palladium(0) (0.010 g, 0.008 mmol) in acetonitrile (2.5 mL) was heated in the microwave for 15 minutes at 150° C. The reaction was diluted with MeOH and passed through a MP-SH resin cartridge (0.5 g), then purified by SPE using a MP-TsOH resin (500 mg) cartridge and the solvent removed in vacuo. The residue was purified by preparative HPLC to afford 2-(2,6-difluorophenyl)-5-(pyridin-2-yl)oxazole-4-carboxamide (0.029 g, 0.10 mmol, 58%) as a white solid. $^1$H NMR (DMSO) δ 7.41 (2H, t), 7.55 (1H, ddd), 7.76 (1H, m), 7.88 (1H, br. s), 8.06 (1H, ddd), 8.32 (1H, dt), 8.77 (1H, ddd), 9.10 (1H, br. s). LCMS (2) Rt: 2.23 min; m/z (ES+) 302.

In a similar manner as described in example F-1 the compounds described in examples F-3 to F-37 were prepared.

Example F-3

2-(2,6-difluorophenyl)-5-(4-(dimethylamino)phenyl)oxazole-4-carboxamide

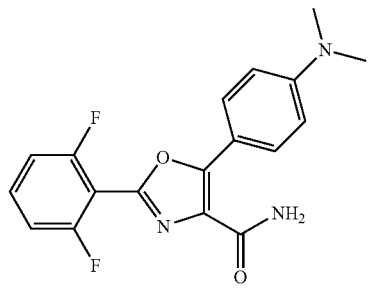 [SMILES: CN(C)c1ccc(-c2oc(-c3c(F)cccc3F)nc2C(N)=O)cc1]

¹H NMR (DMSO) δ 3.01 (6H, s), 6.81 (2H, d), 7.38 (2H, t), 7.57 (1H, br. s), 7.58 (1H, br, s), 7.71 (1H, m), 8.16 (2H, d). LCMS (2) Rt: 3.16 min; m/z (ES+) 344.

Example F-4

2-(2,6-difluorophenyl)-5-(4-morpholinophenyl)oxazole-4-carboxamide

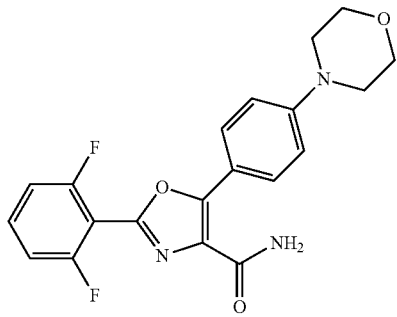 [SMILES: NC(=O)c1nc(-c2c(F)cccc2F)oc1-c1ccc(N2CCOCC2)cc1]

¹H NMR (DMSO) δ 3.28 (4H, m), 3.76 (4H, m), 7.07 (2H, d), 7.38 (2H, t), 7.63 (1H, br. s), 7.64 (1H, br. s), 7.72 (1H, m), 8.17 (2H, d). LCMS (2) Rt: 2.90 min; m/z (ES+) 386.

Example F-5

2-(2,6-difluorophenyl)-5-(thiophen-3-yl)oxazole-4-carboxamide

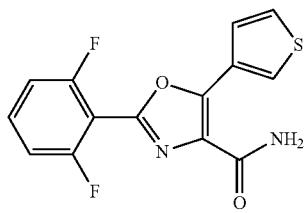 [SMILES: NC(=O)c1nc(-c2c(F)cccc2F)oc1-c1ccsc1]

¹H NMR (DMSO) δ 7.40 (2H, t), 7.73 (4H, m), 7.87 (1H, dd), 8.68 (1H, dd). LCMS (2) Rt: 2.90 min; m/z (ES+) 307.

Example F-6

2-(2,6-difluorophenyl)-5-(4-(methylsulfonyl)phenyl)oxazole-4-carboxamide

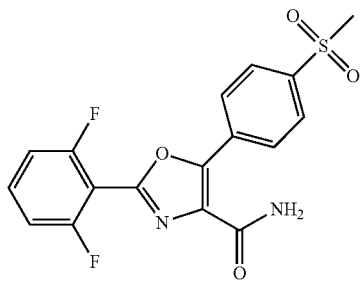 [SMILES: CS(=O)(=O)c1ccc(-c2oc(-c3c(F)cccc3F)nc2C(N)=O)cc1]

¹H NMR (DMSO) δ 3.30 (3H, s), 7.42 (2H, t), 7.77 (1H, m), 7.90 (2H, br. s), 8.09 (2H, d), 8.48 (2H, d). LCMS (2) Rt: 2.46 min; m/z (ES+) 379.

Example F-7

2-(2,6-difluorophenyl)-5-(6-(dimethylamino)pyridin-3-yl)oxazole-4-carboxamide

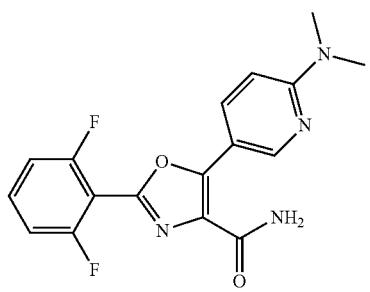 [SMILES: CN(C)c1ccc(-c2oc(-c3c(F)cccc3F)nc2C(N)=O)cn1]

¹H NMR (DMSO) δ 3.11 (6H, s), 6.77 (1H, d), 7.38 (2H, t), 7.62 (1H, br. s), 7.65 (1H, br. s), 7.71 (1H, m), 8.34 (1H, dd), 8.95 (1H, dd). LCMS (2) Rt: 2.37 min; m/z (ES+) 345.

Example F-8

2-(2,6-difluorophenyl)-5-(pyridin-4-yl)oxazole-4-carboxamide

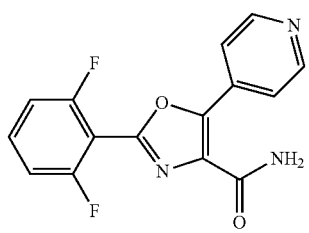 [SMILES: NC(=O)c1nc(-c2c(F)cccc2F)oc1-c1ccncc1]

¹H NMR (DMSO) δ 7.42 (2H, t), 7.77 (1H, m), 7.92 (1H, br. s), 7.94 (1H, br. s), 8.21 (2H, dd), 8.76 (2H, dd). LCMS (2) Rt: 2.18 min; m/z (ES+) 302.

Example F-9

2-(2,6-difluorophenyl)-5-(pyridin-3-yl)oxazole-4-carboxamideH

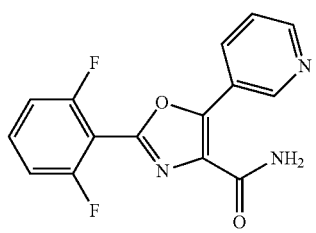 [SMILES: NC(=O)c1nc(-c2c(F)cccc2F)oc1-c1cccnc1]

¹H NMR (DMSO) δ 7.41 (2H, t), 7.59 (1H, ddd), 7.76 (1H, m), 7.85 (2H, br. s), 8.60 (1H, ddd), 8.67 (1H, dd), 9.32 (1H, dd). LCMS (2) Rt: 2.18 min; m/z (ES+) 302.

Example F-10

2-(2,6-difluorophenyl)-5-(4-((4-methylpiperazin-1-yl)methyl)phenyl)oxazole-4-carboxamide

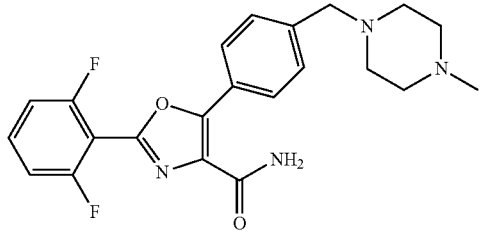 [SMILES: CN1CCN(Cc2ccc(-c3oc(-c4c(F)cccc4F)nc3C(N)=O)cc2)CC1]

The title compound was prepared using 4-((4-methylpiperazin-1-yl)methyl)phenylboronic acid synthesised as described above. ¹H NMR (DMSO) δ 2.15 (3H, s), 2.35 (8H, m), 3.52 (2H, s), 7.40 (2H, t), 7.45 (2H, d), 7.74 (3H, m), 8.18 (2H, d). LCMS (2) Rt: 2.58 min; m/z (ES+) 413.

Example F-11

5-(4-((4-acetylpiperazin-1-yl)methyl)phenyl)-2-(2,6-difluorophenyl)oxazole-4-carboxamide

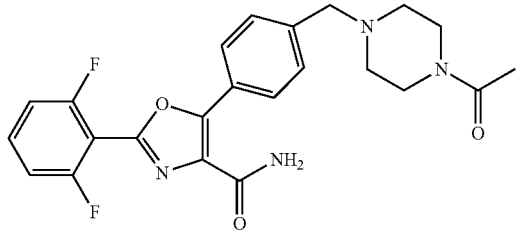 [SMILES: CC(=O)N1CCN(Cc2ccc(-c3oc(-c4c(F)cccc4F)nc3C(N)=O)cc2)CC1]

The title compound was prepared using 4-((4-acetylpiperazin-1-yl)methyl)phenylboronic acid synthesised as described above. ¹H NMR (DMSO) δ 1.91 (3H, s), 2.33 (2H, m), 2.40 (2H, m), 3.44 (4H, m), 3.57 (2H, s), 7.40 (2H, t), 7.48 (2H, d), 7.74 (3H, m), 8.20 (2H, d). LCMS (2) Rt: 2.44 min; m/z (ES+) 441.

Example F-12

2-(2,6-difluorophenyl)-5-(4-((2-morpholinoethoxy)methyl)phenyl)oxazole-4-carboxamide

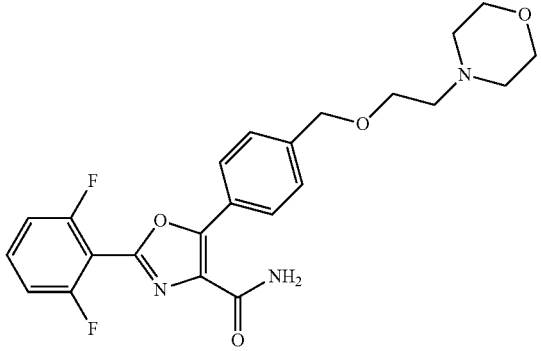 [SMILES: NC(=O)c1nc(-c2c(F)cccc2F)oc1-c1ccc(COCCN2CCOCC2)cc1]

The title compound, prepared using 4-((2-morpholinoethoxy)methyl)phenylboronic acid synthesised as described above, was isolated as the formate salt. ¹H NMR (DMSO) δ 3.53 (6H, m), 4.03 (6H, m), 4.89 (2H, s), 7.42 (2H, t), 7.75 (3H, m), 7.86 (2H, s), 8.38 (2H, d), 8.50 (1H, s). LCMS (2) Rt: 2.46 min; m/z (ES+) 443.

Example F-13

2-(2,6-difluorophenyl)-5-(4-(2-morpholinoethoxy)phenyl)oxazole-4-carboxamide

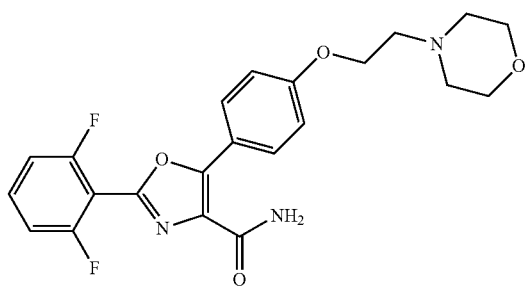 [SMILES: NC(=O)c1nc(-c2c(F)cccc2F)oc1-c1ccc(OCCN2CCOCC2)cc1]

The title compound was prepared using 4-(2-morpholinoethoxy)phenylboronic acid synthesised as described above. ¹H NMR (DMSO) δ 2.48 (4H, t), 2.72 (2H, t), 3.58 (4H, t), 4.17 (2H, t), 7.10 (2H, d), 7.39 (2H, t), 7.68 (1H, br. s), 7.69 (1H, br. s), 7.72 (1H, m 8.22 (2H, d). LCMS (2) Rt: 2.69 min; m/z (ES+) 430.

Example F-14

2-(2,6-difluorophenyl)-5-(4-(2-(piperidin-1-yl)ethoxy)phenyl)oxazole-4-carboxamide

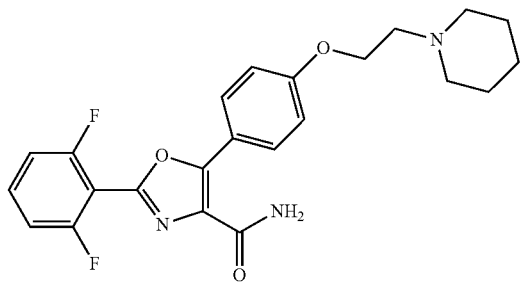 [SMILES: NC(=O)c1nc(-c2c(F)cccc2F)oc1-c1ccc(OCCN2CCCCC2)cc1]

The title compound was prepared using 4-(2-(piperidin-1-yl)ethoxy)phenylboronic acid synthesised as described above. ¹H NMR (DMSO) δ 1.39 (2H, m), 1.76 (4H, m), 2.45 (4H, m), 2.68 (2H, m), 4.15 (2H, t), 7.10 (2H, d), 7.39 (2H, t), 7.68 (1H, br. s), 7.69 (1H, br, s), 7.73 (1H, m), 8.22 (2H, d) ᴴH. LCMS (2) Rt: 3.38 min; m/z (ES+) 428.

Example F-15

2-(2,6-difluorophenyl)-5-(4-(2-(dimethylamino)ethoxy)phenyl)oxazole-4-carboxamide

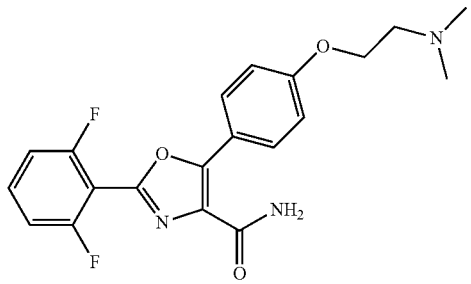 [SMILES: CN(C)CCOc1ccc(-c2oc(-c3c(F)cccc3F)nc2C(N)=O)cc1]

The title compound was prepared using 4-(2-(dimethylamino)ethoxy)phenylboronic acid synthesised as described above. ¹H NMR (DMSO) δ 2.22 (6H, s), 2.64 (2H, t), 4.13 (2H, t), 7.10 (2H, d), 7.39 (2H, t), 7.68 (1H, br. s), 7.69 (1H, br. s), 7.72 (1H, m), 8.22 (2H, d). LCMS (2) Rt: 2.86 min; m/z (ES+) 388.

Example F-16

5-(4-(aminomethyl)phenyl)-2-(2,6-difluorophenyl)oxazole-4-carboxamide

Step a—tert-butyl 4-(4-carbamoyl-2-(2,6-difluorophenyl)oxazol-5-yl)benzylcarbamate

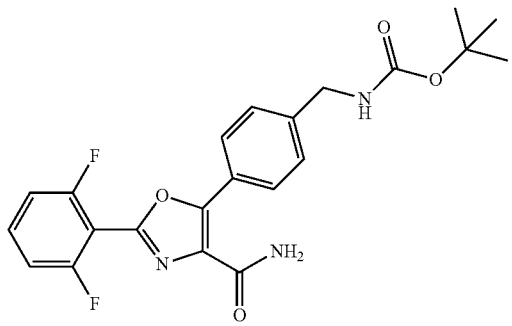 [SMILES: CC(C)(C)OC(=O)NCc1ccc(-c2oc(-c3c(F)cccc3F)nc2C(N)=O)cc1]

¹H NMR (DMSO) δ 1.41 (9H, s), 4.19 (2H, d), 7.38 (2H, d), 7.40 (2H, t), 7.51 (1H, t), 7.74 (3H, m), 8.17 (2H, d). LCMS (2) Rt: 3.14 min; m/z (ES+) 430.

Step b—5-(4-(aminomethyl)phenyl)-2-(2,6-difluorophenyl)oxazole-4-carboxamide

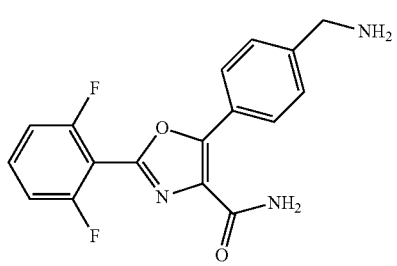 [SMILES: NCc1ccc(-c2oc(-c3c(F)cccc3F)nc2C(N)=O)cc1]

To a solution of tert-butyl 4-(4-carbamoyl-2-(2,6-difluorophenyl)oxazol-5-yl)benzylcarbamate (0.110 g, 0.26 mmol) in DCM (10 mL) was added 4M HCl in dioxane (1.5 mL, 6.0 mmol) and the resulting mixture stirred at room temperature overnight. The solvent was then removed in vacuo. The residue was purified by preparative HPLC to afford 5-(4-(aminomethyl)phenyl)-2-(2,6-difluorophenyl)oxazole-4-carboxamide (0.0366 g, 0.11 mmol, 43%) as a white solid as the formate salt. ¹H NMR (DMSO) δ 3.95 (2H, s), 7.40 (2H, t), 7.55 (2H, d), 7.74 (3H, m), 8.21 (2H, d), 8.33 (1H, s). LCMS (2) Rt: 2.30 min; m/z (ES+) 330.

Example F-17

5-(4-carbamoylphenyl)-2-(2,6-difluorophenyl)oxazole-4-carboxamide

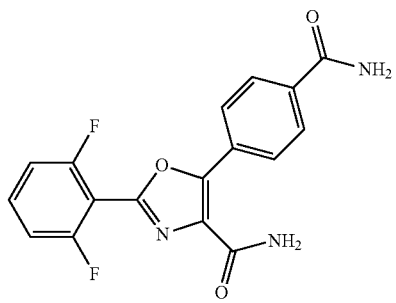 [SMILES: NC(=O)c1ccc(-c2oc(-c3c(F)cccc3F)nc2C(N)=O)cc1]

¹H NMR (DMSO) δ 7.41 (2H, t), 7.53 (1H, br. s), 7.75 (1H, m), 7.81 (2H, br. s), 8.01 (2H, d), 8.12 (1H, br. s), 8.32 (2H, d). LCMS (2) Rt: 2.08 min; m/z (ES+) 344.

Example F-18

2-(2,6-difluorophenyl)-5-(6-methoxypyridin-3-yl)oxazole-4-carboxamide

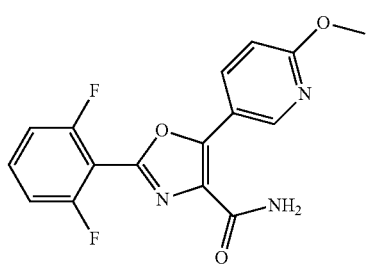 [SMILES: COc1ccc(-c2oc(-c3c(F)cccc3F)nc2C(N)=O)cn1]

¹H NMR (DMSO) δ 3.94 (3H, s), 7.01 (1H, d), 7.40 (2H, t), 7.70-7.80 (3H, m), 8.51 (1H, dd), 9.01 (1H, dd). LCMS (2) Rt: 2.74 min; m/z (ES+) 332.

Example F-19

2-(2,6-difluorophenyl)-5-(6-morpholinopyridin-3-yl)oxazole-4-carboxamide

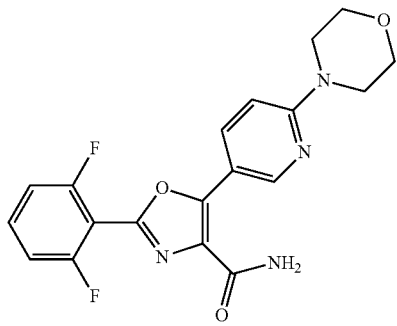 [SMILES: NC(=O)c1nc(-c2c(F)cccc2F)oc1-c1ccc(N2CCOCC2)nc1]

¹H NMR (DMSO) δ 3.60 (4H, m), 3.71 (4H, m), 6.98 (1H, d), 7.39 (2H, t), 7.66 (1H, br. s), 7.68 (1H, br. s), 7.72 (1H, m), 8.39 (1H, dd), 8.97 (1H, d). LCMS (2) Rt: 2.64 min; m/z (ES+) 387.

Example F-20

2-(2,6-difluorophenyl)-5-(4-(morpholinomethyl)phenyl)oxazole-4-carboxamide

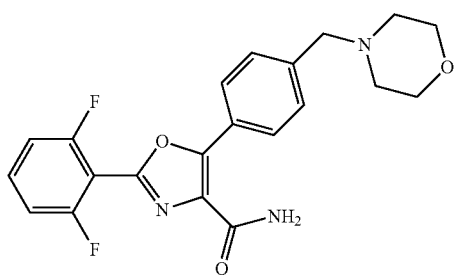 [SMILES: NC(=O)c1nc(-c2c(F)cccc2F)oc1-c1ccc(CN2CCOCC2)cc1]

¹H NMR (DMSO) δ 2.38 (4H, br. t), 3.53 (2H, s), 3.59 (4H, t), 7.40 (2H, t), 7.47 (2H, d), 7.74 (3H, m), 8.19 (2H, d). LCMS (2) Rt: 2.67 min; m/z (ES+) 400.

Example F-21

5-(4-benzenesulfonamide)-2-(2,6-difluorophenyl)oxazole-4-carboxamide

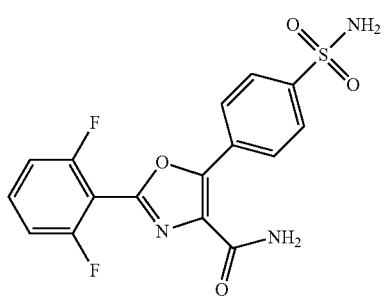 [SMILES: NC(=O)c1nc(-c2c(F)cccc2F)oc1-c1ccc(S(N)(=O)=O)cc1]

¹H NMR (DMSO) δ 7.41 (2H, t), 7.52 (2H, s), 7.76 (1H, m), 7.84 (2H, br. s), 7.96 (2H, d), 8.40 (2H, d). LCMS (2) Rt: 2.25 min; m/z (ES+) 380.

Example F-22

5-(4-aminophenyl)-2-(2,6-difluorophenyl)oxazole-4-carboxamide

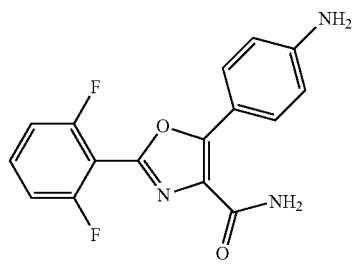 [SMILES: NC(=O)c1nc(-c2c(F)cccc2F)oc1-c1ccc(N)cc1]

¹H NMR (DMSO) δ 5.78 (2H, br. s), 6.64 (2H, d), 7.37 (2H, t), 7.54 (2H, br. s), 7.70 (1H, m), 8.01 (2H, d). LCMS (2) Rt: 2.36 min; m/z (ES+) 316.

Example F-23

5-(4-acetamidophenyl)-2-(2,6-difluorophenyl)oxazole-4-carboxamide

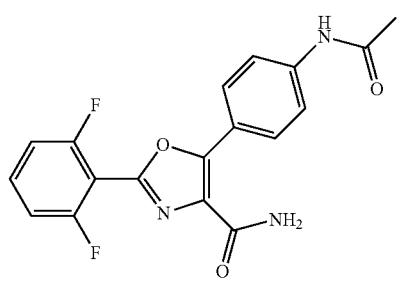 [SMILES: CC(=O)Nc1ccc(-c2oc(-c3c(F)cccc3F)nc2C(N)=O)cc1]

¹H NMR (DMSO) δ 2.09 (3H, s), 7.39 (2H, t), 7.70-7.74 (5H, m), 8.21 (2H, d), 10.24 (1H, br. s). LCMS (2) Rt: 2.28 min; m/z (ES+) 358.

Example F-24

2-(2-chloro-6-fluorophenyl)-5-(4-(2-(piperidin-1-yl)ethoxy)phenyl)oxazole-4-carboxamide

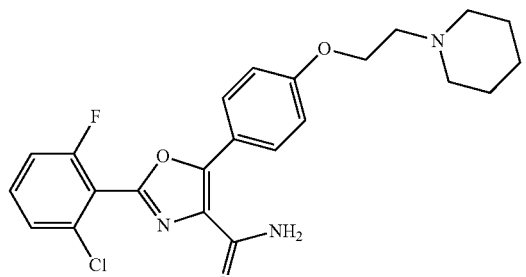

The title compound was prepared using 4-(2-(piperidin-1-yl)ethoxy)phenylboronic acid synthesised as described above. After purification by preparative HPLC the compound was purified by SPE using a MP-TsOH (500 mg) cartridge. ¹H NMR (DMSO) δ 1.38 (2H, m), 1.50 (4H, quin), 2.44 (4H, br. t), 2.68 (2H, t), 4.15 (2H, t), 7.09 (2H, d), 7.52 (1H, ddd), 7.61 (1H, d), 7.64 (1H, br. s), 7.70-7.76 (2H, m), 8.22 (2H, d). LCMS (2) Rt: 3.45 min; m/z (ES+) 444/446.

Example F-25

2-(2,6-dichlorophenyl)-5-(4-(2-(piperidin-1-yl)ethoxy)phenyl)oxazole-4-carboxamide

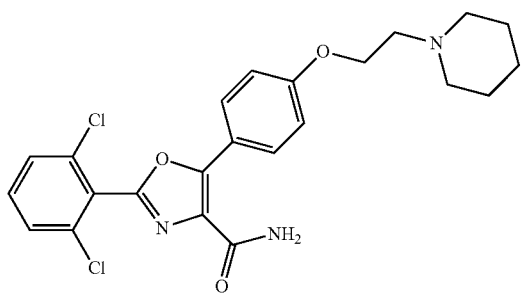 [SMILES: NC(=O)c1nc(-c2c(Cl)cccc2Cl)oc1-c1ccc(OCCN2CCCCC2)cc1]

The title compound was prepared using 4-(2-(piperidin-1-yl)ethoxy)phenylboronic acid synthesised as described above. After purification by preparative HPLC the compound was purified by SPE using a MP-TsOH (500 mg) cartridge. $^1$H NMR (DMSO) δ 1.39 (2H, m), 1.50 (4H, quin), 2.44 (4H, br. t), 2.67 (2H, t), 4.15 (2H, t), 7.08 (2H, d), 7.63 (1H, br. s), 7.68-7.76 (3H, m), 7.78 (1H, br. s), 8.21 (2H, d). LCMS (2) Rt: 3.60 min; m/z 460/462/464.

Example F-26

2-(2-fluorophenyl)-5-(4-(2-(piperidin-1-yl)ethoxy)phenyl)oxazole-4-carboxamide

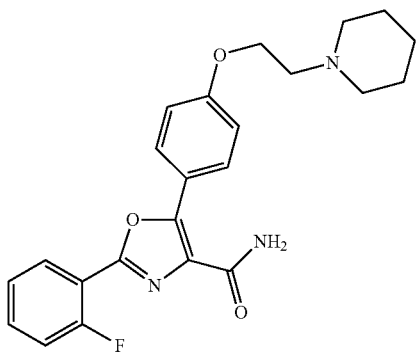 [SMILES: NC(=O)c1nc(-c2ccccc2F)oc1-c1ccc(OCCN2CCCCC2)cc1]

The title compound was prepared using 4-(2-(piperidin-1-yl)ethoxy)phenylboronic acid synthesised as described above. $^1$H NMR (DMSO) δ 1.36-1.42 (2H, m), 1.51 (4H, quin), 2.47 (4H, br s), 2.70 (2H, t), 4.16 (2H, t), 7.10 (2H, d), 7.41-7.49 (2H, m), 7.62-7.68 (2H, m), 7.71 (1H, br s), 8.17 (1H, ddd), 8.30 (2H, d). LCMS (2) Rt: 3.31 min; m/z 410.

Example F-27

2-(2-fluorophenyl)-5-(4-(2-morpholinoethoxy)phenyl)oxazole-4-carboxamide

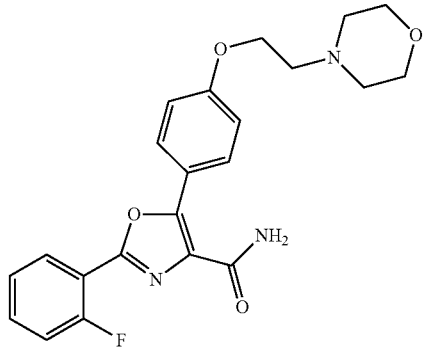 [SMILES: NC(=O)c1nc(-c2ccccc2F)oc1-c1ccc(OCCN2CCOCC2)cc1]

$^1$H NMR (DMSO) δ 2.49 (4H, m), 2.73 (2H, t), 3.59 (4H, t), 4.18 (2H, t), 7.11 (2H, d), 7.41-7.49 (2H, m), 7.43 (1H, ddd), 7.47 (1H, ddd), 7.62-7.68 (2H, m), 7.72 (1H, br s), 8.18 (1H, ddd), 8.30 (2H, d). LCMS (2) Rt: 2.67 min; m/z 412.

Example F-28

2-(2,6-difluorophenyl)-5-(3,4-dimethoxyphenyl)oxazole-4-carboxamide

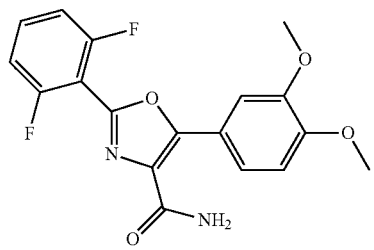 [SMILES: COc1ccc(-c2oc(-c3c(F)cccc3F)nc2C(N)=O)cc1OC]

$^1$H NMR (CDCl$_3$) δ 3.95 (3H, s), 4.00 (3H, s), 5.53 (1H, br s), 6.67 (1H, d), 7.08 (2H, t), 7.26 (1H, br s), 7.47 (1H, tt), 7.92 (1H, dd), 8.35 (1H, d). LCMS (2) Rt: 2.68 min; m/z (ES+) 361.

Example F-29

5-(benzo[d][1,3]dioxol-5-yl)-2-(2,6-difluorophenyl)oxazole-4-carboxamide

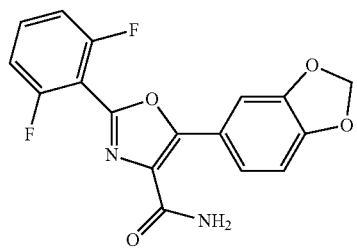 [SMILES: NC(=O)c1nc(-c2c(F)cccc2F)oc1-c1ccc2c(c1)OCO2]

¹H NMR (CDCl₃) δ 5.53 (1H, br s), 6.03 (2H, s), 6.92 (1H, d), 7.08 (2H, t), 7.22 (1H, br s), 7.47 (1H, quin), 7.96 (1H, s), 8.01 (1H, d). LCMS (2) Rt: 2.84 min; m/z (ES+) 345.

Example F-30

2-(2,6-Difluorophenyl)-5-(3-(morpholine-4-carbonyl)phenyl)oxazole-4-carboxamide

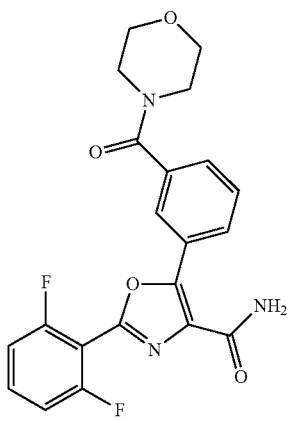 [SMILES: NC(=O)c1nc(-c2c(F)cccc2F)oc1-c1cccc(C(=O)N2CCOCC2)c1]

¹H NMR (DMSO) δ 3.41 (2H, br s), 3.64 (6H, br m), 7.40 (2H, t), 7.53-7.56 (1H, m), 7.63 (1H, t), 7.71-7.79 (3H, m), 8.24-8.26 (1H, m), 8.33 (1H, t). LCMS (2) Rt: 2.27 min; m/z (ES+) 414.

Example F-31

2-(2,6-Difluorophenyl)-5-(3-(piperidine-1-carbonyl)phenyl)oxazole-4-carboxamide

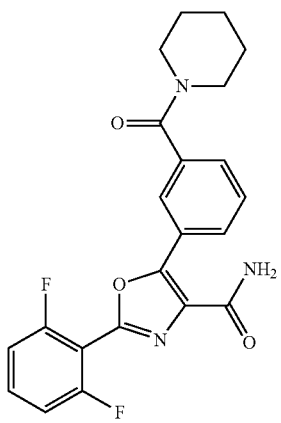 [SMILES: NC(=O)c1nc(-c2c(F)cccc2F)oc1-c1cccc(C(=O)N2CCCCC2)c1]

¹H NMR (DMSO) δ 1.50-1.63 (6H, br m), 3.32 (2H, br m), 3.61 (2H, br m), 7.41 (2H, t), 7.50-7.51 (1H, m), 7.62 (1H, t), 7.71-7.80 (3H, m), 8.23-8.27 (1H, m), 8.31 (1H, s). LCMS (2) Rt: 2.71 min; m/z (ES+) 412.

Example F-32

2-(2,6-difluorophenyl)-5-(4-(2-(piperidin-1-yl)ethylamino)phenyl)oxazole-4-carboxamide Step a—N-(2-(piperidin-1-yl)ethyl)-4-(4,4,5,5-tetramethyl-1,3,2-dioxaborolan-2-yl)benzenamine

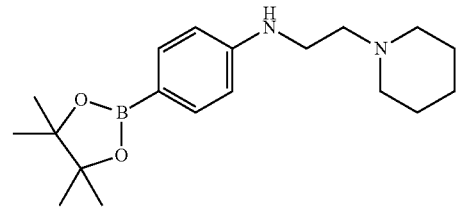 [SMILES: CC1(C)OB(c2ccc(NCCN3CCCCC3)cc2)OC1(C)C]

N-(2-(piperidin-1-yl)ethyl)-4-(4,4,5,5-tetramethyl-1,3,2-dioxaborolan-2-yl)benzenamine was prepared by heating 4-(4,4,5,5-tetramethyl-1,3,2-dioxaborolan-2-yl)benzenamine (0.219 g, 1 mmol), potassium iodide (0.006 g, 0.03 mmol), potassium carbonate (0.060 g, 0.4 mmol) and 1-(2-chloroethyl)-piperidine (0.050 g, 0.3 mmol) in MeCN (2 ml) to 110° C. by microwave irradiation for 10 minutes. The crude reaction was purified by preparative HPLC to give the product as a white solid (0.009 g, 0.027 mmol). LCMS (3) 2.50 min; m/z (ES+) 331.

Step b—2-(2,6-difluorophenyl)-5-(4-(2-(piperidin-1-yl)ethylamino)phenyl)oxazole-4-carboxamide

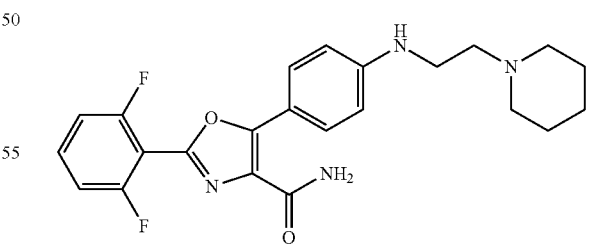

The title compound was prepared from N-(2-(piperidin-1-yl)ethyl)-4-(4,4,5,5-tetramethyl-1,3,2-dioxaborolan-2-yl)benzenamine synthesised as described in Step a above. ¹H NMR (DMSO) δ 1.35-1.45 (2H, m), 1.49-1.58 (4H, m), 2.35-2.45 (4H, m), 2.45-2.55 (2H, m), 3.21 (2H, q), 6.15 (1H, t), 6.70 (2H, d), 7.39 (2H, t), 7.55 (2H, br. s), 7.65-7.75 (1H, m), 8.08 (2H, d). LCMS (2) 3.19 min; m/z (ES+) 427.

Example F-33

2-(2,6-difluorophenyl)-5-(4-(2-(dimethylamino)ethylamino)phenyl)oxazole-4-carboxamide Step a—N-(2-(dimethylamino)ethyl)-4-(4,4,5,5-tetramethyl-1,3,2-dioxaborolan-2-yl)benzenamine

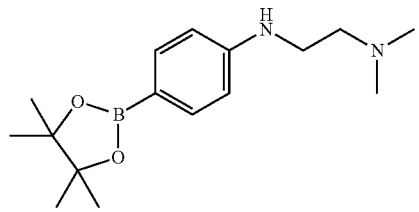

N-(2-(dimethylamino)ethyl)-4-(4,4,5,5-tetramethyl-1,3,2-dioxaborolan-2-yl)benzenamine was prepared by heating 4-(4,4,5,5-tetramethyl-1,3,2-dioxaborolan-2-yl)benzenamine (0.219 g, 1 mmol), potassium iodide (0.006 g, 0.03 mmol), potassium carbonate (0.060 g, 0.4 mmol) and 2-dimethylaminoethyl chloride hydrochloride (0.043 g, 0.3 mmol) in MeCN (2 ml) to 110° C. by microwave irradiation for 10 minutes. The crude reaction was purified by preparative HPLC to give the desired compound as a white solid, (0.025 g, 0.086 mmol). LCMS (3) 2.12 min; m/z (ES+) 291

Step b—2-(2,6-difluorophenyl)-5-(4-(2-(dimethylamino)ethylamino)phenyl)oxazole-4-carboxamide

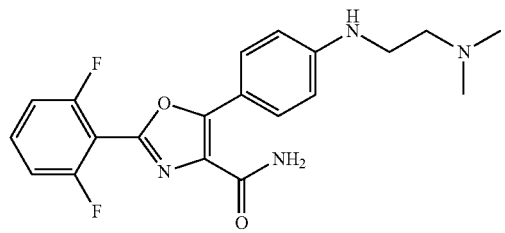 [SMILES: CN(C)CCNc1ccc(-c2oc(-c3c(F)cccc3F)nc2C(N)=O)cc1]

Prepared from N-(2-(dimethylamino)ethyl)-4-(4,4,5,5-tetramethyl-1,3,2-dioxaborolan-2-yl)benzenamine synthesised as described in Step a above. $^1$H NMR (DMSO) δ 2.20 (6H, s), 2.48 (2H, t), 3.19 (2H, q), 6.15 (1H, t), 6.70 (2H, d), 7.39 (2H, t), 7.55 (2H, br. s), 7.65-7.75 (1H, m), 8.08 (2H, d). LCMS (2) 2.65 min; m/z (ES+) 387.

Example F-34

2-(2,6-difluorophenyl)-5-(4-(2-morpholinoethylamino)phenyl)oxazole-4-carboxamide Step a: N-(2-morpholinoethyl)-4-(4,4,5,5-tetramethyl-1,3,2-dioxaborolan-2-yl)benzenamine

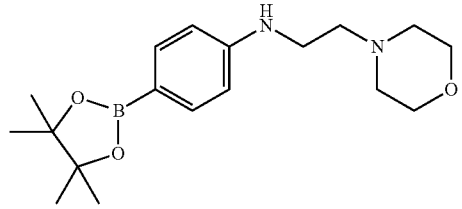 [SMILES: CC1(C)OB(c2ccc(NCCN3CCOCC3)cc2)OC1(C)C]

N-(2-morpholinoethyl)-4-(4,4,5,5-tetramethyl-1,3,2-dioxaborolan-2-yl)benzenamine was prepared by heating 4-(4,4,5,5-tetramethyl-1,3,2-dioxaborolan-2-yl)benzenamine (0.219 g, 1 mmol), potassium iodide (0.006 g, 0.03 mmol), potassium carbonate (0.060 g, 0.4 mmol) and 2-N-(2-chloroethyl)morpholine hydrochloride (0.056 g, 0.3 mmol) in MeCN (2 ml) to 110° C. by microwave irradiation for 10 minutes. The crude reaction was purified by preparative HPLC to give the desired compound as an off-white solid (0.030 g, 0.090 mmol). LCMS (3) 1.91 min; m/z (ES+) 333

Step b: 2-(2,6-difluorophenyl)-5-(4-(2-morpholinoethylamino)phenyl)oxazole-4-carboxamide

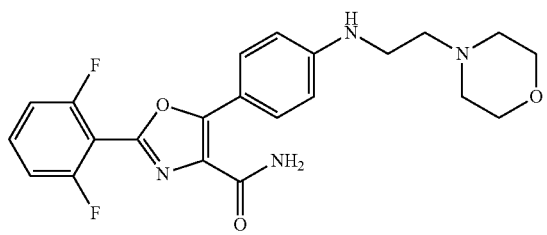 [SMILES: NC(=O)c1nc(-c2c(F)cccc2F)oc1-c1ccc(NCCN2CCOCC2)cc1]

Prepared from N-(2-morpholinoethyl)-4-(4,4,5,5-tetramethyl-1,3,2-dioxaborolan-2-yl)benzenamine synthesised as described in Step a above. $^1$H NMR (DMSO) δ 2.4-2.5 (4H, m), 2.52 (2H, t), 3.21 (2H, q), 3.6 (4H, t), 6.15 (1H, t), 6.70 (2H, d), 7.39 (2H, t), 7.55 (2H, br. s), 7.65-7.75 (1H, m), 8.08 (2H, d). LCMS (2) 2.57 min; m/z (ES+) 429.

Example F-35

2-(2,6-difluorophenyl)-5-(naphthalen-1-yl)oxazole-4-carboxamide

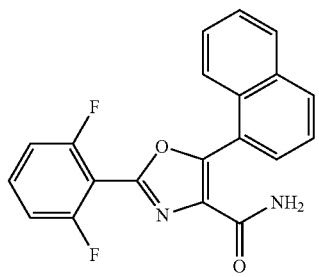 [SMILES: NC(=O)c1nc(-c2c(F)cccc2F)oc1-c1cccc2ccccc12]

$^1$H NMR (DMSO) δ 7.34-7.40 (2H, m), 7.48 (1H, br s), 7.56 (1H, br s), 7.58-7.62 (2H, m), 7.63-7.68 (1H, m), 7.69-7.77 (1H, m), 7.82-7.86 (1H, m), 7.87-7.91 (1H, m), 8.04-8.08 (1H, m), 8.12-8.16 (1H, m). LCMS (2) 2.97 min; m/z (ES+) 351.

97
Example F-36
2-(2,6-difluorophenyl)-5-(1H-indol-4-yl)oxazole-4-carboxamide
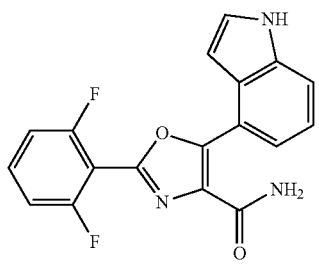 [SMILES: NC(=O)c1nc(-c2c(F)cccc2F)oc1-c1cccc2[nH]ccc12]
$^1$H NMR (DMSO) δ 6.82 (1H, s), 7.42 (1H, t), 7.35-7.42 (2H, m), 7.48-7.59 (4H, m), 7.70-7.80 (1H, m), 8.19 (1H, d), 11.32 (1H, br. s). LCMS (2) 2.49 min; m/z (ES+) 340.
98
Example F-37
2-(2,6-difluorophenyl)-5-(quinolin-8-yl)oxazole-4-carboxamide
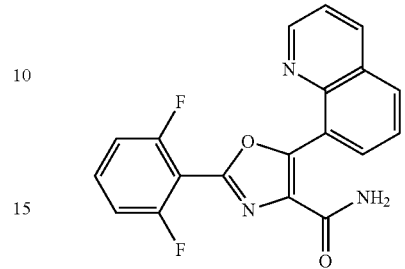
$^1$H NMR (DMSO) δ 7.33-7.40 (3H, m), 7.47 (1H, br. s), 7.61 (1H, dd), 7.68-7.78 (2H, m), 8.06 (1H, dd), 8.19 (1H, dd), 8.48 (1H, dd), 8.90 (1H, dd). LCMS (2) 2.35 min; m/z (ES+) 352.
General Methods G-J
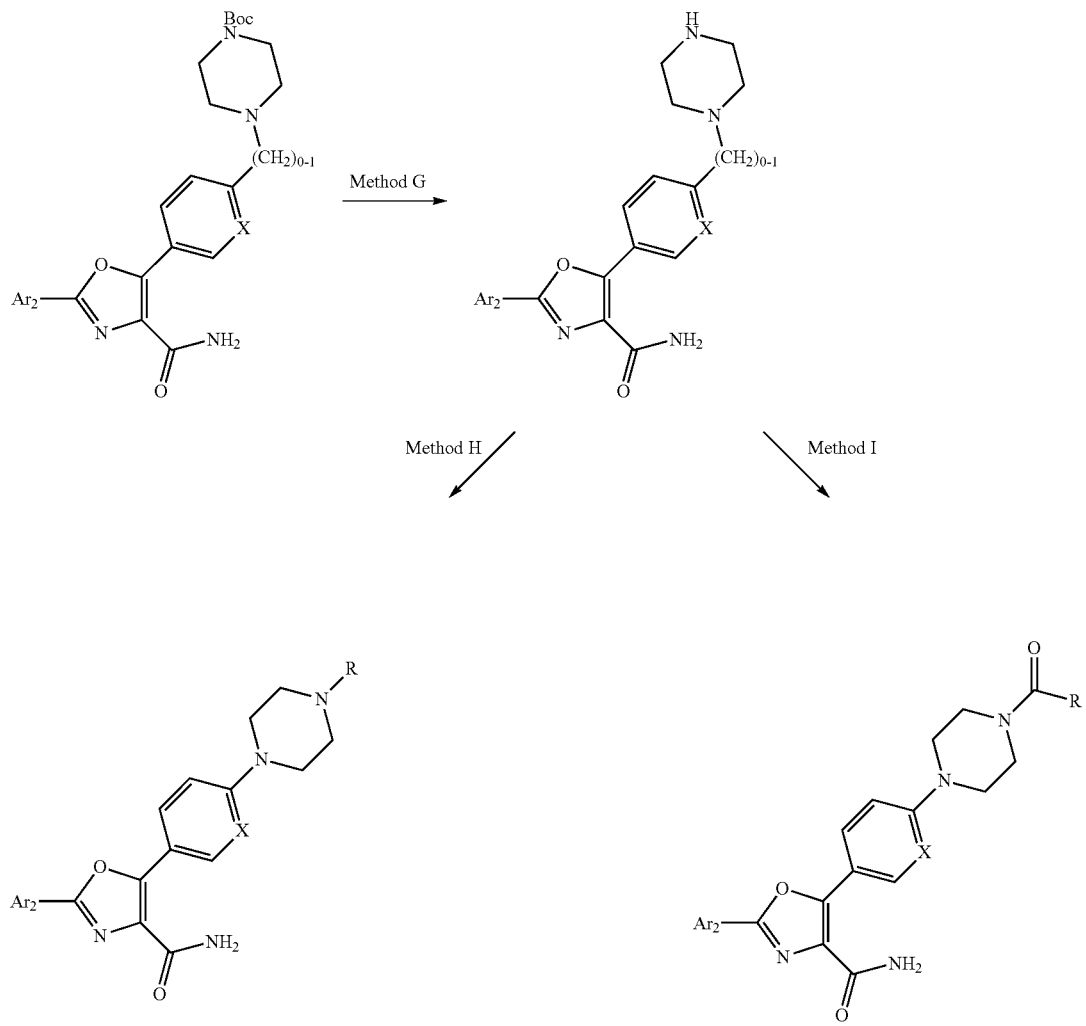

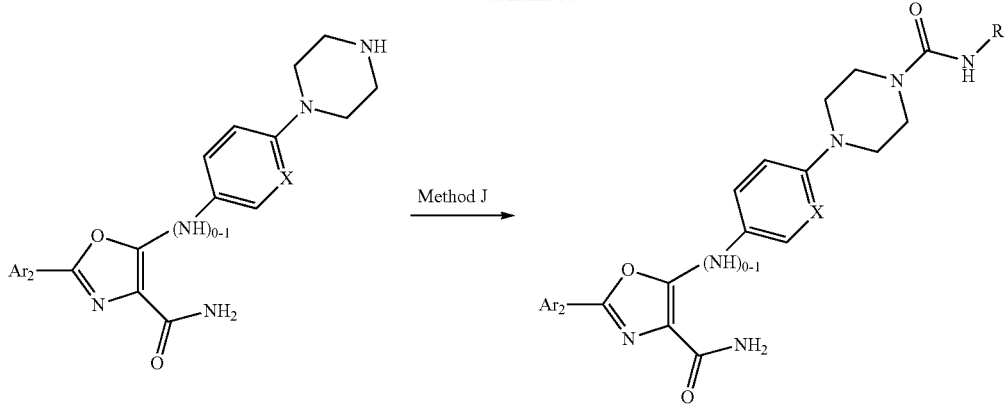

Example G-1

2-(2,6-difluorophenyl)-5-(4-(piperazin-1-ylmethyl)phenyl)oxazole-4-carboxamide Step a—tert-butyl 4-(4-(4-carbamoyl-2-(2,6-difluorophenyl)oxazol-5-yl)benzyl)piperazine-1-carboxylate

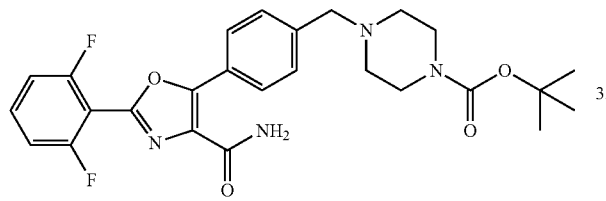

Prepared in a similar manner to the procedure outlined for the synthesis of Example F-1 using tert-butyl 4-(4-(4,4,5,5-tetramethyl-1,3,2-dioxaborolan-2-yl)benzyl)piperazine-1-carboxylate synthesised as described above. The product obtained was used without further purification. LCMS (2) Rt: 3.52 min; m/z (ES+) 499.

Step b—2-(2,6-difluorophenyl)-5-(4-(piperazin-1-ylmethyl)phenyl)oxazole-4-carboxamide

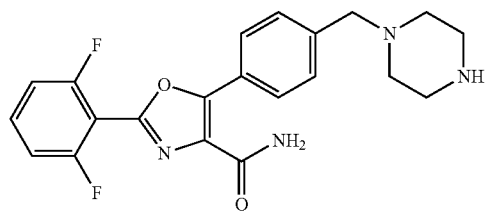 [SMILES: NC(=O)c1nc(-c2c(F)cccc2F)oc1-c1ccc(CN2CCNCC2)cc1]

To a solution of tert-butyl 4-(4-(4-carbamoyl-2-(2,6-difluorophenyl)oxazol-5-yl)benzyl)piperazine-1-carboxylate (0.100 g, 0.2 mmol) in DCM (3 mL) was added 4M HCl in dioxane (2 mL, 8.0 mmol) and the resulting mixture stirred at room temperature overnight. The solvent was removed in vacuo. The residue was purified by preparative HPLC to afford 2-(2,6-difluorophenyl)-5-(4-(piperazin-1-ylmethyl)phenyl)oxazole-4-carboxamide (0.043 g, 0.1 mmol, 50%) as a white solid as the formate salt. $^1$H NMR (DMSO) δ 2.44 (4H, m), 2.88 (4H, m), 3.55 (2H, s), 7.40 (2H, t), 7.47 (2H, d), 7.75 (3H, m), 8.19 (2H, d), 8.32 (1H, s). LCMS (2) Rt: 2.63 min; m/z (ES+) 399.

Example G-2

2-(2,6-difluorophenyl)-5-(6-(piperazin-1-yl)pyridin-3-yl)oxazole-4-carboxamide dihydrochloride Step a—tert-butyl 4-(5-(4-carbamoyl-2-(2,6-difluorophenyl)oxazol-5-yl)pyridin-2-yl)piperazine-1-carboxylate

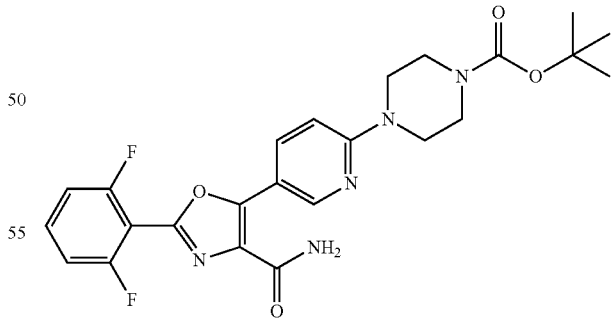

Prepared in a similar manner to the procedure outlined for the synthesis of Example F-1. The product was purified by silica gel column chromatography using a gradient of 30-75% EtOAc in hexanes. $^1$H NMR (CDCl$_3$) δ 1.49 (9H, s), 3.56 (4H, m), 3.67 (4H, m), 5.55 (1H, br. d), 6.70 (1H, d), 7.07 (2H, t), 7.18 (1H, br. d), 7.46 (1H, m), 8.69 (1H, dd), 9.01 (1H, dd). LCMS (1) Rt: 2.31 min; m/z (ES+) 486.

Step b—2-(2,6-difluorophenyl)-5-(6-(piperazin-1-yl)pyridin-3-yl)oxazole-4-carboxamide

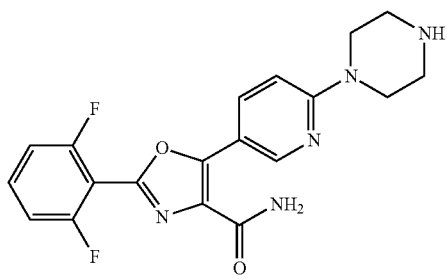 [SMILES: NC(=O)c1nc(-c2c(F)cccc2F)oc1-c1ccc(N2CCNCC2)nc1]

A mixture of tert-butyl 4-(5-(4-carbamoyl-2-(2,6-difluorophenyl)oxazol-5-yl)pyridin-2-yl)piperazine-1-carboxylate (0.227 g, 0.47 mmol) in DCM (3 mL) and 4N HCl in dioxane (2 mL, 8.0 mmol) was stirred at room temperature for 48 hours. The solvent was removed in vacuo to give 2-(2,6-difluorophenyl)-5-(6-(piperazin-1-yl)pyridin-3-yl)oxazole-4-carboxamide (0.211 g, 0.46 mmol, 98%) as a white solid as the dihydrochloride salt. $^1$H NMR (DMSO) δ 3.20 (4H, m), 3.90 (4H, t), 7.11 (1H, d), 7.39 (2H, t), 7.73 (3H, m), 8.44 (1H, dd), 9.0 (1H, d), 9.24 (1H, br. s), 9.30 (1H, br. s). LCMS (2) Rt: 2.38 min; m/z (ES+) 386.

Example G-3

2-(2,6-difluorophenyl)-5-(4-(piperazin-1-yl)phenyl)oxazole-4-carboxamide

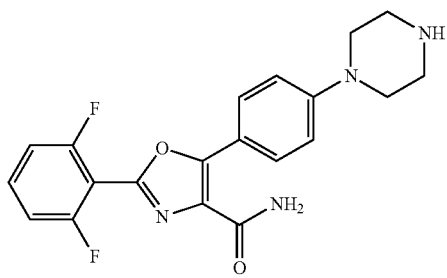 [SMILES: NC(=O)c1nc(-c2c(F)cccc2F)oc1-c1ccc(N2CCNCC2)cc1]

Prepared in a similar manner to the method described in Example G-2. The final product was suspended in saturated sodium bicarbonate solution and extracted with EtOAc and DCM. The combined organic phase was dried over MgSO$_4$ and the solvent removed in vacuo to afford 2-(2,6-difluorophenyl)-5-(4-(piperazin-1-yl)phenyl)oxazole-4-carboxamide as a yellow solid. $^1$H NMR (DMSO) δ 2.84 (4H, m), 3.20 (4H, m), 7.03 (2H, d), 7.38 (2H, t), 7.61 (1H, br. s), 7.62 (1H, br. s), 7.72 (1H, m), 8.15 (2H, d). LCMS (2) Rt: 2.60 min; m/z (ES+) 385.

Example G-4

2-(2-fluorophenyl)-5-(4-(piperazin-1-yl)phenyl)oxazole-4-carboxamide

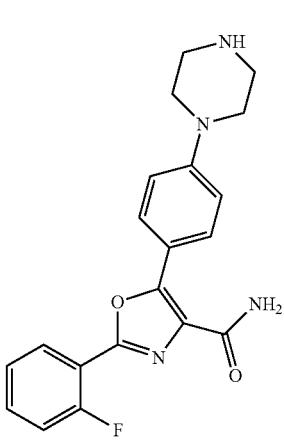 [SMILES: NC(=O)c1nc(-c2ccccc2F)oc1-c1ccc(N2CCNCC2)cc1]

Prepared according to the method described for Example G-3. $^1$H NMR (DMSO) δ 2.85 (4H, t), 3.21 (4H, t), 7.04 (2H, d), 7.40-7.50 (2H, m), 7.60-7.66 (3H, m), 8.16 (1H, m), 8.22 (2H, d). LCMS (2) Rt: 2.32 min; m/z 367.

Example G-5

2-(2-chloro-6-fluorophenyl)-5-(4-(piperazin-1-yl)phenyl)oxazole-4-carboxamide

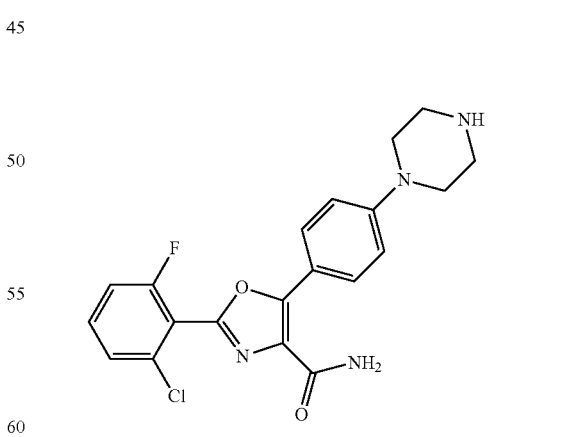

Prepared according to the method described for Example G-3. $^1$H NMR (DMSO) δ 2.84 (4H, m), 3.20 (4H, m), 7.02 (2H, d), 7.52 (1H, ddd), 7.58 (1H, br. s), 7.60 (1H, m), 7.67 (1H, br. s), 7.12 (1H, m), 8.14 (2H, d). LCMS (2) Rt: 2.59 min; m/z (ES+) 401/403.

Example H-1

2-(2,6-difluorophenyl)-5-(4-(4-methylpiperazin-1-yl)phenyl)oxazole-4-carboxamide

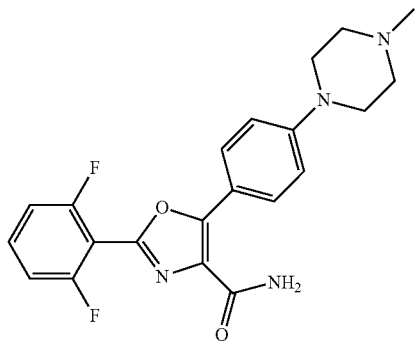 [SMILES: CN1CCN(c2ccc(-c3oc(-c4c(F)cccc4F)nc3C(N)=O)cc2)CC1]

To a stirred suspension of 2-(2,6-difluorophenyl)-5-(4-(piperazin-1-yl)phenyl)oxazole-4-carboxamide (0.025 g, 0.065 mmol) in DCE (2 mL) under an $N_2$ atmosphere at room temperature was added formaldehyde 37% solution (10 uL, 0.12 mmol) followed by sodium triacetoxyborohydride (0.066 g, 0.31 mmol) and the resulting mixture stirred at room temperature for 2 hours. The reaction mixture was diluted with DCM and washed with saturated sodium bicarbonate solution. The aqueous phase was extracted with DCM and the combined organic phases dried over $MgSO_4$ and the solvent removed in vacuo to afford 2-(2,6-difluorophenyl)-5-(4-(4-methylpiperazin-1-yl)phenyl)oxazole-4-carboxamide (0.019 g, 0.048 mmol, 72%) as a white solid. $^1$H NMR ($CDCl_3$) δ 2.36 (3H, s), 2.57 (4H, t), 3.34 (4H, t), 5.49 (1H, br. s), 6.97 (2H, d), 7.07 (2H, t), 7.19 (1H, br. s), 7.45 (1H, m), 8.31 (2H, d). LCMS (2) Rt: 2.75 min; m/z (ES+) 399.

Example H-2

2-(2,6-difluorophenyl)-5-(6-(4-methylpiperazin-1-yl)pyridin-3-yl)oxazole-4-carboxamide

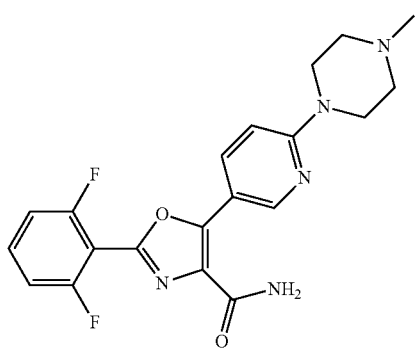 [SMILES: CN1CCN(c2ccc(-c3oc(-c4c(F)cccc4F)nc3C(N)=O)cn2)CC1]

Prepared in a similar manner to that described in Example H-1 except that triethylamine (2.6 equivalents) was added to the reaction prior to the formaldehyde addition. $^1$H NMR ($CDCl_3$) δ 2.35 (3H, s), 2.52 (4H, t), 3.70 (4H, t), 5.12 (1H, br. s), 6.70 (1H, d), 7.07 (2H, t), 7.18 (1H, br. s), 7.46 (1H, m), 8.68 (1H, dd), 8.99 (1H, d). LCMS (2) Rt: 2.54 min; m/z (ES+) 400.

Example I-1

5-(4-(4-acetylpiperazin-1-yl)phenyl)-2-(2,6-difluorophenyl)oxazole-4-carboxamide

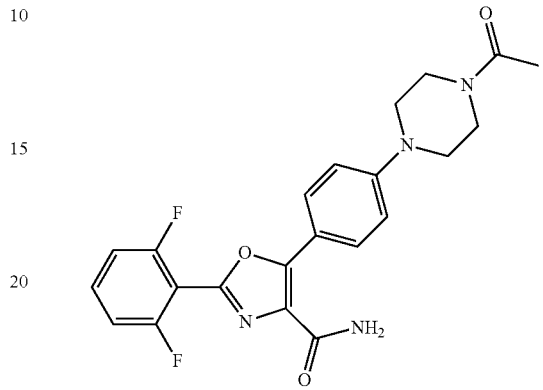

To a solution of 2-(2,6-difluorophenyl)-5-(4-(piperazin-1-yl)phenyl)oxazole-4-carboxamide (0.029 g, 0.075 mmol) in DCM (3 mL) was added triethylamine (12 uL, 0.086 mmol) followed by acetyl chloride (6 uL, 0.084 mmol). The resulting solution was stirred at room temperature for 2 hours when further portion of triethylamine (12 uL, 0.086 mmol) and acetyl chloride (6 uL, 0.084 mmol) were added and the reaction stirred at room temperature for 1 hour. The solvent was then removed in vacuo. The residue was purified by preparative HPLC to afford 5-(4-(4-acetylpiperazin-1-yl)phenyl)-2-(2,6-difluorophenyl)oxazole-4-carboxamide (0.025 g, 0.059 mmol, 78%) as a white solid. $^1$H NMR (DMSO) δ 2.06 (3H, s), 3.28 (2H, m), 3.56 (2H, m, masked by water), 3.59 (4H, m), 7.08 (2H, d), 7.38 (2H, t), 7.63 (1H, br. s), 7.64 (1H, br. s), 7.72 (1H, m), 8.18 (2H, d). LCMS (2) Rt: 2.52 min; m/z (ES+) 427.

Example I-2

5-(6-(4-acetylpiperazin-1-yl)pyridin-3-yl)-2-(2,6-difluorophenyl)oxazole-4-carboxamide

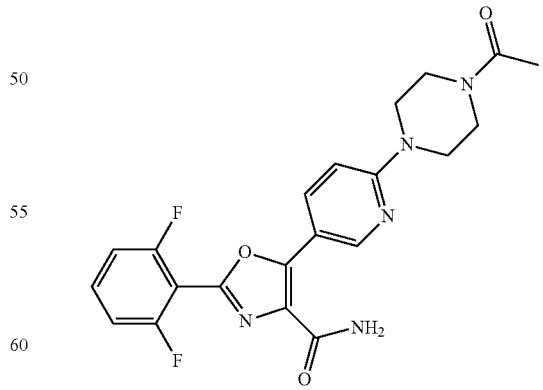

Prepared in a similar manner to that described in Example I-1 except that triethylamine (3.3 equivalents) was initially added to the reaction. $^1$H NMR (DMSO) δ 2.06 (3H, s), 3.56 (4H, m), 3.63 (2H, m), 3.71 (2H, m), 7.00 (1H, d), 7.39 (2H, t), 7.67 (1H, br. s), 7.69 (1H, br. s), 7.72 (1H, m), 8.39 (1H, dd), 8.97 (1H, d), LCMS (2) Rt: 2.34 min; m/z (ES+) 428.

Example J-1

4-(4-(4-carbamoyl-2-(2,6-difluorophenyl)oxazol-5-yl)phenyl)-N-methylpiperazine-1-carboxamide

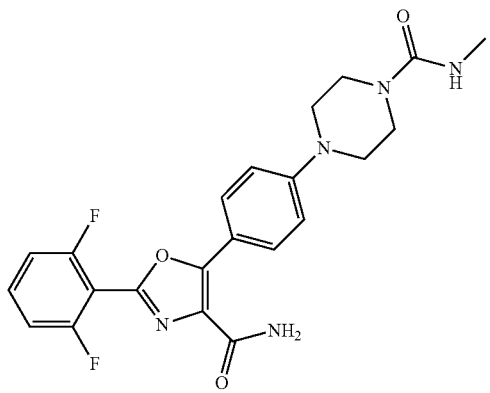 [SMILES: CNC(=O)N1CCN(c2ccc(-c3oc(-c4c(F)cccc4F)nc3C(N)=O)cc2)CC1]

To a suspension of 2-(2,6-difluorophenyl)-5-(4-(piperazin-1-yl)phenyl)oxazole-4-carboxamide (0.029 g, 0.075 mmol) in DCM (3 mL) was added methyl isocyanate (8 uL, 0.136 mmol). The resulting solution was stirred at room temperature overnight. The solvent was removed in vacuo to afford 4-(4-(4-carbamoyl-2-(2,6-difluorophenyl)oxazol-5-yl)phenyl)-N-methylpiperazine-1-carboxamide (0.026 g, 0.059 mmol, 79%) as a yellow solid. $^1$H NMR (DMSO) δ 2.85 (3H, d), 3.34 (4H, m), 3.56 (4H, m), 4.46 (1H, br. q), 5.49 (1H, br. s), 6.95 (2H, d), 7.07 (2H, t), 7.20 (1H, br. s), 7.46 (1H, m), 8.32 (2H, d). LCMS (2) Rt: 2.43 min; m/z (ES+) 442.

Example J-2

4-(5-(4-carbamoyl-2-(2,6-difluorophenyl)oxazol-5-yl)pyridin-2-yl)-N-methylpiperazine-1-carboxamide

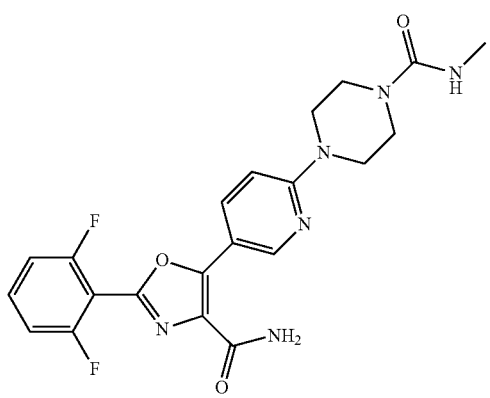 [SMILES: CNC(=O)N1CCN(c2ccc(-c3oc(-c4c(F)cccc4F)nc3C(N)=O)cn2)CC1]

To a suspension of 2-(2,6-difluorophenyl)-5-(6-(piperazin-1-yl)pyridin-3-yl)oxazole-4-carboxamide dihydrochloride (0.060 g, 0.13 mmol) in DCM (3 mL) was added triethylamine (40 uL, 0.29 mmol) followed by methyl isocyanate (12 uL, 0.20 mmol). The resulting solution was stirred at room temperature overnight. The solvent was removed in vacuo. The residue was purified by preparative HPLC and then by SPE using a MP-TsOH resin (500 mg) cartridge to afford 4-(5-(4-carbamoyl-2-(2,6-difluorophenyl)oxazol-5-yl)pyridin-2-yl)-N-methylpiperazine-1-carboxamide (0.0057 g, 0.013 mmol, 10%) as a yellow solid. $^1$H NMR (DMSO) δ 2.58 (3H, d), 3.40 (4H, m), 3.61 (4H, m), 6.54 (1H, br. q), 6.99 (1H, d), 7.38 (2H, t), 7.65 (1H, br. s), 7.67 (1H, br. s), 7.72 (1H, m), 8.37 (1H, dd), 8.95 (1H, d). LCMS (2) Rt: 2.27 min; m/z (ES+) 443.

Example J-3

4-(4-(4-carbamoyl-2-(2,6-difluorophenyl)oxazol-5-ylamino)phenyl)-N-methylpiperazine-1-carboxamide

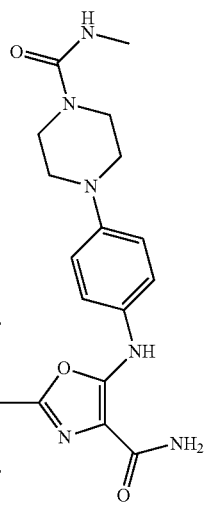

Prepared according to the method described in example J-1 from 2-(2,6-difluorophenyl)-5-(4-(piperazin-1-yl)phenylamino)oxazole-4-carboxamide. $^1$H NMR (DMSO) δ 2.58 (3H, d), 3.03 (4H, t), 3.40 (4H, t), 6.53 (1H, q), 6.96 (2H, d), 7.28 (2H, br. s), 7.29-7.34 (4H, m), 7.62 (1H, m), 9.12 (1H, s). LCMS (2) Rt: 2.13 min; m/z 457.

General Methods K and L

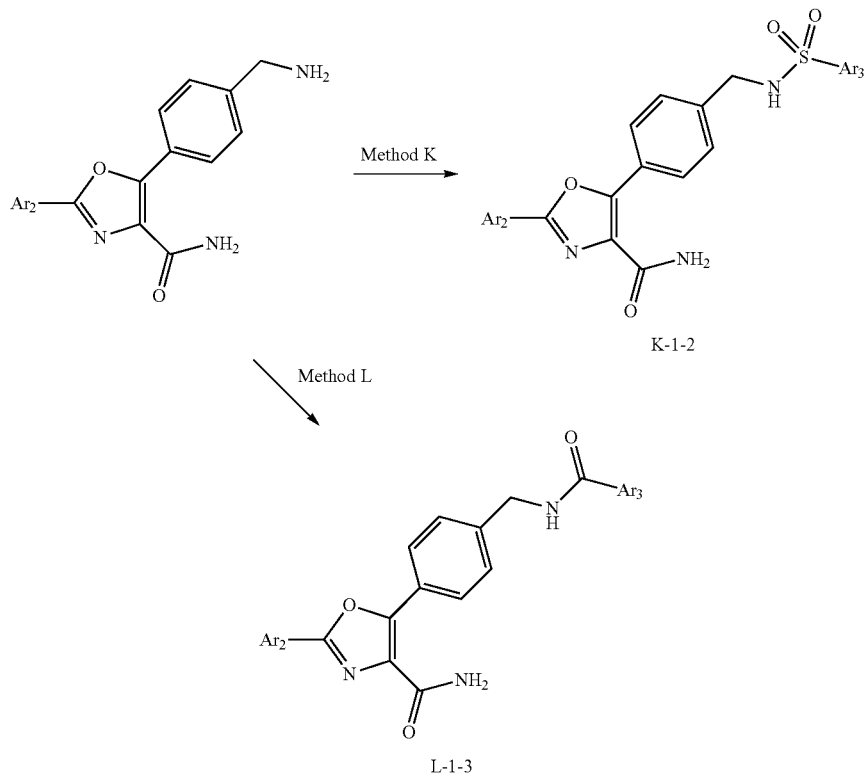

Example K-1

2-(2,6-difluorophenyl)-5-(4-((4-fluorophenylsulfonamido)methyl)phenyl)oxazole-4-carboxamide

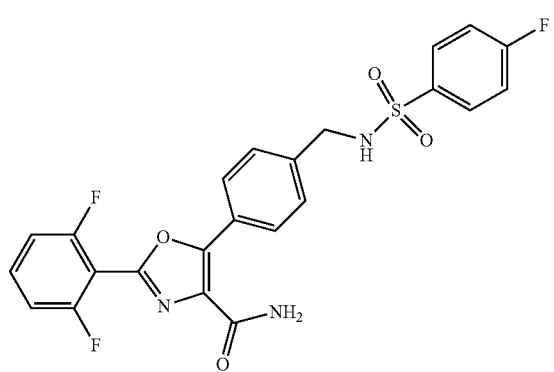 [SMILES: NC(=O)c1nc(-c2c(F)cccc2F)oc1-c1ccc(CNS(=O)(=O)c2ccc(F)cc2)cc1]

To a suspension of 5-(4-(aminomethyl)phenyl)-2-(2,6-difluorophenyl)oxazole-4-carboxamide hydrochloride (0.030 g, 0.082 mmol) in DCM (2 mL) was added triethylamine (25 uL, 0.18 mmol) followed by 4-fluorobenzenesulfonyl chloride (0.016 g, 0.082 mmol) and the resulting mixture stirred at room temperature overnight. Triethylamine (13 uL, 0.093 mmol) followed by 4-fluorobenzenesulfonyl chloride (0.016 g, 0.082 mmol) was then added and the reaction stirred for a further 3 hours. After 2 hours triethylamine (6 uL, 0.043 mmol) and 4-fluorobenzenesulfonyl chloride (0.008 g, 0.041 mmol) was added. The solvent was removed in vacuo and the residue was purified by preparative HPLC to afford 2-(2,6-difluorophenyl)-5-(4-((4-fluorophenylsulfonamido)methyl)phenyl)oxazole-4-carboxamide (0.0230 g, 0.047 mmol, 57%) as a white solid. $^1$H NMR (DMSO) δ 4.07 (2H, d), 7.39 (6H, m), 7.74 (3H, m), 7.85 (2H, m), 8.13 (2H, d), 8.32 (1H, t). LCMS (2) Rt: 3.07 min; m/z (ES+) 488.

In a similar manner as described in example K-1 the compound described in example K-2 was prepared.

Example K-2

2-(2,6-difluorophenyl)-5-(4-(phenylsulfonamidomethyl)phenyl)oxazole-4-carboxamide

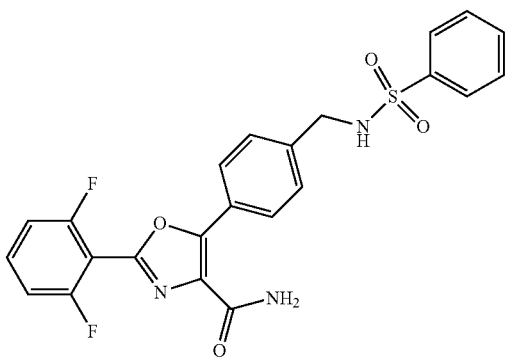 [SMILES: NC(=O)c1nc(-c2c(F)cccc2F)oc1-c1ccc(CNS(=O)(=O)c2ccccc2)cc1]

¹H NMR (DMSO) δ 4.06 (2H, d), 7.38 (2H, d), 7.40 (2H, t), 7.56-7.66 (3H, m), 7.73 (3H, m), 7.82 (2H, m), 8.13 (2H, d), 8.28 (1H, t). LCMS (2) Rt: 3.02 min; m/z (ES+) 470.

Example L-1

5-(4-(benzamidomethyl)phenyl)-2-(2,6-difluorophenyl)oxazole-4-carboxamide

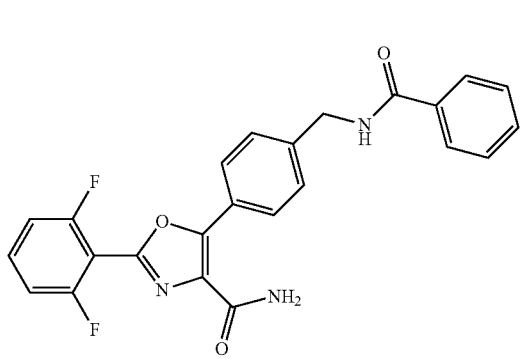 [SMILES: NC(=O)c1nc(-c2c(F)cccc2F)oc1-c1ccc(CNC(=O)c2ccccc2)cc1]

To a suspension of 5-(4-(aminomethyl)phenyl)-2-(2,6-difluorophenyl)oxazole-4-carboxamide hydrochloride (0.030 g, 0.08 mmol) in DCM (2 mL) was added triethylamine (25 uL) followed by benzoyl chloride (11 uL) and the resulting mixture stirred at room temperature for 2 hours The solvent was removed in vacuo and the residue purified by preparative HPLC to afford 5-(4-(benzamidomethyl)phenyl)-2-(2,6-difluorophenyl)oxazole-4-carboxamide (0.0128 g, 0.03 mmol, 36%). ¹H NMR (DMSO) δ 4.54 (2H, d), 7.40 (2H, t), 7.49 (4H, m), 7.55 (1H, m), 7.74 (3H, m), 7.92 (2H, m), 8.18 (2H, d), 9.15 (1H, t). LCMS (2) Rt: 2.82 min; m/z (ES+) 434.

In a similar manner as described in example L-1 the compounds described in examples L-2 to L-3 were prepared.

Example L-2

2-(2,6-difluorophenyl)-5-(4-((4-fluorobenzamido)methyl)phenyl)oxazole-4-carboxamide

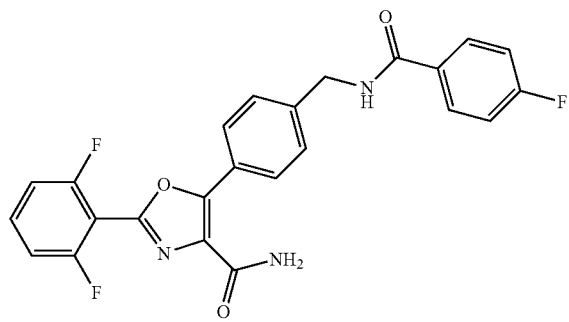 [SMILES: NC(=O)c1nc(-c2c(F)cccc2F)oc1-c1ccc(CNC(=O)c2ccc(F)cc2)cc1]

¹H NMR (DMSO) δ 4.54 (2H, d), 7.32 (2H, t), 7.39 (2H, t), 7.47 (2H, d), 7.73 (3H, m), 7.99 (2H, dd), 8.18 (2H, d), 9.17 (1H, t). LCMS (2) Rt: 2.91 min; m/z (ES+) 452.

Example L-3

2-(2,6-difluorophenyl)-5-(4-((thiophene-2-carboxamido)methyl)phenyl)oxazole-4-carboxamide

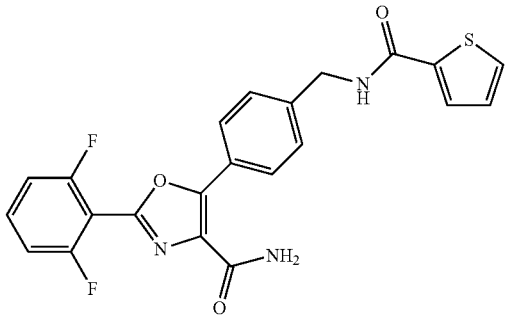 [SMILES: NC(=O)c1nc(-c2c(F)cccc2F)oc1-c1ccc(CNC(=O)c2cccs2)cc1]

¹N NMR (DMSO) δ 4.52 (2H, d), 7.17 (1H, dd), 7.39 (2H, t), 7.46 (2H, d), 7.73 (3H, m), 7.79 (1H, d), 7.83 (1H, d), 8.19 (2H, d), 9.14 (1H, t). LCMS (2) Rt: 2.78 min; m/z (ES+) 440.

General Method M

General Method M comprises the series of reactions set out in Scheme 7 above.

Example M-1

5-(4-methoxyphenyl)-2-(thiophen-2-yl)oxazole-4-carboxamide

Step a—ethyl 5-(4-methoxyphenyl)oxazole-4-carboxylate (see *Org. Lett.* (2006) 8, 5231-5234)

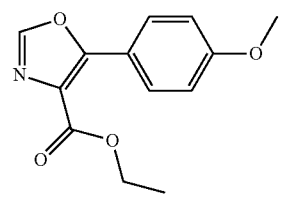 [SMILES: CCOC(=O)c1ncoc1-c1ccc(OC)cc1]

A solution of ethyl isocyanoacetate (2.126 mL, 19.5 mmol) and p-anisole chloride (2.765 g, 16.2 mmol) in acetonitrile (20 mL) was stirred for 20 minutes. 1,8-Diazabicyclo[5.4.0]undec-7-ene (7.329 mL, 48.6 mmol) was then added and the reaction heated in the microwave at 110° C. for 10 minutes. The solvent was then removed in vacuo and the residue purified by silica gel column chromatography using 35% EtOAc in hexane as eluant to afford ethyl 5-(4-methoxyphenyl)oxazole-4-carboxylate (1.211 g, 4.9 mmol, 30%). ¹H NMR (CDCl$_3$) δ 1.41 (3H, t), 3.87 (3H, s), 4.41 (2H, q), 6.99 (2H, d), 7.85 (1H, s), 8.07 (2H, d). LCMS (1) Rt: 1.90 min; m/z (ES+) 248.

Step b—ethyl 2-iodo-5-(4-methoxyphenyl)oxazole-4-carboxylate

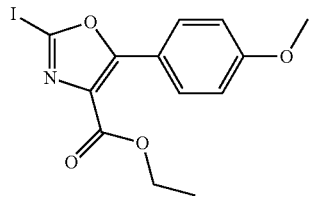 [SMILES: CCOC(=O)c1nc(I)oc1-c1ccc(OC)cc1]

To a solution of ethyl 5-(4-methoxyphenyl)oxazole-4-carboxylate (2.75 g, 11.1 mmol) in anhydrous THF (20 mL) under an N$_2$ atmosphere at −78° C. was added 1M lithium bis(trimethylsilyl)amide in THF (18 mL, 18 mmol), dropwise. The reaction mixture was stirred at −78° C. for one hour. A solution of iodine (5.0 g, 19.7 mmol) in anhydrous THF (10 mL) was added dropwise and the reaction stirred at −78° C. for a further 1 hour. The mixture was then warmed to −10° C. and 10% sodium thiosulfate solution and EtOAc was added. The aqueous phase was extracted with EtOAc and the combined organic phase was washed with brine, dried over MgSO$_4$ and the solvent removed in vacuo. The residue was purified by silica gel column chromatography using a 10-40% EtOAc in hexanes gradient to afford ethyl 2-iodo-5-(4-methoxyphenyl)oxazole-4-carboxylate (3.33 g, 8.9 mmol, 80%) as a white solid. $^1$H NMR (CDCl$_3$) δ 1.40 (3H, t), 3.87 (3H, s), 4.41 (2H, q), 6.98 (2H, d), 8.01 (2H, d). LCMS (1) Rt: 2.13 min; m/z (ES+) 374.

Step c—5-(4-methoxyphenyl)-2-(thiophen-2-yl)oxazole-4-carboxamide

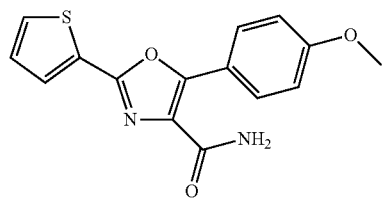 [SMILES: COc1ccc(-c2oc(-c3cccs3)nc2C(N)=O)cc1]

To a mixture of ethyl 2-iodo-5-(4-methoxyphenyl)oxazole-4-carboxylate (0.100 g, 0.27 mmol) and 2-thiophenyl boronic acid (0.069 g, 0.54 mmol) in acetonitrile (2 mL) was added a solution of Pd(dppf)$_2$Cl$_2$ (0.010 g, 0.012 mmol) in acetonitrile (0.2 mL) followed by 1M aqueous sodium carbonate solution (0.535 mL, 0.54 mmol). The resulting reaction mixture was heated at 150° C. in the microwave for 15 minutes and the solvent was then removed in vacuo. The residue was purified by silica gel column chromatography using a gradient of 4-90% EtOAc in hexanes to afford ethyl 5-(4-methoxyphenyl)-2-(thiophen-2-yl)oxazole-4-carboxylate which was used without further purification. LCMS (1) Rt: 2.45 min; m/z (ES+) 330.

To a solution of ethyl 5-(4-methoxyphenyl)-2-(thiophen-2-yl)oxazole-4-carboxylate in MeOH (2 mL) and DCM (0.5 mL) was added 1M aqueous lithium hydroxide solution (2 mL, 2 mmol). The reaction mixture was stirred at 50° C. overnight and then 2M aqueous HCl (0.125 mL) was added and the solvent removed in vacuo to afford 5-(4-methoxyphenyl)-2-(thiophen-2-yl)oxazole-4-carboxylic acid which was used without further purification.

LCMS (1) Rt: 1.34 min; m/z (ES+) 302.

To a solution of 5-(4-methoxyphenyl)-2-(thiophen-2-yl)oxazole-4-carboxylic acid in DCM (2 mL) and DMF (1 mL) was added hydroxybenzotriazole monohydrate (0.022 g, 0.14 mmol) followed by 0.5M ammonia in dioxane (1.3 mL, 0.65 mmol). A solution of 1-(3-(dimethylamino)propyl)-3-ethylcarbodiimide hydrochloride (0.078 g, 0.41 mmol) in DMF/DCM (4:1, 0.5 mL) was added and the reaction stirred at room temperature overnight. The solvents were removed in vacuo and the residue was purified by preparative HPLC to afford 5-(4-methoxyphenyl)-2-(thiophen-2-yl)oxazole-4-carboxamide (0.0128 g, 0.04 mmol, 15%) as a white solid. $^1$H NMR (CDCl$_3$) δ 3.85 (3H, s), 5.53 (1H, br. s), 7.00 (2H, d), 7.16 (1H, dd), 7.17 (1H, br. s), 7.48 (1H, dd), 7.74 (1H, dd), 8.32 (2H, d). LCMS (2) Rt: 2.90 min; m/z (ES+) 301.

Example M-2

5-(4-methoxyphenyl)-2-phenyloxazole-4-carboxamide

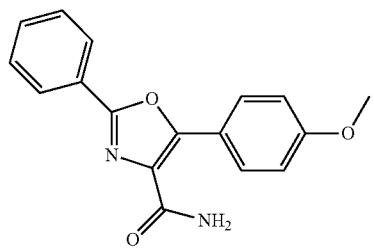 [SMILES: COc1ccc(-c2oc(-c3ccccc3)nc2C(N)=O)cc1]

To a solution of 5-(4-methoxyphenyl)-2-phenyloxazole-4-carboxylic acid (prepared according to the method described for 5-(4-methoxyphenyl)-2-(thiophen-2-yl)oxazole-4-carboxylic acid in Example M-1, 0.032 g, 0.11 mmol) and hydroxybenzotriazole monohydrate (0.02 g, 0.13 mmol) in DCM (2 mL) and DMF (1 mL) was added 0.5M ammonia in dioxane (1 mL, 0.5 mmol), followed by PS-carbodiimide resin. The resulting mixture was stirred at room temperature overnight. The mixture was passed through a MP-CO$_3$ resin cartridge and the solvent removed in vacuo. The residue was purified by preparative HPLC to afford 5-(4-methoxyphenyl)-2-phenyloxazole-4-carboxamide (0.008 g, 0.03 mmol, 27%) as a white solid. $^1$H NMR (DMSO) δ 3.85 (3H, s), 7.10 (2H, d), 7.60 (3H, m), 7.66 (1H, br. s), 7.78 (1H, br. s), 8.14 (2H, m), 8.37 (2H, d). LCMS (2) Rt: 3.16 min; m/z (ES+) 295.

In a similar manner as described in example M-1 the compounds described in examples M-3 to M-11 were prepared.

Example M-3

2-(2-fluorophenyl)-5-(4-methoxyphenyl)oxazole-4-carboxamide

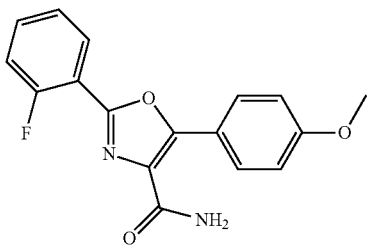 [SMILES: COc1ccc(-c2oc(-c3ccccc3F)nc2C(N)=O)cc1]

¹H NMR (CDCl₃) δ 3.90 (3H, s), 5.58 (1H, br. s), 7.03 (2H, d), 7.24-7.34 (3H, m), 7.51 (1H, m), 8.11 (1H, m), 8.41 (2H, d). LCMS (2) Rt: 3.02 min; m/z (ES+) 313.

Example M-4

2-(1H-indol-4-yl)-5-(4-methoxyphenyl)oxazole-4-carboxamide

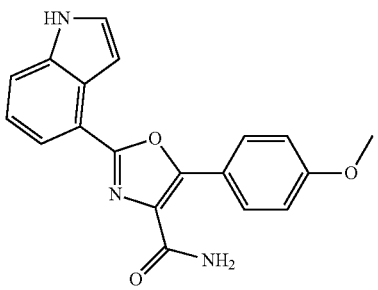 [SMILES: COc1ccc(-c2oc(-c3cccc4[nH]ccc34)nc2C(N)=O)cc1]

¹H NMR (DMSO) δ 3.86 (3H, s), 7.12 (2H, d), 7.28 (1H, dd), 7.37 (1H, m), 7.60 (1H, dd), 7.63 (1H, d), 7.67 (1H, br. s), 7.88 (2H, m), 8.40 (2H, d), 11.53 (1H, s). LCMS (2) Rt: 2.84 min; m/z (ES+) 334.

Example M-5

5-(4-methoxyphenyl)-2-(thiophen-3-yl)oxazole-4-carboxamide

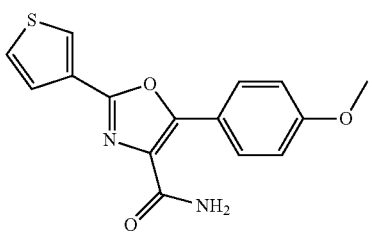 [SMILES: COc1ccc(-c2oc(-c3ccsc3)nc2C(N)=O)cc1]

¹H NMR (CDCl₃) δ 3.88 (3H, s), 5.54 (1H, br. s), 7.00 (2H, d), 7.19 (1H, br. s), 7.44 (1H, dd), 7.65 (1H, dd), 8.01 (1H, dd), 8.32 (2H, d). LCMS (2) Rt: 2.88 min; m/z (ES+) 301.

Example M-6

2-(2-carbamoylphenyl)-5-(4-methoxyphenyl)oxazole-4-carboxamide

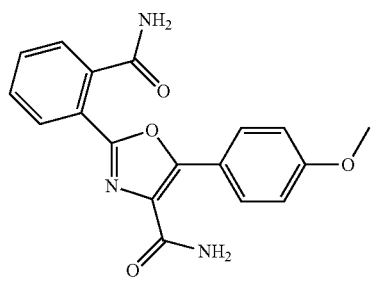 [SMILES: COc1ccc(-c2oc(-c3ccccc3C(N)=O)nc2C(N)=O)cc1]

Prepared using 2-cyanophenyl boronic acid which hydrolysed to the amide under the reaction conditions. ¹H NMR (DMSO) δ 3.84 (3H, s), 7.07 (2H, d), 7.55 (1H, dd), 7.62 (2H, m), 7.68 (1H, br. s), 7.72 (1H, br. s), 8.04 (2H, m), 8.30 (2H, d). LCMS (2) Rt: 1.96 min; m/z (ES+) 338.

Example M-7

2-(3-fluorophenyl)-5-(4-methoxyphenyl)oxazole-4-carboxamide

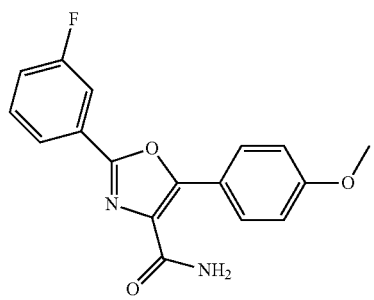 [SMILES: COc1ccc(-c2oc(-c3cccc(F)c3)nc2C(N)=O)cc1]

¹H NMR (CDCl₃) δ 3.91 (3H, s), 5.56 (1H, br. s), 7.04 (2H, d), 7.19-7.23 (2H, m), 7.50 (1H, m), 7.80 (1H, ddd), 7.90 (1H, m), 8.37 (2H, d). LCMS (2) Rt: 3.15 min; m/z (ES+) 313.

Example M-8

2-(4-fluorophenyl)-5-(4-methoxyphenyl)oxazole-4-carboxamide

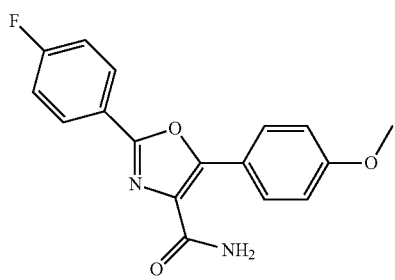 [SMILES: COc1ccc(-c2oc(-c3ccc(F)cc3)nc2C(N)=O)cc1]

¹H NMR (CDCl₃) δ 3.88 (3H, s), 5.56 (1H, br. s), 7.01 (2H, d), 7.17-7.22 (3H, m), 8.09 (2H, dd), 8.33 (2H, d). LCMS (2) Rt: 3.11 min; m/z (ES+) 313.

Example M-9

2-(4-cyanophenyl)-5-(4-methoxyphenyl)oxazole-4-carboxamide

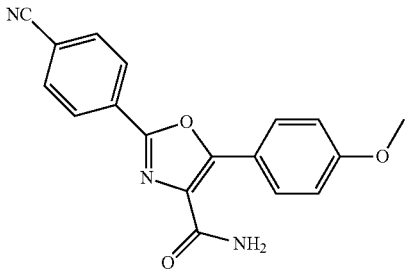 [SMILES: COc1ccc(-c2oc(-c3ccc(C#N)cc3)nc2C(N)=O)cc1]

¹H NMR (DMSO) δ 3.82 (3H, s), 7.10 (2H, d), 7.72 (1H, br. s), 7.87 (1H, br. s), 8.08 (2H, d), 8.30 (2H, d), 8.40 (2H, d). LCMS (2) Rt: 2.92 min; m/z (ES+) 342 (M+Na⁺).

Example M-10

2-(2,4-difluorophenyl)-5-(4-methoxyphenyl)oxazole-4-carboxamide

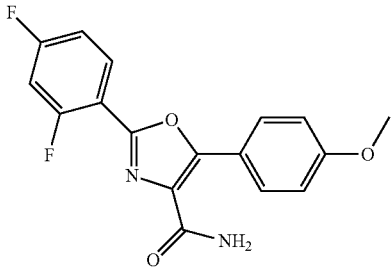 [SMILES: COc1ccc(-c2oc(-c3ccc(F)cc3F)nc2C(N)=O)cc1]

¹H NMR (CDCl₃) δ 3.88 (3H, s), 5.56 (1H, br. s), 6.96-7.06 (4H, m), 7.21 (1H, br. s), 8.09 (1H, m), 8.36 (2H, d). LCMS (2) Rt: 3.11 min; m/z (ES+) 331.

Example M-11

5-(4-methoxyphenyl)-2-(4-(methylsulfonyl)phenyl)oxazole-4-carboxamide

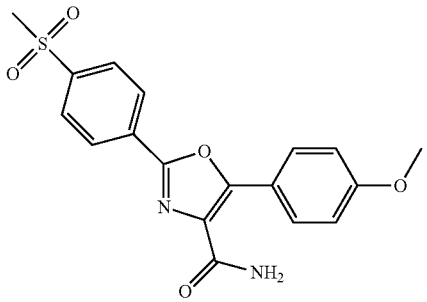

¹H NMR (DMSO) δ 3.31 (3H, s), 3.85 (3H, s), 7.10 (2H, d), 7.71 (1'-1, br. s), 7.87 (1H, br. s), 8.13 (2H, d), 8.36 (2H, d), 8.38 (2H, d). LCMS (2) Rt: 2.47 min; m/z (ES+) 373.

Example M-12

2-(1H-indol-4-yl)-5-(4-(piperazin-1-yl)phenyl)oxazole-4-carboxamide

Step a—ethyl 5-(4-bromophenyl)oxazole-4-carboxylate

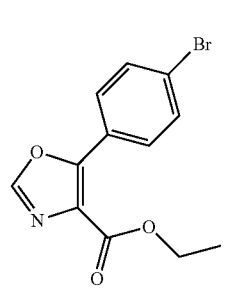 [SMILES: CCOC(=O)c1ncoc1-c1ccc(Br)cc1]

Prepared from 4-bromobenzoyl chloride according to the procedure outlined for ethyl 5-(4-methoxyphenyl)oxazole-4-carboxylate in example M-1. ¹H NMR (DMSO) δ 1.42 (3H, t), 4.42 (2H, q), 7.61 (2H, d), 7.92 (1H, s), 7.99 (2H, d). LCMS (1) Rt: 2.10 min; m/z (ES+) 268/270 MH⁺-Et.

Step b—tert-butyl 4-(4-(4-(ethoxycarbonyl)oxazol-5-yl)phenyl)piperazine-1-carboxylate

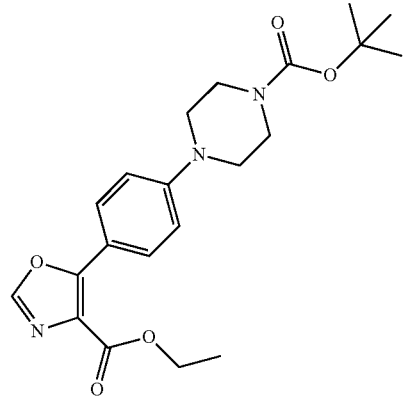 [SMILES: CCOC(=O)c1ncoc1-c1ccc(N2CCN(C(=O)OC(C)(C)C)CC2)cc1]

A solution of tris(dibenzylideneacetone)dipalladium(0) (0.079 g, 0.09 mmol), 9,9-dimethyl-4,5-bis(diphenylphosphino)xanthene (0.100 g, 0.17 mmol), ethyl 5-(4-bromophenyl)oxazole-4-carboxylate (0.500 g, 1.69 mmol), tert-butyl 1-piperazinecarboxylate (0.409 g, 2.20 mmol) and cesium carbonate (0.786 g, 2.41 mmol) in dioxane (25 ml) and t-butanol (25 ml) was degassed, placed under a nitrogen atmosphere and heated under reflux overnight. The solvent was removed in vacuo and the residue partitioned between water and DCM. The organic phase was dried over MgSO₄ and the solvent removed in vacuo. The residue was purified by silica gel column chromatography using 50% EtOAc in hexane as eluant to afford tert-butyl 4-(4-(4-(ethoxycarbonyl)oxazol-5-yl)phenyl)piperazine-1-carboxylate (0.340 g, 0.85 mmol, 50%) of a yellow solid. ¹H NMR (CDCl₃) δ 1.42 (3H, t), 1.49 (9H, s), 3.28 (4H, br. t), 3.59 (4H, br. t), 4.42 (2H, q), 6.95 (2H, d), 7.83 (1H, s), 8.05 (2H, d). LCMS (1) Rt: 2.37 min; m/z (ES+) 402.

Step c—tert-butyl 4-(4-(4-(ethoxycarbonyl)-2-iodooxazol-5-yl)phenyl)piperazine-1-carboxylate

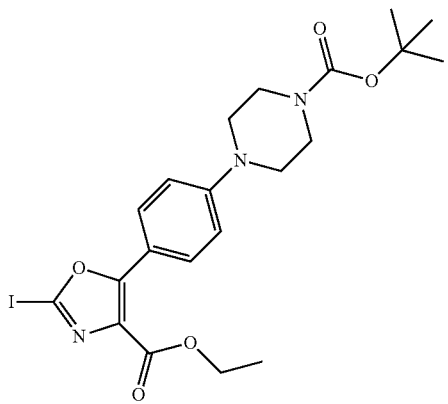 [SMILES: CCOC(=O)c1nc(I)oc1-c1ccc(N2CCN(C(=O)OC(C)(C)C)CC2)cc1]

Prepared from tert-butyl 4-(4-(4-(ethoxycarbonyl)oxazol-5-yl)phenyl)piperazine-1-carboxylate using the procedure described for the synthesis of ethyl 2-iodo-5-(4-methoxyphenyl)oxazole-4-carboxylate in example M-1. ¹H NMR (DMSO) δ 1.40 (3H, t), 1.57 (9H, s), 3.29 (4H, br. t), 3.59 (4H, br. t), 4.41 (2H, q), 6.93 (2H, d), 7.99 (2H, d). LCMS (1) Rt: 2.58 min; m/z (ES+) 528.

Step d—2-(1H-indol-4-yl)-5-(4-(piperazin-1-yl)phenyl)oxazole-4-carboxamide

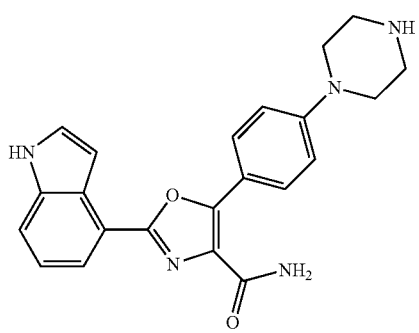 [SMILES: NC(=O)c1nc(-c2cccc3[nH]ccc23)oc1-c1ccc(N2CCNCC2)cc1]

A mixture of ethyl 2-iodo-5-(4-methoxyphenyl)oxazole-4-carboxylate (0.080 g, 0.15 mmol), indole-4-boronic acid (0.048 g, 0.30 mmol), Pd(dppf)₂Cl₂ (0.006 g, 0.007 mmol) and 1M aq. sodium carbonate (0.31 ml, 0.31 mmol) in acetonitrile (2.5 ml) was heated in the microwave at 150° C. for 15 minutes. The reaction mixture was diluted with DCM and washed with 1M NaOH. The organic phase was passed through a MP-SH cartridge, dried over MgSO₄ and the solvent removed in vacuo to afford tert-butyl 4-(4-(4-(ethoxycarbonyl)-2-(1H-indol-4-yl)oxazol-5-yl)phenyl)piperazine-1-carboxylate which was used without further purification. LCMS (1) Rt: 2.61 min; m/z (ES+) 517.

To a solution of tert-butyl 4-(4-(4-(ethoxycarbonyl)-2-(1H-indol-4-yl)oxazol-5-yl)phenyl)piperazine-1-carboxylate in MeOH (10 ml) was added 1M aq KOH (3 ml) and the resulting mixture stirred at 55° C. for 3 hours. The reaction was cooled to room temperature and the methanol removed in vacuo. The reaction mixture was then partitioned between DCM and water and the resulting precipitate collected by filtration to afford 5-(4-(4-(tert-butoxycarbonyl)piperazin-1-yl)phenyl)-2-(1H-indol-4-yl)oxazole-4-carboxylic acid as the potassium salt (0.045 g, 0.09 mmol, 57% two steps). LCMS (1) Rt: 1.66 min; m/z (ES+) 489.

To a solution of 5-(4-(4-(tert-butoxycarbonyl)piperazin-1-yl)phenyl)-2-(1H-indol-4-yl)oxazole-4-carboxylic acid potassium salt (0.045, 0.09 mmol) in DCM (0.9 ml) and DMF (0.7 ml) was added hydroxybenzotriazole monohydrate (0.018 g, 0.12 mmol), 1-[3-(dimethylamino)propyl]-3-ethylcarbodiimide hydrochloride (0.027 g, 0.14 mmol) and 0.5M ammonia in dioxane (0.9 ml, 0.45 mmol) and the resultant mixture stirred overnight at room temperature. The solvent was then removed in vacuo and the residue purified by preparative HPLC to afford tert-butyl 4-(4-(4-carbamoyl-2-(1H-indol-4-yl)oxazol-5-yl)phenyl)piperazine-1-carboxylate (0.027 g, 0.06 mmol, 65%). LCMS (2) Rt: 3.33 min; m/z (ES+) 488.

To a suspension of tert-butyl 4-(4-(4-carbamoyl-2-(1H-indol-4-yl)oxazol-5-yl)phenyl)piperazine-1-carboxylate (0.027 g, 0.06 mmol) in DCM (1 ml) was added 4M HCl in dioxane (0.5 ml, 2.0 mmol) and the reaction stirred at room temperature for 2 hours. The mixture was then diluted with MeOH and purified by SPE using a MP-TsOH cartridge (500 mg) to afford 2-(1H-indol-4-yl)-5-(4-(piperazin-1-yl)phenyl)oxazole-4-carboxamide (0.0078 g, 0.02 mmol, 36%). ¹H NMR (DMSO) δ 2.86 (4H, br. t), 3.22 (4H, br. t), 7.06 (2H, d), 7.21 (1H, t), 7.35 (1H, br. t), 7.56-7.60 (2H, m), 7.62 (1H, d), 7.79 (1H, br. s), 7.86 (1H, dd), 8.30 (2H, d), 11.51 (1H, br. s). LCMS (2) Rt: 2.36 min; m/z (ES+) 388.

Example M-13

5-(4-(piperazin-1-yl)phenyl)-2-(pyridin-3-yl)oxazole-4-carboxamide

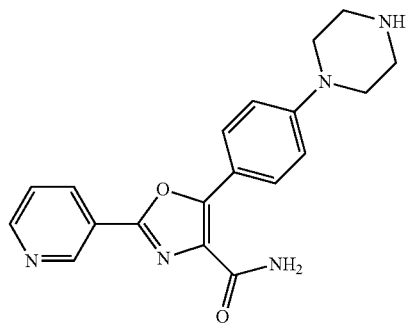 [SMILES: NC(=O)c1nc(-c2cccnc2)oc1-c1ccc(N2CCNCC2)cc1]

Prepared according to the method described in example M-12. ¹H NMR (DMSO) δ 2.85 (4H, m), 3.21 (4H, m), 7.03 (2H, d), 7.61-7.64 (2H, m), 7.76 (1H, br. s), 8.29 (2H, d), 8.45 (1H, ddd), 8.75 (1H, dd), 9.30 (1H, dd). LCMS (2) Rt: 1.74 min; m/z (ES+) 350.

Example M-14

5-(4-(piperazin-1-yl)phenyl)-2-(pyridin-4-yl)oxazole-4-carboxamide

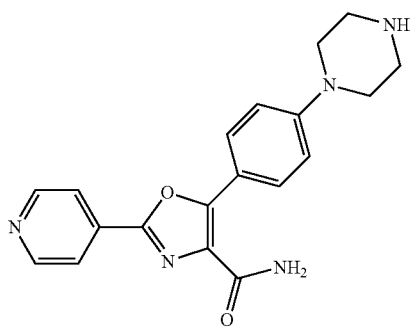 [SMILES: NC(=O)c1nc(-c2ccncc2)oc1-c1ccc(N2CCNCC2)cc1]

Prepared according to the method described for example M-12, except that during the NaOH mediated hydrolysis the reaction was worked up by acidifying the aqueous phase and extracting the product into DCM. ¹H NMR (DMSO) δ 2.86 (4H, t), 3.23 (4H, t), 7.04 (2H, d), 7.62 (1H, br. s), 7.76 (1H, br. s), 8.01 (2H, d), 8.29 (2H, d), 8.79 (2H, d). LCMS (2) Rt: 1.80 min; m/z (ES+) 350.

Example M-15

2-(1H-indol-5-yl)-5-(4-(piperazin-1-yl)phenyl)oxazole-4-carboxamide

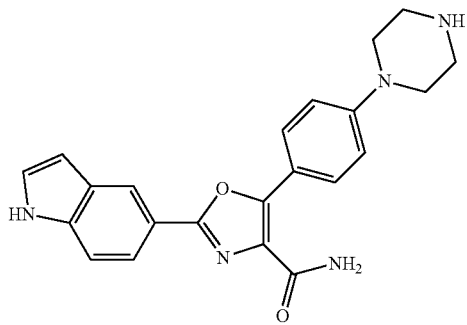 [SMILES: NC(=O)c1nc(-c2ccc3[nH]ccc3c2)oc1-c1ccc(N2CCNCC2)cc1]

Prepared according to the method described in example M-12. ¹H NMR (CD₃OD) δ 3.03 (4H, m), 3.31 (4H, m), 6.61 (1H, d), 7.06 (2H, d), 7.36 (1H, d), 7.53 (1H, d), 7.92 (1H, dd), 8.25 (2H, d), 8.37 (1H, d). LCMS (1) 2.31 min; m/z (ES+) 388.

Example M-16

2-(1H-indol-6-yl)-5-(4-(piperazin-1-yl)phenyl)oxazole-4-carboxamide

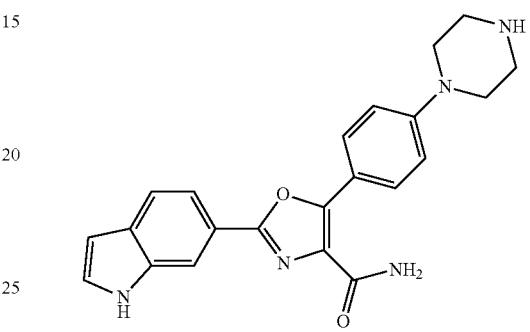

5-(4-(4-(tert-butoxycarbonyl)piperazin-1-yl)phenyl)-2-(1H-indol-6-yl)oxazole-4-carboxylic acid was prepared according to the method described for the synthesis of 5-(4-(4-(tert-butoxycarbonyl)piperazin-1-yl)phenyl)-2-(1H-indol-4-yl)oxazole-4-carboxylic acid in example M-12, except that during the NaOH mediated hydrolysis the reaction was worked up by acidifying the aqueous phase and extracting the product in DCM.

To a solution of 5-(4-(4-(tert-butoxycarbonyl)piperazin-1-yl)phenyl)-2-(1H-indol-6-yl)oxazole-4-carboxylic acid (0.038 g, 0.08 mmol) in DMF (1 ml) was added O-(7-azabenzotriazol-1-yl)-N,N,N',N'-tetramethyluronium hexafluorophosphate (0.036 g, 0.09 mmol) and diisopropylethylamine (0.016 ml, 0.09 mmol). The solution was stirred at room temperature for 5 minutes and then 0.5M ammonia in dioxane (0.31 ml, 0.16 mmol) was added and the resultant mixture stirred at room temperature for 2 hours. The solvent was removed in vacuo and the residue purified by preparative HPLC to afford tert-butyl 4-(4-(4-carbamoyl-2-(1H-indol-6-yl)oxazol-5-yl)phenyl)piperazine-1-carboxylate (0.018 g, 0.04 mmol, 46%). LCMS (2) Rt: 3.39 min; m/z (ES+) 488.

A solution of tert-butyl 4-(4-(4-carbamoyl-2-(1H-indol-6-yl)oxazol-5-yl)phenyl)piperazine-1-carboxylate (0.018 g, 0.04 mmol) in MeOH was loaded onto a MP-TsOH cartridge (500 mg). The cartridge was washed with MeOH and allowed to stand for 2 hours. The cartridge was then washed with 2M ammonia in MeOH and the solvent removed in vacuo. The residue was purified by preparative HPLC to afford 2-(1H-indol-6-yl)-5-(4-(piperazin-1-yl)phenyl)oxazole-4-carboxamide (0.006 g, 0.02 mmol, 50%). ¹H NMR (DMSO) δ 2.85 (4H, t), 3.20 (4H, t), 6.55 (1H, m), 7.04 (2H, d), 7.55 (1H, br.

s), 7.56 (1H, m), 7.68 (1H, br. s), 7.71 (1H, d), 7.77 (1H, dd), 8.15 (1H, s), 8.26 (2H, d), 11.48 (1H, br. s). LCMS (2) Rt: 2.32 min; m/z (ES+) 388.

Example M-17

2-(1H-indazol-4-yl)-5-(4-(piperazin-1-yl)phenyl)oxazole-4-carboxamide

Step a—tert-butyl 4-(4-(4-(ethoxycarbonyl)-2-(1H-indazol-4-yl)oxazol-5-yl)phenyl)piperazine-1-carboxylate

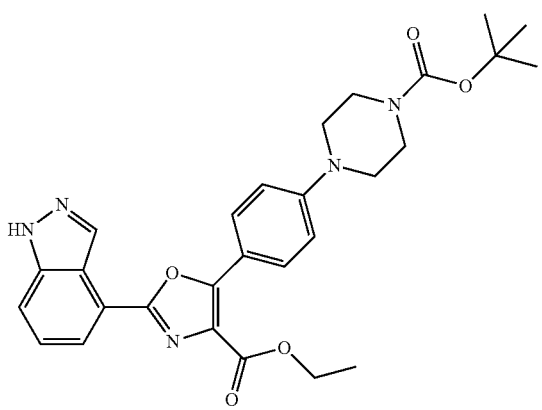 [SMILES: CCOC(=O)c1nc(-c2cccc3[nH]ncc23)oc1-c1ccc(N2CCN(C(=O)OC(C)(C)C)CC2)cc1]

To a mixture of tert-butyl 4-(4-(4-(ethoxycarbonyl)-2-iodooxazol-5-yl)phenyl)piperazine-1-carboxylate (0.080 g, 0.15 mmol), 4-(4,4,5,5-tetramethyl-[1,3,2]-dioxaborolan-2-yl)-1H-indazole (0.080 g, 0.33 mmol) and sodium carbonate (0.048 g, 0.45 mmol) in toluene (0.81 ml), ethanol (0.49 ml) and water (0.23 ml) was added bis(triphenylphosphine)palladium (II) chloride (0.005 g, 0.007 mmol) and the resulting mixture heated in the microwave at 120° C. for 60 minutes followed by an additional 45 minutes. The reaction mixture was diluted with EtOAc and washed with 1M NaOH. The organic phase was passed through a MP-SH cartridge, dried over MgSO$_4$ and the solvent removed in vacuo. The residue was purified by silica gel column chromatography using a 10-100% EtOAc in hexane gradient to afford tert-butyl 4-(4-(4-(ethoxycarbonyl)-2-(1H-indazol-4-yl)oxazol-5-yl)phenyl)piperazine-1-carboxylate (0.037 g, 0.07 mmol, 47%) as a yellow solid. LCMS (2) Rt: 3.57 min; m/z (ES+) 518.

Step b—2-(1H-indazol-4-yl)-5-(4-(piperazin-1-yl)phenyl)oxazole-4-carboxamide

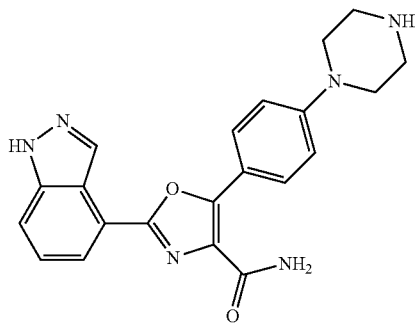 [SMILES: NC(=O)c1nc(-c2cccc3[nH]ncc23)oc1-c1ccc(N2CCNCC2)cc1]

Prepared from tert-butyl 4-(4-(4-(ethoxycarbonyl)-2-(1H-indazol-4-yl)oxazol-5-yl)phenyl)piperazine-1-carboxylate according to the method described in example M-16 except that the final acid mediated Boc group removal is performed as described in example M-12 with 4M HCl in dioxane. $^1$H NMR (DMSO) δ 2.87 (4H, t), 3.23 (4H, t), 7.06 (2H, d), 7.54 (1H, t), 7.59 (1H, br s), 7.76 (1H, d), 7.93 (1H, d), 8.01 (1H, br s), 8.33 (2H, d), 8.98 (1H, s), 13.43 (1H, br s). LCMS (2) Rt: 1.99 min; m/z (ES+) 389.

Example M-18

2-(1H-indazol-4-yl)-5-(4-(piperazin-1-yl)phenyl)oxazole-4-carboxamide

Step a—4-chloro-1H-pyrrolo[2,3-b]pyridine

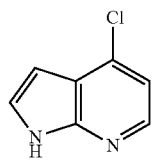

Prepared from 7-Azaindole according to the procedure outlined in the patent WO 03/082289. LCMS (3) Rt: 1.89 min; m/z (ES+) 153/155.

Step b—4-(4,4,5,5-tetramethyl-1,3,2-dioxaborolan-2-yl)-1H-pyrrolo[2,3-b]pyridine

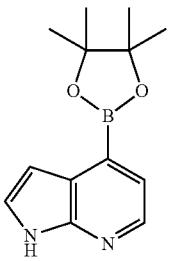 [SMILES: CC1(C)OB(c2ccnc3[nH]ccc23)OC1(C)C]

A solution of 2-(dicyclohexylphosphino)biphenyl (0.287 g, 0.819 mmol), bis(pinacolato)diboron (0.915 g, 3.60 mmol), Acetic acid potassium salt (0.965 g, 9.83 mmol), tris(dibenzylideneacetone)dipalladium(0) (0.030 g, 0.032 mmol) and 4-chloro-1H-pyrrolo[2,3-b]pyridine (0.500 g, 3.28 mmol) in dioxane (10 ml) was degassed, placed under a nitrogen atmosphere and heated under reflux for 3 hours. The solvent was removed in vacuo. The residue was taken up in MeOH and loaded onto a MP-TsOH cartridge (2500 mg). The cartridge was washed with MeOH then with 2M ammonia in MeOH and the solvent reduced in vacuo to afford 4-(4,4,5,5- tetramethyl-1,3,2-dioxaborolan-2-yl)-1H-pyrrolo[2,3-b]pyridine (0.394 g, 1.62 mmol, 48%) of a brown solid. LCMS (2) Rt: 1.39 min; m/z (ES+) 245.

Step c—tert-butyl 4-(4-(4-(ethoxycarbonyl)-2-(1H-pyrrolo[2,3-b]pyridin-4-yl)oxazol-5-yl)phenyl)piperazine-1-carboxylate

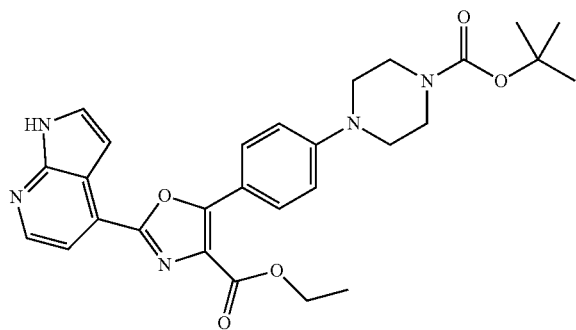 [SMILES: CCOC(=O)c1nc(-c2ccnc3[nH]ccc23)oc1-c1ccc(N2CCN(C(=O)OC(C)(C)C)CC2)cc1]

To a mixture of tert-butyl 4-(4-(4-(ethoxycarbonyl)-2-iodooxazol-5-yl)phenyl)piperazine-1-carboxylate (0.080 g, 0.15 mmol), 4-(4,4,5,5-tetramethyl-1,3,2-dioxaborolan-2-yl)-1H-pyrrolo[2,3-b]pyridine (0.093 g, 0.38 mmol) and sodium carbonate (0.048 g, 0.45 mmol) in toluene (0.81 ml), ethanol (0.49 ml) and water (0.23 ml) was added bis(triphenylphosphine)palladium (II) chloride (0.005 g, 0.007 mmol) and the resulting mixture irradiated in the microwave at 120° C. for 60 minutes. The reaction mixture was diluted with EtOAc and washed with H₂O. The organic phase was passed through a MP-SH cartridge, dried over MgSO₄ and the solvent removed in vacuo. The residue was purified by silica gel column chromatography using a 0-100% EtOAc in hexane gradient to afford tert-butyl 4-(4-(4-(ethoxycarbonyl)-2-(1H-pyrrolo[2,3-b]pyridin-4-yl)oxazol-5-yl)phenyl)piperazine-1-carboxylate (0.070 g, 0.123 mmol, 81%) as a yellow solid. ¹H NMR (CDCl₃) δ 1.46 (3H, t), 1.49 (9H, s), 3.31 (4H, m), 3.61 (4H, m), 4.47 (2H, q), 7.00 (2H, d), 7.24 (1H, m), 7.55 (1H, m), 7.90 (1H, d), 8.18 (2H, d), 8.46 (1H, d), 10.68 (1H, br s). LCMS (3) Rt: 2.63 min; m/z (ES+) 518.

Step d—5-(4-(piperazin-1-yl)phenyl)-2-(1H-pyrrolo[2,3-b]pyridin-4-yl)oxazole-4-carboxamide

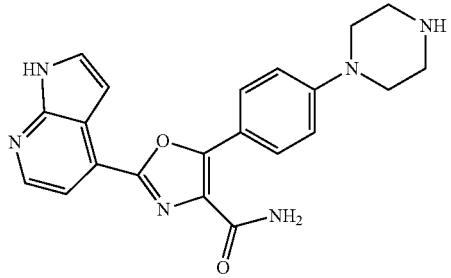 [SMILES: NC(=O)c1nc(-c2ccnc3[nH]ccc23)oc1-c1ccc(N2CCNCC2)cc1]

Prepared from tert-butyl 4-(4-(4-(ethoxycarbonyl)-2-(1H-pyrrolo[2,3-b]pyridin-4-yl)oxazol-5-yl)phenyl)piperazine-1-carboxylate according to the method described in example M-12 step d from the hydrolysis using KOH onwards. The final product was purified using preparative HPLC to yield the desired compound as the formate salt. ¹H NMR (DMSO) δ 2.87 (4H, m), 3.24 (4H, m), 7.06 (2H, d), 7.30 (1H, m), 7.59 (1H, m), 7.71 (1H, m), 7.76 (1H, d), 7.87 (1H, m), 8.31 (3H, m), 8.40 (1H, d), 12.02 (1H, s). LCMS (2) Rt: 1.88 min; m/z (ES+) 389.

General Method N

General Method N comprises the series of reactions set out in Scheme 8 above.

Example N-1

5-(4-methoxyphenyl)-2-(1H-pyrazol-5-yl)oxazole-4-carboxamide

Step a—2-iodo-5-(4-methoxyphenyl)oxazole-4-carboxylic acid

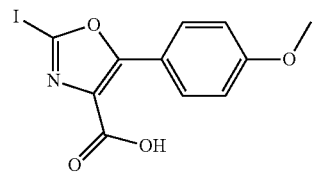 [SMILES: COc1ccc(-c2oc(I)nc2C(=O)O)cc1]

To a solution of ethyl 2-iodo-5-(4-methoxyphenyl)oxazole-4-carboxylate (1.00 g, 2.7 mmol) in DCE (25 mL) was added trimethyl tin hydroxide (1.70 g, 9.4 mmol) and the resultant mixture stirred at 80° C. for 3 hours. Trimethyl tin hydroxide (0.24 g, 1.3 mmol) was then added and the reaction stirred at 80° C. overnight. The reaction was cooled to room temperature and extracted with DCM. The organic phase was washed with 1M aqueous HCl and brine, dried over MgSO₄ and the solvent removed in vacuo to give 2-iodo-5-(4-methoxyphenyl)oxazole-4-carboxylic acid (0.92 g, 2.7 mmol, 99%) as a white solid which was used without further purification. ¹H NMR (CDCl₃) δ 3.88 (3H, s), 6.99 (2H, d), 8.13 (2H, d). LCMS (1) Rt: 1.03 min; m/z (ES+) 346.

Step b—2-iodo-5-(4-methoxyphenyl)oxazole-4-carboxamide

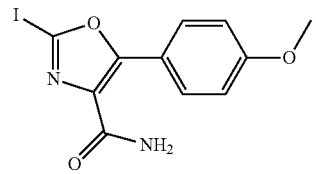 [SMILES: COc1ccc(-c2oc(I)nc2C(N)=O)cc1]

To a solution 2-iodo-5-(4-methoxyphenyl)oxazole-4-carboxylic acid (0.92 g, 2.7 mmol) in DCM (20 mL) and DMF (10 mL) was added hydroxybenzotriazole monohydrate (0.44 g, 2.9 mmol) followed by 0.5M ammonia in dioxane (22 mL, 11.0 mmol) and 1-(3-(dimethylamino)propyl)-3-ethyl-carbodiimide hydrochloride (0.77 g, 4.0 mmol) and the reaction stirred at room temperature overnight. EtOAc was then added and the mixture washed with brine. The organic phase was dried over MgSO₄ and the solvent removed in vacuo. The residue was purified by silica gel column chromatography using gradient of 0-50% EtOAc in DCM to afford 2-iodo-5-(4-methoxyphenyl)oxazole-4-carboxamide (0.66 g, 1.9 mmol, 70%) as a yellow solid. ¹H NMR (CDCl₃) δ 3.79 (3H, s), 5.47 (1H, br. s), 6.90 (2H, d), 6.94 (1H, br. s), 8.14 (2H, d). LCMS (1) Rt: 1.84 min; m/z (ES+) 345.

Step c—5-(4-methoxyphenyl)-2-(1H-pyrazol-5-yl)oxazole-4-carboxamide

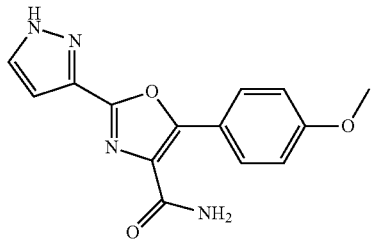 [SMILES: COc1ccc(-c2oc(-c3cc[nH]n3)nc2C(N)=O)cc1]

To a mixture of 2-iodo-5-(4-methoxyphenyl)oxazole-4-carboxamide (0.025 g, 0.07 mmol), 1H-pyrazole-5-boronic acid (0.020 g, 0.18 mmol) and [1,1'-bis(diphenylphosphino)ferrocene]dichloropalladium(II) (0.003 g, 0.004 mmol) in acetonitrile (2 mL) and DMSO (0.5 mL) was added a 1M sodium carbonate solution (0.1 mL, 0.1 mmol) and the reaction heated in the microwave at 150° C. for 15 minutes. A further portion of [1,1'-bis(diphenylphosphino)ferrocene]dichloro-palladium(II) (0.003 g, 0.004 mmol) was added and the mixture heated at 150° C. for a further 10 minutes in the microwave. The reaction was diluted with EtOAc and washed 1M sodium carbonate solution. The aqueous phase was extracted with EtOAc and the combined organic phases were washed with brine, dried over MgSO$_4$ and passed through a MP-SH resin cartridge (500 mg). The solvent was removed in vacuo and the residue purified by preparative HPLC to afford 5-(4-methoxyphenyl)-2-(1H-pyrazol-5-yl)oxazole-4-carboxamide (0.008 g, 0.03 mmol, 38%) as a white solid. $^1$H NMR (DMSO) δ 3.84 (3H, s), 6.90 (1H, br. d), 7.09 (2H, d), 7.62 (1H, br. s), 7.67 (1H, br. s), 7.97 (1H, br. s), 8.27 (2H, br. d), 13.50 (1H, br. s). LCMS (2) Rt: 1.98 min; m/z (ES+) 285.

In a similar manner as described in example N-1 the compounds described in examples N-2 to N-10 were prepared.

Example N-2

5-(4-methoxyphenyl)-2-(1H-pyrazol-4-yl)oxazole-4-carboxamide

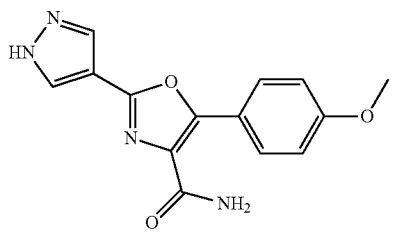 [SMILES: COc1ccc(-c2oc(-c3cn[nH]c3)nc2C(N)=O)cc1]

Prepared using 4-(4,4,5,5-tetramethyl-1,3,2-dioxaborolan-2-yl)-pyrazole-1-carboxylic acid tert-butyl ester which deprotected under the reaction conditions. $^1$H NMR (DMSO) δ 3.84 (3H, s), 7.07 (2H, d), 7.59 (1H, br. s), 7.62 (1H, br. s), 8.09 (1H, br. s), 8.30 (2H, d), 8.50 (1H, br. s), 13.49 (1H, br. s). LCMS (2) Rt: 1.91 min; m/z (ES+) 285.

Example N-3

2-(3-acetamidophenyl)-5-(4-methoxyphenyl)oxazole-4-carboxamide

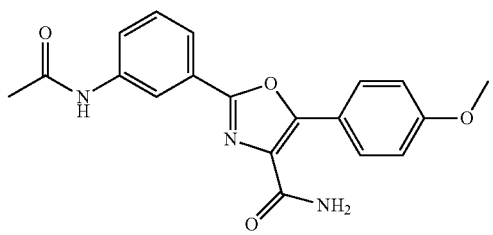 [SMILES: COc1ccc(-c2oc(-c3cccc(NC(C)=O)c3)nc2C(N)=O)cc1]

$^1$H NMR (DMSO) δ 2.09 (3H, s), 3.85 (3H, s), 7.11 (2H, d), 7.51 (1H, t), 7.66 (0.1H, br. s), 7.71 (1H, br. s), 7.76 (1H, ddd), 7.80 (1H, dt), 8.30 (2H, d), 8.36 (1H, br. t), 10.23 (1H, s). H,H LCMS (2) Rt: 2.43 min; m/z (ES+) 352.

Example N-4

5-(4-methoxyphenyl)-2-(4-(trifluoromethyl)phenyl)oxazole-4-carboxamide

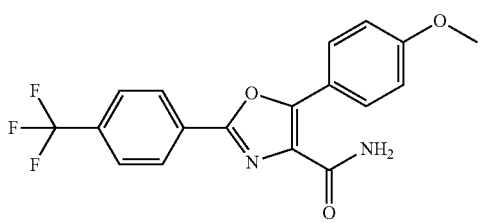 [SMILES: COc1ccc(-c2oc(-c3ccc(C(F)(F)F)cc3)nc2C(N)=O)cc1]

LCMS (2) Rt: 3.41 min; m/z 363.

Example N-5

2-(2-fluoro-4-(trifluoromethyl)phenyl)-5-(4-methoxyphenyl)oxazole-4-carboxamide

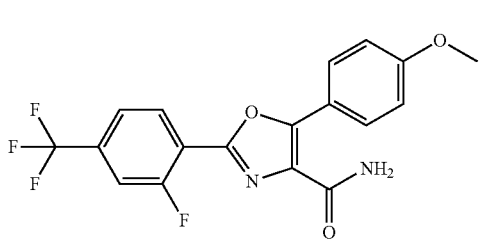 [SMILES: COc1ccc(-c2oc(-c3ccc(C(F)(F)F)cc3F)nc2C(N)=O)cc1]

LCMS (2) Rt: 3.31 min; m/z 381.

Example N-6

2-(2-fluoro-5-(trifluoromethyl)phenyl)-5-(4-methoxyphenyl)oxazole-4-carboxamide

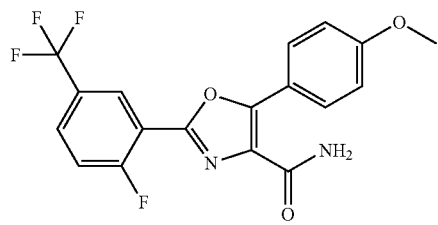 [SMILES: COc1ccc(-c2oc(-c3cc(C(F)(F)F)ccc3F)nc2C(N)=O)cc1]

LCMS (2) Rt: 3.34 min; m/z 381.

Example N-7

2-(2-fluoro-3-(trifluoromethyl)phenyl)-5-(4-methoxyphenyl)oxazole-4-carboxamide

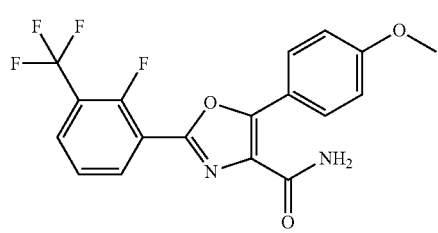 [SMILES: COc1ccc(-c2oc(-c3cccc(C(F)(F)F)c3F)nc2C(N)=O)cc1]

LCMS (2) Rt: 3.33 min; m/z 381.

Example N-8

5-(4-methoxyphenyl)-2-(3-(trifluoromethyl)phenyl)oxazole-4-carboxamide

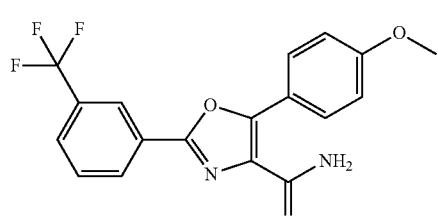

$^1$H NMR (DMSO) δ 3.85 (3H, s), 7.10 (2H, d), 7.67 (1H, br. s), 7.85 (1H, t), 7.90 (1H, br. s), 7.96 (1H, d), 8.40-8.44 (4H, m). LCMS (2) Rt: 3.38 min; m/z 363.

Example N-9

5-(4-methoxyphenyl)-2-p-tolyloxazole-4-carboxamide

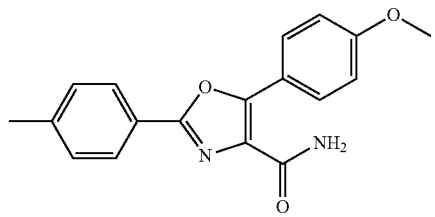

LCMS (2) Rt: 3.22 min; m/z 309.

Example N-10

5-(4-methoxyphenyl)-2-m-tolyloxazole-4-carboxamide

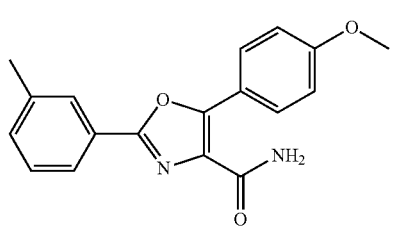 [SMILES: COc1ccc(-c2oc(-c3cccc(C)c3)nc2C(N)=O)cc1]

$^1$H NMR (DMSO) δ 2.43 (3H, s), 3.85 (3H, s), 7.09 (2H, d), 7.40 (1H, d), 7.48 (1H, t), 7.64 (1H, br. s), 7.76 (1H, br. s), 7.93 (1H, d), 7.97 (1H, s), 8.37 (2H, d). LCMS (2) Rt: 3.23 min; m/z 309.

General Method O

General Method O comprises the series of reactions set out in Scheme 9 above.

Example O-1

2-(2,6-difluorophenyl)-5-(phenylamino)oxazole-4-carboxamide

Step a—diethyl 2-(2,6-difluorobenzamido)malonate

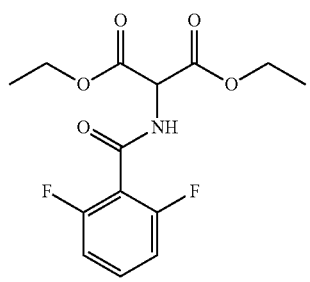 [SMILES: CCOC(=O)C(NC(=O)c1c(F)cccc1F)C(=O)OCC]

To a stirred suspension of 2-amino diethylmalonate hydrochloride (5.00 g, 23.6 mmol) in DCM (200 mL) at 0° C. was added diisopropylethylamine (4.00 mL, 49.1 mmol). To the resulting solution at 0° C. was added a solution of 2,6-difluorobenzoyl chloride (3.00 mL, 25.5 mmol) in DCM (50 mL), dropwise, and the reaction warmed to room temperature and stirred for 1 hour. The solution was washed with 1M aqueous HCl, brine, saturated aqueous sodium bicarbonate and brine, dried over MgSO$_4$ and the solvent removed in vacuo to afford diethyl 2-(2,6-difluorobenzamido)malonate (7.10 g, 22.5 mmol, 95%) as a white solid. $^1$H NMR (CDCl$_3$) δ 1.32 (6H, t), 4.31 (4H, m), 5.35 (1H, d), 6.97 (2H, t), 7.06 (1H, br. d), 7.41 (1H, m).

Step b—ethyl 2-(2,6-difluorophenyl)-5-ethoxyoxazole-4-carboxylate

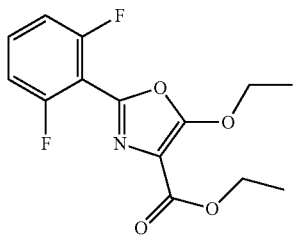 [SMILES: CCOC(=O)c1nc(-c2c(F)cccc2F)oc1OCC]

A solution of diethyl 2-(2,6-difluorobenzamido)malonate (5.00 g, 15.9 mmol) in trifluorotoluene (16 mL) and trifluoroacetic anhydride (8.33 mL, 129.7 mmol) was heated in the microwave at 160° C. for 5 minutes. The solvent was removed in vacuo and the residue purified by silica gel column chromatography using a gradient of 0-90% EtOAc in hexanes to afford ethyl 2-(2,6-difluorophenyl)-5-ethoxyoxazole-4-carboxylate (2.11 g, 7.1 mmol, 45%) as a white solid which was used without further purification. $^1$H NMR (CDCl$_3$) δ 1.39 (3H, t), 1.53 (3H, t), 4.39 (2H, q), 4.58 (2H, q), 7.02 (2H, t), 7.41 (1H, m).

Step c—2-(2,6-difluorophenyl)-5-ethoxyoxazole-4-carboxylic acid

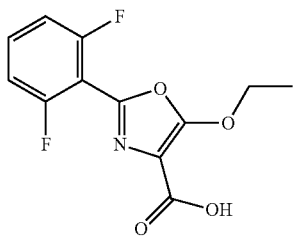 [SMILES: CCOc1oc(-c2c(F)cccc2F)nc1C(=O)O]

A suspension of ethyl 2-(2,6-difluorophenyl)-5-ethoxyoxazole-4-carboxylate (2.10 g, 7.1 mmol) in 1M aqueous potassium hydroxide and heated to 100° C. for 6 hours. The mixture was then cooled to 0° C. and acidified to pH 3 by 2M aqueous HCl. The resulting white solid was filtered, washed with water and dried in a vacuum oven to afford 2-(2,6-difluorophenyl)-5-ethoxyoxazole-4-carboxylic acid (1.28 g, 4.8 mmol, 67%). $^1$H NMR (CD$_3$OD) δ 1.52 (3H, t), 4.61 (2H, q), 7.19 (2H, t), 7.61 (1H, m). LCMS (1) Rt: 1.09 min; m/z (ES+) 270.

Step d—2-(2,6-difluorophenyl)-5-ethoxy-N-phenyloxazole-4-carboxamide

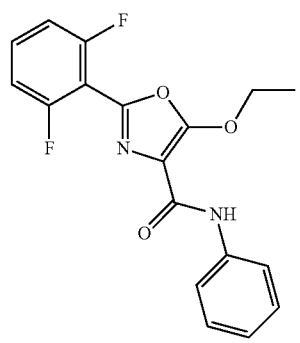 [SMILES: CCOc1oc(-c2c(F)cccc2F)nc1C(=O)Nc1ccccc1]

To a solution of 2-(2,6-difluorophenyl)-5-ethoxyoxazole-4-carboxylic acid (0.10 g, 0.37 mmol) and hydroxybenzotriazole monohydrate (0.06 g, 0.39 mmol) in DCM (4 mL) was added PS-carbodiimide resin (0.36 g, 0.45 mmol, 1.25 mmol/g) followed by aniline (39 uL, 0.43 mmol). The resulting mixture was stirred at room temperature for 4 hours when a further portion of aniline (7 uL, 0.08 mmol) was added and the reaction stirred at room temperature overnight. The mixture was filtered through a silica-carbonate cartridge, followed by a MP-TsOH resin cartridge which was rinsed with DCM and MeOH to afford 2-(2,6-difluorophenyl)-5-ethoxy-N-phenyloxazole-4-carboxamide (0.13 g) which was used without further purification. LCMS (1) Rt: 2.30; m/z (ES+) 345.

Step e—ethyl 2-(2,6-difluorophenyl)-5-(phenylamino)oxazole-4-carboxylate

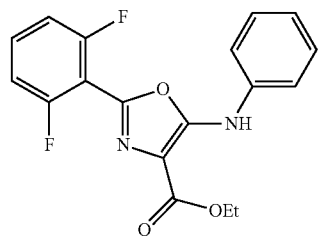 [SMILES: CCOC(=O)c1nc(-c2c(F)cccc2F)oc1Nc1ccccc1]

A solution of 2-(2,6-difluorophenyl)-5-ethoxy-N-phenyloxazole-4-carboxamide (0.13 g, 0.38 mmol) in trifluorotoluene was heated at 180° C. for 5 minutes in the microwave. The solvent was removed in vacuo to give ethyl 2-(2,6-difluorophenyl)-5-(phenylamino)oxazole-4-carboxylate (0.13 g) as a brown solid which was used without further purification. LCMS (1) Rt: 2.40 min; m/z (ES+) 345.

Step f—2-(2,6-difluorophenyl)-5-(phenylamino)oxazole-4-carboxylic acid

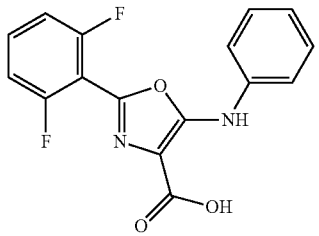 [SMILES: O=C(O)c1nc(-c2c(F)cccc2F)oc1Nc1ccccc1]

To a solution of ethyl 2-(2,6-difluorophenyl)-5-(phenylamino)oxazole-4-carboxylate (0.080 g, 0.23 mmol) in DCE (8 mL) was added trimethyltin hydroxide (0.300 g, 1.66 mmol) and the resulting solution stirred at 80° C. overnight. A further portion of trimethyltin hydroxide (0.168 g, 0.93 mmol) was added and the solution stirred at 80° C. overnight. The reaction was diluted with DCM and washed with 1M aqueous HCl and brine. The organic phase was dried over $MgSO_4$ and solvent removed in vacuo. The residue was purified by silica gel column chromatography using an 8% to 50% EtOAc in hexanes gradient followed by a 5% to 50% MeOH in DCM gradient to afford 2-(2,6-difluorophenyl)-5-(phenylamino)oxazole-4-carboxylic acid (0.030 g, 0.095 mmol, 41% three steps). LCMS (1) Rt: 1.46 min; m/z (ES+) 317.

Step g—2-(2,6-difluorophenyl)-5-(phenylamino)oxazole-4-carboxamide

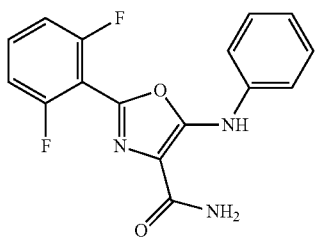 [SMILES: NC(=O)c1nc(-c2c(F)cccc2F)oc1Nc1ccccc1]

To a solution of 2-(2,6-difluorophenyl)-5-(phenylamino)oxazole-4-carboxylic acid (0.030 g, 0.095 mmol) in DCM (3 mL) was added hydroxybenzotriazole monohydrate (0.015 g, 0.098 mmol), 1-[3-(dimethylamino)propyl]-3-ethylcarbodiimide (0.020 g, 0.10 mmol) and 0.5M ammonia in dioxane (0.9 mL, 0.45 mmol). The reaction mixture was stirred at room temperature overnight. Further 1-[3-(dimethylamino)propyl]-3-ethylcarbodiimide (0.007 g, 0.038 mmol) and ammonia in dioxane (0.57 mL, 0.29 mmol) were added and the reaction stirred for 3 hours at room temperature. The solvent was evaporated in vacuo and the residue purified by preparative HPLC to afford 2-(2,6-difluorophenyl)-5-(phenylamino)oxazole-4-carboxamide (0.006 g, 0.019 mmol, 20%) as a white solid. $^1$H NMR (DMSO) δ 7.03 (1H, dd), 7.35 (4H, m), 7.38 (2H, br. s), 7.43 (2H, m), 7.64 (1H, m), 9.34 (1H, br. s). LCMS (2) Rt 2.87 min; m/z (ES+) 338 (M+Na), 299 (M-NH$_2$).

General Method P

General Method P comprises the series of steps set out in Scheme 10 above.

Example P-1

2-(2,6-difluorophenyl)-5-(4-methoxyphenylamino)oxazole-4-carboxamide

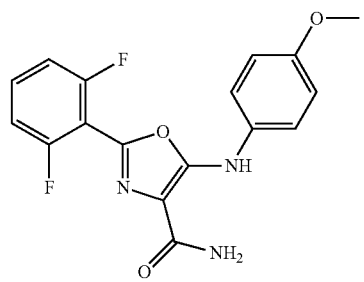 [SMILES: COc1ccc(Nc2oc(-c3c(F)cccc3F)nc2C(N)=O)cc1]

To a stirred, degassed solution of 5-bromo-2-(2,6-difluorophenyl)oxazole-4-carboxamide (0.125 g, 0.41 mmol) in trifluorotoluene (10.5 mL) was added tris(dibenzylideneacetone)dipalladium(0) (0.019 g, 0.02 mmol), (±)-2,2"-bis(diphenylphosphino)-1,1"-binaphthalene (0.026 g, 0.04 mmol), and sodium tert-butoxide (0.059 g, 0.62 mmol). This was followed by addition of p-anisidine (0.076 g, 0.62 mmol) after approximately 3 minutes stirring. The resulting reaction mixture was degassed, placed under an $N_2$ atmosphere and heated in the microwave at 160° C. for 20 minutes. The solution was then washed with 2M aqueous HCl and brine, dried over $MgSO_4$ and then passed through a MP-SH resin cartridge (500 mg). The solvent was removed in vacuo and the residue purified by preparative HPLC to afford 2-(2,6-difluorophenyl)-5-(4-methoxyphenylamino)oxazole-4-carboxamide (0.0037 g, 0.01 mmol, 8%) as a white solid. $^1$H NMR (DMSO) δ 3.74 (3H, s), 6.93 (2H, d), 7.29 (2H, br. s), 7.32 (2H, t), 7.37 (2H, d), 7.62 (1H, m), 9.17 (1H, br. s). LCMS (2) Rt: 2.80 min; m/z (ES+) 346.

General Method Q

General Method Q comprises the series of reactions set out in Scheme 11 above.

Example Q-1

2-(2,6-difluorophenyl)-5-(4-morpholinophenylamino)oxazole-4-carboxamide

Step a—2-(2,6-difluorophenyl)-5-(4-morpholinophenylamino)oxazole-4-carbonitrile

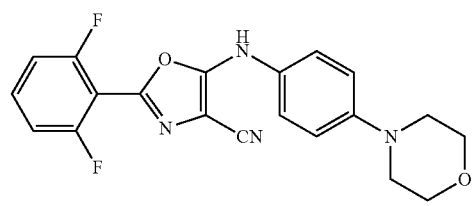 [SMILES: N#Cc1nc(-c2c(F)cccc2F)oc1Nc1ccc(N2CCOCC2)cc1]

A solution of palladium acetate (0.0057 g, 0.025 mmol) and (±)-2,2"-bis(diphenylphosphino)-1,1"-binaphthalene (0.015 g, 0.024 mmol) in DMF (7.1 mL) was stirred at room temperature for 3 minutes. Then 5-bromo-2-(2,6-difluorophenyl)oxazole-4-carbonitrile (0.100 g, 0.35 mmol), 4-morpholinoaniline (0.250 g, 1.40 mmol) and potassium phosphate tribasic (0.149 g, 0.70 mmol) were added and the mixture heated in the microwave for 3 minutes at 180° C. The reaction was diluted with EtOAc and washed with water. The organic phase was passed through a MP-SH resin cartridge, dried over MgSO₄ and the solvent removed in vacuo. The residue was purified by silica gel column chromatography using a gradient 10-100% EtOAc in hexanes to afford 2-(2,6-difluorophenyl)-5-(4-morpholinophenylamino)oxazole-4-carbonitrile (0.035 g, 0.09 mmol, 26%) as an off white solid. ¹H NMR (DMSO) δ 3.08 (4H, t), 3.74 (4H, t), 6.97 (2H, d), 7.24 (2H, d), 7.33 (2H, t), 7.64 (1H, m), 10.58 (1H, s). LCMS (2) Rt: 2.92 min; m/z (ES+) 383.

Step b—2-(2,6-difluorophenyl)-5-(4-morpholinophenylamino)oxazole-4-carboxamide

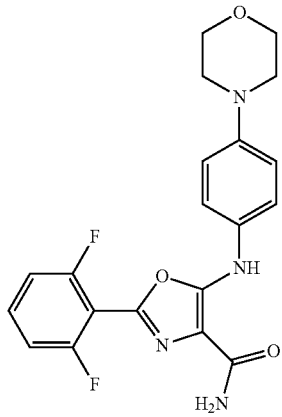 [SMILES: NC(=O)c1nc(-c2c(F)cccc2F)oc1Nc1ccc(N2CCOCC2)cc1]

A solution of 2-(2,6-difluorophenyl)-5-(4-morpholinophenylamino)oxazole-4-carbonitrile (0.035 g, 0.09 mmol) in concentrated sulfuric acid (1.7 mL) was stirred at room temperature for 1.5 hours. The solution was neutralised by pouring into saturated sodium bicarbonate solution. The aqueous phase was extracted with EtOAc. The combined organic phase was dried over MgSO₄ and the solvent removed in vacuo to afford 2-(2,6-difluorophenyl)-5-(4-morpholinophenylamino)oxazole-4-carboxamide (0.031 g, 0.077 mmol, 85%) as a yellow solid. ¹H NMR (DMSO) δ 3.06 (4H, t), 3.73 (4H, t), 6.94 (2H, d), 7.28 (2H, br. s), 7.32 (4H, m), 7.62 (1H, m), 9.13 (1H, s). LCMS (2) Rt: 2.60 min; m/z (ES+) 401.

Example Q-2

2-(2,6-difluorophenyl)-5-(3-morpholinophenylamino)oxazole-4-carboxamide

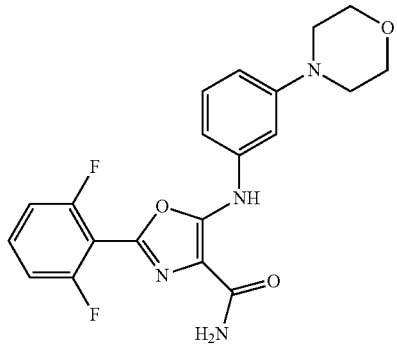 [SMILES: NC(=O)c1nc(-c2c(F)cccc2F)oc1Nc1cccc(N2CCOCC2)c1]

Prepared according to the procedure described in example Q-1. ¹H NMR (DMSO) δ 3.12 (4H, t), 3.75 (4H, t), 6.64 (1H, dd), 6.90 (1H, dd), 7.02 (1H, t), 7.18 (1H, t), 7.34 (2H, t), 7.36 (2H, br. s), 7.63 (1H, m), 9.20 (1H, s). LCMS (2) Rt: 2.59 mins; m/z (ES+) 401.

Example Q-3

2-(2,6-difluorophenyl)-5-(4-(methylsulfonyl)phenylamino)oxazole-4-carboxamide

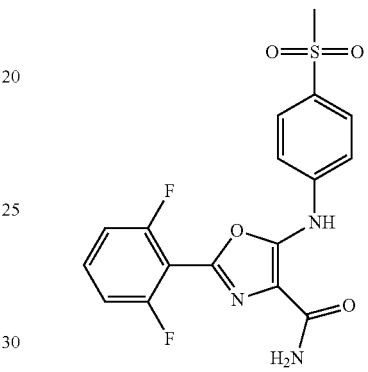

Prepared according to the procedure described in example Q-1. ¹H NMR (DMSO) δ 3.18 (3H, s), 7.35 (2H, t), 7.49 (2H, br. s), 7.58 (2H, d), 7.67 (1H, m), 7.83 (2H, d), 9.86 (1H, s). LCMS (2) Rt: 2.20 min; m/z (ES+) 394.

Example Q-4

2-(2,6-difluorophenyl)-5-(3-(methylsulfonyl)phenylamino)oxazole-4-carboxamide

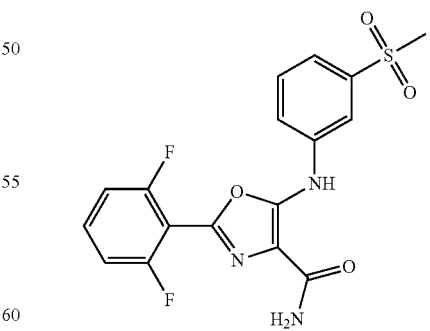

Prepared according to the procedure described in example Q-1. ¹H NMR (DMSO) δ 3.21 (3H, s), 7.34 (2H, t), 7.43 (2H, br. s), 7.53 (1H, d), 7.60 (1H, t, dd), 7.65 (1H, m), 7.73 (1H, d), 7.98 (1H, s), 9.74 (1H, s). LCMS (2) Rt: 2.21 min; m/z 394.

Example Q-5

2-(2,6-difluorophenyl)-5-(2-methoxyphenylamino)oxazole-4-carboxamide

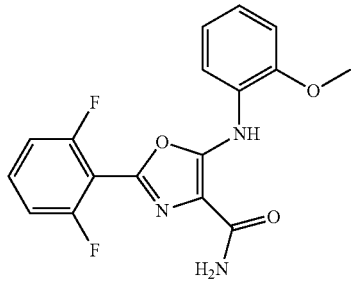 [SMILES: COc1ccccc1Nc1oc(-c2c(F)cccc2F)nc1C(N)=O]

To a suspension of 2-(2,6-difluorophenyl)-5-(2-methoxyphenylamino)oxazole-4-carbonitrile (0.018 g, 0.055 mmol, prepared according to the procedure described for Q-1 step a) in water (4.5 mL) was added 1M aqueous potassium hydroxide (0.27 mL, 0.27 mmol) and the resulting mixture stirred at 140° C. in the microwave for 15 minutes.

The solvent was removed in vacuo and the residue purified by preparative HPLC to afford 2-(2,6-difluorophenyl)-5-(2-methoxyphenylamino)oxazole-4-carboxamide (0.0104 g, 0.030 mmol, 55%). $^1$H NMR (DMSO) δ 3.92 (3H, s), 6.99 (1H, ddd), 7.04 (1H, ddd), 7.12 (1H, dd), 7.35 (2H, t), 7.42 (2H, br. s), 7.64 (1H, m), 7.68 (1H, dd), 9.48 (1H, s). LCMS (2) Rt: 2.86 min; m/z (ES+) 346.

Example Q-6

2-(2,6-difluorophenyl)-5-(3-methoxyphenylamino)oxazole-4-carboxamide

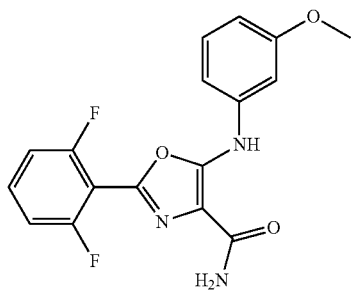 [SMILES: COc1cccc(Nc2oc(-c3c(F)cccc3F)nc2C(N)=O)c1]

Prepared according to the procedure described in example Q-5. $^1$H NMR (DMSO) δ 3.76 (3H, s), 6.61 (1H, dd), 7.00 (1H, dd), 7.07 (1H, t), 7.24 (1H, t), 7.34 (2H, t), 7.38 (2H, br. s), 7.63 (1H, m), 9.31 (1H, s). LCMS (2) Rt: 2.71 min; m/z (ES+) 346.

Example Q-7

2-(2,6-difluorophenyl)-5-(4-(4-methylpiperazin-1-yl)phenylamino)oxazole-4-carboxamide Step a—1-methyl-4-(4-nitrophenyl)piperazine

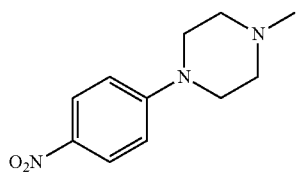

To a solution of 1-methylpiperazine (0.605 ml, 5.45 mmol) in DMF (6.25 ml) was added 4-fluoronitrobenzene (0.750 ml, 7.07 mmol) and potassium carbonate (1.13 g, 8.18 mmol) and the reaction mixture stirred at 90° C. overnight. The reaction was then cooled to room temperature, diluted with DCM and washed with water. The organic phase was dried over MgSO$_4$ and the solvent removed in vacuo. The residue was purified by silica gel silica chromatography using a 0-10% MeOH in DCM gradient to afford 1-methyl-4-(4-nitrophenyl)piperazine (1.03 g, 4.66 mmol, 85%) as a yellow solid. $^1$H NMR (DMSO) δ 2.37 (3H, s), 2.58 (4H, t), 3.45 (4H, t), 6.82 (2H, d), 8.12 (2H, d). LCMS (1) Rt: 1.63 min; m/z (ES+) 222.

Step b—4-(4-methylpiperazin-1-yl)benzenamine

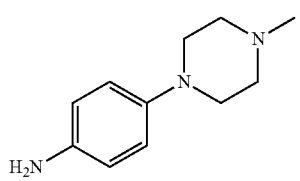 [SMILES: CN1CCN(c2ccc([N+](=O)[O-])cc2)CC1]

A solution of 1-methyl-4-(4-nitrophenyl)piperazine (1.03 g, 4.66 mmol) in MeOH (100 ml) was hydrogenated at 20° C. at atmospheric pressure using an H-Cube (flow rate at 1 ml/min and full hydrogen mode) using a Pd/C cartridge. The solvent was removed in vacuo to afford 4-(4-methylpiperazin-1-yl)benzenamine (0.82 g, 4.29 mmol, 92%) as an off-white solid. $^1$H NMR (CDCl$_3$) δ 2.37 (3H, s), 2.62 (4H, t), 3.09 (4H, t), 3.40 (2H, br. s), 6.65 (2H, d), 6.82 (2H, d). LCMS (1) Rt: 0.98 min; m/z (ES+) 192.

Step c—2-(2,6-difluorophenyl)-5-(4-(4-methylpiperazin-1-yl)phenylamino)oxazole-4-carboxamide

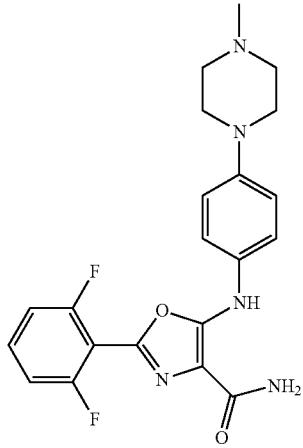 [SMILES: CN1CCN(c2ccc(Nc3oc(-c4c(F)cccc4F)nc3C(N)=O)cc2)CC1]

4-(4-Methylpiperazin-1-yl)benzenamine and 5-bromo-2-(2,6-difluorophenyl)oxazole-4-carbonitrile were reacted together following the procedure set out in example Q-1 to give an intermediate nitrile which was hydrolysed to give the title compound by the method of step b in example Q-1. $^1$H NMR (DMSO) δ 2.21 (3H, s), 2.44 (4H, t), 3.08 (4H, t), 6.92 (2H, d), 7.26-7.34 (6H, m), 7.60 (1H, m), 9.10 (1H, s). LCMS (2) Rt: 2.39 min; m/z (ES+) 414.

Example Q-8

2-(2,6-difluorophenyl)-5-(4-(2-morpholinoethoxy)phenylamino)oxazole-4-carboxamide

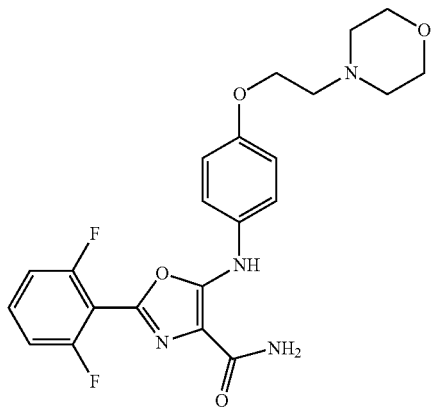 [SMILES: NC(=O)c1nc(-c2c(F)cccc2F)oc1Nc1ccc(OCCN2CCOCC2)cc1]

Prepared according to the procedure described in example Q-5. $^1$H NMR (DMSO) δ 2.46 (4H, m), 2.67 (2H, t), 3.58 (4H, t), 4.06 (2H, t), 6.93 (2H, d), 7.30 (2H, br. s), 7.32-7.36 (4H, m), 7.62 (1H, m), 9.14 (1H, br. s). LCMS (2) Rt: 2.42 min; m/z (ES+) 445.

Example Q-9

5-(4-(4-acetylpiperazin-1-yl)phenylamino)-2-(2,6-difluorophenyl)oxazole-4-carboxamide Step a—1-(4-(4-aminophenyl)piperazin-1-yl)ethanone

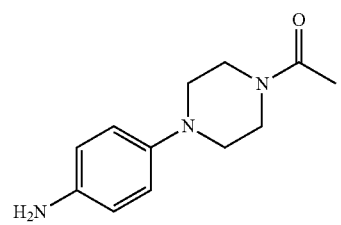 [SMILES: CC(=O)N1CCN(c2ccc(N)cc2)CC1]

The title compound was prepared according to the procedure described for the synthesis of 4-(4-methylpiperazin-1-yl)benzenamine. $^1$H NMR (CDCl$_3$) δ 2.13 (3H, s), 3.00 (4H, m), 3.61 (2H, t), 3.76 (2H, t), 3.20-3.80 (2H, br. s), 6.66 (2H, d), 6.82 (2H, d). LCMS (1) Rt 0.94 min; m/z (ES+) 220.

Step b—5-(4-(4-acetylpiperazin-1-yl)phenylamino)-2-(2,6-difluorophenyl)oxazole-4-carboxamide

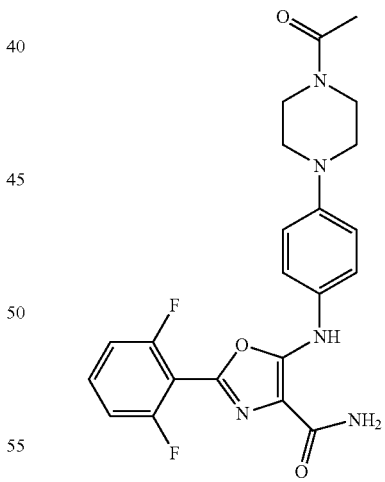

1-(4-(4-Aminophenyl)piperazin-1-yl)ethanone and 5-bromo-2-(2,6-difluorophenyl)oxazole-4-carbonitrile were reacted together following the procedure set out in example Q-1 to give an intermediate nitrile which was hydrolysed to give the title compound by the method of step b in example Q-1. $^1$H NMR (DMSO) δ 2.04 (3H, s), 3.04 (2H, t), 3.11 (2H, t), 3.57 (4H, m), 6.96 (2H, d), 7.29 (2H, br. s), 7.30-7.34 (4H, m), 7.62 (1H, m), 9.14 (1H, s). LCMS (2) Rt: 2.21 min; m/z (ES+) 442.

Example Q-10

2-(2,6-difluorophenyl)-5-(3-(2-morpholinoethoxy)phenylamino)oxazole-4-carboxamide

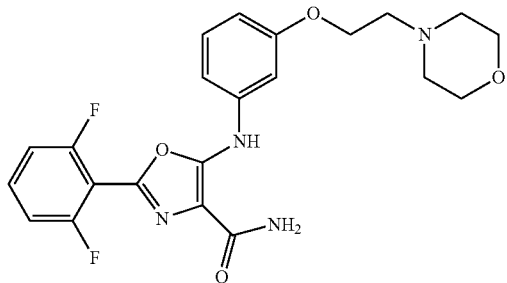 [SMILES: NC(=O)c1nc(-c2c(F)cccc2F)oc1Nc1cccc(OCCN2CCOCC2)c1]

Prepared according to the procedure described in example Q-5. ¹H NMR (DMSO) δ 2.47 (4H, br. t), 2.69 (2H, t), 3.58 (4H, t), 4.09 (2H, t), 6.61 (1H, dd), 7.00 (1H, dd), 7.08 (1H, t), 7.22 (1H, t), 7.33 (2H, t), 7.39 (2H, br. s), 7.64 (1H, m), 9.31 (1H, s). LCMS (2) Rt: 2.54 min; m/z (ES+) 445.

Example Q-11

2-(2,6-difluorophenyl)-5-(4-(piperazin-1-yl)phenylamino)oxazole-4-carboxamide

Step a—tert-butyl 4-(4-aminophenyl)piperazine-1-carboxylate

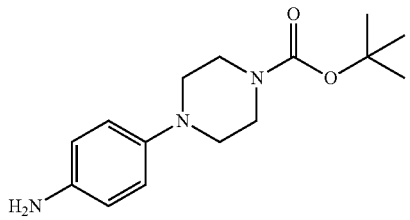 [SMILES: CC(C)(C)OC(=O)N1CCN(c2ccc(N)cc2)CC1]

The title compound was prepared according to the procedure described for the synthesis of 4-(4-methylpiperazin-1-yl)benzenamine. ¹H NMR (CDCl₃) δ 1.48 (9H, s), 3.00 (4H, m), 3.61 (4H, m), 6.66 (2H, d), 6.87 (2H, d). LCMS (1) Rt: 1.75 min; m/z (ES+) 222, 178.

Step b—2-(2,6-difluorophenyl)-5-(4-(piperazin-1-yl)phenylamino)oxazole-4-carboxamide

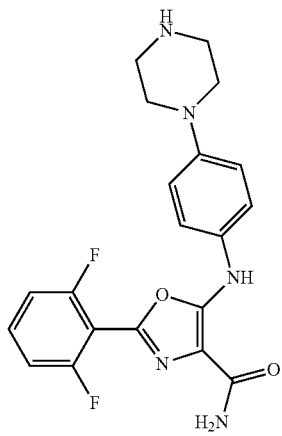 [SMILES: NC(=O)c1nc(-c2c(F)cccc2F)oc1Nc1ccc(N2CCNCC2)cc1]

The title compound was prepared according to the procedure described in example Q-1 from tert-butyl 4-(4-aminophenyl)piperazine-1-carboxylate. Boc deprotection occurred during the acid mediated nitrile hydrolysis. ¹H NMR (DMSO) δ 2.84 (4H, t), 3.01 (4H, m), 6.91 (2H, d), 7.27-7.34 (6H, m), 7.62 (1H, m), 9.10 (1H, br. s). LCMS (2) Rt: 2.09 min; m/z (ES+) 400.

Example Q-12

2-(2,6-difluorophenyl)-5-(3-(piperazin-1-yl)phenylamino)oxazole-4-carboxamide formate salt Step a—tert-butyl 4-(3-aminophenyl)piperazine-1-carboxylate

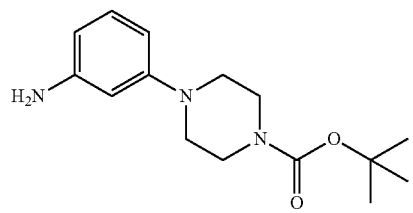 [SMILES: CC(C)(C)OC(=O)N1CCN(c2cccc(N)c2)CC1]

The title compound was prepared according to the procedure described for the synthesis of 4-(4-methylpiperazin-1-yl)benzenamine. The final product was purified by silica gel column chromatography using a 10-100% EtOAc in hexane gradient. ¹H NMR (CDCl₃) δ 1.48 (9H, s), 3.11 (4H, t), 3.57 (4H, t), 6.26 (1H, ddd), 6.30 (1H, m), 6.37 (1H, ddd), 7.06 (1H, t).

Step b—2-(2,6-difluorophenyl)-5-(3-(piperazin-1-yl)phenylamino)oxazole-4-carboxamide formate salt

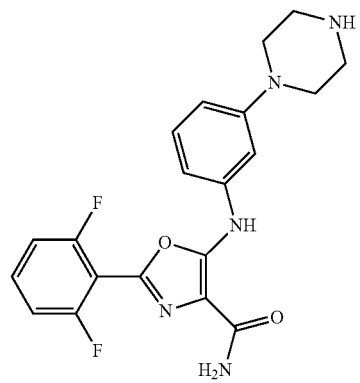 [SMILES: NC(=O)c1nc(-c2c(F)cccc2F)oc1Nc1cccc(N2CCNCC2)c1]

The title compound was prepared according to the procedure described in example Q-1 from tert-butyl 4-(3-aminophenyl)piperazine-1-carboxylate. Boc deprotection occurred during the acid mediated nitrile hydrolysis and the final product was isolated as the formate salt following preparative HPLC. ¹H NMR (DMSO) δ 2.95 (4H, m), 3.16 (4H, m), 6.64 (1H, dd), 6.89 (1H, dd), 7.02 (1H, t), 7.17 (1H, t), 7.34 (2H, t), 7.38 (2H, br. s), 7.63 (1H, m), 8.27 (1H, s, formate), 9.20 (1H, br. s). LCMS (2) Rt: 2.25 min; m/z (ES+) 400.

Example Q-13

2-(2,6-difluorophenyl)-5-(4-(piperidin-1-yl)phenylamino)oxazole-4-carboxamide

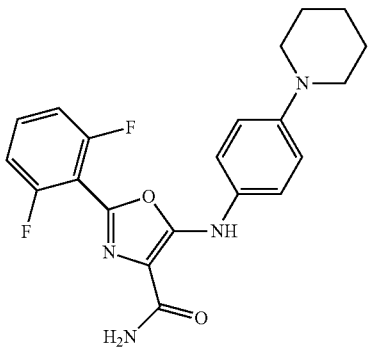 [SMILES: NC(=O)c1nc(-c2c(F)cccc2F)oc1Nc1ccc(N2CCCCC2)cc1]

Prepared according to the procedure described in example Q-1. $^1$H NMR (DMSO) 1.55 (6H, m), 3.07 (4H, t), 6.91 (2H, d), 7.29 (6H, m), 7.61 (1H, m), 9.07 (1H, br. s). LCMS (2) Rt: 3.27 min; m/z (ES+) 399.

Example Q-14

2-(2,6-difluorophenyl)-5-(4-(4-methylpiperazine-1-carbonyl)phenylamino) oxazole-4-carboxamide

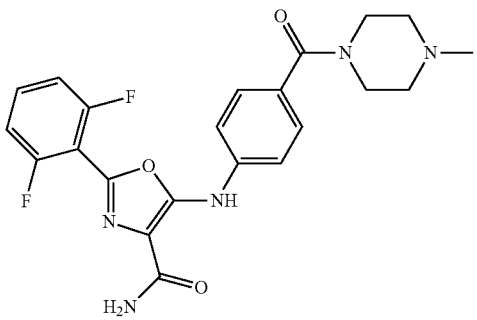 [SMILES: CN1CCN(C(=O)c2ccc(Nc3oc(-c4c(F)cccc4F)nc3C(N)=O)cc2)CC1]

Prepared according to the procedure described in example Q-1. $^1$H NMR (DMSO) δ 2.19 (3H, s), 2.31 (4H, m), 3.49 (4H, m), 7.40 (8H, m), 7.65 (1H, m), 9.54 (1H, br. s). LCMS (2) Rt: 2.07 min; m/z (ES+) 442.

Example Q-15

5-(4-(1,4-diazepan-1-yl)phenylamino)-2-(2,6-difluorophenyl)oxazole-4-carboxamide Step a—tert-butyl 4-(4-aminophenyl)-1,4-diazepane-1-carboxylate

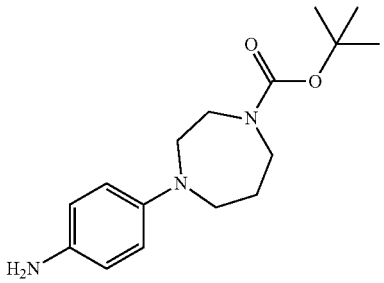 [SMILES: CC(C)(C)OC(=O)N1CCCN(c2ccc(N)cc2)CC1]

The title compound was prepared according to the procedure described for the synthesis of 4-(4-methylpiperazin-1-yl)benzenamine. LCMS (1) Rt: 1.85 min; m/z (ES+) 292.

Step b—5-(4-(1,4-diazepan-1-yl)phenylamino)-2-(2,6-difluorophenyl)oxazole-4-carboxamide

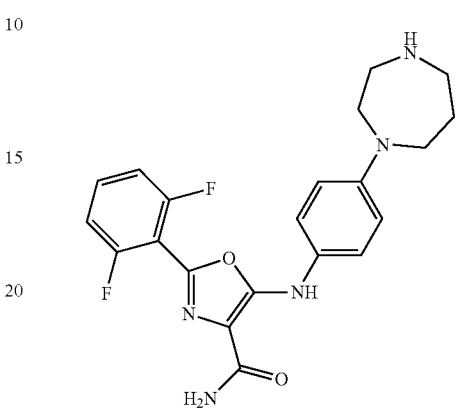

The title compound was prepared from tert-butyl 4-(4-aminophenyl)-1,4-diazepane-1-carboxylate according to the procedure described in example Q-1. $^1$H NMR (CDCl3) δ 1.93 (2H, m), 2.86 (2H, m), 3.06 (2H, m), 3.56 (4H, m), 5.60 (1H, br.s), 6.62 (1H, br.s), 6.69 (2H, d), 7.03 (2H, t), 7.27 (2H, d), 7.37 (1H, m), 8.63 (1H, br.s). LCMS (2) Rt: 2.56 min; m/z (ES+) 414.

Example Q-16

2-(2,6-difluorophenyl)-5-(4-(piperidin-4-yloxy)phenylamino)oxazole-4-carboxamide

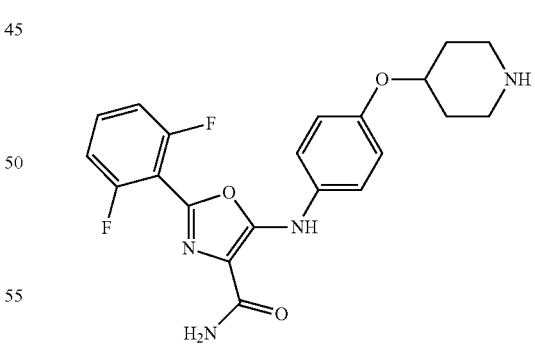

Prepared according to the procedure described in example Q-5, except the Boc group was removed by treatment with 4M HCl in dioxane, prior to the base hydrolysis of the nitrile. $^1$H NMR (CDCl3) δ 1.63 (2H, m), 1.96 (2H, m), 2.70 (2H, m), 3.09 (2H, m), 4.27 (1H, m), 5.31 (1H, br.s), 5.98 (1H, br.s), 6.46 (1H, br.s), 6.84 (2H, d), 6.97 (2H, m), 7.23 (2H, d), 7.33 (1H, m), 8.62 (1H, br.s). LCMS (2) Rt: 2.54 min; m/z (ES+) 415.

Example Q-17

5-(4-(4-aminopiperidin-1-yl)phenylamino)-2-(2,6-difluorophenyl)oxazole-4-carboxamide Step a—tert-butyl 1-(4-aminophenyl)piperidin-4-ylcarbamate

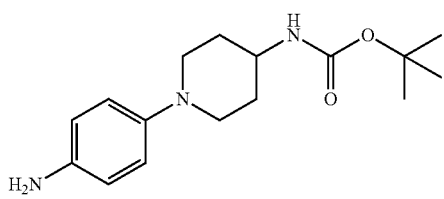 [SMILES: CC(C)(C)OC(=O)NC1CCN(c2ccc(N)cc2)CC1]

The title compound was prepared according to the procedure described for the synthesis of 4-(4-methylpiperazin-1-yl)benzenamine, except that the nitro group reduction was carried out in methanol using 20% w/w of 5% Pd/C under a hydrogen atmosphere for 4 h at room temperature. LCMS (2) Rt: 2.26 min; m/z (ES+) 292.

Step b—5-(4-(4-aminopiperidin-1-yl)phenylamino)-2-(2,6-difluorophenyl)oxazole-4-carboxamide

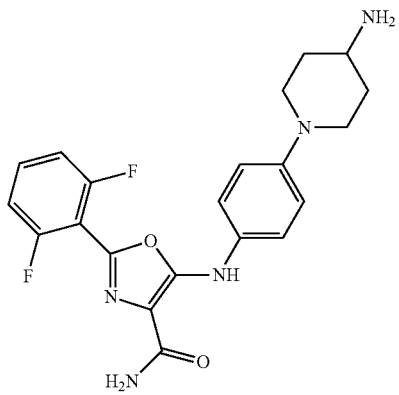 [SMILES: NC(=O)c1nc(-c2c(F)cccc2F)oc1Nc1ccc(N2CCC(N)CC2)cc1]

The title compound was prepared from tert-butyl 1-(4-aminophenyl)piperidin-4-ylcarbamate according to the procedure described in example Q-1. $^1$H NMR (CDCl3) δ 1.45 (2H, m), 1.85 (2H, m), 2.71 (3H, m), 3.52 (2H, m), 5.28 (1H, br.s), 6.43 (1H, br.s), 6.87 (2H, d), 6.96 (2H, t), 7.22 (2H, d), 7.31 (1H, m), 8.59 (1H, br.s). LCMS (2) Rt: 2.30 min; m/z (ES+) 414.

Example Q-18

5-(4-(4-(aminomethyl)piperidin-1-yl)phenylamino)-2-(2,6-difluorophenyl)oxazole-4-carboxamide Step a—tert-butyl (1-(4-aminophenyl)piperidin-4-yl)methylcarbamate

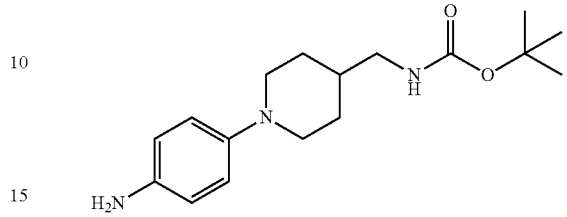

The title compound was prepared according to the procedure described for the synthesis of 4-(4-methylpiperazin-1-yl)benzenamine. $^1$H NMR (CDCl3) δ 1.10 (1H, m), 1.47 (9H, s), 1.79 (4H, m), 2.36 (1H, dd), 2.60 (1H, m), 3.11 (2H, m), 3.36 (2H, m), 4.62 (1H, br.s), 6.67 (2H, d), 6.84 (2H, d). LCMS (2) Rt: 2.45 min; m/z (ES+) 306.

Step b—5-(4-(4-(aminomethyl)piperidin-1-yl)phenylamino)-2-(2,6-difluorophenyl) oxazole-4-carboxamide

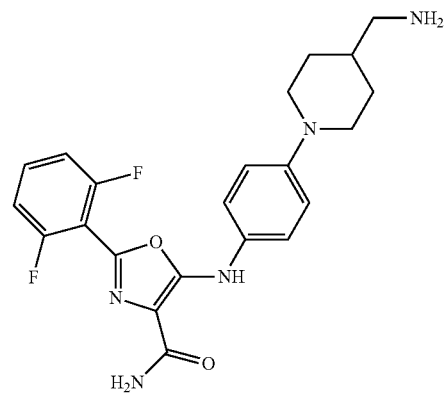 [SMILES: NCC1CCN(c2ccc(Nc3oc(-c4c(F)cccc4F)nc3C(N)=O)cc2)CC1]

The title compound was prepared from tert-butyl (1-(4-aminophenyl)piperidin-4-yl)methylcarbamate according to the procedure described in example Q-1. $^1$H NMR (CDCl3) δ 1.00 (1H, m), 1.72 (4H, m), 2.34 (1H, dd), 2.60 (3H, m), 3.44 (1H, m), 3.56 (1H, m), 5.37 (1H, br.s), 6.49 (1H, br.s), 6.88 (2H, d), 6.96 (2H, t), 7.22 (2H, d), 7.30 (1H, m), 8.60 (1H, br.s). LCMS (2) Rt: 2.49 min; m/z (ES+) 428.

Example Q-19

2-(2,6-difluorophenyl)-5-(4-(3-oxopiperazin-1-yl)phenylamino)oxazole-4-carboxamide Step a—4-(4-aminophenyl)piperazin-2-one

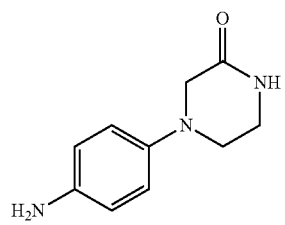 [SMILES: Nc1ccc(N2CCNC(=O)C2)cc1]

The title compound was prepared according to the procedure described for the synthesis of 4-(4-methylpiperazin-1-yl)benzenamine, except that the nitro reduction was carried out in methanol using 20% w/w of 5% Pd/C under a hydrogen atmosphere for 4 h at room temperature. $^1$H NMR (DMSO) δ 3.14 (2H, m), 3.24 (2H, m), 3.45 (2H, s), 4.09 (2H, br.s), 6.52 (2H, d), 6.71 (2H, d), 7.93 (1H, br.s). LCMS (2) Rt: 0.78 min; m/z (ES+) 192.

Step b—2-(2,6-difluorophenyl)-5-(4-(3-oxopiperazin-1-yl)phenylamino)oxazole-4-carboxamide

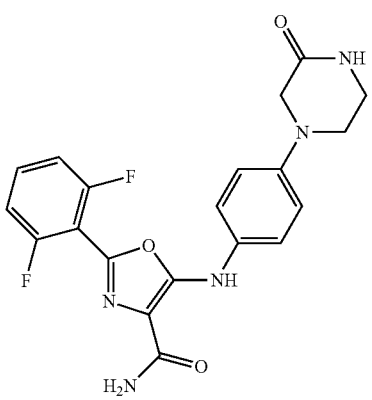 [SMILES: NC(=O)c1nc(-c2c(F)cccc2F)oc1Nc1ccc(N2CCNC(=O)C2)cc1]

The title compound was prepared from 4-(4-aminophenyl)piperazin-2-one according to the procedure described in example Q-1. $^1$H NMR (DMSO) δ 3.30 (4H, m), 3.66 (2H, s), 6.94 (2H, d), 7.31 (6H, m), 7.62 (1H, m), 8.03 (1H, br.s), 9.13 (1H, s). LCMS (2) Rt: 2.08 min; m/z (ES+) 414.

Example Q-20

2-(2,6-difluorophenyl)-5-(4-(dimethylcarbamoyl)phenylamino)oxazole-4-carboxamide

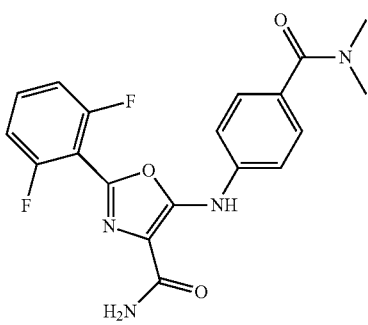 [SMILES: CN(C)C(=O)c1ccc(Nc2oc(-c3c(F)cccc3F)nc2C(N)=O)cc1]

Prepared according to the procedure described in example Q-1. $^1$H NMR (DMSO) δ 2.96 (6H, s), 7.41 (8H, m), 7.65 (1H, m), 9.53 (1H, s). LCMS (2) Rt: 2.24 min; m/z (ES+) 387.

Example Q-21

2-(2,6-difluorophenyl)-5-(4-(piperidine-1-carbonyl)phenylamino)oxazole-4-carboxamide

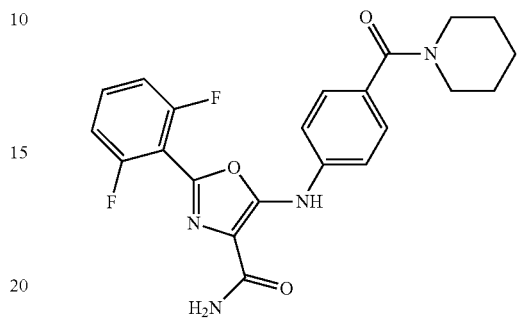

Prepared according to the procedure described in example Q-1. $^1$H NMR (CDCl3) δ 1.70 (6H, br. m), 3.57 (4H, br. m), 5.50 (1H, br.s), 6.60 (1H, br.s), 7.09 (2H, t), 7.43 (5H, m), 9.00 (1H, s). LCMS (2) Rt: 2.68 min; m/z (ES+) 427.

Example Q-22

2-(2,6-difluorophenyl)-5-(4-(piperazine-1-carbonyl)phenylamino)oxazole-4-carboxamide Step a—tert-butyl 4-(4-nitrobenzoyl)piperazine-1-carboxylate

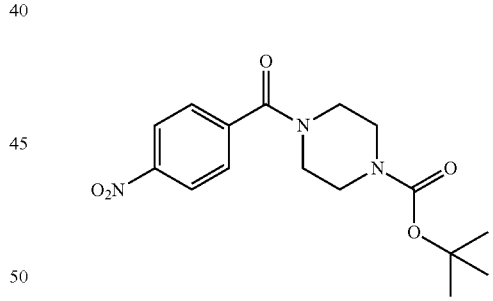

4-Nitrobenzoic acid (1.00 g, 6.00 mmol), tert-butyl 1-piperazinecarboxylate (1.10 g, 6.00 mmol), 1-(3-dimethylaminopropyl)-3-ethylcarbodiimide hydrochloride (1.70 g, 9.00 mmol) and N-methylmorpholine (1.30 ml, 12.00 mmol) were dissolved in dichloromethane (10 ml) and the reaction mixture stirred at 20° C. for 5 h. The reaction was then washed with saturated sodium bicarbonate solution and brine. The organic phase was dried over MgSO$_4$ and the solvent removed in vacuo. The residue was purified by silica gel column chromatography using a 0-50% EtOAc in hexane gradient to afford tert-butyl 4-(4-nitrobenzoyl)piperazine-1-carboxylate (1.88 g, 5.60 mmol, 94%) as a white solid. LCMS (1) Rt: 2.01 min; m/z (ES+) No M+H$^+$, but 280 (-tBu) and 236 (-Boc).

147

Step b—tert-butyl 4-(4-aminobenzoyl)piperazine-1-carboxylate

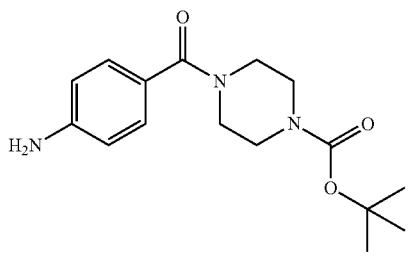 [SMILES: CC(C)(C)OC(=O)N1CCN(C(=O)c2ccc([N+](=O)[O-])cc2)CC1]

A solution of tert-butyl 4-(4-nitrobenzoyl)piperazine-1-carboxylate (1.00 g, 3.00 mmol) in MeOH (60 ml) was hydrogenated at 20° C. at atmospheric pressure using an H-Cube (flow rate at 1 ml/min and full hydrogen mode) using a Pd/C cartridge. The solvent was removed in vacuo to afford tert-butyl 4-(4-aminobenzoyl)piperazine-1-carboxylate (0.85 g, 2.79 mmol, 93%) as a white solid. $^1$H NMR (CDCl$_3$) δ 1.41 (9H, s), 3.38 (4H, m), 3.53 (4H, m), 4.07 (2H, br. s), 6.55 (2H, d), 7.17 (2H, d). LCMS (2) Rt: 2.14 min; m/z (ES+) 306.

Step c—2-(2,6-difluorophenyl)-5-(4-(piperazine-1-carbonyl)phenylamino)oxazole-4-carboxamide

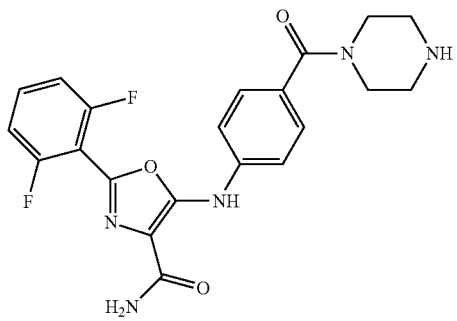 [SMILES: NC(=O)c1nc(-c2c(F)cccc2F)oc1Nc1ccc(C(=O)N2CCNCC2)cc1]

The title compound was prepared from tert-butyl 4-(4-aminobenzoyl)piperazine-1-carboxylate according to the procedure described in example Q-1. $^1$H NMR (CDCl3) δ 2.91 (4H, m), 3.61 (4H, m), 5.44 (1H, br.s), 6.62 (1H, br.s), 7.09 (2H, t), 7.45 (5H, m), 9.02 (1H, s). LCMS (2) Rt: 1.91 min; m/z (ES+) 428.

Example Q-23

2-(2-Fluorophenyl)-5-(4-morpholinophenylamino)oxazole-4-carboxamide

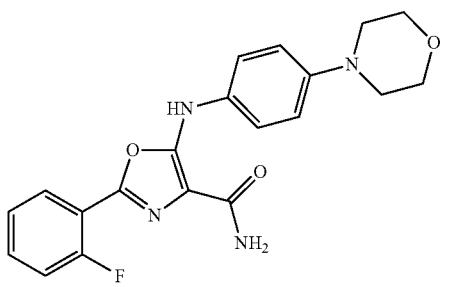 [SMILES: NC(=O)c1nc(-c2ccccc2F)oc1Nc1ccc(N2CCOCC2)cc1]

148

Prepared according to the procedure described in example Q-1. $^1$H NMR (DMSO) δ 3.07 (4H, br t), 3.74 (4H, br t), 6.90 (2H, d), 7.27 (2H, br s), 7.34-7.42 (4H, m), 7.50-7.55 (1H, m), 7.93 (1H, ddd), 9.08 (1H, s). LCMS (2) Rt: 2.59 min; m/z 383.

Example Q-24

5-(4-(1H-imidazol-1-yl)phenylamino)-2-(2,6-difluorophenyl)oxazole-4-carboxamide

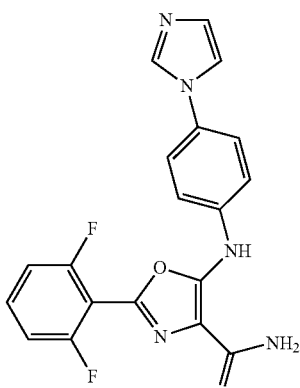

Prepared according to the procedure described in example Q-1. $^1$H NMR (CDCl$_3$) δ 5.42 (1H, br s), 6.61 (1H, br s), 7.08 (2H, dd), 7.20 (1H, s), 7.25 (1H, m), 7.39 (2H, d), 7.45 (1H, m), 7.50 (2H, d), 7.85 (1H, s), 9.00 (1H, s). LCMS (2) Rt: 2.33 min; m/z 382.

Example Q-25

2-(2,6-difluorophenyl)-5-(4-(sulfonamide)phenylamino)oxazole-4-carboxamide

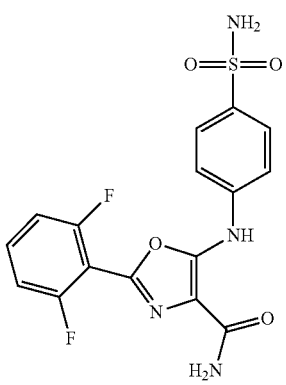 [SMILES: NC(=O)c1nc(-c2c(F)cccc2F)oc1Nc1ccc(S(N)(=O)=O)cc1]

Prepared according to the procedure described in example Q-1. $^1$H NMR (DMSO) δ 7.23 (2H, s), 7.34 (2H, t), 7.44 (2H, s), 7.52 (2H, d), 7.65 (1H, m), 7.74 (2H, d), 9.70 (1H, s). LCMS (2) Rt: 2.05 min; m/z 395.

Example Q-26

2-(2,6-difluorophenyl)-5-(4-(N',N'-dimethylsulfona-mide)phenylamino)oxazole-4-carboxamide

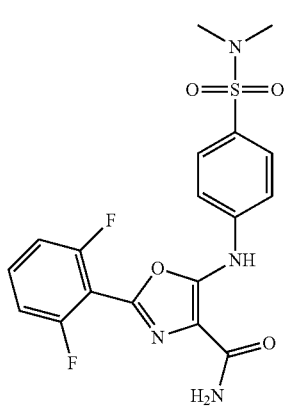 [SMILES: CN(C)S(=O)(=O)c1ccc(Nc2oc(-c3c(F)cccc3F)nc2C(N)=O)cc1]

Prepared according to the procedure described in example Q-1. $^1$H NMR (DMSO) δ 2.58 (6H, s), 7.34 (2H, t), 7.48 (2H, s), 7.58 (2H, d), 7.67 (3H, m), 9.83 (1H, s). LCMS (2) Rt: 2.60 min; m/z 423.

Example Q-27

2-(2,6-difluorophenyl)-5-(4-(N'-methylsulfonamide)phenylamino)oxazole-4-carboxamide

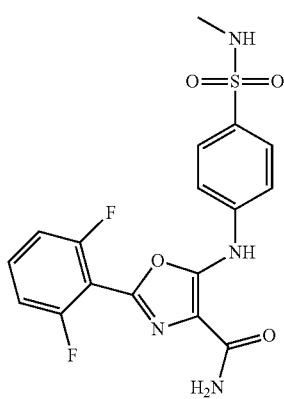 [SMILES: CNS(=O)(=O)c1ccc(Nc2oc(-c3c(F)cccc3F)nc2C(N)=O)cc1]

Prepared according to the procedure described in example Q-1. $^1$H NMR (DMSO) δ 2.39 (3H, d), 7.28 (1H, q), 7.33 (2H, t), 7.45 (2H, s), 7.54 (2H, d), 7.67 (3H, m), 9.76 (1H, s). LCMS (2) Rt: 2.30 min; m/z 409.

Example Q-28

2-(2,6-difluorophenyl)-5-(4-(piperidin-1-ylsulfonyl)phenylamino)oxazole-4-carboxamide

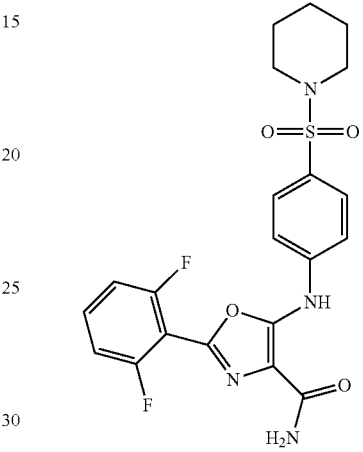

Prepared according to the procedure described in example Q-1. $^1$H NMR (DMSO) δ 1.33 (2H, m), 1.52 (4H, m), 2.84 (4H, m), 7.33 (2H, t), 7.47 (2H, s), 7.56 (2H, d), 7.63 (3H, m), 9.82 (1H, s). LCMS (2) Rt: 3.01 min; m/z 463.

Example Q-29

2-(2,6-difluorophenyl)-5-(4-(morpholinosulfonyl)phenylamino)oxazole-4-carboxamide

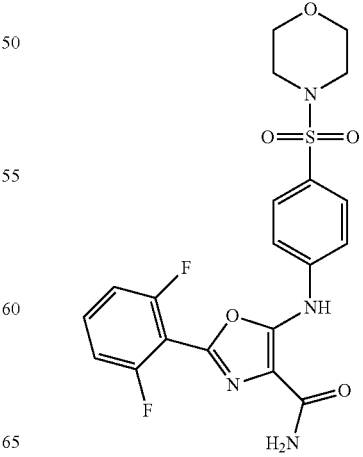

Prepared according to the procedure described in example Q-1. ¹H NMR (DMSO) δ 2.83 (4H, t), 3.61 (4H, t), 7.34 (2H, t), 7.48 (2H, s), 7.62 (5H, m), 9.86 (1H, s). LCMS (2) Rt: 2.55 min; m/z 465.

Example Q-30

5-(4-(1H-1,2,4-triazol-1-yl)phenylamino)-2-(2,6-difluorophenyl)oxazole-4-carboxamide

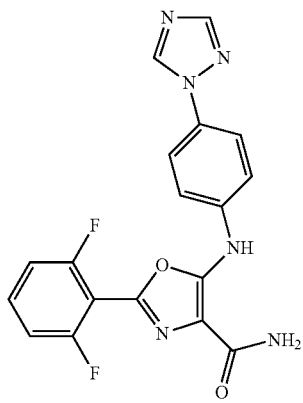

Prepared according to the procedure described in example Q-1. ¹H NMR (DMSO) δ 7.34 (2H, t), 7.40 (2H, br s), 7.61 (3H, m), 7.80 (2H, d), 8.21 (1H, s), 9.22 (1H, s), 9.57 (1H, br s). LCMS (2) Rt: 2.31 min; m/z 383.

Example Q-31

5-(4-(1H-tetrazol-1-yl)phenylamino)-2-(2,6-difluorophenyl)oxazole-4-carboxamide

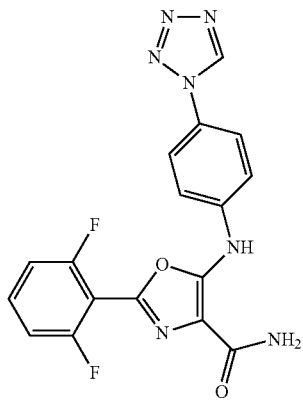 [SMILES: NC(=O)c1nc(-c2c(F)cccc2F)oc1Nc1ccc(-n2cnnn2)cc1]

Prepared according to the procedure described in example Q-1. ¹H NMR (DMSO) δ 7.39 (2H, t), 7.44 (2H, br s), 7.65 (3H, m), 7.85 (2H, d), 9.70 (1H, br s), 10.02 (1H, s). LCMS (2) Rt: 2.39 min; m/z 384.

Example Q-32

2-(2,6-difluorophenyl)-5-(4-(5-oxo-4,5-dihydro-1H-pyrazol-3-yl)phenylamino)oxazole-4-carboxamide

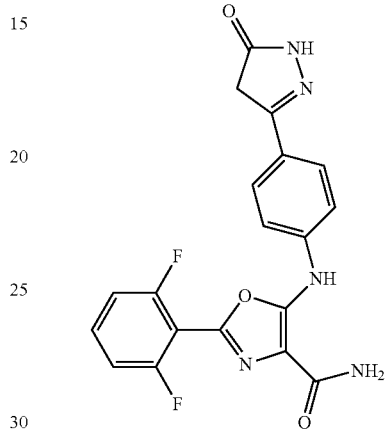

Prepared according to the procedure described in example Q-1. LCMS (2) Rt: 1.58 min; m/z 398.

Example Q-33

2-(2,6-difluorophenyl)-5-(4-(5-(hydroxymethyl)isoxazol-3-yl)phenylamino)oxazole-4-carboxamide

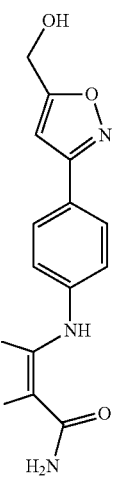

Prepared according to the procedure described in example Q-1. ¹H NMR (DMSO) δ 4.58 (2H, d), 5.70 (1H, t), 6.89 (1H, s), 7.35 (2H, t), 7.41 (2H, br s), 7.53 (2H, d), 7.65 (1H, m), 7.82 (2H, d) 9.58 (1H, br s). LCMS (2) Rt: 2.38 min; m/z 413.

Example Q-34

5-(4-(1H-tetrazol-5-yl)phenylamino)-2-(2,6-difluorophenyl)oxazole-4-carboxamide

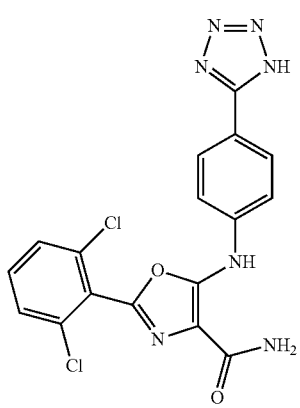 [SMILES: NC(=O)c1nc(-c2c(Cl)cccc2Cl)oc1Nc1ccc(-c2nnn[nH]2)cc1]

Prepared according to the procedure described in example Q-1. $^1$H NMR (DMSO) δ 7.35 (2H, t), 7.43 (2H, br s), 7.57 (2H, d), 7.65 (1H, m), 7.96 (2H, d), 9.63 (1H, br s). LCMS (2) Rt: 1.53 min; m/z 383.

Example Q-35

2-(2,6-dichlorophenyl)-5-(4-(piperazin-1-yl)phenylamino)oxazole-4-carboxamide

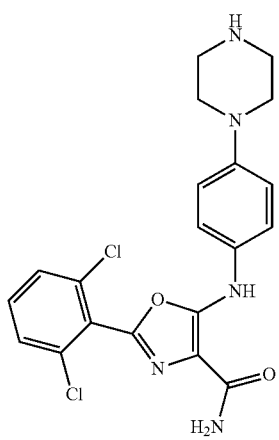 [SMILES: NC(=O)c1nc(-c2c(Cl)cccc2Cl)oc1Nc1ccc(N2CCNCC2)cc1]

Prepared according to the procedure described in example Q-11. $^1$H NMR (DMSO) δ 2.88 (4H, t), 3.02 (4H, t), 6.90 (2H, d), 7.20 (3H, m), 7.40 (1H, br s), 7.61-7.70 (3H, m), 9.05 (1H, br s). LCMS (2) Rt: 2.57 min; m/z 432.

Example Q-36

2-(2-chloro-6-fluorophenyl)-5-(4-(piperazin-1-yl)phenylamino)oxazole-4-carboxamide

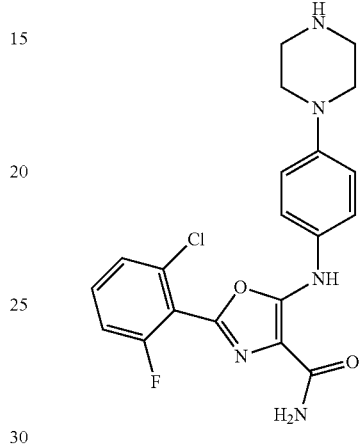

Prepared according to the procedure described in example Q-11. $^1$H NMR (DMSO) δ 2.88 (4H, t), 3.03 (4H, t), 6.91 (2H, d), 7.25 (3H, m), 7.35 (1H, br s), 7.46 (1H, t), 7.54 (1H, d), 7.64 (1H, m), 9.08 (1H, br s). LCMS (2) Rt: 2.44 min; m/z 416.

Example Q-37

2-(2,6-dimethylphenyl)-5-(4-(piperazin-1-yl)phenylamino)oxazole-4-carboxamide

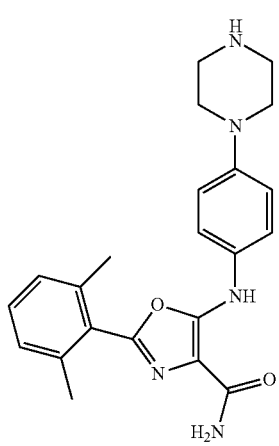 [SMILES: Cc1cccc(C)c1-c1nc(C(N)=O)c(Nc2ccc(N3CCNCC3)cc2)o1]

Prepared according to the procedure described in example Q-11. $^1$H NMR (CD$_3$OD) δ 2.35 (6H, s), 3.35 (8H, m, obscured by CD₃OD peak), 7.06 (2H, d), 7.20 (2H, d), 7.30-7.36 (3H, m), 8.56 (1H, br s). LCMS (2) Rt: 2.64 min; m/z 392.

Example Q-38

5-(1H-benzo[d]imidazol-1-yl)-2-(2,6-difluorophenyl)oxazole-4-carboxamide

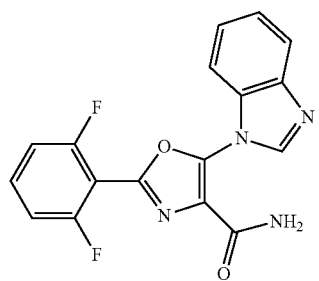 [SMILES: NC(=O)c1nc(-c2c(F)cccc2F)oc1-n1cnc2ccccc21]

Prepared according to the method described in example Q-1, except that the Buchwald coupling was performed at 150° C. for 5 minutes. ¹H NMR (DMSO) δ 7.37-7.44 (4H, m), 7.72-7.78 (2H, m), 7.80-7.83 (1H, m), 7.85 (1H, br. s), 7.88 (1H, br. s), 8.87 (1H, s). LCMS (2) Rt: 2.40 min; m/z (ES+) 341.

Example Q-39

2-(2,6-difluorophenyl)-5-(3,4-dimethoxyphenylamino)oxazole-4-carboxamide

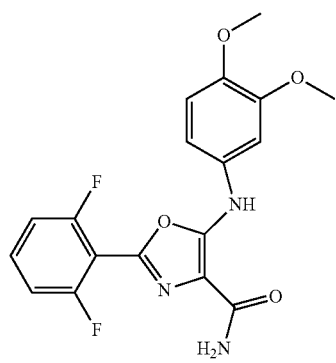 [SMILES: COc1ccc(Nc2oc(-c3c(F)cccc3F)nc2C(N)=O)cc1OC]

Prepared according to the procedure described in example Q-5. ¹H NMR (DMSO) δ 3.73 (3H, s), 3.77 (3H, s), 6.92 (1H, d), 6.98 (1H, dd), 7.14 (1H, d), 7.31 (2H, br s), 7.32 (2H, t), 7.61 (1H, tt), 9.16 (1H, s). LCMS (2) Rt: 2.53 min; m/z (ES+) 376.

Example Q-40

2-(2,6-difluorophenyl)-5-(3,4,5-trimethoxyphenylamino)oxazole-4-carboxamide

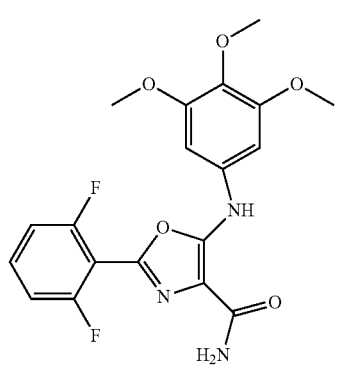 [SMILES: COc1cc(Nc2oc(-c3c(F)cccc3F)nc2C(N)=O)cc(OC)c1OC]

Prepared according to the procedure described in example Q-5. ¹H NMR (DMSO) δ 3.62 (3H, s), 3.78 (6H, s), 6.84 (2H, s), 7.33 (2H, t), 7.36 (2H, br s), 7.61 (1H, tt), 9.22 (1H, s). LCMS (2) Rt: 2.61 min; m/z (ES+) 406.

Example Q-41

5-(benzo[d][1,3]dioxol-5-ylamino)-2-(2,6-difluorophenyl)oxazole-4-carboxamide

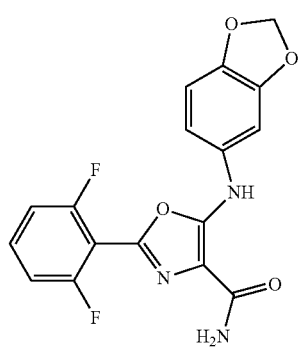 [SMILES: NC(=O)c1nc(-c2c(F)cccc2F)oc1Nc1ccc2c(c1)OCO2]

Prepared according to the procedure described in example Q-5. NMR (DMSO) δ 6.01 (2H, s), 6.89 (2H, s), 7.10 (1H, s), 7.31 (2H, br s), 7.32 (2H, t), 7.62 (1H, tt), 9.20 (1H, s). LCMS (2) Rt: 2.69 min; m/z (ES+) 360.

Example Q-42

2-(2,6-difluorophenyl)-5-(4-(trifluoromethoxy)phenylamino)oxazole-4-carboxamide

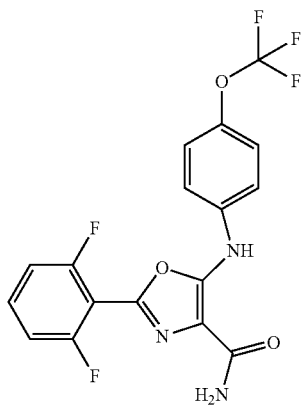 [SMILES: NC(=O)c1nc(-c2c(F)cccc2F)oc1Nc1ccc(OC(F)(F)F)cc1]

Prepared according to the procedure described in example Q-5. $^1$H NMR (DMSO) δ 7.34 (2H, t), 7.38 (2H, d), 7.40 (2H, br s), 7.52 (2H, d), 7.64 (1H, tt), 9.53 (1H, s). LCMS (2) Rt: 3.28 min; m/z (ES+) 400.

Example Q-43

2-(2,6-difluorophenyl)-5-(2-fluoro-4-(methylsulfonyl)phenylamino)oxazole-4-carboxamide

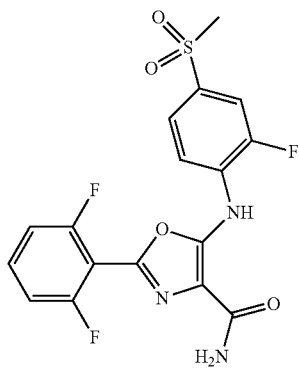 [SMILES: CS(=O)(=O)c1ccc(Nc2oc(-c3c(F)cccc3F)nc2C(N)=O)c(F)c1]

Prepared according to the procedure described in example Q-1. $^1$H NMR (DMSO) δ 3.25 (3H, s), 7.37 (2H, t), 7.62 (2H, br s), 7.68 (1H, tt), 7.77 (1H, dd), 7.82 (1H, t), 7.88 (1H, dd), 9.80 (1H, s). LCMS (2) Rt: 2.40 min; m/z (ES+) 412.

Example Q-44

2-(2,6-difluorophenyl)-5-(2-fluoro-5-(methylsulfonyl)phenylamino)oxazole-4-carboxamide

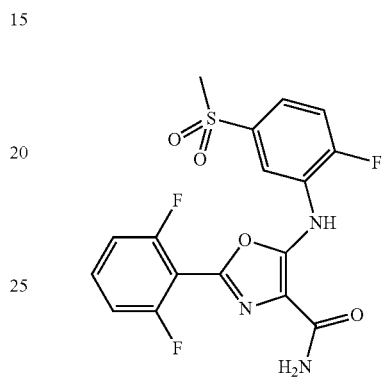

Prepared according to the procedure described in example Q-1. $^1$H NMR (DMSO) δ 3.24 (3H, s), 7.35 (2H, t), 7.56-7.70 (5H, m), 8.18 (1H, d), 9.67 (1H, s). LCMS (2) Rt: 2.30 min; m/z (ES+) 412.

Example Q-45

2-(2,6-difluorophenyl)-5-(pyridin-3-ylamino)oxazole-4-carboxamide

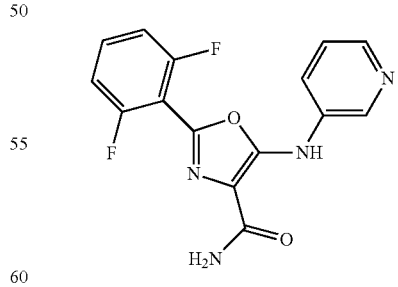

The title compound was prepared according to the procedure described in example Q-1. $^1$H NMR (CDCl$_3$) δ 5.49 (1H, br.s), 6.56 (1H, br.s), 7.00 (2H, t), 7.22 (1H, dd), 7.35 (1H, m), 7.72 (1H, m), 8.25 (1H, dd), 8.61 (1H, d), 8.83 (1H, br.s). LCMS (2) Rt: 2.09 min; m/z (ES+) 317.

Example Q-46

2-(2,6-difluorophenyl)-5-(4-(piperidin-4-yl)phenylamino)oxazole-4-carboxamide

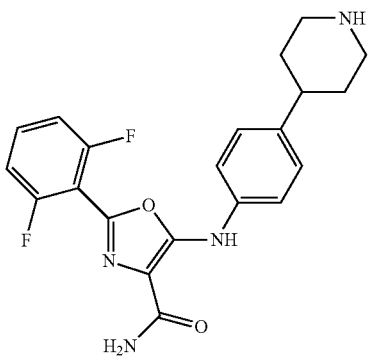 [SMILES: NC(=O)c1nc(-c2c(F)cccc2F)oc1Nc1ccc(C2CCNCC2)cc1]

The title compound was prepared according to the procedure described in example Q-1 from tert-butyl 4-(4-aminophenyl)piperidine-1-carboxylate. Boc deprotection occurred during the acid mediated nitrile hydrolysis. $^1$H NMR (CD$_3$OD) δ 1.79 (2H, m), 1.98 (2H, m), 2.79 (1H, m), 3.03 (2H, m), 3.39 (2H, m), 7.09 (2H, t), 7.18 (2H, d), 7.31 (2H, d), 7.46 (1H, m), 8.44 (1H, s). LCMS (2) Rt: 2.13 min; m/z (ES+) 399.

Example Q-47

2-(2,6-difluorophenyl)-5-(6-(piperazin-1-yl)pyridin-3-ylamino)oxazole-4-carboxamide

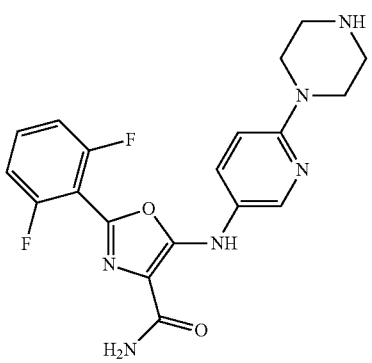 [SMILES: NC(=O)c1nc(-c2c(F)cccc2F)oc1Nc1ccc(N2CCNCC2)nc1]

The title compound was prepared according to the procedure described in example Q-1 from tert-butyl 4-(5-aminopyridin-2-yl)piperazine-1-carboxylate. Boc deprotection occurred during the acid mediated nitrile hydrolysis. $^1$H NMR (CD$_3$OD) δ 3.30 (4H, m), 3.74 (4H, m), 6.97 (1H, dd), 7.18 (2H, t), 7.55 (1H, m), 7.76 (1H, dd), 8.33 (1H, dd), 8.55 (1H, s). LCMS (2) Rt: 1.93 min; m/z (ES+) 401.

Example Q-48

2-(2,6-difluorophenyl)-5-(6-morpholinopyridin-3-ylamino)oxazole-4-carboxamide

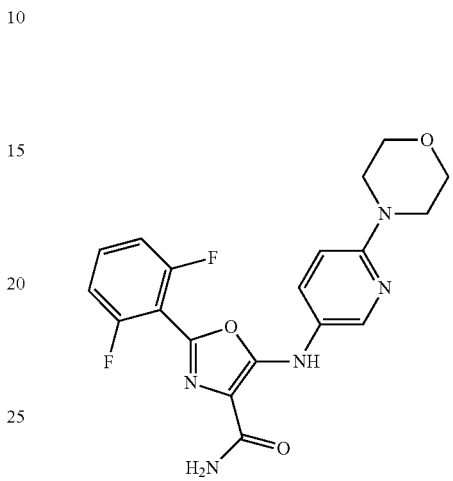

The title compound was prepared according to the procedure described in example Q-1. $^1$H NMR (CDCl$_3$) δ 3.46 (4H, m), 3.84 (4H, m), 6.69 (1H, d), 7.05 (2H, t), 7.40 (1H, m), 7.64 (1H, dd), 8.31 (1H, d). LCMS (2) Rt: 2.33 min; m/z (ES+) 402.

Example Q-49

2-(2,6-difluorophenyl)-5-(6-(4-methylpiperazin-1-yl)pyridin-3-ylamino)oxazole-4-carboxamide

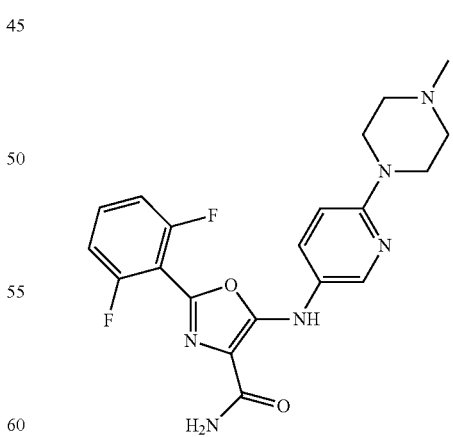

The title compound was prepared according to the procedure described in example Q-1. $^1$H NMR (CDCl$_3$) δ 2.43 (3H, s), 2.68 (4H, m), 3.58 (4H, m), 6.70 (1H, d), 7.04 (2H, t), 7.40 (1H, m), 7.62 (1H, dd), 8.29 (1H, d). LCMS (2) Rt: 2.21 min; m/z (ES+) 415.

Example Q-50

5-(4-((piperidin-4-ylmethyl)carbamoyl)phenylamino)-2-(2,6-difluorophenyl)oxazole-4-carboxamide

Step a—tert-butyl 4-((4-aminobenzamido)methyl)piperidine-1-carboxylate

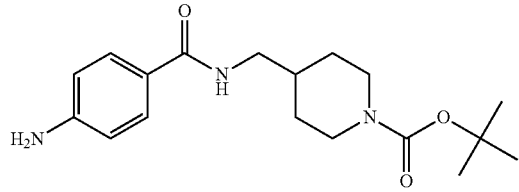 [SMILES: CC(C)(C)OC(=O)N1CCC(CNC(=O)c2ccc(N)cc2)CC1]

To a solution of 4-(aminomethyl)-Boc-piperidine (0.313 g, 1.458 mmol), 4-aminobenzoic acid (0.200 g, 1.458 mmol) and N-methyl morpholine (0.242 mL, 2.187 mmol) in dichloromethane (2 mL) was added 1-(3-dimethylaminopropyl)-3-ethylcarbodiimide hydrochloride (0.422 g, 2.187 mmol) and the reaction mixture stirred at room temperature overnight. The reaction was then washed with water and brine. The organic phase was dried over MgSO$_4$ and the solvent removed in vacuo. The residue was purified by silica gel column chromatography using a 0-100% EtOAc in hexane gradient to afford tert-butyl 4-((4-aminobenzamido)methyl)piperidine-1-carboxylate. LCMS (3) Rt: 1.91 min; m/z (ES+) 334.

Step b—tert-butyl 4-((4-(4-cyano-2-(2,6-difluorophenyl)oxazol-5-ylamino)benzamido)methyl)piperidine-1-carboxylate

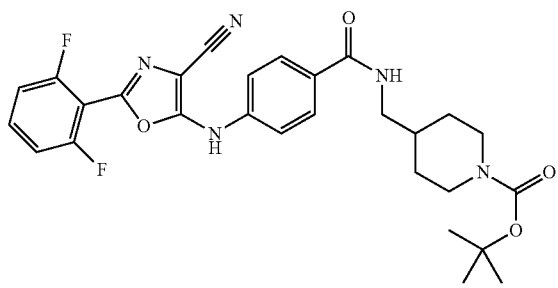 [SMILES: CC(C)(C)OC(=O)N1CCC(CNC(=O)c2ccc(Nc3oc(-c4c(F)cccc4F)nc3C#N)cc2)CC1]

A solution of tris(dibenzylideneacetone)dipalladium(0) (0.019 g, 0.021 mmol) and 9,9-dimethyl-4,5-bis(diphenylphosphino)xanthene (0.011 g, 0.021 mmol) in nBuOH:dioxane (1:1) (5 mL) was stirred at room temperature for 3 minutes. Then 5-bromo-2-(2,6-difluorophenyl)oxazole-4-carbonitrile (0.080 g, 0.281 mmol), tert-butyl 4-((4-aminobenzamido)methyl)piperidine-1-carboxylate (0.250 g, 1.40 mmol) and cesium carbonate (0.108 g, 0.561 mmol) were added and the mixture heated in the microwave for 3 minutes at 140° C. The reaction was diluted with EtOAc and washed with water. The organic phase was passed through a thiol resin cartridge, dried over MgSO$_4$ and the solvent removed in vacuo. The residue was purified by preparative HPLC to afford tert-butyl 4-((4-(4-cyano-2-(2,6-difluorophenyl)oxazol-5-ylamino)benzamido)methyl)piperidine-1-carboxylate (0.035 g, 0.09 mmol, 26%) as a light yellow solid. LCMS (2) Rt: 3.09 min; m/z (ES+) 538.

Step c—5-(4-((piperidin-4-ylmethyl)carbamoyl)phenylamino)-2-(2,6-difluorophenyl) oxazole-4-carboxamide

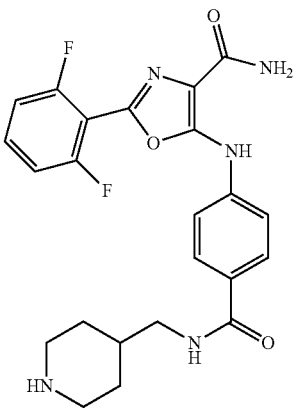 [SMILES: NC(=O)c1nc(-c2c(F)cccc2F)oc1Nc1ccc(C(=O)NCC2CCNCC2)cc1]

A solution of tert-butyl 4-((4-(4-cyano-2-(2,6-difluorophenyl)oxazol-5-ylamino)benzamido)methyl)piperidine-1-carboxylate (0.028 g, 0.052 mmol) in concentrated sulfuric acid (1 mL) was stirred at room temperature for 1.5 hours. The solution was neutralised by pouring into saturated sodium bicarbonate solution. The aqueous phase was then basified to pH14 with 5M NaOH and extracted with EtOAc. The combined organic phases were dried over MgSO$_4$ and the solvent removed in vacuo to afford 5-(4-((piperidin-4-ylmethyl)carbamoyl)phenylamino)-2-(2,6-difluorophenyl)oxazole-4-carboxamide (0.003 g, 0.007 mmol, 14%) as a yellow solid. $^1$H NMR (CD$_3$OD) δ 1.51 (2H, m), 2.00 (3H, m), 2.99 (2H, t), 3.35 (2H, m), 3.45 (2H, m), 7.22 (2H, t), 7.53 (2H, d), 7.60 (1H, m), 7.87 (2H, d), 8.55 (1H, br s). LCMS (2) Rt: 1.85 min; m/z (ES+) 456.

Example Q-51

5-(4-((3-aminopropyl)carbamoyl)phenylamino)-2-(2,6-difluorophenyl)oxazole-4-carboxamide

Step a—tert-butyl 3-(4-aminobenzamido)propylcarbamate

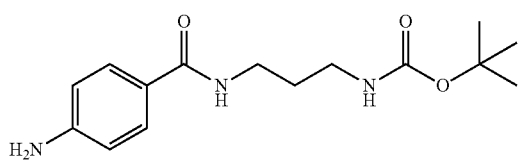 [SMILES: CC(C)(C)OC(=O)NCCCNC(=O)c1ccc(N)cc1]

The title compound was prepared according to the procedure described for the synthesis of tert-butyl 4-((4-aminobenzamido)methyl)piperidine-1-carboxylate. LCMS (3) Rt: 1.69 min; m/z (ES+) 294.

Step b—S-(4-((3-aminopropyl)carbamoyl)phenylamino)-2-(2,6-difluorophenyl)oxazole-4-carboxamide

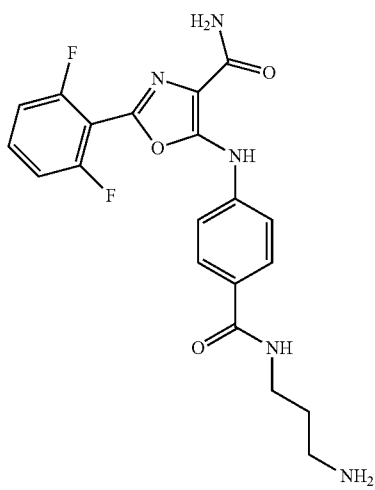 [SMILES: NCCCNC(=O)c1ccc(Nc2oc(-c3c(F)cccc3F)nc2C(N)=O)cc1]

Prepared according to the procedure described in example Q-50 (steps b and c). ¹H NMR (CD₃OD) δ, 1.97 (2H, quin), 3.01 (2H, t), 3.52 (2H, t), 7.22 (2H, t), 7.52 (2H, d), 7.60 (1H, m), 7.88 (2H, d), 8.57 (1H, br s). LCMS (2) Rt: 1.74 min; m/z (ES+) 416.

Example Q-52

5-(4-((2-aminoethyl)carbamoyl)phenylamino)-2-(2,6-difluorophenyl)oxazole-4-carboxamide Step a—tert-butyl 2-(4-aminobenzamido)ethylcarbamate

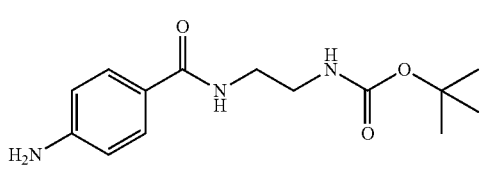 [SMILES: CC(C)(C)OC(=O)NCCNC(=O)c1ccc(N)cc1]

The title compound was prepared according to the procedure described for the synthesis of tert-butyl 4-((4-aminobenzamido)methyl)piperidine-1-carboxylate. LCMS (3) Rt: 1.60 min; m/z (ES+) 280.

Step b—S-(4-((2-aminoethyl)carbamoyl)phenylamino)-2-(2,6-difluorophenyl)oxazole-4-carboxamide

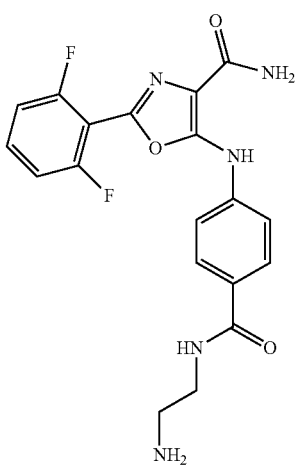 [SMILES: NCCNC(=O)c1ccc(Nc2oc(-c3c(F)cccc3F)nc2C(N)=O)cc1]

Prepared according to the procedure described in example Q-50 (steps b and c). ¹H NMR (CD₃OD) δ 3.17 (2H, t), 3.67 (2H, t), 7.22 (2H, t), 7.53 (2H, d), 7.60 (1H, m), 7.91 (2H, d), 8.56 (1H, s). LCMS (2) Rt: 1.74 min; m/z (ES+) 402.

Example Q-53

(R)-2-(2,6-difluorophenyl)-5-(4-(piperidin-3-ylcarbamoyl)phenylamino)oxazole-4-carboxamide Step a—(R)-tert-butyl 3-(4-aminobenzamido)piperidine-1-carboxylate

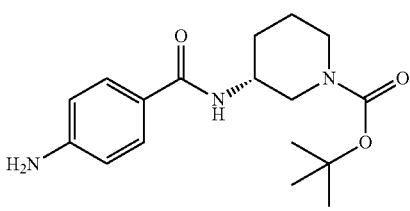 [SMILES: CC(C)(C)OC(=O)N1CCC[C@@H](NC(=O)c2ccc(N)cc2)C1]

The title compound was prepared according to the procedure described for the synthesis of tert-butyl 4-((4-aminobenzamido)methyl)piperidine-1-carboxylate. LCMS (3) Rt: 1.88 min; m/z (ES+) 320.

Step b—(R)-2-(2,6-difluorophenyl)-5-(4-(piperidin-3-ylcarbamoyl)phenylamino)oxazole-4-carboxamide

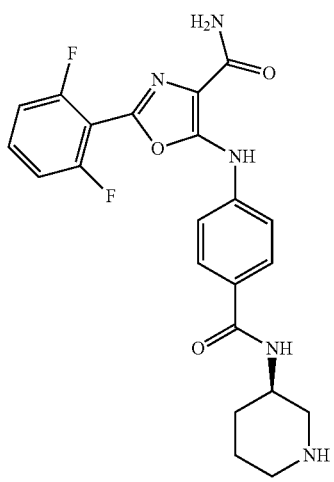 [SMILES: NC(=O)c1nc(-c2c(F)cccc2F)oc1Nc1ccc(C(=O)N[C@@H]2CCCNC2)cc1]

Prepared according to the procedure described in example Q-50 (steps b and c). ¹H NMR (DMSO) δ 1.50 (2H, t), 1.71 (1H, m), 1.84 (1H, m), 2.57 (1H, m), 2.92 (1H, d), 3.07 (1H, d), 3.90 (2H, m), 7.34 (2H, t), 7.43 (2H, br s), 7.47 (2H, d), 7.64 (1H, m), 7.83 (2H, d), 8.14 (1H, d), 8.32 (1H, s). LCMS (2) Rt: 1.96 min; m/z (ES+) 442.

Example Q-54

(S)-2-(2,6-difluorophenyl)-5-(4-(piperidin-3-ylcarbamoyl)phenylamino)oxazole-4-carboxamide Step a—(S)-tert-butyl 3-(4-aminobenzamido)piperidine-1-carboxylate

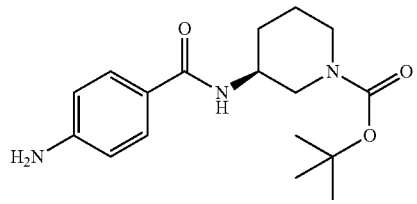 [SMILES: CC(C)(C)OC(=O)N1CCC[C@H](NC(=O)c2ccc(N)cc2)C1]

The title compound was prepared according to the procedure described for the synthesis of tert-butyl 4-((4-aminobenzamido)methyl)piperidine-1-carboxylate. LCMS (3) Rt: 1.89 min; m/z (ES+) 320.

Step b—(S)-2-(2,6-difluorophenyl)-5-(4-(piperidin-3-ylcarbamoyl)phenylamino)oxazole-4-carboxamide

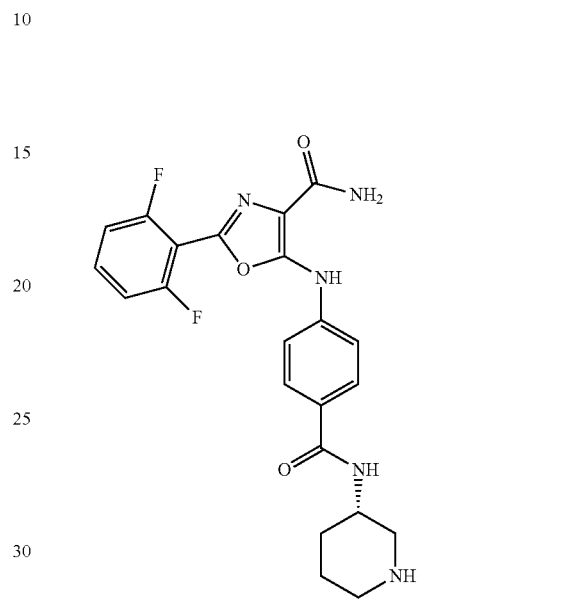

Prepared according to the procedure described in example Q-50 (steps b and c). ¹H NMR (DMSO) δ 1.50 (2H, t), 1.72 (1H, m), 1.84 (1H, m), 2.57 (1H, m), 2.91 (1H, d), 3.07 (1H, d), 3.92 (2H, m), 7.34 (2H, t), 7.43 (2H, br s), 7.47 (2H, d), 7.64 (1H, m), 7.83 (2H, d), 8.15 (1H, d), 8.31 (1H, s). LCMS (2) Rt: 1.95 min; m/z (ES+) 442.

Example Q-55

(R)-5-(4-((piperidin-3-ylmethyl)carbamoyl)phenylamino)-2-(2,6-difluorophenyl)oxazole-4-carboxamide Step a—(R)-tert-butyl 3-((4-aminobenzamido)methyl)piperidine-1-carboxylate

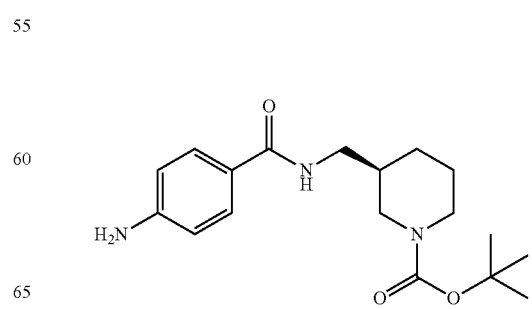

The title compound was prepared according to the procedure described for the synthesis of tert-butyl 4-((4-aminobenzamido)methyl)piperidine-1-carboxylate. LCMS (3) Rt: 1.93 min; m/z (ES+) 334.

Step b—(R)-5-(4-((piperidin-3-ylmethyl)carbamoyl)phenylamino)-2-(2,6-difluorophenyl) oxazole-4-carboxamide

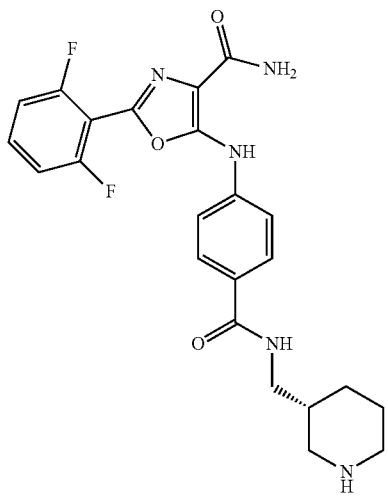 [SMILES: NC(=O)c1nc(-c2c(F)cccc2F)oc1Nc1ccc(C(=O)NC[C@@H]2CCCNC2)cc1]

Prepared according to the procedure described in example Q-50 (steps b and c). ¹H NMR (CD₃OD) δ 1.46 (2H, m), 1.74 (1H, m), 1.96 (2H, m), 2.10 (1H, m), 2.75 (1H, t), 2.92 (1H, t), 3.36 (3H, m), 7.21 (2H, t), 7.51 (2H, d), 7.58 (1H, m), 7.86 (2H, d), 8.52 (1H, br s). LCMS (2) Rt: 1.85 min; m/z (ES+) 456.

Example Q-56

2-(2,6-difluorophenyl)-5-(4-(piperidin-1-ylmethyl)phenylamino)oxazole-4-carboxamide

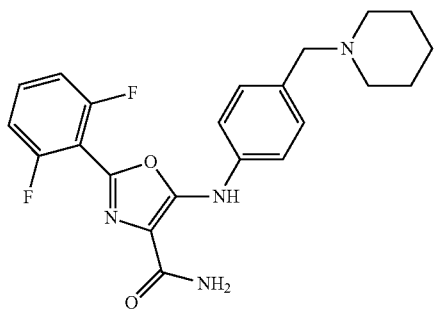 [SMILES: NC(=O)c1nc(-c2c(F)cccc2F)oc1Nc1ccc(CN2CCCCC2)cc1]

Prepared according to the procedure described in example (steps b and c). ¹H NMR (CD₃OD) δ 1.55 (2H, m), 1.71 (4H, quin), 2.79 (4H, m), 3.82 (2H, br s), 7.19 (2H, t), 7.39 (2H, d), 7.45 (2H, d), 7.56 (1H, m). LCMS (2) Rt: 3.12 min; m/z (ES+) 413.

Example Q-57

2-(2-chloro-6-fluorophenyl)-5-(4-(1-methylpiperazine-4-carbonyl)phenylamino)oxazole-4-carbonitrile

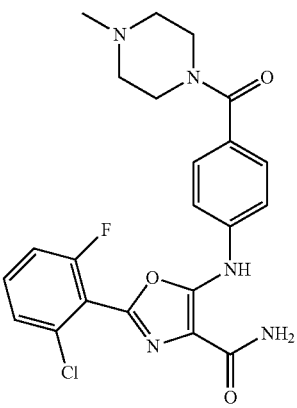 [SMILES: CN1CCN(C(=O)c2ccc(Nc3oc(-c4c(F)cccc4Cl)nc3C(N)=O)cc2)CC1]

Prepared according to the method described for example Q-1. ¹H NMR (CD₃OD) δ 2.35 (3H, s), 2.45-2.55 (4H, m), 3.60-3.70 (4H, br. s), 7.28-7.35 (1H, m), 7.40-7.50 (5H, m), 7.55-7.61 (1H, m). LCMS (2) 2.14 min; m/z (ES+) 458, 460.

Example Q-58

2-(1H-indazol-4-yl)-5-(4-(methylsulfonyl)phenylamino)oxazole-4-carboxamide

Step a—mixture of methyl 1-(4-methoxybenzyl)-1H-indazole-4-carboxylate and methyl 2-(4-methoxybenzyl)-2H-indazole-4-carboxylate

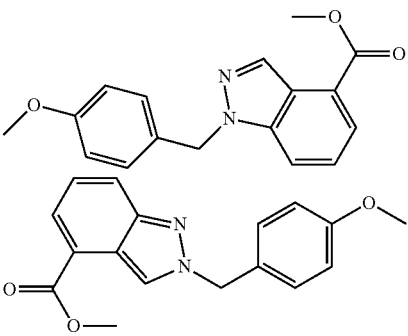

To a solution of methyl 1H-indazole-4-carboxylate (0.90 g, 5.11 mmol) in anhydrous DMF (40 ml) was added NaH, as a 60% suspension in mineral oil (0.31 g, 5.11 mmol). After stirring at room temperature for 5 minutes, 4-methoxybenzyl chloride (1.15 ml, 5.11 mmol) was added and the reaction stirred for a further hour. The reaction was then diluted with DCM and washed with water and brine before being dried over Na₂SO₄ and concentrated to a clear oil. Flash chromatography on silica gel, using a gradient of 0-35% EtOAc in hexanes as eluant, gave 1.22 g (4.12 mmol, 81%) of an approximate one to one mixture of the two regioisomers. LCMS (3) 2.31 and 2.41 min; m/z (ES+) 297.

Step b—mixture of 1-(4-methoxybenzyl)-1H-indazole-4-carboxylic acid and 2-(4-methoxybenzyl)-2H-indazole-4-carboxylic acid

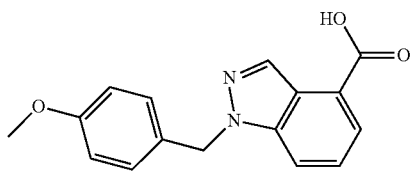

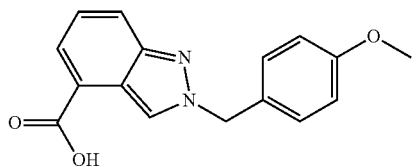

A mixture of methyl 1-(4-methoxybenzyl)-1H-indazole-4-carboxylate and methyl 2-(4-methoxybenzyl)-2H-indazole-4-carboxylate (1.22 g, 4.12 mmol) was taken up in MeOH (13 ml) and to the solution were added THF (6.5 ml) and 1M aqueous NaOH solution (6.5 ml). The reaction was stirred at room temperature overnight then acidified to pH1 with 2M HCl and the resulting precipitate filtered off and dried under vacuum to give 1.07 g (3.79 mmol, 92%) of white solid. LCMS (3) 1.32 and 1.47 min; m/z (ES−) 281.

Step c—mixture of 2-(1-(4-methoxybenzyl)-1H-indazol-4-yl)-5-aminooxazole-4-carbonitrile and 2-(2-(4-methoxybenzyl)-2H-indazol-4-yl)-5-aminooxazole-4-carbonitrile

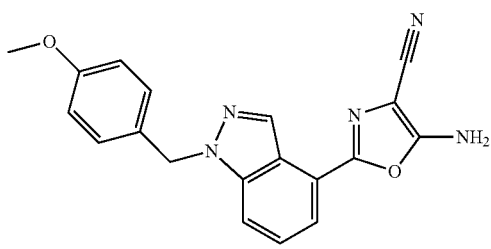

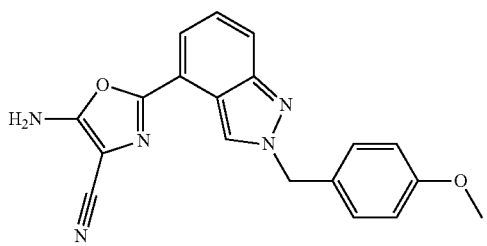

A mixture of 1-(4-methoxybenzyl)-1H-indazole-4-carboxylic acid and 2-(4-methoxybenzyl)-2H-indazole-4-carboxylic acid (1.07 g, 3.79 mmol) was taken up in a mixture of DCM (10 ml) and DMF (100 μl) and then oxalyl chloride (0.38 ml, 4.55 mmol) was added dropwise. After stirring at room temperature for 2 hours the solvent was removed in vacuo and the residue dissolved in NMP (5 ml). To this solution was added aminomalononitrile tosylate (1.15 g, 4.55 mmol) and the reaction heated to 120° C. under microwave irradiation for a period of 5 minutes. The reaction mixture was then diluted with DCM and washed with water. The resulting white precipitate was filtered off and dried in vacuo to give 1.1 g (3.20 mmol, 84%) of a white powdery solid containing a mixture of the two regioisomers. LCMS (3) 2.15 and 2.25 min; m/z (ES−) 344.

Step d—mixture of 2-(1-(4-methoxybenzyl)-1H-indazol-4-yl)-5-bromooxazole-4-carbonitrile and 2-(2-(4-methoxybenzyl)-2H-indazol-4-yl)-5-bromooxazole-4-carbonitrile

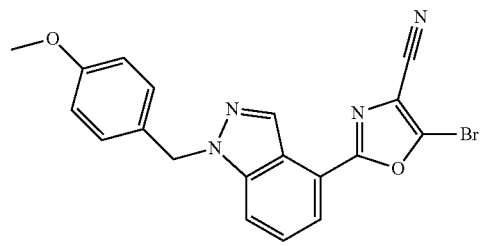

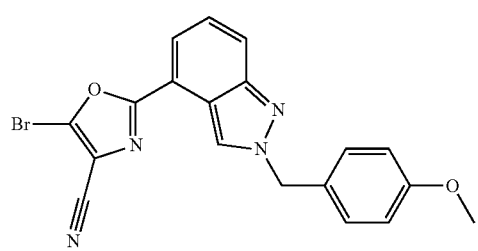

Copper (II) bromide (1.40 g, 6.40 mmol) was suspended in anhydrous acetonitrile (30 ml) under a nitrogen atmosphere at 0° C. Tert-butyl nitrite (0.87 ml, 3.52 mmol) was added, followed by the portionwise addition of a mixture of 2-(1-(4-methoxybenzyl)-1H-indazol-4-yl)-5-aminooxazole-4-carbonitrile and 2-(2-(4-methoxybenzyl)-2H-indazol-4-yl)-5-aminooxazole-4-carbonitrile (1.1 g, 3.20 mmol). The reaction was stirred at 0° C. for 30 minutes and then warmed to room temperature and stirred for a further 30 minutes. The reaction was diluted with diethyl ether and washed with 2M HCl and brine before being dried over $Na_2SO_4$, concentrated in vacuo and purified by flash chromatography (silica gel, 10-50% EtOAc in hexanes as eluant) to give the desired mixture of regioisomers as a yellow solid, 0.500 g (1.2 mmol, 38%). LCMS (3) broad peak at 2.66 min; m/z (ES−) 408.

Step e—mixture of 2-(1-(4-methoxybenzyl)-1H-indazol-4-yl)-5-(4-(methylsulfonyl)phenylamino)oxazole-4-carbonitrile and 2-(2-(4-methoxybenzyl)-2H-indazol-4-yl)-5-(4-(methylsulfonyl)phenylamino)oxazole-4-carbonitrile

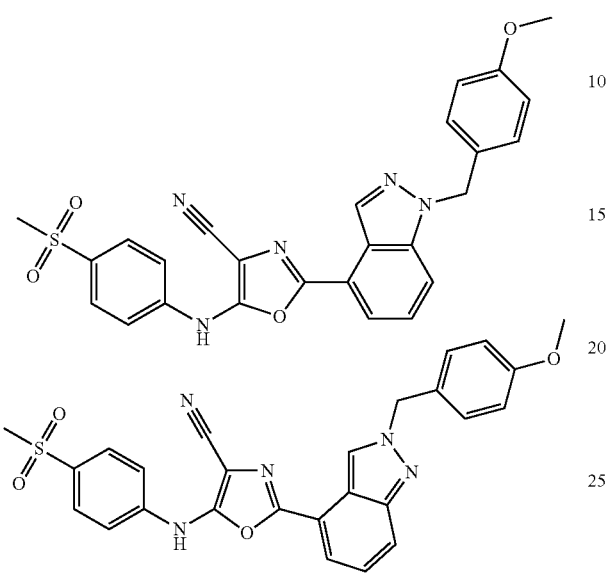

Palladium acetate (0.006 g, 0.026 mmol) and BINAP (0.016 mmol, 0.026 mmol) were dissolved in DMF (5 ml) and stirred at RT for 5 minutes. 2-(1-(4-Methoxybenzyl)-1H-indazol-4-yl)-5-bromoxazole-4-carbonitrile and 2-(2-(4-methoxybenzyl)-2H-indazol-4-yl)-5-bromooxazole-4-carbonitrile (0.150 g, 0.37 mmol), 4-(methylsulfonyl)benzenamine (0.063 g, 0.37 mmol) and potassium phosphate tribasic (0.160 g, 0.73 mmol) were then added and the reaction heated under microwave irradiation to 140° C. for a period of 5 minutes. The crude reaction mixture was purified by prep-HPLC to give a mixture of the two regioisomers as a yellow powder, 0.024 g (0.044 mmol, 12%). LCMS (3) 2.24 min (broad peak); m/z (ES−) 498.

Step f—2-(3a,7a-dihydro-1H-indazol-4-yl)-5-(4-(methylsulfonyl)phenylamino)oxazole-4-carboxamide

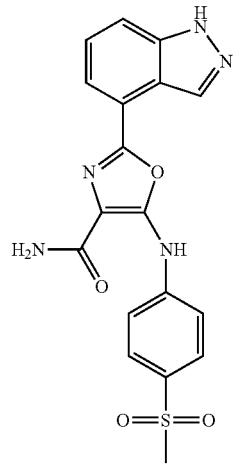 [SMILES: CS(=O)(=O)c1ccc(Nc2oc(-c3cccc4[nH]ncc34)nc2C(N)=O)cc1]

A mixture of 2-(1-(4-methoxybenzyl)-1H-indazol-4-yl)-5-(4-(methylsulfonyl)phenylamino)oxazole-4-carbonitrile and 2-(2-(4-methoxybenzyl)-2H-indazol-4-yl)-5-(4-(methylsulfonyl)phenylamino)oxazole-4-carbonitrile (0.024 g, 0.044 mmol) was taken up in TFA (1 ml) and heated to 140° C. under microwave irradiation for a period of 30 minutes. The TFA was then removed in vacuo and the residue purified by prep-HPLC to furnish the title compound as a yellow solid (0.0027 g, 0.0068 mmol, 15%), $^1$H NMR (CD$_3$OD) δ 3.20 (3H, s), 7.40-7.55 (2H, m), 7.6-7.8 (3H, m), 7.80-7.95 (2H, m), 8.92 (1H, s), 13.35 (1H, s) LCMS (2) 1.99 min; m/z (ES+) 397.

Example Q-59

2-(1H-indazol-4-yl)-5-(4-(piperazin-1-yl)phenylamino)oxazole-4-carboxamide

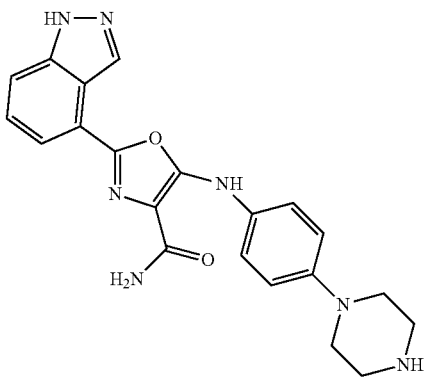 [SMILES: NC(=O)c1nc(-c2cccc3[nH]ncc23)oc1Nc1ccc(N2CCNCC2)cc1]

The title compound was prepared according to the procedure for Q-58 above.

$^1$H NMR (DMSO) δ 2.85-2.95 (4H, m), 3.05-3.15 (4H, m), 6.85-6.95 (2H, m), 7.35 (2H, br. s), 7.40-7.50 (1H, m), 7.55-7.70 (4H, m), 8.28 (1H, s), 9.35 (1H, s) LCMS (2) 1.90 min; m/z (ES+) 404.

Example Q-60

2-(1H-indazol-4-yl)-5-(4-(4-(2,2,2-trifluoroacetyl)piperazin-1-yl)phenylamino)oxazole-4-carboxamide

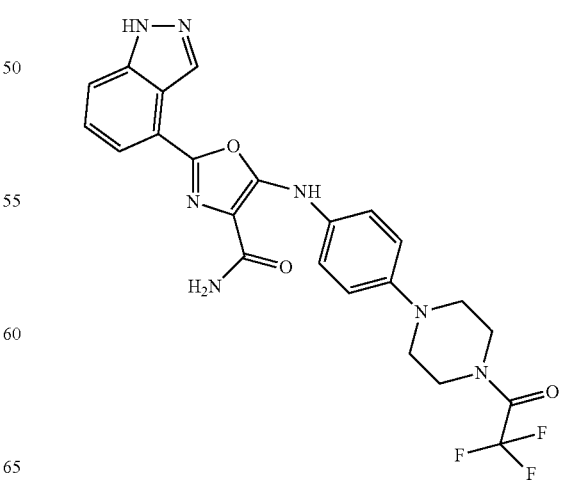

The title compound was isolated as a byproduct from the synthesis of 2-(1H-indazol-4-yl)-5-(4-(piperazin-1-yl)phenylamino)oxazole-4-carboxamide, described in Q-59 above. ¹H NMR (DMSO) δ 2.90-3.00 (4H, m), 3.05-3.15 (4H, m), 6.95-7.05 (2H, m), 7.25 (1H, br. s), 7.38-7.52 (4H, m), 7.55-7.65 (2H, m), 8.28 (1H, s), 8.85 (1H, s) LCMS (2) 1.84 min; m/z (ES+) 500.

General Method R

General Method R comprises the series of steps set out in Scheme 12 above.

Example R-1

5-(4-methoxyphenyl)-2-(phenylamino)oxazole-4-carboxamide

Step a—5-(4-methoxyphenyl)-2-(phenylamino)oxazole-4-carboxylic acid

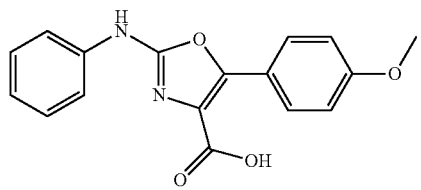 [SMILES: COc1ccc(-c2oc(Nc3ccccc3)nc2C(=O)O)cc1]

To a mixture of ethyl 2-iodo-5-(4-methoxyphenyl)oxazole-4-carboxylate (0.030 g, 0.080 mmol), tris(dibenzylideneacetone)dipalladium(0) (0.004 g, 0.004 mmol), 2-dicyclohexylphosphino-2',4',6'-tri-iso-propyl-1,1'-biphenyl (0.006 g, 0.013 mmol) and potassium carbonate (0.040 g, 0.29 mmol) in anhydrous DMF (1 mL) was added aniline (0.041 g, 0.44 mmol). The resulting mixture was stirred and degassed at room temperature for 5 minutes and then heated in the microwave at 150° C. for 10 minutes. The crude reaction mixture was passed through a MP-SH resin cartridge and then purified by SPE using a MP-TsOH resin cartridge to afford, after eluting with 2M ammonia in MeOH, ethyl 5-(4-methoxyphenyl)-2-(phenylamino)oxazole-4-carboxylate which was used without further purification. LCMS (1) 2.30 min; m/z (ES+) 339.

To a stirred solution of ethyl 5-(4-methoxyphenyl)-2-(phenylamino)oxazole-4-carboxylate in MeOH (5 mL) at 55° C. was added 1M aqueous potassium hydroxide solution (2.075 mL, 2.08 mmol) and the reaction mixture stirred at 55° C. overnight. The reaction was cooled to room temperature and the MeOH removed in vacuo. The remaining solution was diluted with water and washed with DCM. The aqueous phase was acidified with 2M aqueous HCl (2 mL) and extracted with EtOAc. The combined organic phase was washed with brine, dried over MgSO₄ and the solvent removed in vacuo to afford 5-(4-methoxyphenyl)-2-(phenylamino)oxazole-4-carboxylic acid (0.012 g, 0.039 mmol, 48%) as a white solid which was used without further purification. LCMS (1) Rt: 1.44 min; m/z (ES+) 311.

Step b—5-(4-methoxyphenyl)-2-(phenylamino)oxazole-4-carboxamide

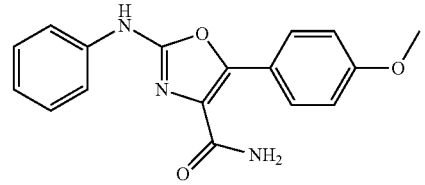 [SMILES: COc1ccc(-c2oc(Nc3ccccc3)nc2C(N)=O)cc1]

To a stirred solution of 5-(4-methoxyphenyl)-2-(phenylamino)oxazole-4-carboxylic acid (0.012 g, 0.039 mmol), 1-hydroxybenzotriazole hydrate (0.009 g, 0.059 mmol) and 1-(3-dimethylaminopropyl)-3-ethylcarbodiimide hydrochloride (0.011 g, 0.057 mmol) in DMF (5 mL) was added a 0.5M ammonia in dioxane solution (0.116 mL, 0.058 mmol) and the resulting mixture stirred at room temperature overnight. The solvent was removed in vacuo and the residue purified by preparative HPLC to afford 5-(4-methoxyphenyl)-2-(phenylamino)oxazole-4-carboxamide (0.0045 g, 0.015 mmol, 38%). ¹H NMR (DMSO) δ 3.82 (3H, s), 6.98 (1H, t), 7.04 (2H, d), 7.33 (2H, t), 7.51 (1H, br, s), 7.60 (1H, br, s), 7.73 (2H, d), 8.16 (2H, d), 10.40 (1H, s). LCMS (2) Rt: 2.67 min; m/z (ES+) 310.

In a similar manner as described in example R-1 the compounds described in examples R-2 to R-9 were prepared.

Example R-2

5-(4-methoxyphenyl)-2-(2-methoxyphenylamino)oxazole-4-carboxamide

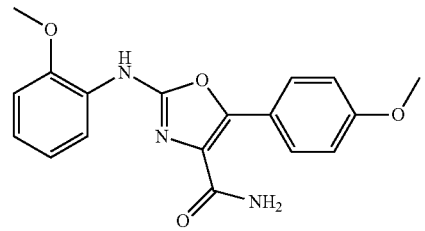 [SMILES: COc1ccc(-c2oc(Nc3ccccc3OC)nc2C(N)=O)cc1]

¹H NMR (DMSO) δ 3.81 (3H, s), 3.86 (3H, s), 7.00 (3H, m), 7.02 (2H, d), 7.48 (1H, br, s), 7.55 (1H, br, s) 8.19 (2H, d), 8.30 (1H, d), 9.30 (1H, s). LCMS (2) Rt: 2.84 min; m/z (ES+) 340.

Example R-3

5-(4-methoxyphenyl)-2-(3-methoxyphenylamino)oxazole-4-carboxamide

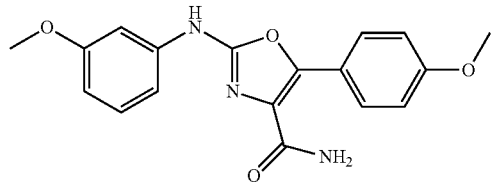

¹H NMR (DMSO) δ 3.77 (3H, s), 3.82 (3H, s), 6.57 (1H, m), 7.04 (2H, d), 7.22 (1H, m), 7.25 (1H, m), 7.33 (1H, d), 7.48 (1H, br, s), 7.51 (1H, br, s), 8.14 (2H, d), 10.40 (1H, s). LCMS (2) Rt: 2.69 min; m/z (ES+) 340.

Example R-4

5-(4-methoxyphenyl)-2-(4-methoxyphenylamino)oxazole-4-carboxamide

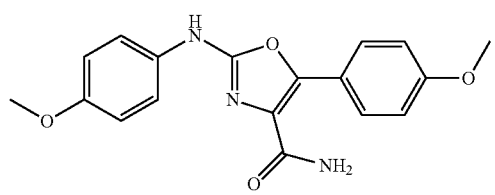

¹H NMR (DMSO) δ 3.73 (3H, s), 3.81 (3H, s), 6.90 (2H, d), 7.02 (2H, d), 7.48 (1H, br, s), 7.53 (1H, br, s) 7.64 (2H, d), 8.14 (2H, d), 10.17 (1H, s). LCMS (2) Rt: 2.62 min; m/z (ES+) 340.

Example R-5

2-(o-toluidino)-5-(4-methoxyphenyl)oxazole-4-carboxamide

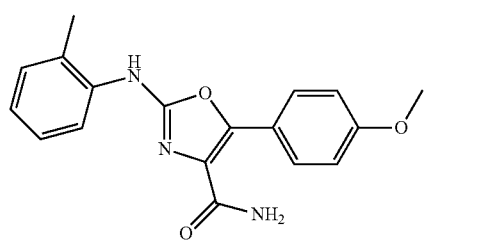 [SMILES: COc1ccc(-c2oc(Nc3ccccc3C)nc2C(N)=O)cc1]

¹H NMR (DMSO) δ 2.30 (3H, s), 3.80 (3H, s), 7.00 (1H, t), 7.01 (2H, d), 7.21 (2H, m), 7.38 (1H, br, s), 7.48 (1H br, s), 7.98 (1H, d), 7.40 (2H, d), 9.33 (1H, s). LCMS (2) Rt: 2.78 min; m/z (ES+) 324.

Example R-6

2-(m-toluidino)-5-(4-methoxyphenyl)oxazole-4-carboxamide

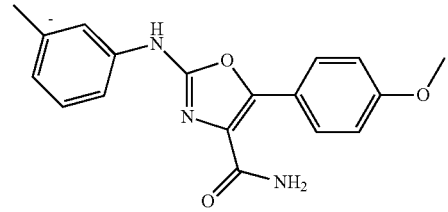

¹H NMR (DMSO) δ 2.31 (3H, s), 3.80 (3H, s), 6.78 (1H, d), 7.02 (2H, d), 7.19 (1H, t), 7.44 (1H, br, s), 7.51 (1H, s), 7.55 (1H, d), 7.57 (1H, br, s), 8.13 (2H, d), 10.29 (1H, s). LCMS (2) Rt: 2.83 min; m/z (ES+) 324.

Example R-7

2-(p-toluidino)-5-(4-methoxyphenyl)oxazole-4-carboxamide

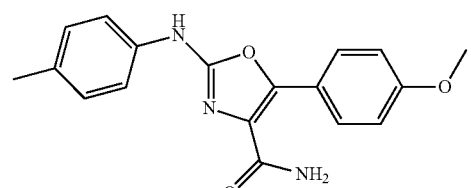

¹H NMR (DMSO) δ 2.26 (3H, s), 3.81 (3H, s), 7.02 (2H, d), 7.12 (2H, d), 7.51 (1H, br, s), 7.57 (1H, br, s), 7.60 (2H, d), 8.14 (2H, d), 10.27 (1H, s). LCMS (2) Rt: 2.82 min; m/z (ES+) 324.

Example R-8

2-(2-fluorophenylamino)-5-(4-methoxyphenyl)oxazole-4-carboxamide

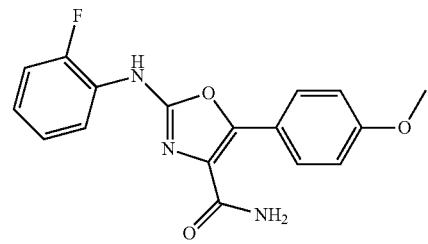 [SMILES: COc1ccc(-c2oc(Nc3ccccc3F)nc2C(N)=O)cc1]

¹H NMR (DMSO) δ 3.81 (3H, s), 7.04 (3H, m), 7.21 (2H, m), 7.51 (1H, br s), 7.59 (1H, br s), 8.17 (2H, d), 8.42 (1H, m), 10.15 (1H, s). LCMS (2) Rt: 2.77 min; m/z 328.

Example R-9

2-(2,6-difluorophenylamino)-5-(4-methoxyphenyl)oxazole-4-carboxamide

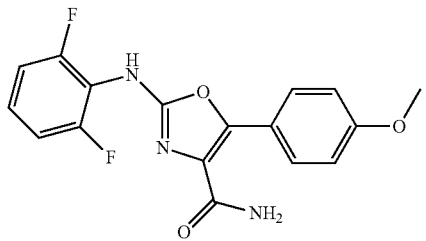 [SMILES: COc1ccc(-c2oc(Nc3c(F)cccc3F)nc2C(N)=O)cc1]

For this example the catalyst system employed during step a was tris(dibenzylideneacetone)dipalladium(0) and 9,9-dimethyl-4,5-bis(diphenylphosphino)xanthene with cesium carbonate as a base. The reaction mixture was irradiated in the microwave for 15 minutes at 150° C. ¹H NMR (DMSO) δ 3.79 (3H, s), 7.00 (2H, d), 7.14 (1H, br s), 7.32 (2H, t), 7.35 (1H, m), 7.43 (1H, br s), 8.02 (2H, d), 9.84 (1H, br s). LCMS (2) Rt: 1.84 min; m/z 346.

Example R-10

2-(o-toluidino)-5-(4-(piperazin-1-yl)phenyl)oxazole-4-carboxamide

Step a—tert-butyl 4-(4-(2-(o-toluidino)-4-(ethoxycarbonyl)oxazol-5-yl)phenyl)piperazine-1-carboxylate

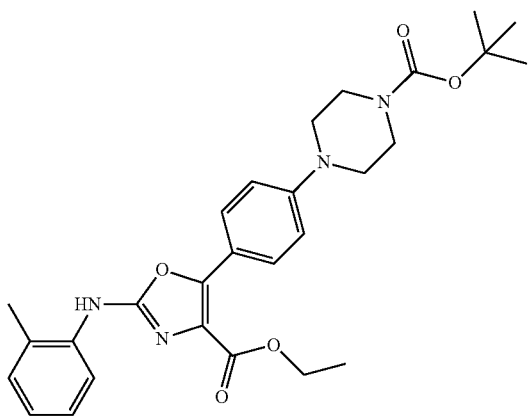 [SMILES: CCOC(=O)c1nc(Nc2ccccc2C)oc1-c1ccc(N2CCN(C(=O)OC(C)(C)C)CC2)cc1]

A mixture of tert-butyl 4-(4-(4-(ethoxycarbonyl)-2-iodooxazol-5-yl)phenyl)piperazine-1-carboxylate (0.06 g, 0.11 mmol), o-toluidine (0.061 ml, 0.57 mmol), tris(dibenzylideneacetone)dipalladium(0) (0.005 g, 0.005 mmol), 2-(dicyclohexylphosphino)-2',4',6'-tri-1-propyl-1,1'-biphenyl (0.011 g, 0.02 mmol) and potassium carbonate (0.063 g, 0.46 mmol) in DMF (1.5 ml) was degassed and heated in the microwave at 150° C. for 20 minutes. The reaction mixture was diluted with EtOAc and washed with water (×2). The organic phase was passed through a MP-SH cartridge, dried over MgSO₄ and the solvent removed in vacuo. The residue was purified by silica gel column chromatography using 10-90% EtOAc in hexane as gradient to afford tert-butyl 4-(4-(2-(o-toluidino)-4-(ethoxycarbonyl)oxazol-5-yl)phenyl)piperazine-1-carboxylate (0.030 g, 0.06 mmol, 52%). LCMS (1) Rt: 2.63 min; m/z (ES+) 507.

Step b—2-(o-toluidino)-5-(4-(4-(tert-butoxycarbonyl)piperazin-1-yl)phenyl)oxazole-4-carboxylic acid

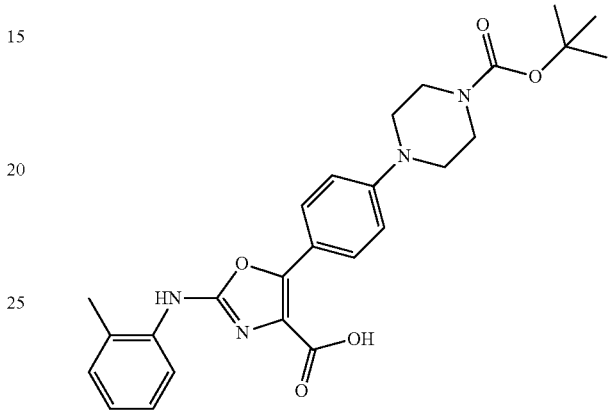

To a solution of tert-butyl 4-(4-(2-(o-toluidino)-4-(ethoxycarbonyl)oxazol-5-yl)phenyl)piperazine-1-carboxylate (0.042 g, 0.08 mmol) in DCE (2 ml) was added trimethyltin hydroxide (0.140 g, 0.77 mmol) and the resulting mixture was heated at 80° C. overnight. The reaction was cooled to room temperature and diluted with DCM. The organic phase was washed with water. The combined aqueous phase was extracted with DCM and the combined organic phase dried over MgSO₄ and the solvent removed in vacuo to afford 2-(o-toluidino)-5-(4-(4-(tert-butoxycarbonyl)piperazin-1-yl)phenyl)oxazole-4-carboxylic acid (0.038 g, 0.08 mmol, 96%). LCMS (1) Rt: 1.89 min; m/z (ES+) 479.

Step c—tert-butyl 4-(4-(2-(o-toluidino)-4-carbamoyloxazol-5-yl)phenyl)piperazine-1-carboxylate

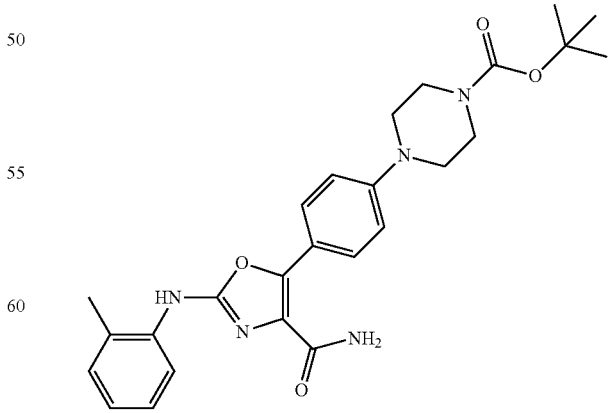

To a solution of 2-(o-toluidino)-5-(4-(4-(tert-butoxycarbonyl)piperazin-1-yl)phenyl)oxazole-4-carboxylic acid (0.038, 0.08 mmol) in DCM (0.8 ml) and DMF (0.6 ml) was added hydroxybenzotriazole monohydrate (0.016 g, 0.10 mmol), 1-[3-(dimethylamino)propyl]-3-ethylcarbodiimide hydrochloride (0.024 g, 0.13 mmol) and 0.5M ammonia in dioxane (0.8 ml, 0.4 mmol) and the resultant mixture stirred overnight at room temperature. A further portion each of hydroxybenzotriazole monohydrate (0.016 g, 0.10 mmol), 1-[3-(dimethylamino)propyl]-3-ethylcarbodiimide hydrochloride (0.024 g, 0.13 mmol) and 0.5M ammonia in dioxane (0.8 ml, 0.4 mmol) was added and the resultant mixture stirred for 5 hours at room temperature, followed by the addition of hydroxybenzotriazole monohydrate (0.008 g, 0.05 mmol), 1-[3-(dimethylamino)propyl]-3-ethylcarbodiimide hydrochloride (0.012 g, 0.065 mmol) and 0.5M ammonia in dioxane (0.4 ml, 0.2 mmol) and the reaction mixture was stirred overnight. The solvent was then removed in vacuo and the residue purified by preparative HPLC to afford tert-butyl 4-(4-(2-(o-toluidino)-4-carbamoyloxazol-5-yl)phenyl)piperazine-1-carboxylate (0.012 g, 0.025 mmol, 32%). LCMS (2) Rt: 3.41 min; m/z (ES+) 478.

Step d—2-(o-toluidino)-5-(4-(piperazin-1-yl)phenyl)oxazole-4-carboxamide

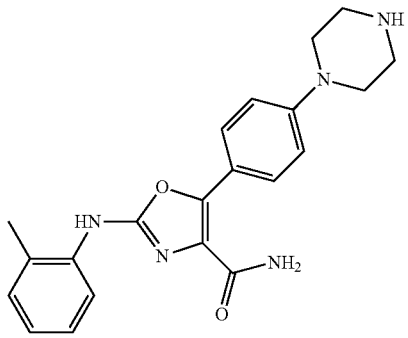 [SMILES: Cc1ccccc1Nc1nc(C(N)=O)c(-c2ccc(N3CCNCC3)cc2)o1]

To a solution of tert-butyl 4-(4-(2-(o-toluidino)-4-carbamoyloxazol-5-yl)phenyl)piperazine-1-carboxylate (0.012 g, 0.025 mmol) in DCM (0.5 ml) was added 0.5M HCl in dioxane (0.25 ml, 0.125 mmol) and the resulting solution stirred at room temperature for 2 hours. The mixture was then diluted with MeOH and purified by SPE using a MP-TsOH (500 mg) cartridge to afford 2-(o-toluidino)-5-(4-(piperazin-1-yl)phenyl)oxazole-4-carboxamide (0.0087 g, 0.023 mmol, 92%). $^1$H NMR (DMSO) δ 2.30 (3H, s), 2.84 (4H, m), 3.15 (4H, m), 6.97-7.01 (3H, m). 7.19-7.23 (2H, m), 7.32 (1H, br. d), 7.41 (1H, br. d), 7.99 (1H, dd), 8.07 (2H, d), 9.26 (1H, s). LCMS (2) Rt: 2.32 min; m/z (ES+) 378.

Example R-11

2-(2-methoxyphenylamino)-5-(4-(piperazin-1-yl)phenyl)oxazole-4-carboxamide

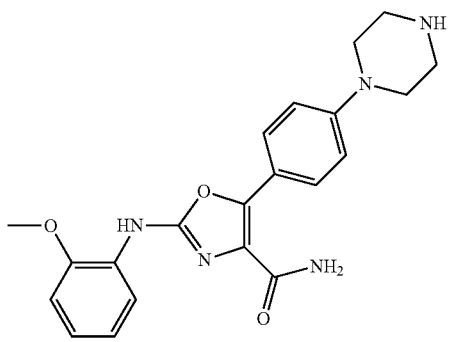 [SMILES: COc1ccccc1Nc1nc(C(N)=O)c(-c2ccc(N3CCNCC3)cc2)o1]

Prepared according to the method described in example R-10. $^1$H NMR (DMSO) δ 2.87 (4H, m), 3.18 (4H, m), 3.87 (3H, s), 6.94-7.05 (5H, m), 7.43 (1H, br. d), 7.51 (1H, br. d), 8.12 (2H, d), 8.31 (1H, m), 9.26 (1H, s). LCMS (2) Rt: 2.36 min; m/z (ES+) 394.

Example R-12

2-(3-methoxyphenylamino)-5-(4-(piperazin-1-yl)phenyl)oxazole-4-carboxamide

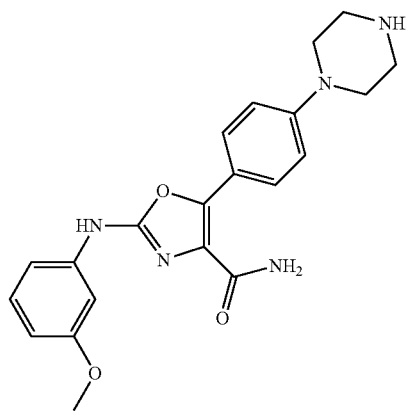 [SMILES: COc1cccc(Nc2nc(C(N)=O)c(-c3ccc(N4CCNCC4)cc3)o2)c1]

Prepared according to the method described in example R-10. $^1$H NMR (DMSO) δ 2.86 (4H, t), 3.18 (4H, t), 3.77 (3H, s), 6.56 (1H, dd), 6.99 (2H, d), 7.21 (1H, d), 7.25 (1H, m), 7.32 (1H, dd), 7.41 (1H, br. s), 7.43 (1H, br. s), 8.06 (2H, d), 10.32 (1H, s). LCMS (2) Rt: 2.31 min; m/z (ES+) 394.

Example R-13

2-(2,6-difluorophenylamino)-5-(4-(piperazin-1-yl)phenyl)oxazole-4-carboxamide

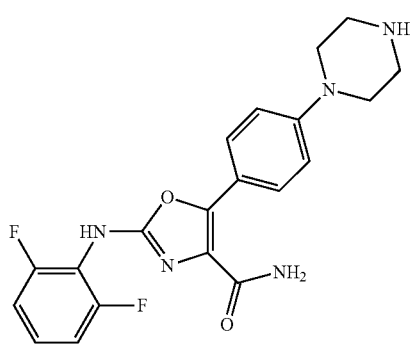 [SMILES: NC(=O)c1nc(Nc2c(F)cccc2F)oc1-c1ccc(N2CCNCC2)cc1]

Prepared according to the method described in example R-10 with the exception that in step a 9,9-dimethyl-4,5-bis(diphenylphosphino)xanthene was used in place of 2-(dicyclohexylphosphino)-2',4',6'-tri-1-propyl-1,1'-biphenyl. $^1$H NMR (CD₃OD) δ 3.01 (4H, m), 3.26 (4H, m), 6.98 (2H, d), 7.09 (2H, t), 7.29 (1H, m), 8.00 (2H, d). LCMS (2) Rt: 1.95 min; m/z (ES+) 400.

Example R-14

5-(4-(piperazin-1-yl)phenyl)-2-(pyridin-3-ylamino)oxazole-4-carboxamide

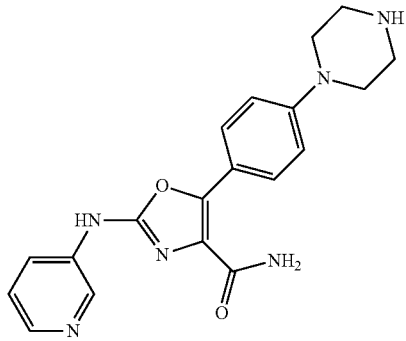 [SMILES: NC(=O)c1nc(Nc2cccnc2)oc1-c1ccc(N2CCNCC2)cc1]

Prepared according to the method described in example R-13 with the exception that step c was performed as follows:
To a solution of 5-(4-(4-(tert-butoxycarbonyl)piperazin-1-yl)phenyl)-2-(pyridin-3-ylamino)oxazole-4-carboxylic acid (0.046 g, 0.1 mmol) in DMF (1 ml) was added O-(7-azabenzotriazol-1-yl)-N,N,N',N'-tetramethyluronium hexafluorophosphate (0.065 g, 0.17 mmol), diisopropylethylamine (0.03 ml, 0.17 mmol) and 0.5M NH₃ in dioxane (0.6 ml, 0.3 mmol) and the resultant mixture stirred at room temperature overnight. A further portion of O-(7-azabenzotriazol-1-yl)-N,N,N',N'-tetramethyluronium hexafluorophosphate (0.020 g, 0.05 mmol), diisopropylethylamine (0.01 ml, 0.056 mmol) and 0.5M NH₃ in dioxane (0.2 ml, 0.1 mmol) was added and the reaction stirred for 1 hour. The solvent was removed in vacuo and the residue purified by preparative HPLC to afford tert-butyl 4-(4-(4-carbamoyl-2-(pyridin-3-ylamino)oxazol-5-yl)phenyl)piperazine-1-carboxylate (0.006 g, 0.013 mmol, 13%). LCMS (2) Rt: 2.64 min; m/z (ES+) 465.
¹H NMR (DMSO) δ 2.84 (4H, t), 3.16 (4H, t), 6.99 (2H, d), 7.35 (1H, dd), 7.44 (1H, br s), 7.66 (1H, br s), 8.07 (2H, d), 8.19 (1H, dd), 8.35 (1H, dd), 8.77 (1H, d), 10.60 (1H, br s). LCMS (2) Rt: 1.62 min; m/z (ES+) 365.

Example R-15

2-(1H-indazol-5-ylamino)-5-(4-(piperazin-1-yl)phenyl)oxazole-4-carboxamide

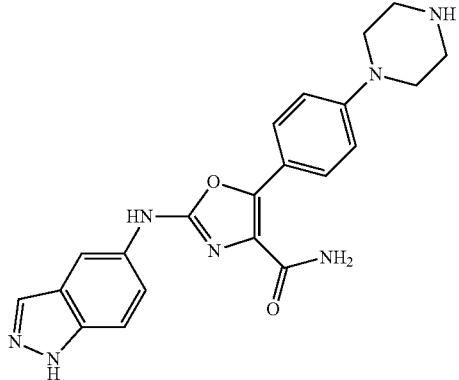 [SMILES: NC(=O)c1nc(Nc2ccc3[nH]ncc3c2)oc1-c1ccc(N2CCNCC2)cc1]

Prepared according to the method described in example R-14 from 1-Boc-5-aminoindazole (the Boc group was removed under the Buchwald coupling conditions).
¹H NMR (DMSO) δ 3.17 (4H, m), 3.41 (4H, m), 7.07 (2H, d), 7.45-7.50 (2H, m), 7.52 (1H, br s), 7.64 (1H, br. s), 8.01 (1H, s), 8.13 (2H, d), 8.37 (1H, dd), 10.30 (1H, s), 12.94 (1H, br. s). LCMS (2) Rt: 1.75 min; m/z (ES+) 404.

Example R-16

2-(1H-indazol-6-ylamino)-5-(4-(piperazin-1-yl)phenyl)oxazole-4-carboxamide

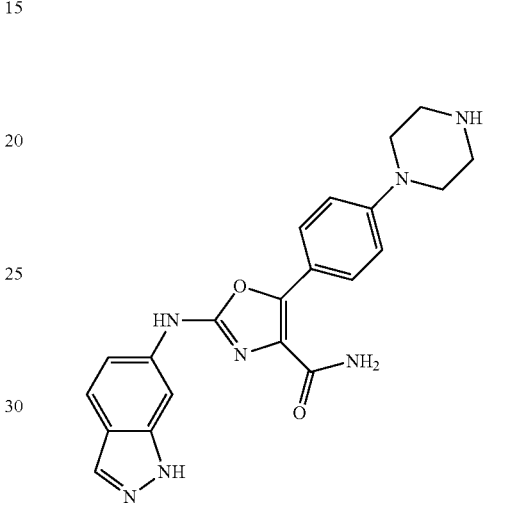

Prepared according to the method described in example R-14 from 1-Boc-6-aminoindazole (the Boc group was removed under the Buchwald coupling conditions). ¹H NMR (DMSO) δ 3.06 (4H, m), 3.32 (4H, m), 7.05 (2H, d), 7.26 (1H, dd), 7.41 (1H, br. s), 7.62 (1H, br. s), 7.67 (1H, d), 7.96 (1H, s), 8.11 (3H, m), 10.54 (1H, s), 12.74 (1H, br. s). LCMS (2) Rt: 1.83 min; m/z (ES+) 404.

Example R-17

2-(1-benzyl-1H-pyrazol-4-ylamino)-5-(4-(piperazin-1-yl)phenyl)oxazole-4-carboxamide

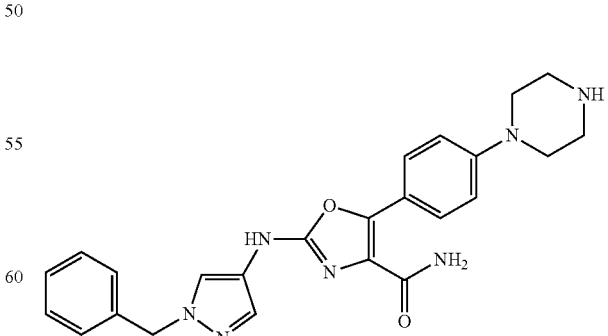

Prepared according to the method described for R-14. ¹H NMR (DMSO) δ 2.84 (4H, t), 3.15 (4H, m), 5.29 (2H, s), 6.97 (2H, d), 7.23 (2H, m), 7.29 (1H, m), 7.35 (2H, m), 7.44 (1H, br. d), 7.49 (1H, d), 7.59 (1H, br. d), 8.05 (2H, d), 8.30 (1H, d), 10.06 (1H, s). LCMS (2) Rt: 2.15 min; m/z (ES+) 444.

Example R-18

2-(1-benzyl-1H-pyrazol-5-ylamino)-5-(4-(piperazin-1-yl)phenyl)oxazole-4-carboxamide

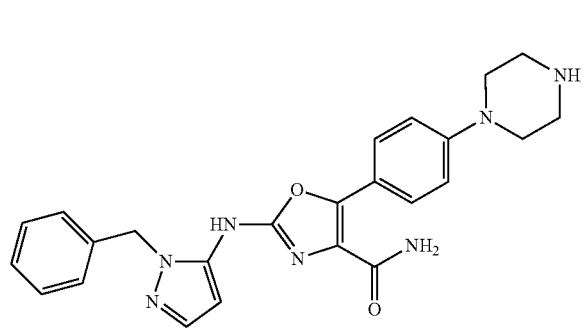 [SMILES: NC(=O)c1nc(Nc2ccnn2Cc2ccccc2)oc1-c1ccc(N2CCNCC2)cc1]

Prepared according to the method described for R-14 using 1-benzyl-1H-pyrazol-5-amine (see Chem. Ber. 1968, 101, 3265-3277). $^1$H NMR (DMSO) δ 2.84 (4H, t), 3.15 (4H, m), 5.38 (2H, s), 6.62 (1H, d), 6.96 (2H, d), 7.09 (2H, m), 7.23 (1H, m), 7.30 (2H, m), 7.36 (1H, br. s), 7.38 (1H, br. s), 7.41 (1H, d), 8.01 (2H, d). LCMS (2) Rt: 2.06 min; m/z (ES+) 444.

Example R-19

2-(1H-pyrazol-4-ylamino)-5-(4-(piperazin-1-yl)phenyl)oxazole-4-carboxamide

Step a—tert-butyl 4-amino-1H-pyrazole-1-carboxylate

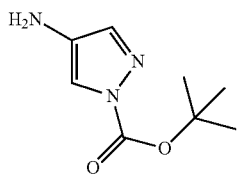

To a stirred mixture of 4-nitro-1H-pyrazole (2.10 g, 19 mmol, see WO2006/044821) and 4-dimethylaminopyridine (0.23 g, 2 mmol) in DCM (210 ml) was added di-tert-butyl-dicarbonate (4.86 g, 22 mmol) and the resulting solution stirred at room temperature for 1 hour. The reaction mixture was washed with 1M HCl, dried over MgSO$_4$ and the solvent removed in vacuo to afford tert-butyl 4-nitro-1H-pyrazole-1-carboxylate (4.03 g, 19 mmol, 100%) as a white solid. $^1$H NMR (DMSO) δ 1.61 (9H, s), 8.54 (1H, s), 9.32 (1H, s). LCMS (2) Rt: 2.46 min.

A solution of tert-butyl 4-nitro-1H-pyrazole-1-carboxylate (1.0 g, 4.7 mmol) in MeOH (120 ml) was passed through the H-Cube with full hydrogen mode at 60° C. and 1 bar with a 10% Pd/C cartridge using 1 ml/min flow rate. The solution was then passed through the H-Cube for a second time using identical conditions and the solvent removed in vacuo to afford tert-butyl 4-amino-1H-pyrazole-1-carboxylate (0.82 g, 4.5 mmol, 95%). $^1$H NMR (DMSO) δ 1.54 (9H, s), 4.42 (2H, s), 7.33 (1H, s), 7.35 (1H, s). LCMS (2) Rt: 1.45 min; m/z (ES+) 206 M+Na$^+$.

Step b—2-(1H-pyrazol-4-ylamino)-5-(4-(4-(tert-butoxycarbonyl)piperazin-1-yl)phenyl)oxazole-4-carboxylic acid

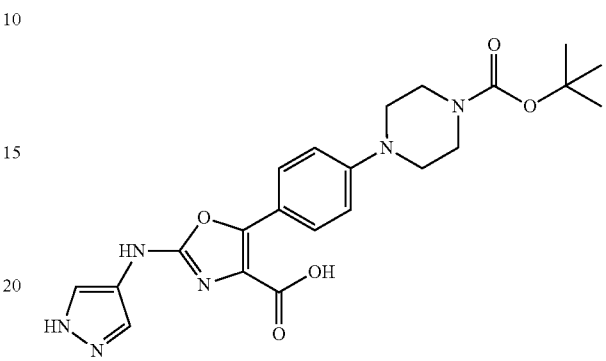

A mixture of tert-butyl 4-(4-(4-(ethoxycarbonyl)-2-iodooxazol-5-yl)phenyl)piperazine-1-carboxylate (0.150 g, 0.28 mmol), tert-butyl 4-amino-1H-pyrazole-1-carboxylate (0.261 g, 1.42 mmol), cesium carbonate (0.462 g, 2.39 mmol), tris(dibenzylideneacetone)dipalladium(0) (0.012 g, 0.013 mmol) and 9,9-dimethyl-4,5-bis(diphenylphosphino)xanthene (0.0165 g, 0.029 mmol) in $^t$BuOH (4.5 ml) and dioxane (4.5 ml) was degassed, placed under a nitrogen atmosphere and then stirred under reflux overnight. The reaction mixture was passed through a MP-SH cartridge and the solvent removed in vacuo. The residue was partitioned between water and EtOAc and the aqueous phase extracted with EtOAc and DCM. The combined organic phases were dried over MgSO$_4$ and the solvent removed in vacuo. The residue was purified by preparative HPLC to afford 2-(1H-pyrazol-4-ylamino)-5-(4-(4-(tert-butoxycarbonyl)piperazin-1-yl)phenyl)oxazole-4-carboxylic acid (0.033 g, 0.073 mmol, 26%). LCMS (2) Rt: 1.68 min; m/z (ES+) 455.

Step c—2-(1H-pyrazol-4-ylamino)-5-(4-(piperazin-1-yl)phenyl)oxazole-4-carboxamide

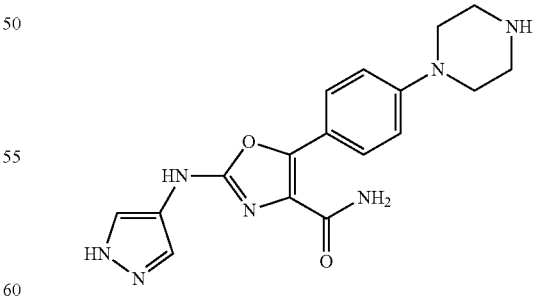

Prepared as described in steps c and d of example R-14 from 2-(1H-pyrazol-4-ylamino)-5-(4-(4-(tert-butoxycarbonyl)piperazin-1-yl)phenyl)oxazole-4-carboxylic acid. $^1$H NMR (CD$_3$OD) δ 2.91 (4H, m), 3.20 (4H, m, part obscured by CD$_3$OD peak), 6.93 (2H, d), 7.47 (1H, s), 7.72 (1H, s), 8.08 (2H, d). LCMS (2) Rt: 1.42 min; m/z (ES+) 354.

General Method S

General Method S comprises the series of steps set out in Scheme 13 above.

Example S-1

2-(2,6-difluorophenyl)-5-(4-(2-(4-methylpiperazin-1-yl)ethoxy)phenyl)oxazole-4-carboxamide Step a—2-(2,6-difluorophenyl)-5-(4-hydroxyphenyl)oxazole-4-carboxamide

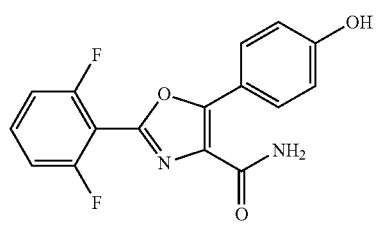 [SMILES: NC(=O)c1nc(-c2c(F)cccc2F)oc1-c1ccc(O)cc1]

To a mixture of 5-bromo-2-(2,6-difluorophenyl)oxazole-4-carboxamide (0.060 g, 0.20 mmol), 4-hydroxyphenylboronic acid (0.055 g, 0.40 mmol) and 1,1'-bis(diphenylphosphino)ferrocene-palladium(II)dichloride (0.008 g, 0.01 mmol) in MeCN (4 ml) was added 1M aqueous $Na_2CO_3$ (0.4 ml, 0.4 mmol). The reaction was heated via microwave irradiation to 150° C. and held at this temperature for 15 minutes. The reaction was then diluted with EtOAc and washed with 2M HCl. The organic layer was dried over $Na_2SO_4$ and concentrated in vacuo. The resulting residue was purified by silica gel flash chromatography using 5-70% EtOAc in hexane as eluant to furnish 2-(2,6-difluorophenyl)-5-(4-hydroxyphenyl)oxazole-4-carboxamide (0.050 g, 0.16 mmol, 80%) as an off white powder. LCMS (1) 1.73 min; m/z (ES−) 315.

Step b—5-(4-(2-chloroethoxy)phenyl)-2-(2,6-difluorophenyl)oxazole-4-carboxamide

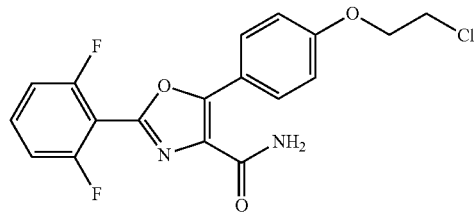 [SMILES: NC(=O)c1nc(-c2c(F)cccc2F)oc1-c1ccc(OCCCl)cc1]

To a solution of 2-(2,6-difluorophenyl)-5-(4-hydroxyphenyl)oxazole-4-carboxamide (0.100 g, 0.316 mmol) in DMF (5 ml) were added potassium carbonate (0.220 g, 1.58 mmol) and 1,2-dichloroethane (0.50 ml, 6.32 mmol). The reaction was heated to 130° C. via microwave irradiation and held at that temperature for 1 hour. The reaction was then diluted with EtOAc, washed with water and brine and dried over $Na_2SO_4$ before being concentrated in vacuo. The resulting residue was purified by silica gel flash chromatography using 0-50% EtOAc in hexane as eluant to afford 5-(4-(2-chloroethoxy)phenyl)-2-(2,6-difluorophenyl)oxazole-4-carboxamide (0.11 g, 0.29 mmol, 92%) as a white solid. LCMS (1) 2.25 min; m/z (ES+) 379/381.

Step c—2-(2,6-difluorophenyl)-5-(4-(2-(4-methylpiperazin-1-yl)ethoxy)phenyl)oxazole-4-carboxamide

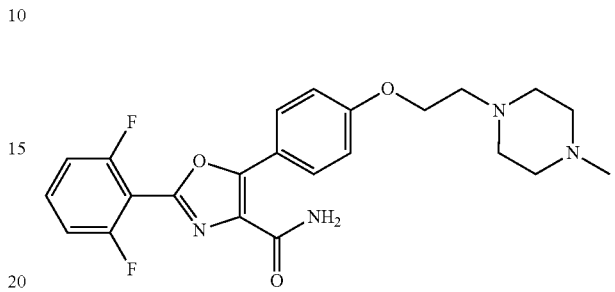

To a solution of 5-(4-(2-chloroethoxy)phenyl)-2-(2,6-difluorophenyl)oxazole-4-carboxamide (0.020 g, 0.053 mmol) in DMSO (1 ml) were added N-methylpiperazine (11 μl, 0.106 mmol) and triethylamine (12 μl, 0.106 mmol). The reaction was heated to 150° C. via microwave irradiation and held at that temperature for 25 minutes. Purification was performed by preparative HPLC to afford 2-(2,6-difluorophenyl)-5-(4-(2-(4-methylpiperazin-1-yl)ethoxy)phenyl)oxazole-4-carboxamide (0.0024 g, 0.0054 mmol, 10%) as an off white powder. $^1$H NMR (CD$_3$OD) δ 2.57 (3H, s), 2.76-2.96 (10H, m), 4.24 (2H, t), 7.06 (2H, m), 7.22 (2H, m), 7.64 (1H, m), 8.26 (2H, m). LCMS (2) 2.25 min; m/z (ES+) 443.

The compounds described in examples S-2 to S-11 were prepared in a similar manner as described in example S-1

Example S-2

2-(2-fluoro-6-(4-methylpiperazin-1-yl)phenyl)-5-(4-(2-(4-methylpiperazin-1-yl)ethoxy)phenyl)oxazole-4-carboxamide

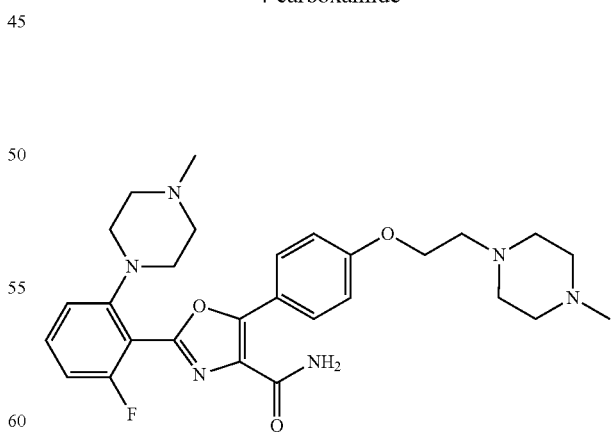

Isolated as a by-product from the synthesis of example S-1. $^1$H NMR (CD$_3$OD) δ 2.56 (3H, s), 2.70 (3H, s), 2.82-2.96 (10H, m), 3.06-3.14 (4H, br, s), 3.20 (4H, t), 4.22 (2H, t), 6.98-7.12 (4H, m), 7.54 (1H, m), 8.23 (2H, m). LCMS (2) 2.34 min; m/z (ES+) 523.

Example S-3

2-(2-fluoro-6-(4-hydroxypiperidin-1-yl)phenyl)-5-(4-(2-(4-hydroxypiperidin-1-yl)ethoxy)phenyl)oxazole-4-carboxamide

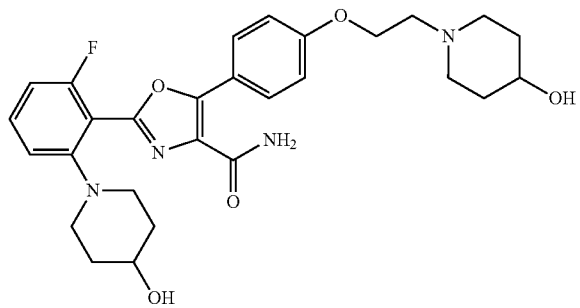 [SMILES: NC(=O)c1nc(-c2c(F)cccc2N2CCC(O)CC2)oc1-c1ccc(OCCN2CCC(O)CC2)cc1]

Isolated as a by-product from the synthesis of example S-4. ¹H NMR (CD₃OD) δ 1.51 (2H, m), 1.84 (4H, m), 2.06 (2H, m), 2.82 (2H, m), 3.08 (2H, m), 3.23 (2H, m), 3.41 (4H, m), 3.67 (1H, m), 3.92 (1H, m), 4.41 (2H, t), 6.91 (1H, m), 7.05 (1H, d), 7.12 (2H, m), 7.52 (1H, m), 8.3 (2H, m). LCMS (2) 2.27 min; m/z (ES+) 525.

Example S-4

2-(2,6-difluorophenyl)-5-(4-(2-(4-hydroxypiperidin-1-yl)ethoxy)phenyl)oxazole-4-carboxamide

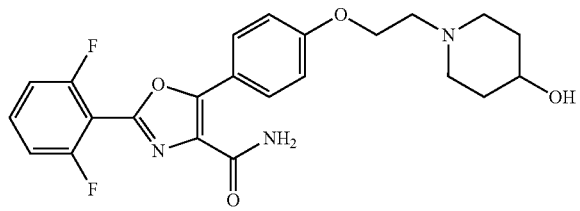 [SMILES: NC(=O)c1nc(-c2c(F)cccc2F)oc1-c1ccc(OCCN2CCC(O)CC2)cc1]

¹H NMR (CD₃OD) δ 1.80-1.90 (2H, m), 2.06-2.14 (2H, m), 3.10-3.20 (2H, br. m), 3.42-3.50 (4H, m), 3.90-3.98 (1H, br. m), 4.44 (2H, t), 7.12-7.16 (2H, m), 7.20-7.27 (2H, m), 7.60-7.70 (1H, m), 8.28-8.32 (2H, m). LCMS (2) 2.40 min; m/z (ES+) 444.

Example S-5

(S)-2-(2,6-difluorophenyl)-5-(4-(2-(2-(hydroxymethyl)pyrrolidin-1-yl)ethoxy)phenyl)oxazole-4-carboxamide

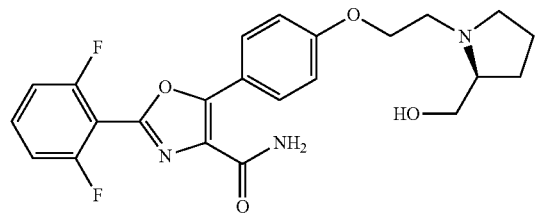 [SMILES: NC(=O)c1nc(-c2c(F)cccc2F)oc1-c1ccc(OCCN2CCC[C@H]2CO)cc1]

¹H NMR (CD₃OD) δ 1.82-1.92 (1H, m), 1.96-2.12 (2H, m), 2.14-2.24 (1H, m), 3.10-3.18 (1H, m), 3.40-3.52 (2H, m), 3.63-3.70 (1H, m), 3.71-3.86 (3H, m), 4.41 (2H, t), 7.12-7.16 (2H, m), 7.20-7.27 (2H, m), 7.61-7.69 (1H, m), 8.28-8.32 (2H, m). LCMS (2) 2.68 min; m/z (ES+) 444.

Example S-6

(R)-2-(2,6-difluorophenyl)-5-(4-(2-(2-(hydroxymethyl)pyrrolidin-1-yl)ethoxy)phenyl)oxazole-4-carboxamide

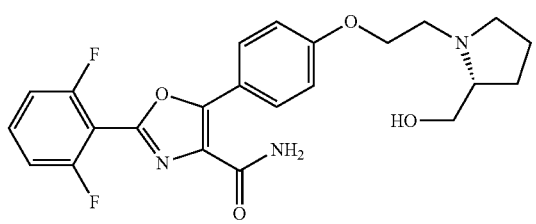 [SMILES: NC(=O)c1nc(-c2c(F)cccc2F)oc1-c1ccc(OCCN2CCC[C@@H]2CO)cc1]

¹H NMR (CD₃OD) δ 1.82-1.92 (1H, m), 1.96-2.12 (2H, m), 2.14-2.24 (1H, m), 3.10-3.18 (1H, m), 3.40-3.52 (2H, m), 3.63-3.70 (1H, m), 3.71-3.86 (3H, m), 4.41 (2H, t), 7.12-7.16 (2H, m), 7.20-7.27 (2H, m), 7.61-7.69 (1H, m), 8.28-8.32 (2H, m). LCMS (2) 2.67 min; m/z (ES+) 444.

Example S-7

2-(2,6-difluorophenyl)-5-(4-(2-(4-(2-hydroxyethyl)piperazin-1-yl)ethoxy)phenyl)oxazole-4-carboxamide

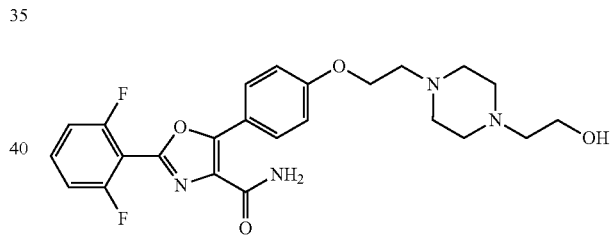

¹H NMR (CD₃OD) δ 2.88-2.96 (4H, br, s), 2.99 (4H, q), 3.06-3.14 (4H, br, s), 3.82 (2H, t), 4.27 (2H, t), 7.06-7.11 (2H, m), 7.20-7.26 (2H, m), 7.60-7.68 (1H, m), 8.24-8.30 (2H, m). LCMS (2) 2.22 min; m/z (ES+) 473.

Example S-8

2-(2,6-difluorophenyl)-5-(4-(2-((2-hydroxyethyl)(methyl)amino)ethoxy)phenyl)oxazole-4-carboxamide

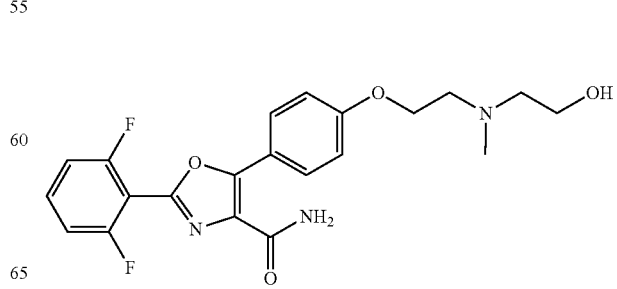

¹H NMR (CD₃OD) δ 2.84 (3H, s), 3.18 (2H, t), 3.46 (2H, t), 3.87 (2H, t), 4.40 (2H, t), 7.12-7.16 (2H, m), 7.20-7.26 (2H, m), 7.60-7.68 (1H, m), 8.26-8.31 (2H, m). LCMS (2) 2.43 min; m/z (ES+) 418.

Example S-9

2-(2,6-difluorophenyl)-5-(4-(2-(3-oxopiperazin-1-yl)ethoxy)phenyl)oxazole-4-carboxamide

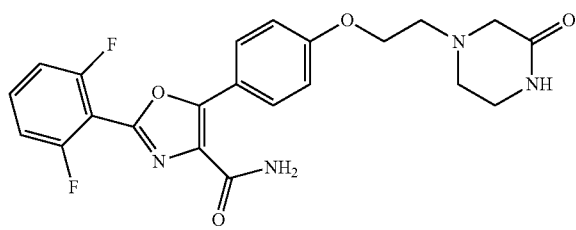 [SMILES: NC(=O)c1nc(-c2c(F)cccc2F)oc1-c1ccc(OCCN2CCNC(=O)C2)cc1]

¹H NMR (CD₃OD) δ 2.87 (2H, t), 2.96 (2H, t), 3.30 (2H, s), 3.37 (2H, t), 4.26 (2H, t), 7.07-7.11 (2H, m), 7.20-7.26 (2H, m), 7.60-7.68 (1H, m), 8.24-8.29 (2H, m). LCMS (2) 2.20 min; m/z (ES+) 443.

Example S-10

1-(2-(4-(4-carbamoyl-2-(2,6-difluorophenyl)oxazol-5-yl)phenoxy)ethyl)piperidine-4-carboxamide

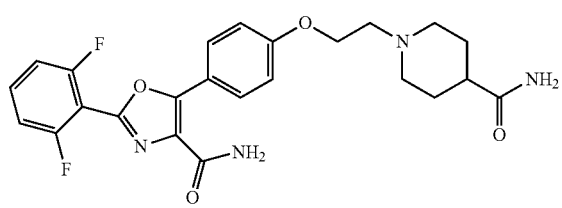 [SMILES: NC(=O)c1nc(-c2c(F)cccc2F)oc1-c1ccc(OCCN2CCC(C(N)=O)CC2)cc1]

¹H NMR (CD₃OD) δ 1.82-1.98 (4H, m), 2.32-2.42 (1H, m), 2.48-2.58 (2H, m), 3.10 (2H, t), 3.27-3.32 (2H, br. s), 4.31 (2H, t), 7.08-7.14 (2H, m), 7.20-7.27 (2H, m), 7.60-7.68 (1H, m), 8.26-8.30 (2H, m). LCMS (2) 2.33 min; m/z (ES+) 471.

Example S-11

5-(4-(2-(benzyl(methyl)amino)ethoxy)phenyl)-2-(2,6-difluorophenyl)oxazole-4-carboxamide

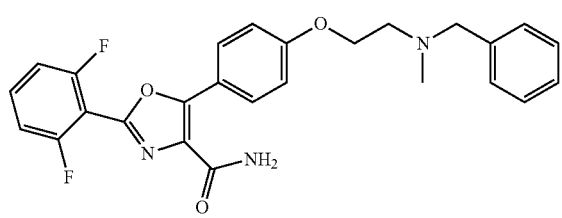 [SMILES: CN(CCOc1ccc(-c2oc(-c3c(F)cccc3F)nc2C(N)=O)cc1)Cc1ccccc1]

¹N NMR (CD₃OD) δ 2.41 (3H, s), 2.94 (2H, t), 3.73 (2H, s), 4.24 (2H, t), 7.02-7.08 (2H, m), 7.16-7.40 (7H, m), 7.60-7.68 (1H, m), 8.23-8.28 (2H, m). LCMS (2) 3.63 min; m/z (ES+) 464.

Example S-12

2-(2,6-difluorophenyl)-5-(4-(3-(piperidin-1-yl)propoxy)phenyl)oxazole-4-carboxamide

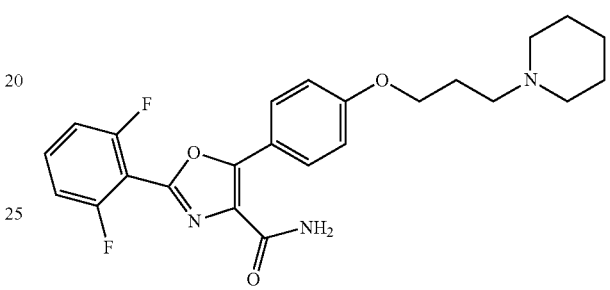

¹H NMR (DMSO) δ 1.36-1.44 (2H, m) 1.53 (4H, quin), 1.92 (2H, quin), 2.42-2.48 (4H, br. s), 3.51 (2H, t), 4.10 (2H, t), 7.06-7.11 (2H, m), 7.35-7.42 (2H, m), 7.66 (2H, br. s), 7.70-7.77 (1H, m), 8.21-8.25 (2H, m). LCMS (2) 3.38 min; m/z (ES+) 442.

Example S-13

2-(2,6-difluorophenyl)-5-(4-(3-morpholinopropoxy)phenyl)oxazole-4-carboxamide

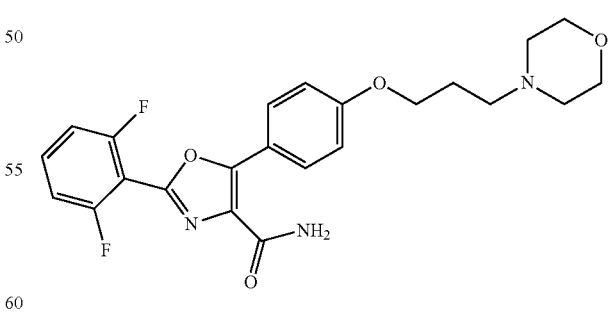

¹H NMR (DMSO) δ 1.90 (2H, quin), 2.34-2.40 (4H, br. s), 2.44 (2H, t), 3.58 (4H, t), 4.10 (2H, t), 7.06-7.11 (2H, m), 7.36-7.42 (2H, m), 7.66 (1H, br. s), 7.68 (1H, br, s), 7.69-7.76 (1H, m), 8.20-8.25 (2H, m). LCMS (2) 2.82 min; m/z (ES+) 444.

Example S-14

2-(2,6-difluorophenyl)-5-(4-(piperidin-4-ylmethoxy)phenyl)oxazole-4-carboxamide

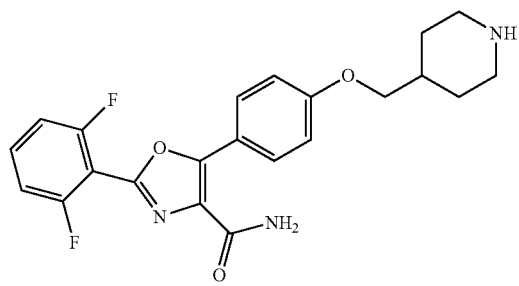 [SMILES: NC(=O)c1nc(-c2c(F)cccc2F)oc1-c1ccc(OCC2CCNCC2)cc1]

The title compound was prepared by alkylation of 2-(2,6-difluorophenyl)-5-(4-hydroxyphenyl)oxazole-4-carboxamide with benzyl 4-(bromomethyl)piperidine-1-carboxylate according to the procedure described in example S-1, step b, followed by subsequent deprotection using the H-cube hydrogenation system (full $H_2$ mode, 10% Pd\C catalyst, 1 ml/min, 20° C., 0.05M in MeOH). NMR (DMSO) δ 1.30-1.50 (2H, m), 1.85 (2H, d), 1.90-2.10 (1H, m), 2.71-2.81 (2H, m), 3.21 (2H, d), 3.92 (2H, d), 7.05-7.15 (2H, m), 7.35-7.45 (2H, m), 7.60-7.80 (3H, m), 8.21-8.30 (2H, m). LCMS (2) 3.13 min; m/z (ES+) 414.

Example S-15

2-(2,6-difluorophenyl)-5-(4-(morpholin-2-ylmethoxy)phenyl)oxazole-4-carboxamide

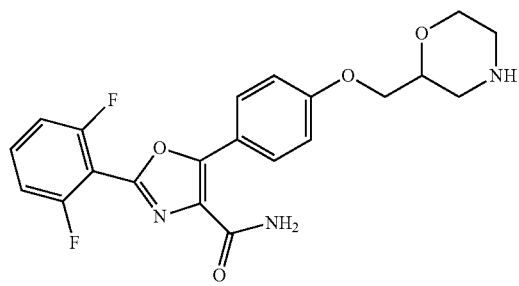 [SMILES: NC(=O)c1nc(-c2c(F)cccc2F)oc1-c1ccc(OCC2CNCCO2)cc1]

The title compound was prepared by alkylation of 2-(2,6-difluorophenyl)-5-(4-hydroxyphenyl)oxazole-4-carboxamide with 2-chloromethyl-4-benzylmorpholine, according to the procedure described in example S-1, step b, followed by subsequent deprotection using the H-cube hydrogenation system (full $H_2$ mode, 10% Pd\C catalyst, 1 ml/min, 0.05M in MeOH, 70° C.). $^1$H NMR (DMSO) δ 2.59-2.70 (2H, m), 2.90-3.00 (2H, m), 3.41-3.51 (1H, m), 3.69-3.79 (2H, m), 4.00 (2H, d), 7.05-7.15 (2H, m), 7.35-7.45 (2H, m), 7.60-7.80 (3H, m), 8.21-8.30 (2H, m). LCMS (2) 2.38 min; m/z (ES+) 416.

Example S-16

2-(2,6-difluorophenyl)-5-(4-(2-((2-hydroxyethyl)(propyl)amino)ethoxy)phenyl)oxazole-4-carboxamide

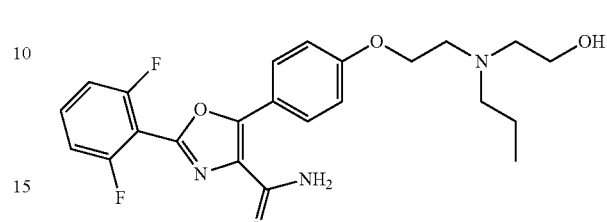

$^1$H NMR (DMSO) δ 0.85 (3H, t), 1.42 (2H, sextet), 2.50 (2H, t), 2.60 (2H, t), 2.88 (2H, t), 3.48 (2H, t), 4.11 (2H, t), 7.05-7.15 (2H, m), 7.35-7.45 (2H, m), 7.60-7.80 (3H, m), 8.20-8.30 (2H, m). LCMS (2) 2.94 min; m/z (ES+) 446.

Example S-17

2-(2,6-difluorophenyl)-5-(4-(2-(3-hydroxypiperidin-1-yl)ethoxy)phenyl)oxazole-4-carboxamide

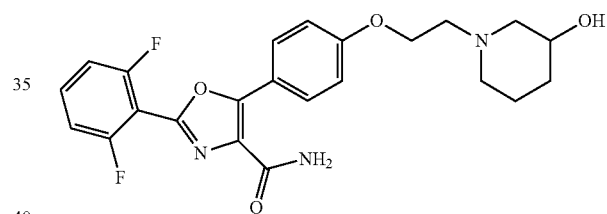

$^1$H NMR (DMSO) δ 1.00-1.11 (1H, m), 1.35-1.50 (1H, m), 1.57-1.65 (1H, m), 1.75-1.85 (2H, m), 1.90-2.00 (1H, m), 2.70-2.80 (3H, m), 2.90-2.98 (1H, m), 3.40-3.52 (1H, m), 4.15 (2H, t), 4.62 (1H, br. s), 7.05-7.15 (2H, m), 7.35-7.45 (2H, m), 7.60-7.80 (3H, m), 8.20-8.30 (2H, m). LCMS (2) 2.51 min; m/z (ES+) 444.

Example S-18

2-(2,6-difluorophenyl)-5-(4-(2-(4-(hydroxymethyl)piperidin-1-yl)ethoxy)phenyl)oxazole-4-carboxamide

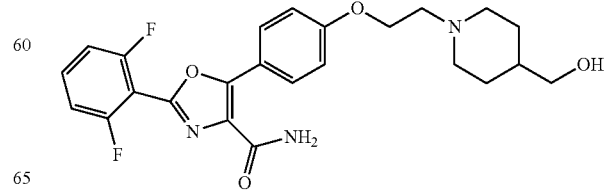

¹H NMR (DMSO) δ 1.08-1.20 (2H, m), 1.28-1.40 (1H, m), 1.60-1.70 (2H, m), 2.00 (2H, t), 2.70 (2H, t), 2.90-3.00 (2H, m), 3.22 (2H, d), 4.15 (2H, t), 7.05-7.15 (2H, m), 7.35-7.45 (2H, m), 7.60-7.80 (3H, m), 8.20-8.30 (2H, m). LCMS (2) 2.57 min; m/z (ES+) 458.

Example S-19

2-(2,6-difluorophenyl)-5-(4-(2-(ethyl(2-hydroxyethyl)amino)ethoxy)phenyl)oxazole-4-carboxamide

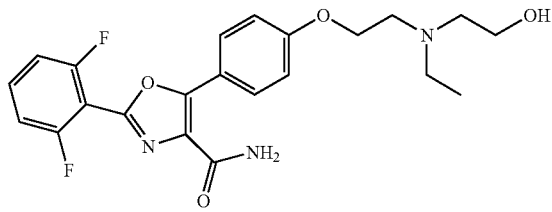 [SMILES: CCN(CCO)CCOc1ccc(-c2oc(-c3c(F)cccc3F)nc2C(N)=O)cc1]

¹H NMR (DMSO) δ 0.98 (3H, t), 2.57-2.64 (4H, m), 2.87 (2H, t), 3.48 (2H, t), 4.11 (2H, t), 7.05-7.15 (2H, m), 7.35-7.45 (2H, m), 7.60-7.80 (3H, m), 8.20-8.30 (2H, m). LCMS (2) 2.66 min; m/z (ES+) 432.

Example S-20

2-(2,6-difluorophenyl)-5-(4-(2-(methylamino)ethoxy)phenyl)oxazole-4-carboxamide

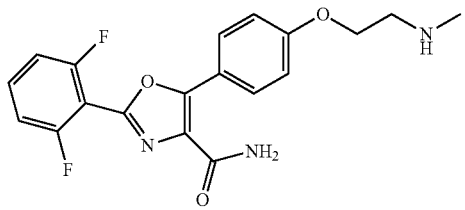 [SMILES: CNCCOc1ccc(-c2oc(-c3c(F)cccc3F)nc2C(N)=O)cc1]

The title compound was prepared by reaction of 5-(4-(2-chloroethoxy)phenyl)-2-(2,6-difluorophenyl)oxazole-4-carboxamide with N-methylbenzylamine, according to the procedure described in example S-1, step c, followed by deprotection with the H-cube hydrogenation system (full H₂ mode, 10% Pd\C catalyst, 1 ml/min, 60° C., 0.05M in MeOH). ¹H NMR (DMSO) δ 2.35 (3H, s), 2.87 (2H, t), 4.10 (2H, t), 7.05-7.15 (2H, m), 7.35-7.45 (2H, m), 7.60-7.80 (3H, m), 8.20-8.30 (2H, m). LCMS (2) 2.55 min; m/z (ES+) 374.

Example S-21

2-(2,6-difluorophenyl)-5-(4-(2-(2-hydroxyethylamino)ethoxy)phenyl)oxazole-4-carboxamide

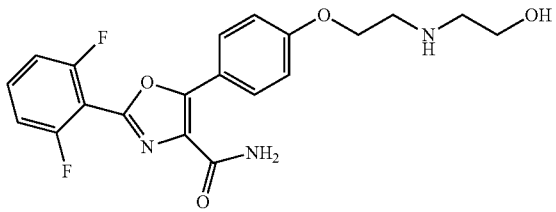 [SMILES: NC(=O)c1nc(-c2c(F)cccc2F)oc1-c1ccc(OCCNCCO)cc1]

The title compound was prepared by reaction of 5-(4-(2-chloroethoxy)phenyl)-2-(2,6-difluorophenyl)oxazole-4-carboxamide with 2-(benzylamino)ethanol, according to the procedure described in example S-1, step c, followed by deprotection with the H-cube hydrogenation system (full H₂ mode, 10% Pd\C catalyst, 1 ml/min, 60° C., 0.05M in MeOH). ¹H NMR (DMSO) δ 2.79 (2H, t), 3.17 (2H, t), 3.55 (2H, t), 4.20 (2H, t), 7.05-7.15 (2H, m), 7.35-7.45 (2H, m), 7.60-7.80 (3H, m), 8.20-8.30 (2H, m). LCMS (2) 2.17 min; m/z (ES+) 404.

General Method T

General Method T comprises the series of steps set out in Scheme 14 above.

Example T-1

2-(2,6-difluorophenyl)-5-(4-(2-hydroxy-3-(piperidin-1-yl)propoxy)phenyl)oxazole-4-carboxamide Step a—2-(2,6-difluorophenyl)-5-(4-(oxiran-2-ylmethoxy)phenyl)oxazole-4-carboxamide

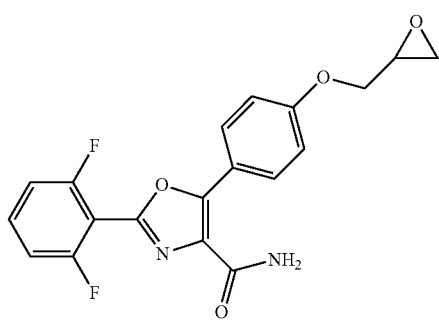 [SMILES: NC(=O)c1nc(-c2c(F)cccc2F)oc1-c1ccc(OCC2CO2)cc1]

To a solution of 2-(2,6-difluorophenyl)-5-(4-hydroxyphenyl)oxazole-4-carboxamide (0.100 g, 0.316 mmol) in DMF (5 ml) was added K₂CO₃ (0.066 g, 0.474 mmol). The resulting mixture was stirred at room temperature for 30 minutes, after which time epichlorohydrin (0.044 g, 0.474 mmol) was added. The reaction was heated to 100° C., stirred at this temperature for 2 h and then diluted with EtOAc before being washed with water and brine. Drying over Na₂SO₄ and removal of solvent under vacuum gave 2-(2,6-difluorophenyl)-5-(4-(oxiran-2-ylmethoxy)phenyl)oxazole-4-carboxamide (0.102 g, 0.274 mmol, 87%) as a golden oil. LCMS (1) 2.00 min; m/z (ES+) 374.

Step b—2-(2,6-difluorophenyl)-5-(4-(2-hydroxy-3-(piperidin-1-yl)propoxy)phenyl)oxazole-4-carboxamide To a solution of 2-(2,6-difluorophenyl)-5-(4-(oxiran-2-ylmethoxy)phenyl)oxazole-4-carboxamide (0.025 g, 0.0671 mmol) in MeOH (1 ml) was added piperidine (0.017 g, 0.201 mmol). The reaction was heated to 100° C. via microwave irradiation and held at this temperature for 15 minutes. The crude reaction was then purified by preparative HPLC to give 2-(2,6-difluorophenyl)-5-(4-(2-hydroxy-3-(piperidin-1-yl) propoxy)phenyl)oxazole-4-carboxamide (0.0036 g, 0.0079 mmol, 12%) as an off white powder. $^1$H NMR (DMSO) δ 1.34-1.41 (2H, m), 1.46-1.54 (4H, m), 2.35-2.48 (6H, m), 3.92-4.01 (2H, m), 4.04-4.08 (1H, m), 7.08-7.12 (2H, m), 7.34-7.41 (2H, m), 7.66 (1H, br. s), 7.68 (1H, br, s), 7.69-7.76 (1H, m), 8.20-8.24 (2H, m). LCMS (2) 3.06 min; m/z (ES+) 458.

In a similar manner as described in example T-1 the compounds described in examples T-2 to T-4 were prepared.

Example T-2

2-(2,6-difluorophenyl)-5-(4-(2-hydroxy-3-morpholinopropoxy)phenyl)oxazole-4-carboxamide

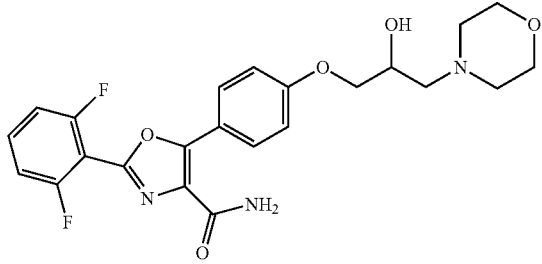 [SMILES: NC(=O)c1nc(-c2c(F)cccc2F)oc1-c1ccc(OCC(O)CN2CCOCC2)cc1]

$^1$H NMR (DMSO) δ 2.35-2.50 (6H, m), 3.56 (4H, t), 3.94-4.02 (2H, m), 4.05-4.10 (1H, m), 7.08-7.12 (2H, m), 7.36-7.42 (2H, m), 7.66 (1H, br. s), 7.68 (1H, br, s), 7.70-7.76 (1H, m), 8.20-8.26 (2H, m). LCMS (2) 2.44 min; m/z (ES+) 460.

Example T-3

2-(2,6-difluorophenyl)-5-(4-(2-hydroxy-3-(4-methylpiperazin-1-yl)propoxy)phenyl)oxazole-4-carboxamide

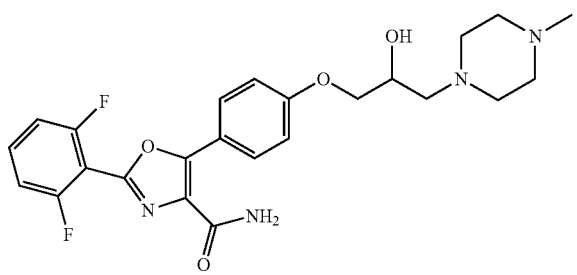 [SMILES: CN1CCN(CC(O)COc2ccc(-c3oc(-c4c(F)cccc4F)nc3C(N)=O)cc2)CC1]

$^1$H NMR (DMSO) δ 2.16 (3H, s), 2.28-2.40 (6H, m), 2.40-2.50 (4H, m), 3.92-4.00 (2H, m), 4.03-4.09 (1H, m), 7.07-7.12 (2H, m), 7.34-7.42 (2H, m), 7.66 (1H, br. s), 7.68 (1H, br, s), 7.70-7.76 (1H, m), 8.20-8.26 (2H, m). LCMS (2) 2.37 min; m/z (ES+) 473.

Example T-4

2-(2,6-difluorophenyl)-5-(4-(2-hydroxy-3-(4-hydroxypiperidin-1-yl)propoxy)phenyl)oxazole-4-carboxamide

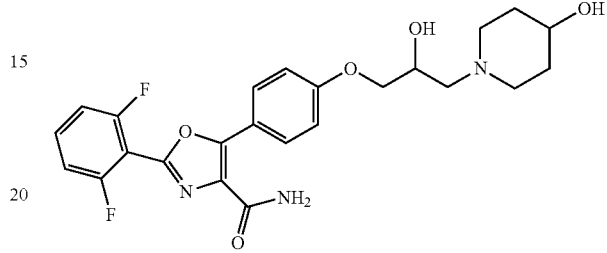

$^1$H NMR (DMSO) δ 1.36-1.46 (2H, m), 1.68-1.76 (2H, m), 2.15-2.26 (3H, m), 2.40-2.46 (1H, m), 2.76-2.86 (2H, m), 3.42-3.50 (1H, m), 3.92-4.02 (2H, m), 4.03-4.08 (1H, m), 7.07-7.12 (2H, m), 7.34-7.41 (2H, m), 7.66 (2H, br s), 7.68-7.76 (1H, m), 8.20-8.25 (2H, m). LCMS (2) 2.28 min; m/z (ES+) 474.

General Method U

General Method U comprises the series of steps set out in Scheme 15 above.

Example U-1

4-(4-carbamoyl-2-(2,6-difluorophenyl)oxazol-5-ylamino)benzoic acid

Step a—4-(4-cyano-2-(2,6-difluorophenyl)oxazol-5-ylamino)benzoic acid

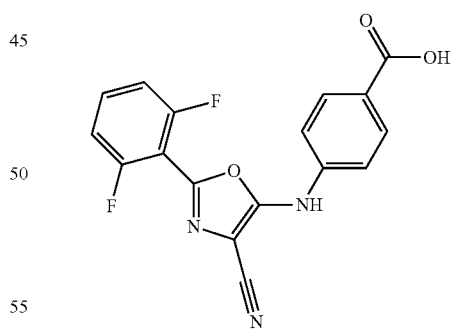

A solution of tris(dibenzylideneacetone)dipalladium(0) (0.337 g, 0.368 mmol) and 9,9-dimethyl-4,5-bis(diphenylphosphino)xanthene (0.213 g, 0.368 mmol) in n-butanol: dioxane (1:1) (5 mL) was stirred at room temperature for 3 minutes. Then 5-bromo-2-(2,6-difluorophenyl)oxazole-4-carbonitrile (1.50 g, 5.262 mmol), 4-aminobenzoic acid (2.165 g, 15.787 mmol) and cesium carbonate (3.429 g, 10.525 mmol) were added and the mixture heated in the microwave for 3 minutes at 140° C. The reaction was diluted with EtOAc and washed with water. The organic phase was passed through an MP-SH cartridge, dried over MgSO$_4$ and the solvent removed in vacuo. The residue was purified by column chromatography using a 20-45% EtOAc:hexane gradient then further purified by trituration of the solid in DCM:hexane (1:1) to afford 4-(4-cyano-2-(2,6-difluorophenyl)oxazol-5-ylamino)benzoic acid (0.251 g, 0.735 mmol, 14%) as a light yellow solid. $^1$H NMR (DMSO) δ 7.34 (2H, t), 7.40 (2H, d), 7.66 (1H, m), 7.92 (2H, d), 11.16 (1H, br s), 12.76 (1H, br s). LCMS (3) Rt: 1.53 min; m/z (ES+) 342.

Step b—4-(4-carbamoyl-2-(2,6-difluorophenyl)oxazol-5-ylamino)benzoic acid

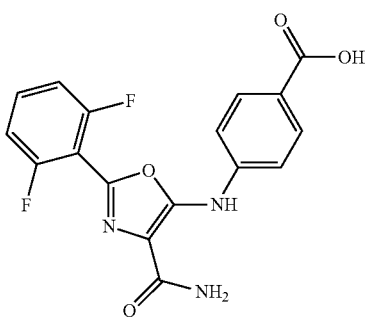 [SMILES: NC(=O)c1nc(-c2c(F)cccc2F)oc1Nc1ccc(C(=O)O)cc1]

A solution of 4-(4-cyano-2-(2,6-difluorophenyl)oxazol-5-ylamino)benzoic acid (0.962 g, 2.819 mmol) in concentrated sulfuric acid (5 mL) was stirred at room temperature for 1.5 hours. The reaction mixture was added to ice water and a precipitate formed. The precipitate was isolated by filtration and the remaining aqueous layer extracted with ethyl acetate. The organic layer was combined with the precipitate and reduced in vacuo to yield 4-(4-carbamoyl-2-(2,6-difluorophenyl)oxazol-5-ylamino)benzoic acid (0.580 g, 1.614 mmol, 57%) as a yellow solid. $^1$H NMR (DMSO) δ 7.35 (2H, t), 7.46 (4H, m), 7.65 (1H, m), 7.87 (2H, d), 9.71 (1H, s), 12.64 (1H, br s). LCMS (2) Rt: 1.37 min; m/z (ES+) 360.

Example U-2

2-(2,6-difluorophenyl)-5-(4-(morpholine-4-carbonyl)phenylamino)oxazole-4-carboxamide Step a—2-(2,6-difluorophenyl)-5-(4-(morpholine-4-carbonyl)phenylamino)oxazole-4-carbonitrile

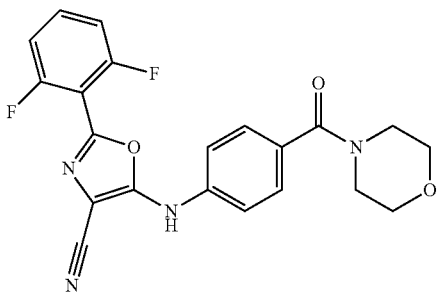 [SMILES: N#Cc1nc(-c2c(F)cccc2F)oc1Nc1ccc(C(=O)N2CCOCC2)cc1]

To a solution of 4-(4-cyano-2-(2,6-difluorophenyl)oxazol-5-ylamino)benzoic acid (0.020 g, 0.059 mmol), O-(7-azabenzotriazol-1-yl)-N,N,N',N'-tetramethyluronium hexafluorophosphate (0.022 g, 0.059 mmol), and diisopropylethylamine (0.020 mL, 0.117 mmol) in N,N-dimethylformide (2 mL) was added morpholine (0.005 mL, 0.059 mmol) and the reaction mixture stirred at room temperature for 16 hours. The reaction was then diluted with EtOAc washed with 1M HCl, water and brine. The organic phase was dried over MgSO$_4$ and the solvent removed in vacuo. The residue was purified by preparative HPLC to afford 2-(2,6-difluorophenyl)-5-(4-(morpholine-4-carbonyl)phenylamino)oxazole-4-carbonitrile (0.009 g, 0.022 mmol, 37%) as a yellow solid. LCMS (2) Rt: 2.38 min; m/z (ES+) 411.

Step b—2-(2,6-difluorophenyl)-5-(4-(morpholine-4-carbonyl)phenylamino)oxazole-4-carboxamide

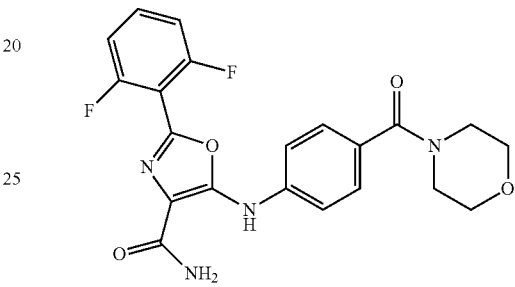

A solution of 2-(2,6-difluorophenyl)-5-(4-(morpholine-4-carbonyl)phenylamino)oxazole-4-carbonitrile (0.009 g, 0.022 mmol) in concentrated sulfuric acid (0.5 m L) was stirred at room temperature for 1.5 hours. The solution was neutralised by pouring into saturated sodium bicarbonate solution. The aqueous phase was then basified to pH14 using 5M NaOH and extracted with EtOAc. The combined organic phase was dried over MgSO$_4$ and the solvent removed in vacuo to afford 2-(2,6-difluorophenyl)-5-(4-(morpholine-4-carbonyl)phenylamino)oxazole-4-carboxamide (0.007 g, 0.017 mmol, 77%) as a yellow solid. $^1$H NMR (DMSO) δ 3.51 (4H, m), 3.58 (4H, m), 7.32-7.47 (8H, m), 7.64 (1H, m), 9.55 (1H, s). LCMS (2) Rt: 2.14 min; m/z (ES+) 429.

Example U-3

5-(4-((2-(methylamino)ethyl)carbamoyl)phenylamino)-2-(2,6-difluorophenyl) oxazole-4-carboxamide

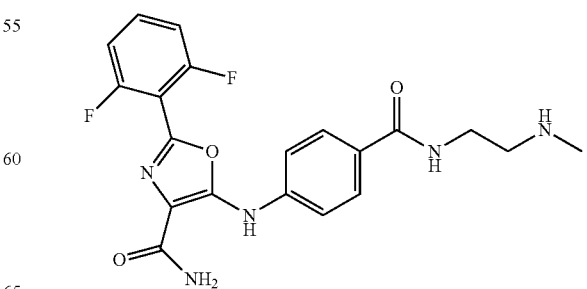

Prepared according to the procedure described in example U-2. ¹H NMR (DMSO) δ 2.30 (3H, s), 2.64 (2H, t), 3.32 (2H, t), 7.34 (2H, t), 7.39 (2H, br s), 7.45 (2H, d), 7.64 (1H, m), 7.81 (2H, d), 8.28 (1H, t). LCMS (2) Rt: 2.00 min; m/z (ES+) 416.

Example U-4

5-(4-((3-(methylamino)propyl)carbamoyl)phenylamino)-2-(2,6-difluorophenyl) oxazole-4-carboxamide

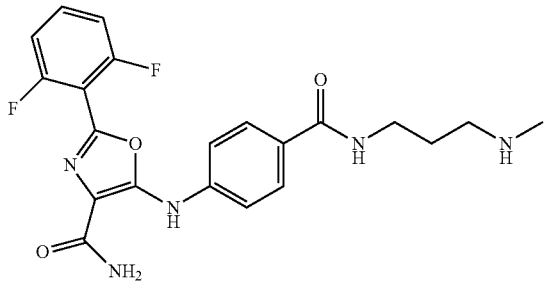 [SMILES: CNCCCNC(=O)c1ccc(Nc2oc(-c3c(F)cccc3F)nc2C(N)=O)cc1]

Prepared according to the procedure described in example U-2. ¹H NMR (DMSO) δ 1.65 (2H, quin), 2.29 (3H, s), 2.53 (2H, m), 3.28 (2H, m), 7.33 (2H, t), 7.45 (2H, d), 7.51 (2H, br s), 7.63 (1H, m), 7.79 (2H, d), 8.40 (1H, t). LCMS (2) Rt: 2.07 min; m/z (ES+) 430.

Example U-5

5-(4-(((4-benzylmorpholin-2-yl)methyl)carbamoyl)phenylamino)-2-(2,6-difluorophenyl)oxazole-4-carboxamide

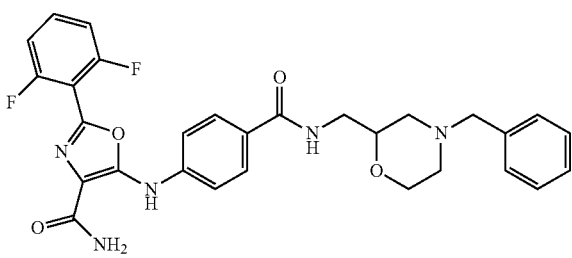 [SMILES: NC(=O)c1nc(-c2c(F)cccc2F)oc1Nc1ccc(C(=O)NCC2CN(Cc3ccccc3)CCO2)cc1]

Prepared according to the procedure described in example U-2. ¹H NMR (DMSO) δ 1.83 (1H, t), 2.05 (1H, t), 2.57 (1H, d), 2.78 (1H, d), 3.28 (2H, m), 3.52-3.59 (3H, m), 3.61 (1H, m), 3.78 (1H, d), 7.23 (1H, m), 7.29-7.37 (6H, m), 7.45 (4H, m), 7.65 (1H, m), 7.80 (2H, d), 8.42 (1H, t), 9.60 (1H, s). LCMS (2) Rt: 2.72 min; m/z (ES+) 548.

Example U-6

(R)-2-(2,6-difluorophenyl)-5-(4-(pyrrolidin-3-ylcarbamoyl)phenylamino)oxazole-4-carboxamide

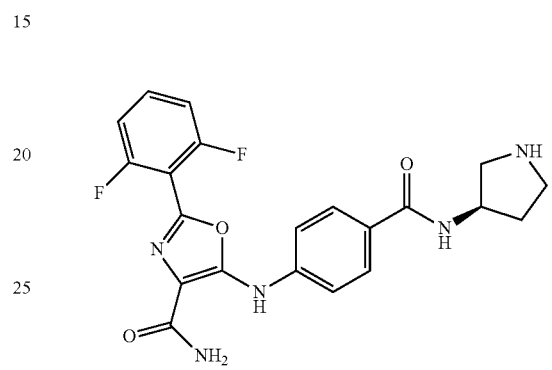

Prepared according to the procedure described in example U-2. ¹H NMR (DMSO) δ 1.68 (1H, m), 1.98 (1H, m), 2.71 (1H, m), 2.78 (1H, m), 2.96 (2H, m), 4.31 (1H, m), 7.34 (2H, t), 7.37-7.52 (4H, m), 7.63 (1H, m), 7.82 (2H, d), 8.21 (1H, d). LCMS (2) Rt: 2.04 min; m/z (ES+) 428.

Example U-7

(S)-2-(2,6-difluorophenyl)-5-(4-(pyrrolidin-3-ylcarbamoyl)phenylamino)oxazole-4-carboxamide

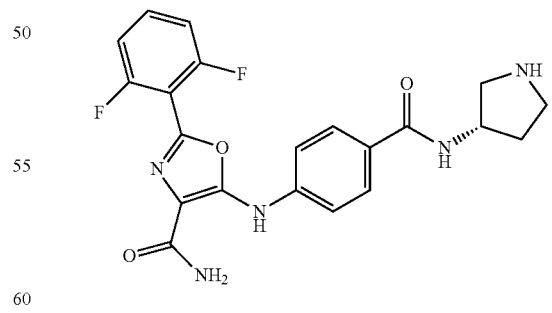

Prepared according to the procedure described in example U-2. ¹H NMR (DMSO) δ 1.68 (1H, m), 1.98 (1H, m), 2.71 (1H, m), 2.78 (1H, m), 2.96 (2H, m), 4.31 (1H, m), 7.34 (2H, t), 7.37-7.52 (4H, m), 7.63 (1H, m), 7.82 (2H, d), 8.21 (1H, d). LCMS (2) Rt: 2.05 min; m/z (ES+) 428.

Example U-8

5-(4-((2-(dimethylamino)ethyl)carbamoyl)phenylamino)-2-(2,6-difluorophenyl) oxazole-4-carboxamide

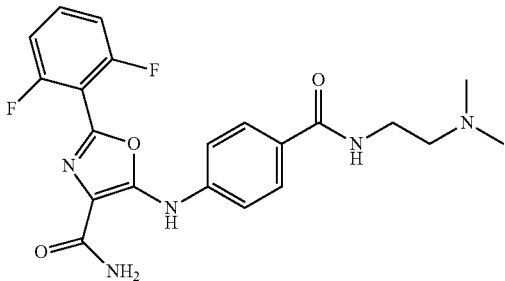 [SMILES: CN(C)CCNC(=O)c1ccc(Nc2oc(-c3c(F)cccc3F)nc2C(N)=O)cc1]

Prepared according to the procedure described in example U-2. ¹H NMR (CD₃OD) δ 2.40 (6H, d), 2.68 (2H, t), 3.56 (2H, t), 7.20 (2H, t), 7.51 (2H, d), 7.58 (1H, m), 7.86 (2H, d). LCMS (2) Rt: 2.14 min; m/z (ES+) 430.

Example U-9

5-(4-((2-morpholinoethyl)carbamoyl)phenylamino)-2-(2,6-difluorophenyl)oxazole-4-carboxamide

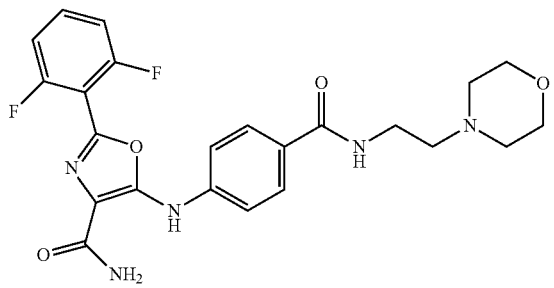 [SMILES: NC(=O)c1nc(-c2c(F)cccc2F)oc1Nc1ccc(C(=O)NCCN2CCOCC2)cc1]

Prepared according to the procedure described in example U-2. NMR (CD₃OD) δ 2.45 (4H, m), 2.51 (2H, t), 3.45 (2H, t), 3.61 (4H, t), 7.11 (2H, t), 7.41 (2H, d), 7.47 (1H, m), 7.76 (2H, d). LCMS (2) Rt: 2.03 min; m/z (ES+) 472.

Example U-10

2-(2,6-difluorophenyl)-5-(4-(quinuclidin-3-ylcarbamoyl)phenylamino)oxazole-4-carboxamide

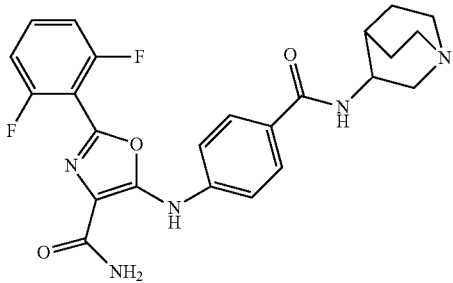 [SMILES: NC(=O)c1nc(-c2c(F)cccc2F)oc1Nc1ccc(C(=O)NC2CN3CCC2CC3)cc1]

Prepared according to the procedure described in example U-2. ¹H NMR (CD₃OD) δ 1.63 (1H, m), 1.84 (2H, m), 1.98 (1H, m), 2.11 (1H, m), 2.85-3.02 (4H, m); 3.10 (1H, m), 3.41 (1H, m), 4.19 (1H, m), 7.20 (2H, t), 7.52 (2H, d), 7.58 (1H, m), 7.88 (2H, d). LCMS (2) Rt: 2.27 min; m/z (ES+) 468.

Example U-11

5-(4-((8-methyl-8-aza-bicyclo[3.2.1]octan-3-yl)carbamoyl)phenylamino)-2-(2,6-difluorophenyl)oxazole-4-carboxamide

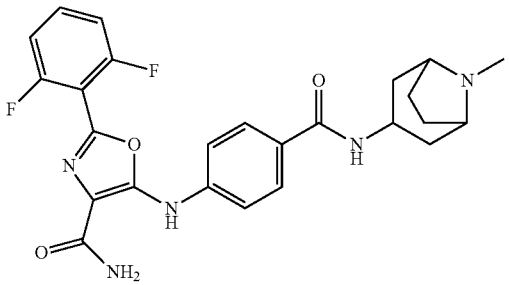 [SMILES: CN1C2CCC1CC(NC(=O)c1ccc(Nc3oc(-c4c(F)cccc4F)nc3C(N)=O)cc1)C2]

Prepared according to the procedure described in example U-2. ¹H NMR (CD₃OD) δ 2.10-2.33 (8H, m), 2.53 (3H, s), 3.48 (2H, m), 4.09 (1H, t), 7.24 (2H, t), 7.55 (2H, d), 7.61 (1H, m), 7.83 (2H, d). LCMS (2) Rt: 2.28 min; m/z (ES+) 482.

Example U-12

(R)-2-(2,6-difluorophenyl)-5-(4-(2-(hydroxymethyl)pyrrolidine-1-carbonyl)phenylamino)oxazole-4-carboxamide

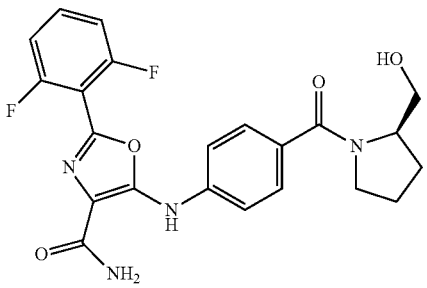 [SMILES: NC(=O)c1nc(-c2c(F)cccc2F)oc1Nc1ccc(C(=O)N2CCC[C@@H]2CO)cc1]

To a solution of 4-(4-carbamoyl-2-(2,6-difluorophenyl)oxazol-5-ylamino)benzoic acid (0.040 g, 0.111 mmol), O-(7-Azabenzotriazol-1-yl)-N,N,N',N'-tetramethyluronium hexafluorophosphate (0.042 g, 0.111 mmol), and diisopropylethylamine (0.038 mL, 0.222 mmol) in DMF (0.35 mL) was added D-prolinol (0.011 mL, 0.111 mmol) and the reaction mixture stirred at room temperature for 6 hours. The reaction was reduced in vacuo. The residue was purified by preparative HPLC to afford the white solid (R)-2-(2,6-difluorophenyl)--

5-(4-(2-(hydroxymethyl)pyrrolidine-1-carbonyl)phenylamino)oxazole-4-carboxamide (0.018 g, 0.040 mmol, 36%). $^1$H NMR (DMSO) δ 1.68 (1H, m), 1.90 (3H, m), 3.61-3.32 (4H, m), 4.13 (1H, br s), 4.75 (1H, t), 7.50-7.31 (8H, m), 7.64 (1H, m), 9.50 (1H, br s). LCMS (2) Rt: 2.10 min; m/z (ES+) 443.

Example U-13

(S)-2-(2,6-difluorophenyl)-5-(4-(2-(hydroxymethyl)pyrrolidine-1-carbonyl)phenylamino)oxazole-4-carboxamide

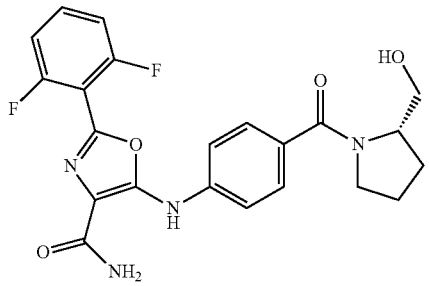 [SMILES: NC(=O)c1nc(-c2c(F)cccc2F)oc1Nc1ccc(C(=O)N2CCC[C@H]2CO)cc1]

Prepared according to the procedure described in example U-12. $^1$H NMR (DMSO) δ 1.68 (1H, m), 1.90 (3H, m), 3.61-3.32 (4H, m), 4.13 (1H, br s), 4.75 (1H, t), 7.50-7.31 (8H, m), 7.64 (1H, m), 9.50 (1H, br s). LCMS (2) Rt: 2.11 min; m/z (ES+) 443.

Example U-14

2-(2,6-difluorophenyl)-5-(4-(2-(hydroxymethyl)piperidine-1-carbonyl)phenylamino) oxazole-4-carboxamide

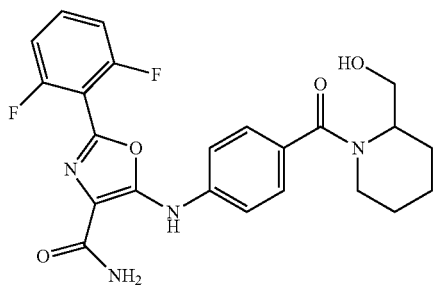 [SMILES: NC(=O)c1nc(-c2c(F)cccc2F)oc1Nc1ccc(C(=O)N2CCCCC2CO)cc1]

Prepared according to the procedure described in example U-12. $^1$H NMR (DMSO) δ 1.74-1.30 (6H, m), 2.92 (1H, m), 3.49 (1H, m), 3.61 (1H, m), 4.10 (2H, br m), 4.75 (1H, t), 7.41-7.31 (6H, m), 7.43 (2H, d), 7.64 (1H, m), 9.41 (1H, br s). LCMS (2) Rt: 2.21 min; m/z (ES+) 457.

Example U-15

2-(2,6-difluorophenyl)-5-(4-(3-hydroxypiperidine-1-carbonyl)phenylamino)oxazole-4-carboxamide

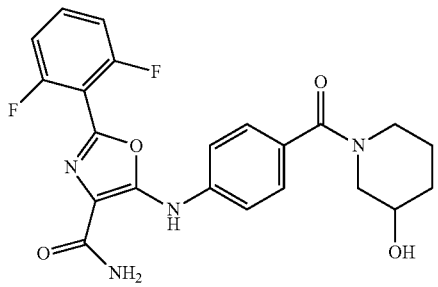 [SMILES: NC(=O)c1nc(-c2c(F)cccc2F)oc1Nc1ccc(C(=O)N2CCCC(O)C2)cc1]

Prepared according to the procedure described in example U-12. $^1$H NMR (DMSO) δ 1.40 (2H, m), 1.69 (1H, m), 1.86 (1H, m), 3.08-2.75 (2H, m), 3.49 (1H, m), 4.06 (2H, br m), 4.87 (1H, br s), 7.38-7.31 (6H, m), 7.43 (2H, d), 7.64 (1H, m), 9.48 (1H, br s). LCMS (2) Rt: 2.03 min; m/z (ES+) 443.

Example U-16

5-(4-((2-hydroxyethyl)carbamoyl)phenylamino)-2-(2,6-difluorophenyl)oxazole-4-carboxamide

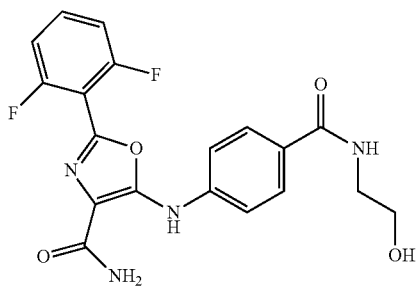 [SMILES: NC(=O)c1nc(-c2c(F)cccc2F)oc1Nc1ccc(C(=O)NCCO)cc1]

Prepared according to the procedure described in example U-12. $^1$H NMR (DMSO) δ 3.31 (2H, q), 3.49 (2H, q), 4.72 (1H, t), 7.34 (2H, t), 7.42 (2H, br s), 7.46 (2H, d), 7.64 (1H, m), 7.83 (2H, d), 8.31 (1H, br t), 9.57 (1H, br s). LCMS (2) Rt: 1.83 min; m/z (ES+) 403.

Example U-17

5-(4-((3-hydroxypropyl)carbamoyl)phenylamino)-2-(2,6-difluorophenyl)oxazole-4-carboxamide

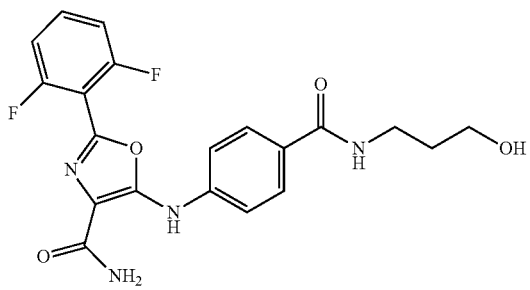 [SMILES: NC(=O)c1nc(-c2c(F)cccc2F)oc1Nc1ccc(C(=O)NCCCO)cc1]

Prepared according to the procedure described in example U-12. $^1$H NMR (DMSO) δ 1.66 (2H, quin), 3.30 (2H, q), 3.45 (2H, q), 4.45 (1H, t), 7.34 (2H, t), 7.39 (2H, br s), 7.48 (2H, d), 7.64 (1H, m), 7.81 (2H, d), 8.29 (1H, br t), 9.55 (1H, br s). LCMS (2) Rt: 1.90 min; m/z (ES+) 417.

Example U-18

5-(4-((1-methylpiperidin-4-yl)carbamoyl)phenylamino)-2-(2,6-difluorophenyl) oxazole-4-carboxamide

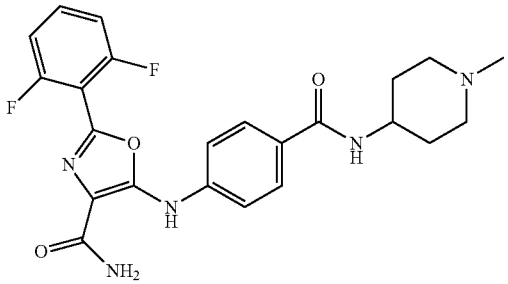 [SMILES: CN1CCC(NC(=O)c2ccc(Nc3oc(-c4c(F)cccc4F)nc3C(N)=O)cc2)CC1]

Prepared according to the procedure described in example U-12. $^1$H NMR (DMSO) δ 1.58 (2H, q), 1.75 (2H, d), 1.97 (2H, t), 2.18 (3H, s), 2.78 (2H, d), 3.72 (1H, br m), 7.34 (2H, t), 7.40 (2H, br s), 7.47 (2H, d), 7.65 (1H, m), 7.84 (2H, d), 8.11 (1H, d). LCMS (2) Rt: 2.09 min; m/z (ES+) 456.

Example U-19

2-(2,6-difluorophenyl)-5-(4-(3-(hydroxymethyl)morpholine-4-carbonyl)phenylamino)oxazole-4-carboxamide

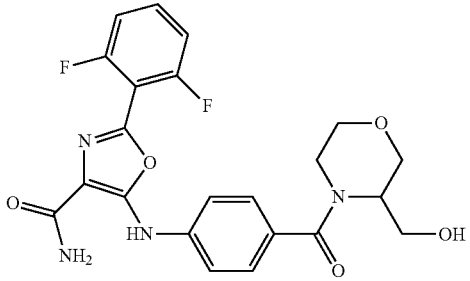 [SMILES: NC(=O)c1nc(-c2c(F)cccc2F)oc1Nc1ccc(C(=O)N2CCOCC2CO)cc1]

Prepared according to the procedure described in example U-12. $^1$H NMR (CD$_3$OD) δ 3.31 (2H, m), 3.53 (1H, m), 3.63 (1H, m), 3.86 (5H, m), 7.20 (2H, t), 7.50 (4H, m), 7.56 (1H, m). LCMS (2) Rt: 1.92 min; m/z (ES+) 459.

Example U-20 tert-butyl 4-(4-(4-carbamoyl-2-(2,6-difluorophenyl)oxazol-5-ylamino)benzamido) piperidine-1-carboxylate

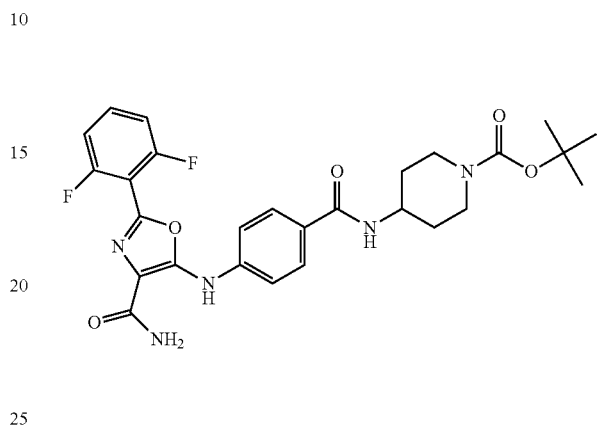

Prepared according to the procedure described in example U-12. $^1$H NMR (DMSO) δ 1.41 (11H, m), 1.75 (2H, d), 2.83 (2H, br m), 3.94 (3H, m), 7.34 (2H, t), 7.42 (2H, br s), 7.46 (2H, d), 7.64 (1H, m), 7.82 (2H, d), 8.14 (1H, d), 9.57 (1H, br s). LCMS (2) Rt: 2.83 min; m/z (ES+) 542.

Example U-21

2-(2,6-difluorophenyl)-5-(4-(piperidin-4-ylcarbamoyl)phenylamino)oxazole-4-carboxamide

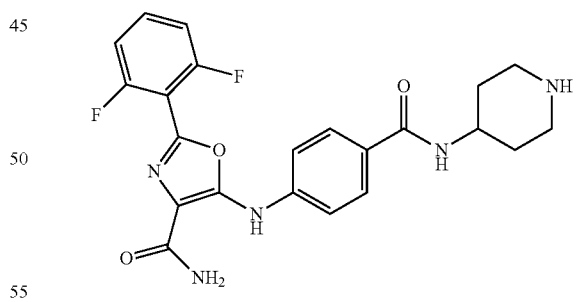

To tert-butyl 4-(4-(4-carbamoyl-2-(2,6-difluorophenyl)oxazol-5-ylamino)benzamido) piperidine-1-carboxylate (0.019 g, 0.036 mmol) was added 1M HCl in dioxane and the reaction mixture stirred at room temperature for 2 hours. The reaction mixture was reduced in vacuo, taken up in methanol and purified by SPE using a MP-TsOH cartridge (500 mg) to generate 2-(2,6-difluorophenyl)-5-(4-(piperidin-4-ylcarbamoyl)phenylamino) oxazole-4-carboxamide (0.014 g, 0.031 mmol, 98%) as a white solid. $^1$H NMR (DMSO) δ 1.45 (2H, q), 1.75 (2H, d), 2.58 (2H, t), 3.00 (2H, d), 3.84 (1H, m), 7.33 (2H, t), 7.40 (2H, br s), 7.46 (2H, d), 7.64 (1H, m), 7.83 (2H, d), 8.11 (1H, d). LCMS (2) Rt: 1.87 min; m/z (ES+) 442.

Example U-22 tert-butyl (4-(4-(4-carbamoyl-2-(2,6-difluorophenyl)oxazol-5-ylamino)benzoyl) morpholin-2-yl)methyl-carbamate

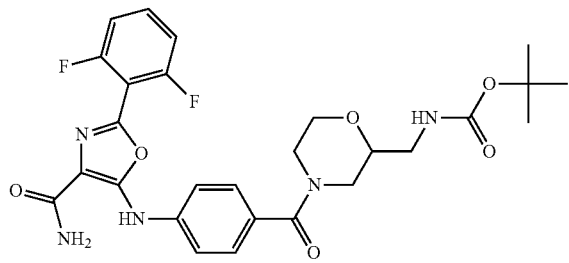 [SMILES: CC(C)(C)OC(=O)NCC1CN(C(=O)c2ccc(Nc3oc(-c4c(F)cccc4F)nc3C(N)=O)cc2)CCO1]

Prepared according to the procedure described in example U-12. $^1$H NMR (CD$_3$OD) δ 1.38 (11H, br m), 2.98 (2H, br m), 3.15 (2H, m), 3.51 (1H, m), 3.58 (1H, m), 3.94 (1H, br m), 7.21 (2H, t), 7.47 (2H, d), 7.53 (2H, d), 7.59 (1H, m). LCMS (2) Rt: 2.54 min; m/z (ES+) 558.

Example U-23

5-(4-(2-(aminomethyl)morpholine-4-carbonyl)phenylamino)-2-(2,6-difluorophenyl) oxazole-4-carboxamide

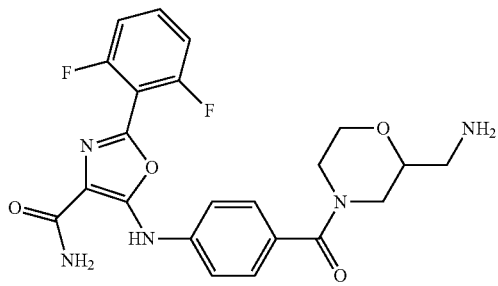 [SMILES: NCC1CN(C(=O)c2ccc(Nc3oc(-c4c(F)cccc4F)nc3C(N)=O)cc2)CCO1]

Prepared according to the procedure described in example U-21. $^1$H NMR (DMSO) δ 2.76 (1H, br m), 2.84 (1H, br m), 3.10 (1H, br m), 3.53-3.45 (3H, m), 3.69 (2H, m), 3.89 (1H, br m), 7.34 (2H, t), 7.42-7.37 (4H, m), 7.47 (2H, d), 7.65 (1H, m). LCMS (2) Rt: 1.86 min; m/z (ES+) 458.

Example U-24

2-(2,6-difluorophenyl)-5-(4-(2-(2-hydroxyethyl)-1-methylpiperazine-4-carbonyl)phenylamino)oxazole-4-carboxamide

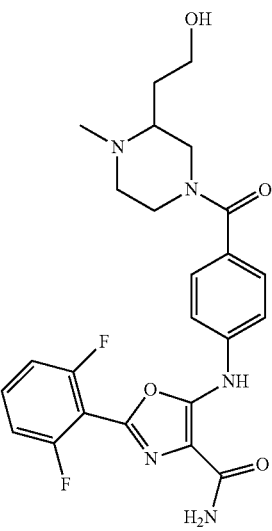 [SMILES: CN1CCN(C(=O)c2ccc(Nc3oc(-c4c(F)cccc4F)nc3C(N)=O)cc2)CC1CCO]

2-(1-methylpiperazin-2-yl)ethanol was prepared by dissolving methyl 2-(1-methyl-3-oxopiperazin-2-yl)acetate (0.500 g, 2.50 mmol, prepared according to Abelman et al., Tetrahedron Letters, 44 (2003), 1823-1826) in THF (10 ml) followed by addition of LiAlH$_4$ (2M in THF, 3.12 ml, 6.24 mmol). The resulting solution was refluxed for 2 h, concentrated in vacuo, basified to pH12 with 1M NaOH solution and filtered through a celite pad. The filtrate was purified by SPE using a TsOH cartridge to give 2-(1-methylpiperazin-2-yl)ethanol as a golden oil (0.125 g, 0.87 mmol). 2-(2,6-difluorophenyl)-5-(4-(2-(2-hydroxyethyl)-1-methylpiperazine-4-carbonyl)phenylamino)oxazole-4-carboxamide was then prepared using the method described in example U-12. $^1$H NMR (CD$_3$OD) δ 1.35-1.40 (1H, m), 1.92-2.05 (1H, m), 2.10-2.20 (2H, m), 2.36 (3H, s), 2.30-2.38 (1H, m), 2.85-2.95 (2H, m), 3.25-3.35 (2H, m), 3.55-3.65 (2H, br. s), 7.15-7.25 (2H, m), 7.42-7.48 (2H, m), 7.50-7.60 (3H, m) LCMS (2) 1.96 min; m/z (ES+) 486.

Example U-25

2-(2,6-difluorophenyl)-5-(4-(2-(hydroxymethyl)-1-methylpiperazine-4-carbonyl)phenylamino)oxazole-4-carboxamide

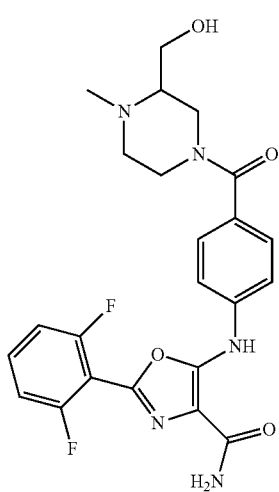 [SMILES: CN1CCN(C(=O)c2ccc(Nc3oc(-c4c(F)cccc4F)nc3C(N)=O)cc2)CC1CO]

The above compound was synthesised by the method given in example U-12 using (1-methylpiperazin-2-yl)methanol (cf. WO 2005/026152) as a starting material. $^1$H NMR (CD$_3$OD) δ 1.45-1.52 (2H, m), 2.40-2.50 (1H, m), 2.50-2.60 (4H, m), 2.95-3.08 (1H, m), 3.10-3.30 (2H, m), 3.65-3.80 (2H, m), 7.18-7.25 (2H, m), 7.48-7.55 (4H, m), 7.56-7.65 (1H, m). LCMS (2) 1.82 min; m/z (ES+) 472.

Example U-26

(R)-2-(2,6-difluorophenyl)-5-(4-(3-(hydroxymethyl)-1-methylpiperazine-4-carbonyl)phenylamino)oxazole-4-carboxamide

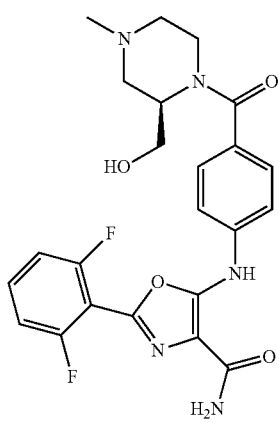 [SMILES: CN1CCN(C(=O)c2ccc(Nc3oc(-c4c(F)cccc4F)nc3C(N)=O)cc2)[C@@H](CO)C1]

The above compound was synthesised by the method given in example U-12 using (R)-(4-methylpiperazin-2-yl)methanol (cf. Falomi and Giacomelli, SYNLETT, 1996, p 143-144) as a starting material. $^1$H NMR (CD$_3$OD) δ 2.22 (1H, dt), 2.30-2.40 (4H, m), 2.90-3.00 (1H, m), 3.05-3.15 (1H, m), 3.25-3.35 (3H, m, partially obscured by solvent peak), 3.75-3.85 (1H, br. s), 3.89-3.98 (1H, m), 7.18-7.25 (2H, m), 7.48-7.54 (4H, m), 7.56-7.62 (1H, m) LCMS (2) 1.94 min; m/z (ES+) 472.

Example U-27

(S)-2-(2,6-difluorophenyl)-5-(4-(3-(hydroxymethyl)-1-methylpiperazine-4-carbonyl)phenylamino)oxazole-4-carboxamide

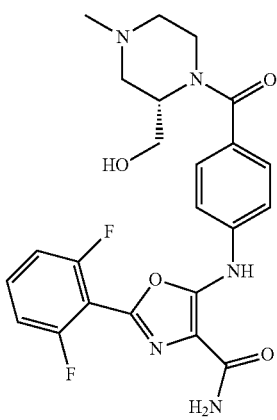 [SMILES: CN1CCN(C(=O)c2ccc(Nc3oc(-c4c(F)cccc4F)nc3C(N)=O)cc2)[C@H](CO)C1]

The above compound was synthesised by the method given in example U-12 using (S)-(4-methylpiperazin-2-yl)methanol (cf. Falomi and Giacomelli, SYNLETT, 1996, p 143-144) as a starting material. $^1$H NMR (CD$_3$OD) δ 2.22 (1H, dt), 2.30-2.40 (4H, m), 2.90-3.00 (1H, m), 3.05-3.15 (1H, m), 3.25-3.35 (3H, m, partially obscured by solvent peak), 3.75-3.85 (1H, br. s), 3.89-3.98 (1H, m), 7.18-7.25 (2H, m), 7.48-7.54 (4H, m), 7.56-7.62 (1H, m) LCMS (2) 1.94 min; m/z (ES+) 472.

General Method V

General Method V comprises the series of steps set out in Scheme 16 above.

Example V-1

5-(4-aminophenylamino)-2-(2,6-difluorophenyl)oxazole-4-carboxamide

Step a—2-(2,6-difluorophenyl)-5-(4-nitrophenylamino)oxazole-4-carbonitrile

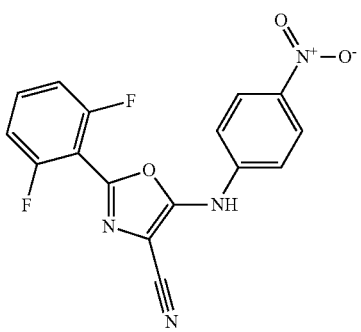 [SMILES: N#Cc1nc(-c2c(F)cccc2F)oc1Nc1ccc([N+](=O)[O-])cc1]

Prepared according to the procedure described in example U-1, step a. LCMS (2) Rt: 2.70 min; m/z (ES+) 343.

Step b—5-(4-aminophenylamino)-2-(2,6-difluorophenyl)oxazole-4-carbonitrile

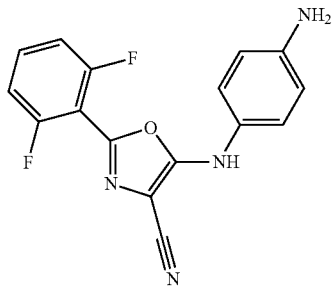 [SMILES: N#Cc1nc(-c2c(F)cccc2F)oc1Nc1ccc(N)cc1]

A solution of 2-(2,6-difluorophenyl)-5-(4-nitrophenylamino)oxazole-4-carbonitrile (0.435 g, 1.271 mmol) in 50:50 MeOH:EtOAc (10 ml) was hydrogenated using a 10% Pd/C catalyst at 30° C. at atmospheric pressure using the Thales H-Cube at a flow rate of 1 ml/min. The organic layer was then reduced in vacuo to yield 5-(4-aminophenylamino)-2-(2,6-difluorophenyl)oxazole-4-carbonitrile (0.360 g, 1.153 mmol, 90%). ¹H NMR (CD₃OD) δ 6.74 (2H, d), 7.10 (2H, d), 7.14 (2H, t), 7.55 (1H, m). LCMS (2) Rt: 2.47 min; m/z (ES+) 313.

Step c—5-(4-aminophenylamino)-2-(2,6-difluorophenyl)oxazole-4-carboxamide

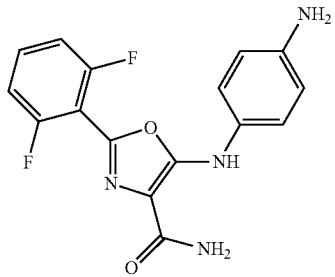 [SMILES: NC(=O)c1nc(-c2c(F)cccc2F)oc1Nc1ccc(N)cc1]

Prepared according to the procedure described in example Q-50, part c. ¹H NMR (DMSO) δ 4.94 (2H, br s), 6.53 (2H, d), 7.07 (2H, d), 7.21 (2H, br s), 7.29 (2H, t), 7.59 (1H, m), 8.87 (1H, br s). LCMS (2) Rt: 2.14 min; m/z (ES+) 331.

Example V-2

N-(4-(4-carbamoyl-2-(2,6-difluorophenyl)oxazol-5-ylamino)phenyl)-4-methyl piperazine-1-carboxamide Step a—N-(4-(4-cyano-2-(2,6-difluorophenyl)oxazol-5-ylamino)phenyl)-4-methylpiperazine-1-carboxamide

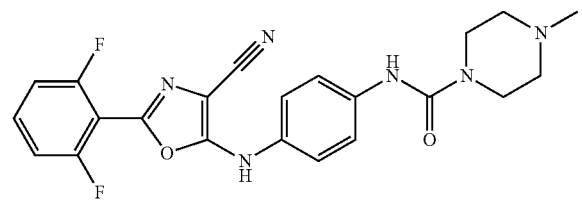 [SMILES: CN1CCN(C(=O)Nc2ccc(Nc3oc(-c4c(F)cccc4F)nc3C#N)cc2)CC1]

To a solution of 5-(4-aminophenylamino)-2-(2,6-difluorophenyl)oxazole-4-carbonitrile (0.020 g, 0.064 mmol), and diisopropylethylamine (0.011 mL, 0.064 mmol) in DCM (1 mL) was added 1,1''-carbonyldiimidazole (0.031 g, 0.192 mmol) and the reaction mixture stirred at room temperature for 15 minutes. To the reaction mixture was then added N-methyl piperazine (0.025 mL, 0.192 mmol) and the reaction mixture stirred for 1 hour. The reaction mixture was partitioned between water and DCM. The organic layer was reduced in vacuo to yield N-(4-(4-cyano-2-(2,6-difluorophenyl)oxazol-5-ylamino)phenyl)-4-methylpiperazine-1-carboxamide (0.019 g, 0.042 mmol, 66%). LCMS (2) Rt: 2.32 min; m/z (ES+) 439.

Step b—N-(4-(4-carbamoyl-2-(2,6-difluorophenyl)oxazol-5-ylamino)phenyl)-4-methyl piperazine-1-carboxamide

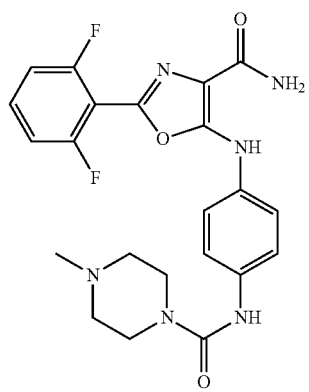 [SMILES: CN1CCN(C(=O)Nc2ccc(Nc3oc(-c4c(F)cccc4F)nc3C(N)=O)cc2)CC1]

Prepared according to the procedure described in example Q-50, part c. ¹H NMR (DMSO) δ 2.20 (3H, s), 2.31 (4H, t), 3.42 (4H, t), 7.34-7.27 (6H, m), 7.41 (2H, d), 7.62 (1H, m), 8.47 (1H, br s), 9.18 (1H, br s). LCMS (2) Rt: 2.05 min; m/z (ES+) 457.

Example V-3

2-(2,6-difluorophenyl)-5-(4-(3-(methylamino)propanamido)phenylamino)oxazole-4-carboxamide Step a—tert-butyl 3-(4-(4-cyano-2-(2,6-difluorophenyl)oxazol-5-ylamino)phenylamino)-3-oxopropyl(methyl)carbamate

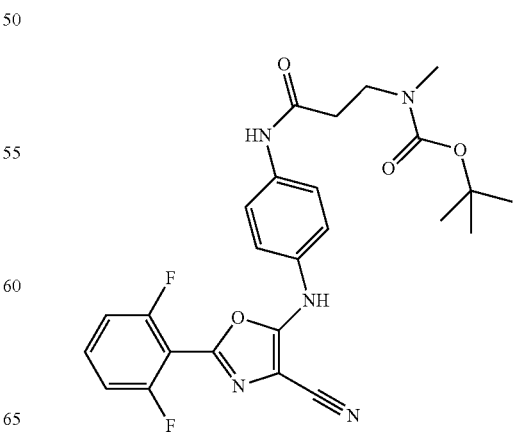

To a solution of N-(tert-butoxycarbonyl)-3-methylaminopropanoic acid (0.022 g, 0.11 mmol) in DMF (1.25 ml) were added O-(7-azabenzotriazol-1-yl)-N,N,N',N'-tetramethyluronium hexafluorophosphate (0.040 g, 0.11 mmol) and diisopropylethylamine (0.018 ml, 0.11 mmol) followed by 5-(4-aminophenylamino)-2-(2,6-difluorophenyl)oxazole-4-carbonitrile (0.030 g, 0.10 mmol) and the resultant mixture stirred at room temperature overnight. A further portion of N-(tert-butoxycarbonyl)-3-methylaminopropanoic acid (0.022 g, 0.11 mmol), O-(7-azabenzotriazol-1-yl)-N,N,N',N'-tetramethyluronium hexafluorophosphate (0.040 g, 0.11 mmol) and diisopropylethylamine (0.018 ml, 0.11 mmol) was added and the reaction stirred for 2 hours at room temperature. The solvent was removed in vacuo and the residue purified by preparative HPLC to afford tert-butyl 3-(4-(4-cyano-2-(2,6-difluorophenyl)oxazol-5-ylamino)phenylamino)-3-oxopropyl(methyl)carbamate (0.021 g, 0.04 mmol, 44%) as a white solid. LCMS (2) Rt: 3.03 min; m/z (ES+) 498.

Step b—2-(2,6-difluorophenyl)-5-(4-(3-(methylamino)propanamido)phenylamino)oxazole-4-carboxamide

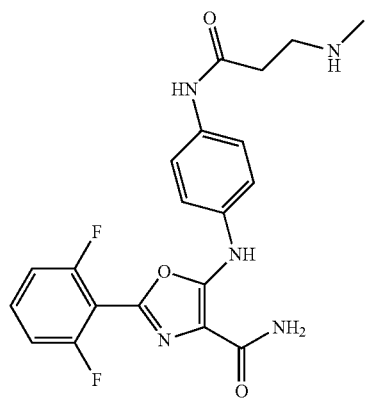 [SMILES: CNCCC(=O)Nc1ccc(Nc2oc(-c3c(F)cccc3F)nc2C(N)=O)cc1]

A solution of tert-butyl 3-(4-(4-cyano-2-(2,6-difluorophenyl)oxazol-5-ylamino)phenylamino)-3-oxopropyl(methyl)carbamate (0.021 g, 0.04 mmol) in concentrated sulfuric acid (1 ml) was stirred at room temperature overnight. The reaction was basified by addition to sat. sodium bicarbonate and then addition of 6M NaOH (to ~pH12). The aqueous phase was then extracted with EtOAc, the combined organic phases dried over MgSO$_4$ and the solvent removed in vacuo. The residue was purified by preparative HPLC to afford 2-(2,6-difluorophenyl)-5-(4-(3-(methylamino)propanamido)phenylamino)oxazole-4-carboxamide (0.0038 g, 0.009 mmol, 22%). $^1$H NMR (CD$_3$OD) δ 2.64 (3H, s), 2.73 (2H, t), 3.20 (2H, masked by CD$_3$OD peak), 7.08 (2H, t), 7.29 (2H, d), 7.45 (1H, m), 7.48 (2H, d), 8.45 (1H, br. s). LCMS (2) Rt: 2.28 min; m/z (ES+) 416.

Example V-4

N-(4-(4-carbamoyl-2-(2,6-difluorophenyl)oxazol-5-ylamino)phenyl)piperidine-3-carboxamide

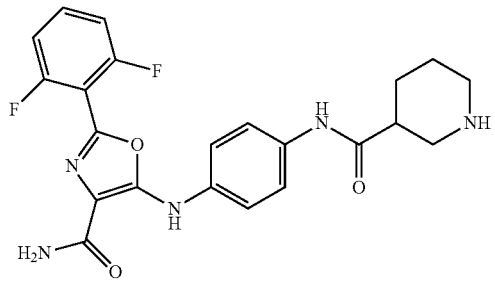 [SMILES: NC(=O)c1nc(-c2c(F)cccc2F)oc1Nc1ccc(NC(=O)C2CCCNC2)cc1]

Prepared according to the procedure descried in example V-2. LCMS (2) Rt: 2.40 min; m/z (ES+) 442.

General Method X

General Method X comprises the series of steps set out in Scheme 17 above.

Example X-1

2-(2,6-Difluorophenyl)-5-(3-(morpholinomethyl)phenyl)oxazole-4-carboxamide

Step a—2-(2,6-difluorophenyl)-5-(3-formylphenyl)oxazole-4-carboxamide

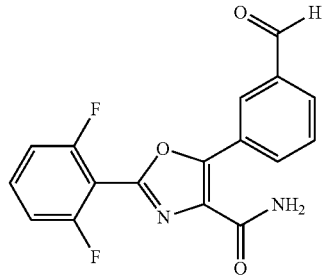 [SMILES: NC(=O)c1nc(-c2c(F)cccc2F)oc1-c1cccc(C=O)c1]

Prepared according to the method described in example F-1. $^1$H NMR (DMSO) δ 7.39-7.43 (2H, m), 7.74-7.83 (4H, m), 8.03-8.05 (1H, m), 8.59 (1H, m), 8.72-8.73 (1H, m), 10.10 (1H, s). LCMS (3) Rt: 2.18 min; m/z (ES+) 329.

Step b—2-(2,6-Difluorophenyl)-5-(3-(morpholinomethyl)phenyl)oxazole-4-carboxamide

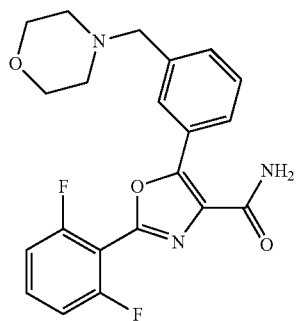 [SMILES: NC(=O)c1nc(-c2c(F)cccc2F)oc1-c1cccc(CN2CCOCC2)c1]

To a solution of 2-(2,6-difluorophenyl)-5-(3-formylphenyl)oxazole-4-carboxamide (0.050 g, 0.152 mmol), morpholine (0.027 mL, 0.305 mmol) and sodium triacetoxyborohydride (0.014 g, 0.228 mmol) in 1,2-dichloroethane (6 mL) was added acetic acid (0.013 mL, 0.228 mmol) at room temperature. The resulting mixture was stirred at room temperature for 2 h and then quenched with saturated sodium bicarbonate. The aqueous layer was extracted with ethyl acetate and the combined organic extracts dried over MgSO4 and concentrated in vacuo to give a residue that was purified by preparative HPLC to afford 2-(2,6-difluorophenyl)-5-(3-(morpholinomethyl)phenyl)oxazole-4-carboxamide (0.022 g, 0.056 mmol, 37%) as a white solid. $^1$H NMR (DMSO) δ 2.39 (4H, br m), 3.54 (2H, br m), 3.59 (4H, t), 7.38-7.45 (3H, m), 7.50 (1H, t), 7.71-7.78 (3H, m), 8.13-8.17 (2H, m). LCMS (2) Rt: 2.62 min; m/z (ES+) 400.

In a similar manner as described in example X-1 the compounds described in examples X-2 to X-4 were prepared.

Example X-2

2-(2,6-Difluorophenyl)-5-(3-((3-oxopiperazin-1-yl)methyl)phenyl)oxazole-4-carboxamide

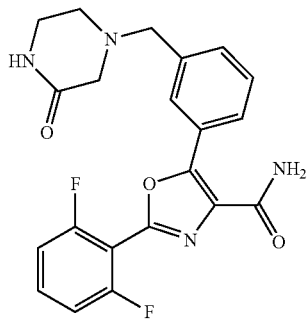 [SMILES: NC(=O)c1nc(-c2c(F)cccc2F)oc1-c1cccc(CN2CCNC(=O)C2)c1]

$^1$H NMR (DMSO) δ 2.57 (2H, br t), 2.96 (2H, s), 3.15-3.18 (2H, m), 3.62 (2H, s), 7.38-7.46 (3H, m), 7.49-7.53 (1H, m), 7.71-7.78 (4H, m), 8.15-8.18 (2H, m). LCMS (2) Rt: 2.18 min; m/z (ES+) 413.

Example X-3

2-(2,6-Difluorophenyl)-5-(3-(piperazin-1-ylmethyl)phenyl)oxazole-4-carboxamide formate salt

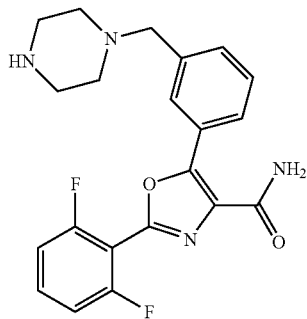 [SMILES: NC(=O)c1nc(-c2c(F)cccc2F)oc1-c1cccc(CN2CCNCC2)c1]

Modified Procedure;

Prepared using 1-boc-piperazine, with the following modification to the procedure used in example X-1: the crude reaction was passed through MP-TsOH cartridge and washed with methanol. After 3 h the cartridge was washed with 2M ammonia solution in methanol. The methanol solution was concentrated to give a residue that was purified by preparative HPLC to afford the product as the formate salt. $^1$H NMR (DMSO) δ 2.42 (4H, br m), 2.83 (4H, t), 3.54 (2H, s), 7.38-7.43 (3H, m), 7.47-7.51 (1H, m), 7.72-7.78 (2H, m), 8.11-8.15 (2H, m), 8.35 (2H, s). LCMS (2) Rt: 2.18 min; m/z (ES+) 399.

Example X-4

5-(3-((2-(Aminomethyl)morpholino)methyl)phenyl)-2-(2,6-difluorophenyl)oxazole-4-carboxamide formate salt

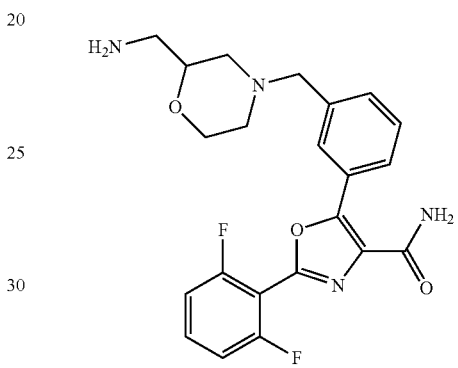

Prepared using 1-tert-butyl morpholin-2-ylmethylcarbamate according to the procedure described in example X-3 to afford the product as the formate salt. $^1$H NMR (DMSO) δ 1.87 (1H, t), 2.11-2.17 (1H, m), 2.67-2.70 (3H, m), 2.78-2.82 (1H, m), 3.48-3.53 (2H, m), 3.55-3.60 (2H, m), 3.80-3.83 (1H, m), 7.38-7.40 (2H, m), 7.43-7.46 (1H, m), 7.48-7.52 (1H, m), 7.60 (211, br s), 7.70-7.76 (1H, m), 8.12-8.15 (2H, m), 8.34 (1H, br s). LCMS (2) Rt: 2.21 mins; m/z (ES+) 429.

Biological Activity

FLT4—Enzyme Inhibition

FLT4 Enzyme:

A GST-kinase fusion protein of 70 KDa was produced using sf9 baculovirus expression system, with a construct expressing the human FLT4 (789-1207) with an amino terminal GST tag. The protein was purified by affinity chromatography using glutathione-agarose followed by separation on a gel filtration column.

FLT4 Kinase Assay:

FLT4 enzyme activity is determined using a Dissociation Enhanced Lanthanide Fluorescent Immunoassay (DELFIA) with a peptide substrate derived from the MET (Tyr 1253) peptide ARDMYDKEYYSVHNKTGAKA with a core sequence M<u>Y</u>DKE<u>YY</u>S.

The amount of phosphorylated peptide produced is detected by means of a phospho-Tyrosine specific Europium-labelled antibody using Time-Resolved Fluorescence at Excitation 360-35 nm and Emission 620-35 nm.

Enzyme Reaction:

Assay reactions are set up in a 25 uL final volume on a 96 well plate. FLT4-GST enzyme (Sareum) at 34 nM is incubated with varying concentrations of inhibitor in 2.5% DMSO, 1 uM peptide Biotin-DMYDKEYYSVHNKTG (custom made) and 30 μM ATP in 60 mM HEPES pH 7.5, 20 mM MgCl$_2$, 5 mM MnCl$_2$, 1.25 mM DTT and 0.01% Triton X-100. The reaction is allowed to proceed for 30 minutes at room temperature before stopping with 100 uL Stop solution comprising of 100 mM EDTA, 1×BSA blocker in TBS (Perbio) and 0.05% Surfact-Amps20 (Perbio).

Detection Step:

The stopped reaction is transferred to a black 96-well Neutravidin-coated plate (Perbio) and incubated for 30 minutes to capture the biotinylated peptide substrate. After washing wells 3 times with 200 uL TBS/T buffer, Anti-Phospho-Tyr-100 antibody labelled with Eu—N$_1$ (Perkin Elmer AD0159) is added to all wells for 60 minutes at room temperature. After a repeat washing step, DELFIA Enhancement solution (Perkin Elmer) is added to all wells for 5 minutes and the fluorescence measured on a plate reader Analyst HT (Molecular Devices).

The % inhibition of the activity is calculated and plotted in order to determine the concentration of test compound required to inhibit 50% of the enzyme activity (IC$_{50}$).

By means of the protocol set out above, it was found that the compounds of Examples A-13, A-16, B-2, D-1, E-1, E-2, E-3, E-4, F-1, F-3, F-4, F-5, F-6, F-7, F-8, F-9, F-10, F-11, F-12, F-13, F-14, F-15, F16, F-17, F-21, F-22, F-23, F-24, F-25, F-26, F-27, F-28, F-30, F-31, F-32, F-33, F-34, G-1, G-2, G-3, G-4, G-5, H-1, H-2, I-1, I-2, J-1, J-2, J-3, K-1, K-2, L-1, L-3, M-1, M-2, M-3, M-4, M-5, M-12, M-13, M-14, M-15, M-16, M-17, M-18, N-1, N-2, N-3, O-1, P-1, Q-2, Q-3, Q-4, Q-5, Q-7, Q-8, Q-9, Q-10, Q-11, Q-12, Q-13, Q-14, Q-15, Q-16, Q-17, Q-18, Q-19, Q-20, Q-21, Q-22, Q-23, Q-24, Q-25, Q-26, Q-27, Q-28, Q-29, Q-30, Q-31, Q-32, Q-33, Q-34, Q-35, Q-36, Q-37, Q-38, Q-39, Q-40, Q-42, Q-43, Q-44, Q-45, Q-46, Q-47, Q-48, Q-49, Q-50, Q-51, Q-52, Q-53, Q-54, Q-55, Q-56, Q-57, Q-58, Q-59, Q-60, R-1, R-2, R-4, R-5, R-6, R-8, R-10, R-11, R-12, R-13, R-14, R-15, R-16, R-17, R-18, R-19, S-1, S-4, S-5, S-6, S-7, S-8, S-9, S-10, S-11, S-12, S-13, S-14, S-15, S-16, S-17, S-18, S-19, S-20, S-21, T-1, T-2, T-3, T-4, U-1, U-2, U-3, U-4, U-5, U-6, U-7, U-8, U-9, U-10, U-11, U-12, U-13, U-14, U-15, U-16, U-17, U-18, U-19, U-20, U-21, U-22, U-23, U-24, U-25, U-26, U-27, V-1, V-2, V-3 and V-4 each have IC$_{50}$ values less than 10 μM or exhibit greater than 50% inhibition at a concentration of 10 μM, whereas the compounds of Examples A-1, A-2, A-3, A-4, A-5, A-6, A-7, A-8, A-9, A-10, A-11, A-12, A-14, A-15, A-17, A-19, A-20, B-1, B-3, B-4, B-5, C-1, F-2, F-19, F-20, F-29, M-9, N-7, N-10, Q-6, Q41, S-3, X-1, X-2, X-3 and X-4 each have IC$_{50}$ values less than 100 μM or exhibit greater than 50% inhibition at a concentration of 100 μM.

FLT3 Enzyme Inhibition

FLT3 Enzyme:

A GST-kinase fusion protein of 70 KDa was produced using sf9 baculovirus expression system, with a construct expressing the human FLT3 (564-993) with an amino terminal GST tag. The protein was purified by one-step affinity chromatography using glutathione-agarose.

FLT3 Kinase Assay:

FLT3 enzyme activity is determined using a Dissociation Enhanced Lanthanide Fluorescent Immunoassay (DELFIA) with a peptide substrate derived from the Gastrin Precursor (Tyr 87) peptide LEEEEEAYGWMDFGRRS with a core sequence: EA<u>Y</u>GW.

The amount of phosphorylated peptide produced is detected by means of a phospho-Tyrosine specific Europium-labelled antibody using Time-Resolved Fluorescence at Excitation 360-35 nm and Emission 620-35 nm.

Enzyme Reaction:

Assay reactions are set up in a 25 uL final volume on a 96 well plate. FLT3-GST enzyme (Sareum) at 9 nM is incubated with varying concentrations of inhibitor in 2.5% DMSO, 0.25 uM peptide: Biotin-LEEEEEAYGWMDFGRRS and 30 uM ATP in 60 mM HEPES pH 7.5, 80 mM MgCl$_2$, 80 mM MnCl$_2$, 1.25 mM DTT and 0.01% Triton X-100. The reaction is allowed to proceed for 30 minutes at room temperature before stopping with 100 μL Stop solution comprising of 100 mM EDTA, 1×BSA blocker in TBS (Perbio) and 0.05% Surfact-Amps20 (Perbio).

Detection Step:

The stopped reaction is transferred to a black 96-well Neutravidin-coated plate (Perbio) and incubated for 30 minutes to capture the biotinylated peptide substrate. After washing wells 3 times with 200 uL TBS/T buffer, Anti-Phospho-Tyr-100 antibody labelled with Eu—N$_1$ (Perkin Elmer AD0159) is added to all wells for 60 minutes at room temperature. After a repeat washing step, DELFIA Enhancement solution (Perkin Elmer) is added to all wells for 5 minutes and the fluorescence measured on a plate reader Analyst HT (Molecular Devices).

The % inhibition of the activity is calculated and plotted in order to determine the concentration of test compound required to inhibit 50% of the enzyme activity (IC$_{50}$).

By means of the protocol set out above, it was found that the compounds of Examples B-2, F-13, F-14, F-15, F-22, F-24, F-25, F-26, F-27, G-2, G-3, G-4, G-5, H-1, H-2, I-1, I-2, J-1, J-2, J-3, M-4, M-12, M-17, P-1, Q-1, Q-2, Q-3, Q-7, Q-8, Q-9, Q-10, Q-11, Q-12, Q-13, Q-14, Q-15, Q-16, Q-19, Q-20, Q-21, Q-22, Q-26, Q-23, Q-24, Q-25, Q-27, Q-29, Q-31, Q-32, Q-34, Q-35, Q-36, Q-37, Q-47, Q-56, Q-57, Q-58, Q-60, R-1, R-2, R-3, R-5, R-8, R-11, R-12, R-13, R-14, R-15, R-16, R-17, S-6, S-7, S-8, S-9, S-10, S-11, S-12, S-13, T-1, T-2, T-3, T-4 and U-1, U-5, U-12, U-13, U-14, U-15, U-16, U-17, U-18, U-19, U-20, U-21, U-22, U-23, U-24, U-25, U-26, U-27, V-2, V-3 and V-4 each have IC$_{50}$ values less than 10 μM or exhibit greater than 50% inhibition at a concentration of 10 μM, whereas the compounds of Examples E-3, E-4, F-2, F-7, F-9, F-10, F-11, F-12, F-16, F-19, G-1, M-2, M-3, M-9, M-11, N-2, N-3, N-7, N-8, Q-28, Q-30, Q-33, S-1, S-2, S-3, S-4 and S-5 each have an IC$_{50}$ value of less than 100 μM or exhibit greater than 50% inhibition at a concentration of 100 μM.

Aurora A Inhibition

Aurora A Enzyme:

The HIS-kinase fusion protein of 45 KDa was produced using sf9 baculovirus expression system, with a construct expressing the human Aurora A (1-403) with an amino terminal Histidine tag. The protein was purified by one-step affinity chromatography using nickel-agarose Aurora A Kinase Assay:

Aurora A enzyme activity is determined using a Dissociation Enhanced Lanthanide Fluorescent Immunoassay (DELFIA) with the peptide substrate (Biotin-A-G-A-G-R-R-R-S-L-L-E-L-H-K-R) containing residues surrounding the Ser 137 of PLK1 enzyme.

The amount of phosphorylated peptide produced is detected by means of a phospho-Tyrosine specific Europium-labelled antibody using Time-Resolved Fluorescence at Excitation 360-35 nm and Emission 620-35 nm.

Enzyme Reaction:

Assay reactions are set up in a 25 uL final volume on a 96 well plate. Aurora enzyme (Sareum) at 500 μM is incubated with varying concentrations of inhibitor in 2.5% DMSO, 1 uM peptide (Biotin-A-G-A-G-R-R-R-S-L-L-E-L-H-K-R) (custom made), 30 uM ATP in 12.5 mM HEPES pH 7.5, 1.25 mM $MgCl_2$, 0.5 mM DTT and 0.1% Tween. The reaction is allowed to proceed for 30 minutes at room temperature before stopping with 100 µL Stop solution comprising of 100 mM EDTA, 1×BSA blocker in TBS (Perbio) and 0.05% Surfact-Amps20 (Perbio).

Detection Step:

The stopped reaction is transferred to a black 96-well Neutravidin-coated plate (Perbio) and incubated for 30 minutes to capture the biotinylated peptide substrate. After washing wells 3 times with 200 uL TBS/T buffer, Anti-Phospho PLK (Ser137) antibody (CST 5070) is added to all wells and incubated for 60 minutes at room temperature. After repeating the washing step, the plate is further incubated for one hour with Europium-labelled anti-rabbit antibody (Perkin Elmer AD0105). The wash step is repeated for a final time before DELFIA Enhancement solution (Perkin Elmer) is added to all wells for 5 minutes and the fluorescence measured on a plate reader Analyst HT (Molecular Devices).

The % inhibition of the activity is calculated and plotted in order to determine the concentration of test compound required to inhibit 50% of the enzyme activity ($IC_{50}$).

By means of the protocol set out above, it was found that the compounds of Examples A-18, F-8, F-10, F-11, F-12, F-13, F-14, F-15, F-16, F-17, F-22, F-24, F-25, F-26, F-27, F-32, F-33, F-34, G-1, G-2, G-3, G-4, G-5, H-1, H-2, I-1, I-2, J-1, J-2, J-3, M-12, M-13, M-14, M-15, M-16, M-17, M-18, N-1, N-2, O-1, Q-1, Q-2, Q-3, Q-4, Q-7, Q-8, Q-9, Q-10, Q-11, Q-12, Q-14, Q-15, Q-16, Q-17, Q-18, Q-19, Q-20, Q-21, Q-22, Q-23, Q-24, Q-25, Q-26, Q-27, Q-29, Q-30, Q-31, Q-32, Q-33, Q-34, Q-35, Q-36, Q-37, Q-45, Q-46, Q-47, Q-48, Q-49, Q-50, Q-51, Q-52, Q-53, Q-54, Q-55, Q-56, Q-57, Q-58, Q-59, Q-60, R-1, R-2, R-5, R-6, R-8, R-9, R-10, R-11, R-12, R-13, R-14, R-15, R-16, R-17, R-18, S-1, S-4, S-5, S-6, S-7, S-8, S-9, S-10, S-12, S-13, S-14, S-15, S-16, S-17, S-18, S-19, S-20, S-21, T-1, T-2, T-3, T-4, U-1, U-2, U-3, U-4, U-5, U-6, U-7, U-8, U-9, U-10, U-11, U-12, U-13, U-14, U-15, U-16, U-17, U-18, U-19, U-21, U-22, U-23, U-24, U-25, U-26, U-27, V-2, V-3 and V-4 each have $IC_{50}$ values less than 10 µM or exhibit greater than 50% inhibition at a concentration of 10 µM, whereas the compounds of Examples A-2, A-3, A-4, A-5, A-6, A-7, A-8, A-10, A-11, A-12, A-13, A-14, A-15, A-16, B-1, B-2, B-3, B-4, B-5, C-1, E-2, E-3, E-4, F-3, F-5, F-9, F-23, F-31, F-35, F-36, F-37, M-3, M-4, M-6, N-4, N-5, N-6, N-7, N-8, N-9, N-10, Q-5, Q-6, Q-13, Q-28, Q-39, Q-41, Q-42, Q-43, Q-44, R-3, R-4, S-2, S-3, S-11 and U-20 each have $IC_{50}$ values less than 100 µM or exhibit greater than 50% inhibition at a concentration of 100 µM.

Anti-Proliferative Activity

The anti-proliferative activities of compounds of the invention are determined by measuring the ability of the compounds to inhibition of cell growth in a number of cell lines. Inhibition of cell growth is measured using the Alamar Blue assay (Nociari et al., *Journal of Immunological Methods* (1998) 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds for a further 72 hours. At the end of the incubation period 10% (v/v) Alamar Blue is added and incubated for a further 6 hours prior to determination of fluorescent product at Excitation 535 nm and Emission 590 nm. In the case of the non-proliferating cell assay cells are maintained at confluence for 96 hour prior to the addition of inhibitor compounds for a further 72 hours. The number of viable cells is determined by Alamar Blue assay as before. All cell lines are obtained from ECACC (European Collection of cell Cultures).

The compounds of examples F-13, G-3, G-5, J-3, M-12, M-17, Q-3, Q-7, Q-8, Q-9, Q-11, Q-14, Q-36, Q-57, R-11 and R-13 have been tested in the above assay against HCT116 cells and each have cell proliferation $IC_{50}$ values of less than 10 µM.

The compounds of examples G-3, G-5, M-12, M-17, Q-3, Q-11, Q-14, Q-26, Q-28, Q-36, Q-57, R-13 have been tested in the above assay against A549 human lung carcinoma cells and have each been found to have $IC_{50}$ values of less than 10 µM or exhibit greater than 50% inhibition of cell growth at a concentration of 10 µM.

Pharmaceutical Formulations

Example (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in a known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/mL) and mannitol (50 mg/mL), sterile filtering the solution and filling into sealable 1 mL vials or ampoules.

(iv) Subcutaneous Injection Formulation

A composition for sub-cutaneous administration is prepared by mixing a compound of the formula (I) with pharmaceutical grade corn oil to give a concentration of 5 mg/mL. The composition is sterilised and filled into a suitable container.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound which is an amide having the formula (4a):

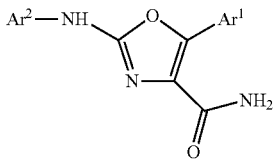

or a salt, N-oxide or tautomer thereof; wherein
Ar¹ is selected from substituted monocyclic 5- and 6-membered aryl and heteroaryl rings containing up to 2 heteroatoms selected from O, N and S, each of the aryl and heteroaryl rings being optionally substituted by one or more substituents R¹;
Ar² is a monocyclic or bicyclic 5- to 10-membered aryl or heteroaryl group containing up to 4 heteroatoms selected from O, N and S and being optionally substituted by one or more substituents R²;
R¹ is halogen; cyano; nitro; a group $R^a$-$R^b$; or a 3 to 8-membered carbocyclic or heterocyclic ring containing up to 4 heteroatoms selected from O, N and S and being optionally substituted by one or more substituents R³;
$R^a$ is a bond, O, CO, $X^1C(X^2)$, $C(X^2)X^1$, $X^1C(X^2)X^1$, S, SO, SO₂, NR$^c$, SO₂NR$^c$ or NR$^c$SO₂;
$R^b$ is:
hydrogen; or
a 3 to 8-membered carbocyclic or heterocyclic ring containing up to 4 heteroatoms selected from O, N and S and being optionally substituted by one or more substituents R³; or
a C$_{1-12}$ acyclic hydrocarbon group optionally substituted by one or more substituents selected from hydroxy; oxo; halogen; cyano; nitro; carboxy; amino; N(R$^c$)₂; and 3 to 8-membered carbocyclic or heterocyclic rings containing up to 4 heteroatoms selected from O, N and S and being optionally substituted by one or more substituents R³; wherein one to three but not all of the carbon atoms of the C$_{1-12}$ acyclic hydrocarbon group may optionally be replaced by O, CO, $X^1C(X^2)$, $C(X^2)X^1$, $X^1C(X^2)X^1$, S, SO, SO₂, NR$^c$, SO₂NR$^c$ or NR$^c$SO₂;
R$^c$ is hydrogen or a C$_{1-4}$ hydrocarbon group;
X¹ is O, S or NR$^c$;
X² is =O, =S or =NR$^c$;
R² is halogen; cyano; nitro; or a group $R^a$-$R^d$;
$R^d$ is hydrogen; a C$_{1-4}$ alkyl group optionally substituted by one or more fluorine atoms; or a benzyl group wherein the benzene ring of the benzyl group is optionally substituted with one to three substituents selected from halogen, cyano, C$_{1-4}$ alkyl and C$_{1-4}$ alkoxy, and wherein the C$_{1-4}$ alkyl and C$_{1-4}$ alkoxy substituents on the benzene ring are each optionally substituted with one or more fluorine atoms;
R³ is X²; halogen; cyano; nitro; a group $R^a$-$R^e$; or a 3 to 7-membered carbocyclic or heterocyclic ring containing up to 4 heteroatoms selected from O, N and S and being optionally substituted by a group R⁴;
R$^e$ is:
hydrogen; or
a C$_{1-6}$ acyclic hydrocarbon group optionally substituted by one or more substituents selected from hydroxy; oxo; halogen; cyano; nitro; carboxy; amino; and N(R$^c$)₂; wherein one to three but not all of the carbon atoms of the C$_{1-6}$ acyclic hydrocarbon group may optionally be replaced by O, S, SO, SO₂, NR$^c$, $X^1C(X^2)$, $C(X^2)X^1$ or $X^1C(X^2)X^1$; or
a benzyl group wherein the benzene ring of the benzyl group is optionally substituted with one to three substituents selected from halogen, cyano, C$_{1-4}$ alkyl and C$_{1-4}$ alkoxy, and wherein the C$_{1-4}$ alkyl and C$_{1-4}$ alkoxy groups are each optionally substituted with one or more fluorine atoms; and
R⁴ is selected from halogen, cyano, nitro and a group $R^a$-$R^d$;
provided that Ar¹ is other than a 2-aminopyridin-4-yl or 2-amino-pyrimidin-4-yl group wherein the 2-amino moiety is optionally substituted;
and that Ar²—NH— does not form an optionally substituted quinoxalin-4-ylamino group.

2. A compound according to claim 1 wherein, in Ar¹, the aryl or heteroaryl ring is substituted by 0, 1 or 2 substituents R¹.

3. A compound according to claim 1 wherein R¹ is selected from halogen; cyano; or a group $R^{aa}$-$R^{bb}$;
$R^{aa}$ is a bond, O, CO, OC(O), C(O)O, NR$^{cc}$C(O), C(O)NR$^{cc}$, NR$^{cc}$, OC(O)O, NR$^{cc}$C(O)O, OC(O)NR$^{cc}$, NR$^{cc}$C(O)NR$^{cc}$, S, SO, SO₂, SO₂NR$^{cc}$ or NR$^{cc}$SO₂
wherein
$R^{bb}$ is:
hydrogen; or
a 3 to 8-membered non-aromatic carbocyclic or heterocyclic ring containing up to 2 heteroatoms selected from O, N and S and being optionally substituted by one or more substituents R$^{3a}$; or
a 5- or 6-membered aryl or heteroaryl group containing up to 4 heteroatoms selected from O, N and S and being optionally substituted by one or more substituents R$^{3a}$; or
a C$_{1-12}$ acyclic hydrocarbon group optionally substituted by one or more substituents selected from:
hydroxy;
oxo;
halogen;
cyano;
carboxy;
N(R$^{cc}$)₂;
3 to 8-membered non-aromatic carbocyclic or heterocyclic rings containing up to 2 heteroatoms selected from O, N and S and being optionally substituted by one or more substituents R$^{3a}$;
5- or 6-membered aryl or heteroaryl groups each containing up to 4 heteroatoms selected from O, N and S and being optionally substituted by one or more substituents R$^{3a}$;
wherein one to three but not all of the carbon atoms of the C$_{1-12}$ acyclic hydrocarbon group may optionally be replaced by O, CO, OC(O), NR$^{cc}$C(O), OC(NR$^{cc}$), C(O)O, C(O)NR$^{cc}$, NR$^{cc}$, OC(O)O, NR$^{cc}$C(O)O, OC(NR$^{cc}$)O, OC(O)NR$^{cc}$, NR$^{cc}$C(O) NR$^{cc}$, S, SO, SO₂, NR$^{cc}$, SO₂NR$^{cc}$ and NR$^{cc}$SO₂;
R$^{cc}$ is hydrogen or a saturated C$_{1-4}$ hydrocarbon group;
R$^{3a}$ is oxo; halogen; cyano; a group $R^{aa}$-$R^{ee}$; or a 3 to 8-membered carbocyclic or heterocyclic ring containing up to 2 heteroatoms selected from O, N and S and being optionally substituted by $C_{1-4}$ alkyl, $C_{1-4}$ acyl, $C_{1-4}$ alkoxycarbonyl or $C_{1-4}$ alkylsulphonyl;

$R^{ee}$ is:
- hydrogen; or
- a $C_{1-6}$ acyclic saturated hydrocarbon group optionally substituted by one or more substituents selected from hydroxy; oxo; halogen; cyano; carboxy; and $N(R^{cc})_2$; or
- a benzyl group wherein the benzene ring of the benzyl group is optionally substituted with one to three substituents selected from halogen, cyano, $C_{1-4}$ alkyl and $C_{1-4}$ alkoxy, and wherein the $C_{1-4}$ alkyl and $C_{1-4}$ alkoxy groups are each optionally substituted with one or more fluorine atoms.

4. A compound according to claim 1 wherein $R^1$ is selected from:

halogen;

$CO_2R^5$ wherein $R^5$ is hydrogen or $C_{1-6}$ alkyl;

$SO_2R^5$;

$C_{1-4}$ alkyl optionally substituted by hydroxy or $C_{1-2}$ alkoxy or one or more fluorine atoms;

$C_{1-4}$ alkoxy optionally substituted by hydroxy or $C_{1-2}$ alkoxy or one or more fluorine atoms; or a group Q, C(O)NHQ, HNC(O)Q, C(O)NH-Alk-Q, HNC(O)-Alk-Q, NH-Alk-Q, $CH_2Q$, S(O)Q, $SO_2Q$, C(O)Q or O-Alk(OH)$_p$-Q where Alk is a straight or branched chain alkylene group of 2 to 5 carbon atoms and p is 0 or 1 provided that there are at least 2 carbon atoms in line between O and Q, or OH and Q, or O and OH;

and Q is selected from:
- a saturated or partially unsaturated 4 to 8 membered heterocyclic ring $Het^1$ containing a nitrogen ring member and optionally a further heteroatomic ring member selected from O, N and S, wherein the heterocyclic ring $Het^1$ is optionally substituted by one or more substituents selected from =O, OH, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl; and
- a 5- or 6-membered monocyclic heteroaryl ring containing 1 to 4 heteroatom ring members selected from O, N and S, of which at least one is N, the heteroaryl ring being optionally substituted by one or more substituents selected from OH, halogen, CN, $CF_3$, $C_{1-4}$ alkyl, hydroxy-$C_{1-4}$ alkyl, amino-$C_{1-4}$ alkyl, mono- or di-$C_{1-4}$ alkylamino-$C_{1-4}$ alkyl, amino, mono- or di-$C_{1-4}$ alkylamino, $C_{1-4}$ acyl, $C_{1-4}$ alkoxycarbonyl, $C_{1-4}$ alkylsulphonyl, aminocarbonyl, and mono- and di-$C_{1-4}$ alkylaminocarbonyl.

5. A compound according to claim 1 wherein $Ar^2$ is selected from optionally substituted monocyclic 5- and 6-membered aryl and heteroaryl rings containing up to 2 heteroatoms selected from O, N and S, and optionally substituted bicyclic 6.5 fused rings containing up to 3 heteroatoms selected from O, N and S.

6. A compound according to claim 5 wherein $Ar^2$ is selected from:
- (a) the group consisting of phenyl, thiophene, furan, indole, indazole, benzoimidazole, benzofuran, pyridine, pyrrolopyridine and pyrazole, each optionally substituted by one or more substituents $R^2$; or
- (b) the group consisting of phenyl, thiophene, furan, indole, indazole, benzoimidazole, benzofuran, pyridine and pyrazole, each optionally substituted by one or more substituents $R^2$.

7. A compound according to claim 1 in the form of a salt.

8. A pharmaceutical composition comprising a compound as defined in claim 1 and a pharmaceutically acceptable carrier.

* * * * *